US008632994B2

(12) United States Patent
Winther et al.

(10) Patent No.: US 8,632,994 B2
(45) Date of Patent: Jan. 21, 2014

(54) METHODS AND COMPOSITIONS FOR IMMUNO-HISTOCHEMICAL DETECTION

(75) Inventors: Lars Winther, Smoerum (DK); Anthony Lionel Knoll, Ventura, CA (US); Kellyann Weckworth, Santa Barbara, CA (US); Uffe Lovborg, Santa Barbara, CA (US)

(73) Assignee: Dako Denmark A/S, Glostrup (DK)

( * ) Notice: Subject to any disclaimer, the term of this patent is extended or adjusted under 35 U.S.C. 154(b) by 1017 days.

(21) Appl. No.: 10/999,102

(22) Filed: Nov. 30, 2004

(65) Prior Publication Data

US 2005/0208529 A1  Sep. 22, 2005

Related U.S. Application Data

(60) Provisional application No. 60/525,960, filed on Dec. 1, 2003, provisional application No. 60/570,800, filed on May 14, 2004.

(51) Int. Cl.
*G01N 33/53* (2006.01)

(52) U.S. Cl.
USPC ............... 435/40.5; 435/7.1; 435/40.52

(58) Field of Classification Search
None
See application file for complete search history.

(56) References Cited

U.S. PATENT DOCUMENTS

| 4,017,597 | A | * | 4/1977 | Reynolds | ............... 435/7.92 |
| 4,609,707 | A | * | 9/1986 | Nowinski et al. | ............ 525/54.1 |
| 4,711,955 | A | * | 12/1987 | Ward et al. | ................ 536/25.32 |
| 5,296,347 | A | | 3/1994 | LaMotte, III | |
| 5,543,332 | A | * | 8/1996 | Lihme et al. | ................... 436/528 |
| 5,585,089 | A | | 12/1996 | Queen et al. | |
| 5,843,725 | A | | 12/1998 | Sledziewski et al. | |
| 6,287,785 | B1 | | 9/2001 | Shinoki et al. | |
| 7,115,727 | B2 | * | 10/2006 | Faris et al. | ................... 536/23.1 |

FOREIGN PATENT DOCUMENTS

| DE | 196 34 730 A1 | 3/1998 |
| EP | 0 269 451 A2 | 6/1988 |
| EP | 0 589 877 B1 | 11/1996 |
| EP | 0 436 597 B1 | 4/1997 |
| EP | 594772 | 5/1999 |
| EP | 0 623 679 B1 | 6/2003 |
| EP | 0 368 684 B2 | 9/2004 |
| FR | 2 596 867 A1 | 10/1987 |
| WO | WO 93/01498 | 1/1993 |
| WO | WO 93/17335 | 9/1993 |

(Continued)

OTHER PUBLICATIONS

Harlow, E. and Lane, D., Antibodies: A Laboratory Manual (1988) Cold Spring Harbor Laboratory Press, Cold Spring Harbor, NY, pp. 359 and 361-420.*

(Continued)

*Primary Examiner* — Christine Foster

(74) *Attorney, Agent, or Firm* — Finnegan, Henderson, Farabow, Garrett & Dunner L.L.P.

(57) ABSTRACT

The invention relates to methods and compositions of detecting a biological marker in a sample. In certain embodiments, the methods and compositions comprise a first binding agent that specifically binds to a biological marker in a sample; a second binding agent linked to a first polymer, wherein the second binding agent specifically binds to the first binding agent; a third binding agent linked to a second polymer, wherein the third binding agent specifically binds to the second binding agent; and a detectable substance. In certain embodiments the biological markers are detected immunologically.

49 Claims, 80 Drawing Sheets

GaR-HRP-polymer

Rabbit anti DNP polymer

DNP labelled mouse antibody

(56) References Cited

FOREIGN PATENT DOCUMENTS

| WO | WO 97/00446 | | 1/1997 | |
|---|---|---|---|---|
| WO | WO 98/18488 | | 5/1998 | |
| WO | WO 00/07019 | * | 2/2000 | ............ G01N 33/531 |

OTHER PUBLICATIONS

Dodson et al. "Modern methods for diagnostic immunocytochemistry" Current Diagnostic Pathology (2002) vol. 8, 113-122.*

Harlow, E. and Lane, D., Antibodies: A Laboratory Manual (1988) Cold Spring Harbor Laboratory Press, Cold Spring Harbor, NY, pp. 319, 321, 344, 359 and 361-420.*

Altmann et al., Insect Cells As Hosts for the Expression of Recombinant Glycoproteins, *Glycoconjugate Journal*, 1999 vol. 16. pp. 109-123.

Ausebel et al., Current Protocols in Molecular Biology, *John Wiley & Sons, Inc.*, 1995 vol. 3, Section 2, Section 4, Section 6, Unit 14.7.

Coons et al., Immunological Properties of an Antibody Containing a Fluorescent Group, *Proc. Soc. Exp. Biol. Med.*, 1941 vol. 47, pp. 200-202.

Dakocytomation Catalog, May 2004, p. 198.

Jones et al., "Replacing the Complemantarity-Determining Regions in a Human Antibody With Those From a Mouse", *Nature*, 1986 vol. 321, pp. 522-524.

Kang et al., Linkage of Recognition and Replication Functions by Assembling Combinatorial Antibody Fab Libaries Along Phage Surfaces, *Proc. Natl. Acad. Sci. USA*, 1991 vol. 88, pp. 4363-4366.

Kohler et al., Continuous Cultures of Fused Cells Secreting Antibody of Predefined Specificity, *Nature*, 1975 vol. 256, pp. 495-497.

Kost et al., Recombinant Baculoviruses As Expression Vectors for Insect and Mammalian Cells, *Current Opinion in Biotechnology*, 1999 vol. 10: pp. 428-433.

Marks et al., By-Passing Immunization: Building High Affinity Human Antibodies by Chain Shuffling, *Bio/Technology*, 1992 vol. 10, pp. 779-793.

McCafferty et al., Phage Antibodies: Filamentous Phage Displaying Antibody Variable Domains, *Nature*, 1990 vol. 348, pp. 552-554.

Mokry, Versatility of Immunohistochemical Reactions: Comprehensive Survey of Detection Systems, *ACTA MEDICA*, 1996 vol. 39 pp. 129-140.

Nakane et al., Enzyme-Labeled Antibodies: Preparation and Application for the Localization of Antigens, *The Journal of Histochemistry and Cytochemistry*, 1996 vol. 14, pp. 929-931.

Nielsen, Peptide Nucleic Acid: A Versatile Tool in Genetic Diagnostics and Molecular Biology, *Current Opinion in Biotechnology*, 2001 vol. 12 pp. 16-20.

Riechmann et al., Reshaping Human Antibodies for Therapy, *Nature*, 1988 vol. 332, pp. 323-327.

Sambrook et al., Hybridization to Nitrocellulose Filters Containing Replicas of Bacterial Colonies, Molecular Cloning: *Laboratory Manual*, $2^{nd}$ ed. 1989 vol. 1, pp. 1.101-104, Chapters 7, 9, Section 10.6-12 and 11.

Sorensen et al., Functionalized LNA (Locked Nucleic Acid): High-Affinity Hybridization of Oligonucleotides Containing N-Acylated and N-Alkylated 2'-Amino-LNA Monomers, *Chem. Commun.* 2003 vol. 21 pp. 2130-2131.

Tatusova et al., BLAST 2 Sequences, A New Tool for Comparing Protein and Nucleotide Sequences, *FEMS Microbiology Letters* 1999 vol. 174 pp. 247-250.

Waterhouse et al., Combinatorial Infection and In Vivo Recombination: A Strategy for Making large Phage Antibody Repertoires, *Nucleic Acids Research*, 1993 vol. 21, No. 9 pp. 2265-2266.

Altshul et al., "Gapped BLAST and PSI-BLAST: a new generation of protein database search programs," *Nucleic Acids Res*. 25:3389-3402 (1997).

Shi et al., "Antigen retrieval immunohistochemistry: past, present, and future," *J Histochem Cytochem*, 45(3):327 (1997).

Rullier A. et al., "Immunohistochemical detection of HCV in cirrhosis, dysplastic nodules, and hepatocellular carcinomas with parallel-tissue quantitiative RT-PCR," Mod. Pathol., 14:496-505 (2001).

Savinainen K.J. et al., "Expression and gene copy number analysis of *ERBB2* oncogene in prostate cancer," American Journal of Pathology, 160:339-45 (2002).

Shi S.R. et al., "Sensitivity and detection efficiency of a novel two-step detection system (PowerVision) for immunohistochemistry," Applied Immunohistochemistry & Molecular Morphology, 7:201-208 (1999).

Wiedom K.H., "EnVision+, a new dextran polymer-based signal enhancement technique for in situ hybridization (ISH)," The Journal of Histochemistry & Cytochemistry, 49:1067-71 (2001).

* cited by examiner

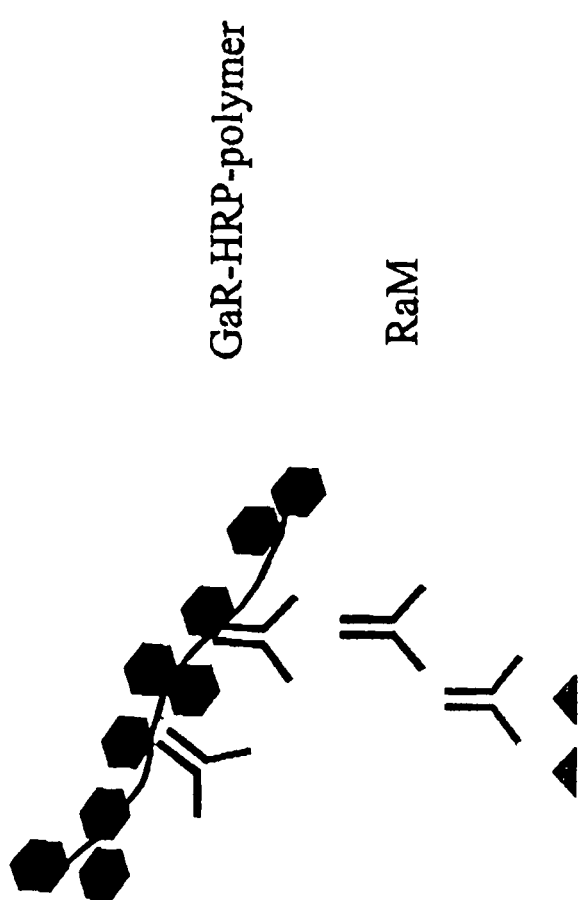

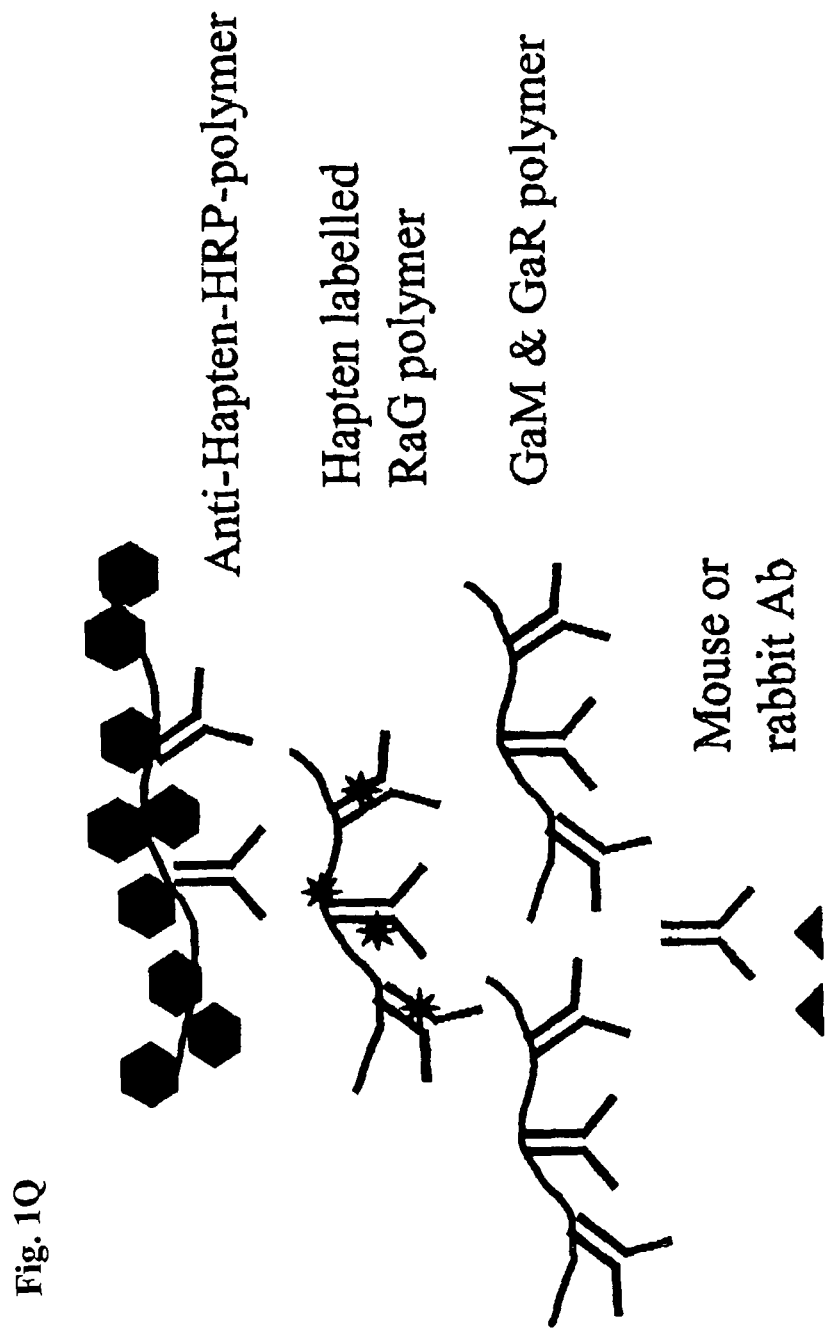

METHODS AND COMPOSITIONS FOR IMMUNO-HISTOCHEMICAL DETECTION

This application claims priority to U.S. provisional application No. 60/525,960 filed on Dec. 1, 2003 and U.S. provisional application No. 60/570,800 filed on May 14, 2004.

In certain embodiments the invention relates to the detection of biological markers using immunological techniques. In certain specific embodiments the invention relates to the detection of biological markers using immuno-histochemistry or cytology.

Detection of a target biological marker in a biological sample or specimen may be achieved by contacting the target with a molecule which specifically binds to the target. The molecule may be, for example, a protein or a nucleic acid probe (e.g. for use in in situ hybridization or Southern or northern blots). The molecule may be linked, either directly or indirectly to a detectable substance, thus permitting the staining and detection of the target contained in a biological sample. Detectable substances that are commonly used include dyes such as Texas red, and FITC, as well as radioactive isotopes, metal particles and enzymes which upon catalysis of a specific substrate permit colormetric detection of the target biological marker (see e.g. Coons et al. 1941, *Proc Soc Exp Biol Med* 47:200; Nakane and Pierce 1966, *J Histochem Cytochem* 14:929). One system for the detection of biological markers relies on immunologically derived molecules which specifically bind to a desired target biological marker in a sample.

Immunologically based detection of biological markers advantageously exploits the specificity of immune derived proteins such as antibodies for specific biological markers of interest. Typically the antibody will recognize a specific epitope on the target biological marker which permits the target to be distinguished and thus detected from other biological markers contained within a given biological sample or specimen. A variety of formats capable of detecting biological markers of interest are known, including enzyme linked immuno-assays (ELISA), flow cytometry, western blots, radioimmunoassay (RIA) and immunohistochemistry (IHC) (see e.g. Janeway et al. *Immunobiology* $5^{th}$ edition, Garland Publishing, N.Y. NY). All of these techniques are useful in research as well as in the detection and diagnosis of a variety of diseases and conditions.

IHC specifically provides a method of detecting a biological marker in a sample or tissue specimen in situ (see Mokry 1996, *ACTA MEDICA* 39:129). The overall cellular integrity of the sample is maintained in IHC, thus allowing detection of both the presence and location of the biological marker of interest. Typically a sample is fixed with formalin and paraffin-embedded and cut into sections for viewing by light microscopy. The intensity of the signal obtained correlates with the level of expression of the target molecule in the sample. Early methods for performing IHC relied solely on direct detection. Direct detection means the detectable agent, e.g., a fluorescent dye, was linked directly to the primary antibody (i.e. the antibody that specifically binds to the target biological marker). The limitation of this method was that biological markers expressed at low levels produced a weak detection signal. Attempts to overcome this limitation included linking multiple copies of the primary antibody to a dextran polymer conjugated with an enzyme such as horse radish peroxidase (EPOS®) (Dakocytomation, Carpenteria, Calif.) (see Dakocytomation catalog).

Other attempts to overcome this problem included addition of a second antibody. To amplify the detection, the primary antibody was not labeled. Instead, application of a secondary antibody, linked to a detectable substance, which specifically bound to the primary antibody was added to the method. Multiple copies of the secondary antibody could bind the primary antibody thus enhancing the signal. This method is known as the indirect detection.

Several products which exploit indirect detection for use in IHC are commercially available. Examples include Envision™+ (Dakocytomation, Carpenteria, Calif.) (see Dakocytomation catalog) which provides secondary antibodies linked to a polymer conjugated with horse radish peroxidase (HRP) or Alkaline Peroxidase (AP). A dual linked version of Envision™ Systems (Envision™+) is also available. The dual link provides for two different secondary antibodies linked to two different polymers, where each of the polymers is conjugated to an enzyme such as HRP. The two secondary antibodies specifically bind to antibodies from different species (e.g. rabbit and mouse), thus providing flexibility in the choice of a primary antibody. Powervision® (Immunovision, Springdale, Ariz.) also uses a secondary antibody linked to a polymer conjugated with an enzyme. Non-biotin amplification (NBA)™ kit (Zymed Laboratories Inc., South San Francisco, Calif.) provides for a secondary antibody conjugated to a hapten (fluorescein) and a tertiary antibody, which specifically binds to the hapten where the tertiary antibody is conjugated with HRP. HistoFine® (Nichirei Corp, Tokyo, Japan) provides for an F(ab) linked to a polymer conjugated with an enzyme such as HRP. Also known in the art are detection systems relying on secondary antibodies linked to haptens such as biotin. In this system, the secondary antibody is contacted with a biotin binding partner such as avidin or streptavidin which is conjugated to HRP.

Despite the variety of commercial products available for performing IHC, the need still exists for methods and compositions which provide increased sensitivity in the detection of biological markers normally present at low levels in a sample, e.g., by IHC. Increased sensitivity would be useful in particular, when a condition or a disease is associated with a decrease in the amount of expression of biological markers as compared to normal.

In certain embodiments, the invention provides for a more sensitive method, compared to known methods, of detecting a biological marker in a sample, e.g., by IHC. Increased sensitivity may provide a stronger detection signal generated from a stained sample. Increased sensitivity may permit the use of less reagents, e.g., a primary antibody, a secondary antibody when performing IHC or other immunologically based detection methods, and less reagent may provide for a reduction in unspecific background staining. Alternatively the increased sensitivity may be utilized to perform a faster protocol.

In some embodiments, the invention provides a composition useful for detecting a biological marker in a sample comprising a first binding agent which specifically binds to a biological marker in a sample, (e.g., a primary antibody, a nucleic acid probe) a second binding agent which specifically binds to the first binding agent, (e.g. a secondary antibody), and a third binding agent which specifically binds to the second binding agent, (e.g., a tertiary antibody). At least one of the binding agents may be linked to a polymer or the binding agents themselves may be polymerizable, e.g., derivatized and polymerized. The conjugated polymer may be linked with a detectable substance. In some embodiments, at least one of the second binding agent and the third binding agent may be linked to a detectable substance or a hapten or both a detectable substance and a hapten. The invention also provides a method of detecting a biological marker in a sample comprising contacting the sample with the composition of the invention.

In some embodiments, the invention provides a composition comprising at least a primary antibody, a secondary antibody and a tertiary antibody, where at least one of the tertiary antibody and the secondary antibody is linked to a polymer conjugated to a detectable substance or is itself derivatized and then polymerized, optionally with a detectable substance. The composition is useful in detecting biological markers in a sample by IHC. The composition is also useful for detecting markers associated with a disease or condition, e.g., a protein expressed at higher levels in a cell or tissue sample derived from a subject having a disease compared to a cell or a tissue sample derived from a subject not having the disease.

In certain embodiments, the invention provides for a method of detecting a biological marker in a sample comprising:
 a) contacting the sample with at least one first binding agent such that the first binding agent binds to the sample and forms a first complex;
 b) contacting the first complex of a) with at least one second binding agent which specifically binds to the at least one first binding agent such that a second complex is formed and, wherein the at least one second binding agent is optionally linked to at least one first polymer, or is polymerizable without the addition of a polymer backbone;
 c) contacting the second complex of b) with
  i) at least one third binding agent wherein the at least one third binding agent is linked to at least one second polymer, or is polymerizable without the addition of a polymer backbone, and wherein the third binding agent specifically binds to the second binding agent;
  wherein at least one detectable agent is linked to at least one of
   1) the at least one third binding agent;
   2) the at least one second polymer; and
   3) both the at least one third binding agent and the at least one second polymer
   such that the third binding agent binds to the second complex of b) and forms a third complex; and
 d) detecting the third complex of c).

In certain embodiments, the invention provides for a method of detecting a biological marker in a sample comprising
 a) contacting the sample with at least one primary antibody, chosen from a mouse antibody and a rabbit antibody such that the at least one primary antibody binds to the sample forming a first complex;
 b) contacting the complex of a) with
  i) at least one first secondary goat antibody linked to a first dextran polymer, the first secondary goat antibody comprising an antigen binding domain which specifically binds to a mouse antibody; and/or
  ii) at least one second secondary goat antibody linked to a second dextran polymer, the second secondary goat antibody comprising an antigen binding domain which specifically binds to a rabbit antibody; such that the at least one secondary antibody binds to the complex of a) forming a second complex;
 c) contacting the second complex of b) with
  i) at least one tertiary rabbit antibody linked to a third dextran polymer, the at least one tertiary rabbit antibody comprising an antigen binding domain which specifically binds to a goat antibody;
  wherein at least one horse radish peroxidase molecule is linked to at least one of
   1) the at least one tertiary antibody;
   2) the at least one second polymer; and
   3) both the at least one tertiary antibody and the at least one second polymer
   such that the at least one tertiary antibody binds to the second complex of b) and forms a third complex; and
 d) detecting the third complex of c).

In certain embodiments, the invention provides for a method of detecting a biological marker in a sample comprising
 a) contacting the sample with at least one primary mouse antibody such that the at least one primary mouse antibody binds to the sample forming a first complex;
 b) contacting the first complex of a) with at least one rabbit antibody comprising an antigen binding domain which specifically binds to a mouse antibody such that the at least one rabbit antibody binds to the complex of a) forming a second complex;
 c) contacting the second complex of b) with
  i) at least one tertiary goat antibody linked to a dextran polymer, the at least one tertiary goat antibody comprising an antigen binding domain which specifically binds to a rabbit antibody;
  wherein at least one horse radish peroxidase molecule is linked to at least one of
   1) the at least one tertiary antibody;
   2) the at least one second polymer; and
   3) both the at least one tertiary antibody and the at least one second polymer
   such that the at least one tertiary antibody binds to the second complex of b) and forms a third complex; and
 d) detecting the third complex of c).

In certain embodiments, the invention provides for a method of detecting a biological marker in a sample comprising
 a) contacting the sample with at least one primary mouse antibody such that the at least one primary mouse antibody binds to the sample forming a first complex;
 b) contacting the complex of a) with at least one secondary rabbit antibody linked to a first dextran polymer, the at least one secondary rabbit antibody comprising an antigen binding domain which specifically reacts with a mouse antibody such that at least one secondary antibody binds to the complex of a) forming a second complex, where optionally, the first dextran polymer is linked to at least one horse radish peroxidase molecule, or the at least one secondary rabbit antibody is linked to at least one horse radish peroxidase molecule, or both the first dextran polymer and the at least one secondary rabbit antibody are each linked to at least one horse radish peroxidase molecule;
 c) contacting the second complex of b) with
  i) at least one first tertiary goat antibody linked to a second dextran polymer, the at least one first tertiary goat antibody comprising an antigen binding domain which specifically reacts with a rabbit antibody; and
  ii) at least one second tertiary goat antibody linked to a third dextran polymer, the at least one second tertiary goat antibody comprising an antigen binding domain which specifically reacts with a mouse antibody;
  wherein at least one horse radish peroxidase molecule is linked to at least one of
   1) any at least one tertiary antibody;
   2) the second dextran polymer;
   3) the third dextran polymer;

4) both the second dextran molecule and the third dextran molecule; and
5) any at least one tertiary antibody and both the second dextran molecule and the third dextran molecule such that the tertiary antibody binds to the second complex of b) and forms a third complex; and
d) detecting the third complex of c).

In certain embodiments, the invention provides for a method of detecting a biological marker in a sample comprising a) contacting the sample with at least one primary antibody, chosen from a mouse antibody and a rabbit antibody such that the at least one primary antibody binds to the sample forming a first complex;
b) contacting the complex of a) with
  i) at least one first secondary goat antibody linked to a first dextran polymer, the first secondary goat antibody comprising an antigen binding domain which specifically binds to a mouse antibody;
  ii) at least one second secondary goat antibody linked to a second dextran polymer, the second secondary goat antibody comprising an antigen binding domain which specifically binds to a rabbit antibody;
  wherein at least one hapten molecule is linked to at least one of
    1) the at least one secondary goat antibody;
    2) at least one of the first and second dextran molecule; and
    3) the at least one secondary goat antibody and at least one of the first and second dextran molecule
  such that the at least one secondary antibody binds to the complex of a) forming a second complex;
c) contacting the second complex of b) with
  i) at least one tertiary antibody, chosen from a rabbit antibody, a mouse antibody, a rat antibody, a porcine antibody and a goat antibody, linked to a third dextran polymer, the at least one tertiary antibody comprising an antigen binding domain which specifically reacts with the at least one hapten molecule of b);
  wherein at least one horse radish peroxidase molecule is linked to at least one of
    1) the tertiary antibody;
    2) the at least one third polymer; and
    3) both the tertiary antibody and the at least one third polymer
  such that the tertiary antibody binds to the second complex of b) and forms a third complex; and
d) detecting the third complex of c).

In one embodiment, the invention provides a composition comprising:
a) at least one primary antibody;
b) at least one secondary antibody, optionally linked to a first polymer, the at least one secondary antibody comprising an antigen binding domain which specifically binds to the primary antibody; and
c) at least one tertiary antibody linked to at least one second polymer wherein a detectable agent is linked to at least one of
  i) the at least one tertiary antibody;
  ii) the at least one the second polymer; and
  iii) both the tertiary antibody and at the least one second polymer.

The invention also contemplates compositions comprising binding agents, e.g., antibodies and polymers depicted and described in FIG. 1A-1L infra.

It is to be understood that both the foregoing general description and the following detailed description are exemplary and explanatory only and are not restrictive of the invention, as claimed.

DESCRIPTION OF THE EMBODIMENTS

A. Definitions

Figure 1A:
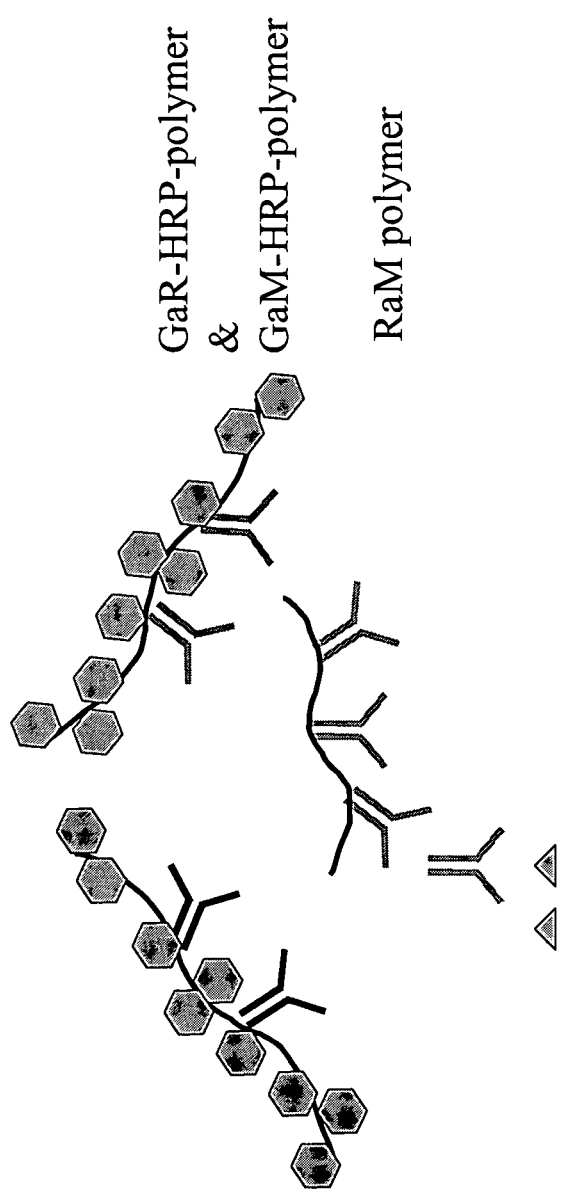
FIG. 1A-1T depict schematic illustrations of various conjugate combinations: (A) target biological marker on tissue, primary antibody, polymeric rabbit anti mouse secondary antibody and a mixture of goat anti mouse and goat anti rabbit secondary antibodies (Envision™+) (Dakocytomation, Carpenteria, Calif.); (B) target biological marker on tissue, primary antibody, polymeric conjugate containing rabbit anti mouse secondary antibody and horseradish peroxidase, and a mixture of polymeric conjugates containing goat anti mouse and horseradish peroxidase and goat anti mouse secondary antibodies and horseradish peroxidase (Envision™+) (Dakocytomation, Carpenteria, Calif.); (C) target biological marker on tissue, primary antibody, a mixture of polymeric conjugates containing goat anti mouse secondary antibody and goat anti rabbit secondary antibody, and a polymeric conjugate containing rabbit anti goat and horseradish; (D) target biological marker on tissue, primary antibody, a rabbit anti mouse secondary antibody, and a polymeric conjugate containing goat anti rabbit and horseradish peroxidase; (E) target biological marker on tissue, primary antibody, a mixture of hapten labeled polymeric conjugates containing goat anti mouse secondary antibody and hapten labeled goat anti rabbit secondary antibody, and a polymeric conjugate containing anti hapten antibody and horseradish peroxidase; (F) target biological marker on tissue, primary antibody, a mixture of polymeric conjugates containing goat anti mouse secondary antibody and goat anti rabbit secondary antibody, and a polymeric conjugate containing rabbit anti goat and alkaline phosphatase (ALP); (G) target biological marker on tissue, primary mouse antibody, a DNP labeled polymeric conjugate containing goat anti mouse secondary antibody, and a polymeric conjugate containing rabbit anti DNP antibody and horseradish peroxidase; (H) target biological marker on tissue, DNP labeled mouse primary antibody, a polymeric conjugate containing rabbit anti DNP antibody, and a polymeric conjugate containing goat anti rabbit secondary antibody and horseradish peroxidase; (I) target biological marker on tissue, polymeric conjugate containing primary mouse antibody, polymeric conjugate containing goat anti mouse secondary antibody and goat anti rabbit secondary antibody, and a polymeric conjugate containing rabbit anti goat and alkaline phosphatase; (J) target biological marker on tissue, myc tagged primary antibody fragment, a polymeric conjugate containing mouse anti myc antibody, and a polymeric conjugate containing goat anti mouse and horseradish peroxidase; (K) two target biological markers on tissue, the first recognized by two primary mouse antibodies, a polymeric conjugate containing swine anti mouse and horseradish peroxidase, and the second marker being recognized by primary rabbit antibodies and a polymeric conjugates containing goat anti rabbit secondary antibody, and a polymeric conjugate containing rabbit anti goat and alkaline phosphatase; (L) two target biological markers on tissue, the first recognized by primary mouse antibody, a polymeric conjugate containing goat anti mouse secondary antibody, and a polymeric conjugate containing swine anti goat secondary antibody and alkaline phosphatase, and the second marker being recognized by a hapten labeled probe against a gene target, a polymeric conjugate containing rabbit anti hapten antibody and a polymeric conjugate containing swine anti rabbit and horseradish peroxidase; (M) two target biological markers on tissue, the first recognized by primary mouse antibody, a polymeric conjugate containing goat anti mouse secondary antibody, and a polymeric conjugate containing swine anti goat antibody and gold particles, and the second marker being recognized by a hapten labeled probe against a gene target, a polymeric conjugate containing rabbit anti hapten antibody and a polymeric conjugate containing swine anti rabbit labeled with multiple fluorescent Fitc molecules; (N) target biological marker on tissue recognized by mouse or rabbit primary antibody, a mixture of polymeric conjugates containing hapten labeled goat anti mouse secondary antibody and horseradish peroxidase, and hapten labeled goat anti rabbit secondary antibody and horseradish peroxidase, and a polymeric conjugate containing anti hapten antibody and horseradish peroxidase; (O) target biological marker on tissue recognized by mouse primary antibody, a polymeric conjugate containing goat anti mouse secondary antibody and rabbit anti hapten, and hapten labeled polymeric conjugate containing alkaline phosphatase; (P) target biological marker on tissue recognized by hapten no. 1 labeled probe against a gene target, a polymeric conjugate containing antibody against hapten no. 1 and antibody against hapten no. 2, polymeric conjugate containing hapten no 2 and alkaline phosphatase; (Q) target biological marker on tissue recognized by mouse or rabbit primary antibody, a mixture of polymeric conjugates containing goat anti mouse antibody and goat anti rabbit antibodies, and hapten labeled rabbit anti goat antibody, and a polymeric conjugate containing anti hapten antibody and horseradish peroxidase; (R) target biological marker on tissue recognized by mouse or rabbit primary antibody, a mixture of polymeric conjugates containing goat anti mouse antibody and horseradish peroxidase and goat anti rabbit antibodies and horseradish peroxidase, and hapten labeled rabbit anti goat secondary antibody and horseradish peroxidase, and a polymeric conjugate containing anti hapten antibody and horseradish peroxidase; (S) target biological marker on tissue recognized by mouse or rabbit primary antibody, a mixture of polymeric conjugates containing Texas red labeled goat anti mouse antibody and Texas red labeled goat anti rabbit antibodies, and hapten labeled rabbit anti goat antibody, and a polymeric conjugate containing anti hapten antibody and multiple Texas red fluorescent molecules; (T) two target biological markers on tissue, the first recognized by Texas red labeled primary mouse antibody, a polymeric conjugate containing goat anti mouse secondary antibody and multiple Texas red molecules, and a polymeric conjugate containing swine anti goat antibody and glucose oxidase enzymes, and the second marker being recognized by a FITC labeled probe against a gene target, a polymeric conjugate containing anti hapten antibody-and multiple Pacific blue fluorescent molecules, and a polymeric conjugate containing anti Pacific blue antibody and horseradish peroxidase.
Figure 1B:
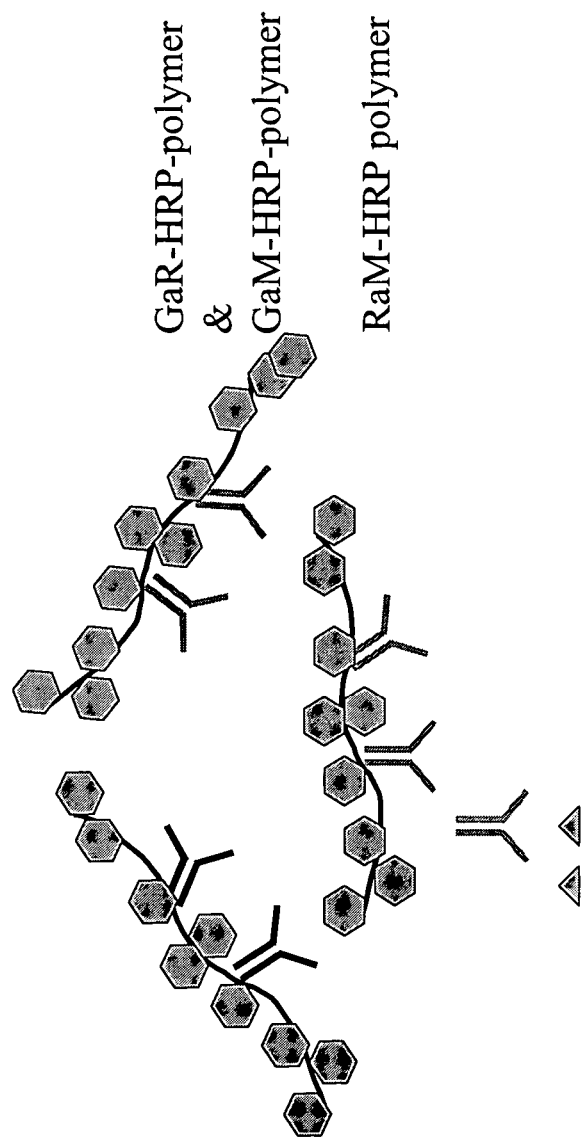
Figure 1C:
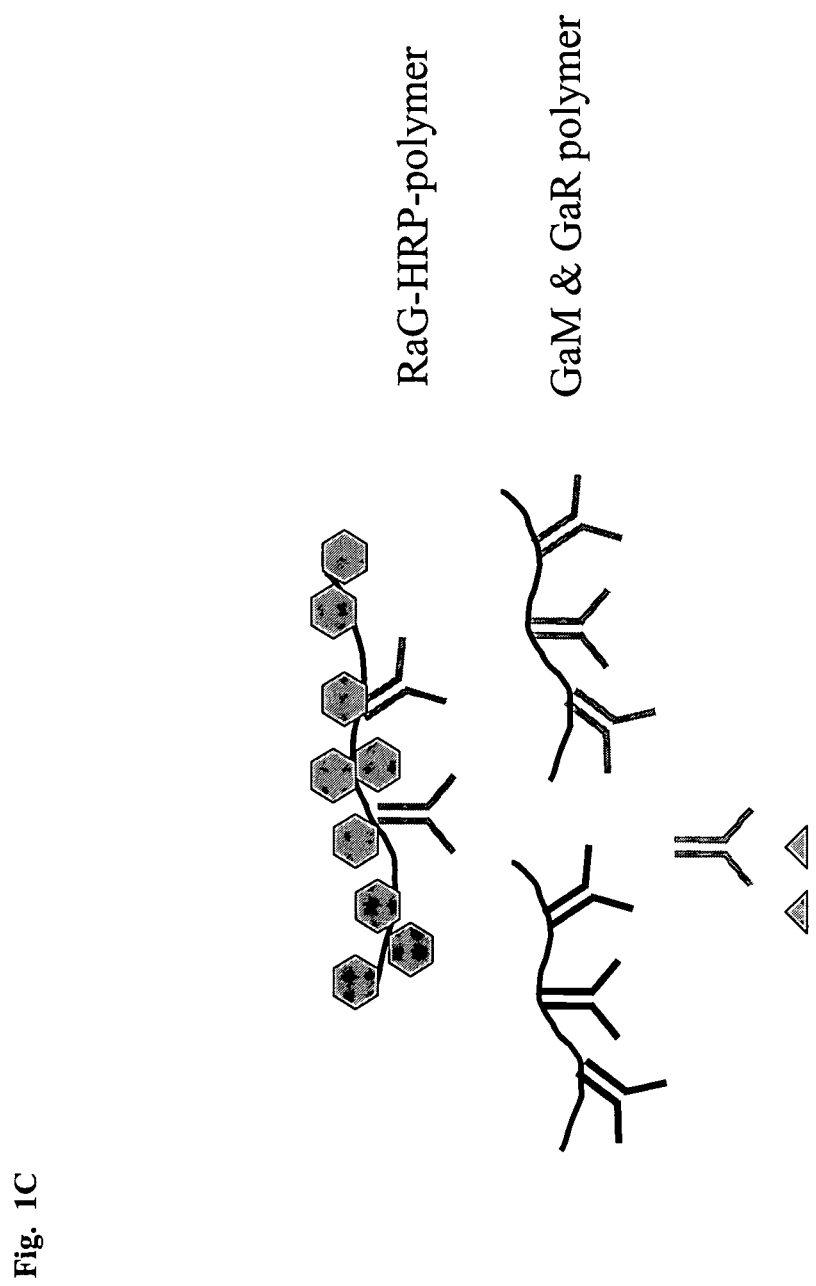
Figure 1E:
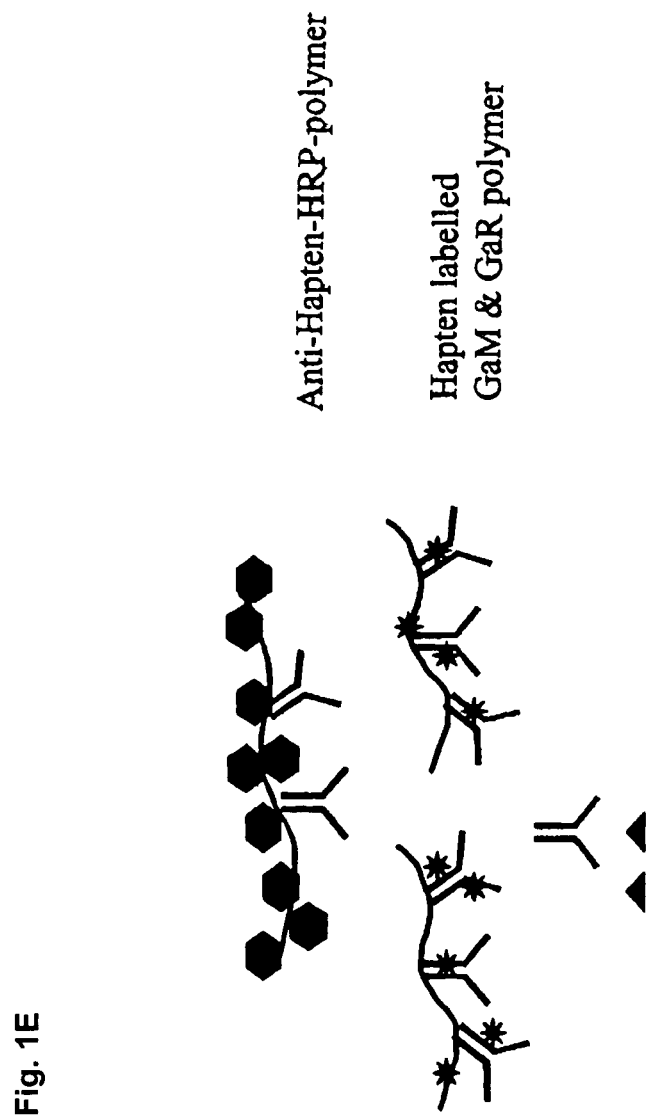
Figure 1F:
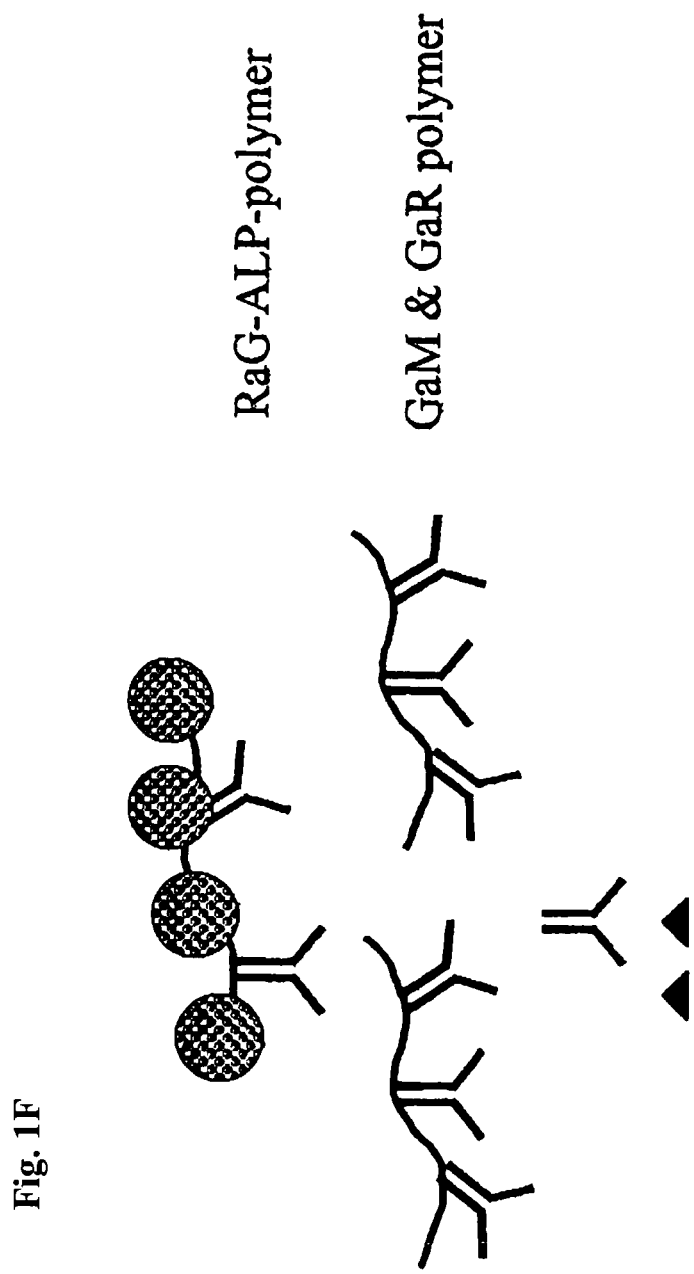
Figure 1G:
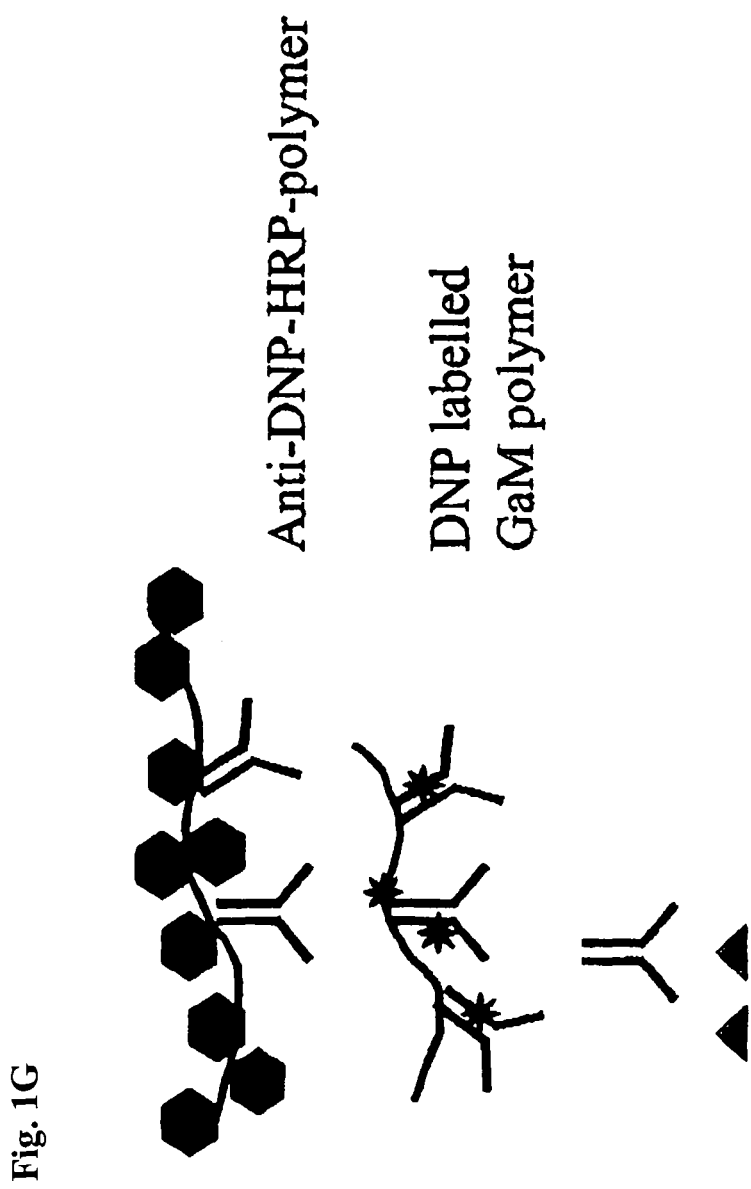
Figure 1H:
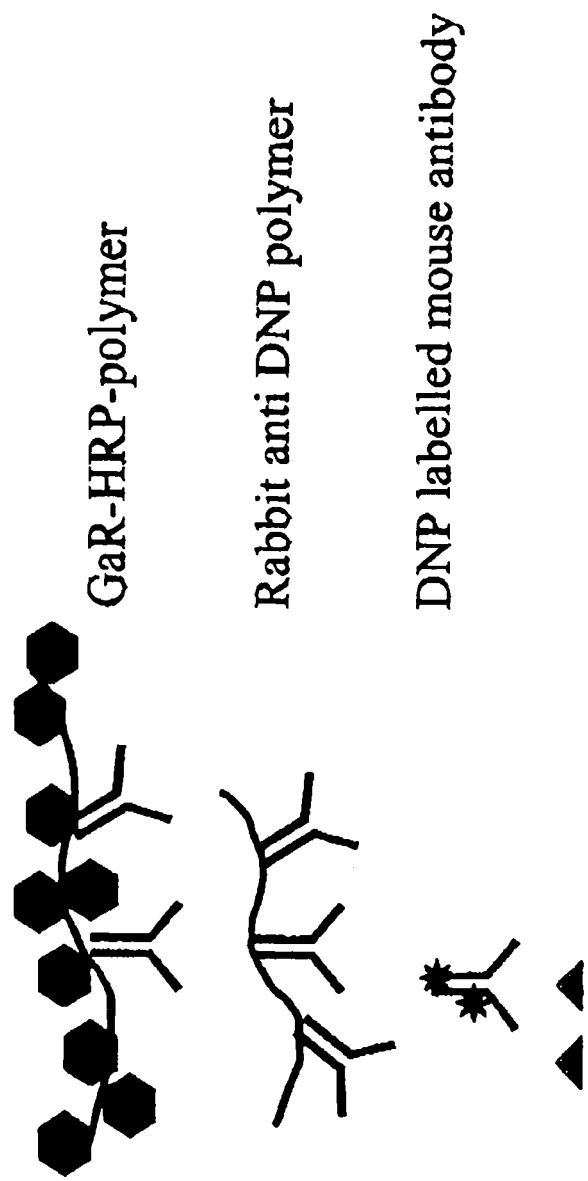
Figure 1I:
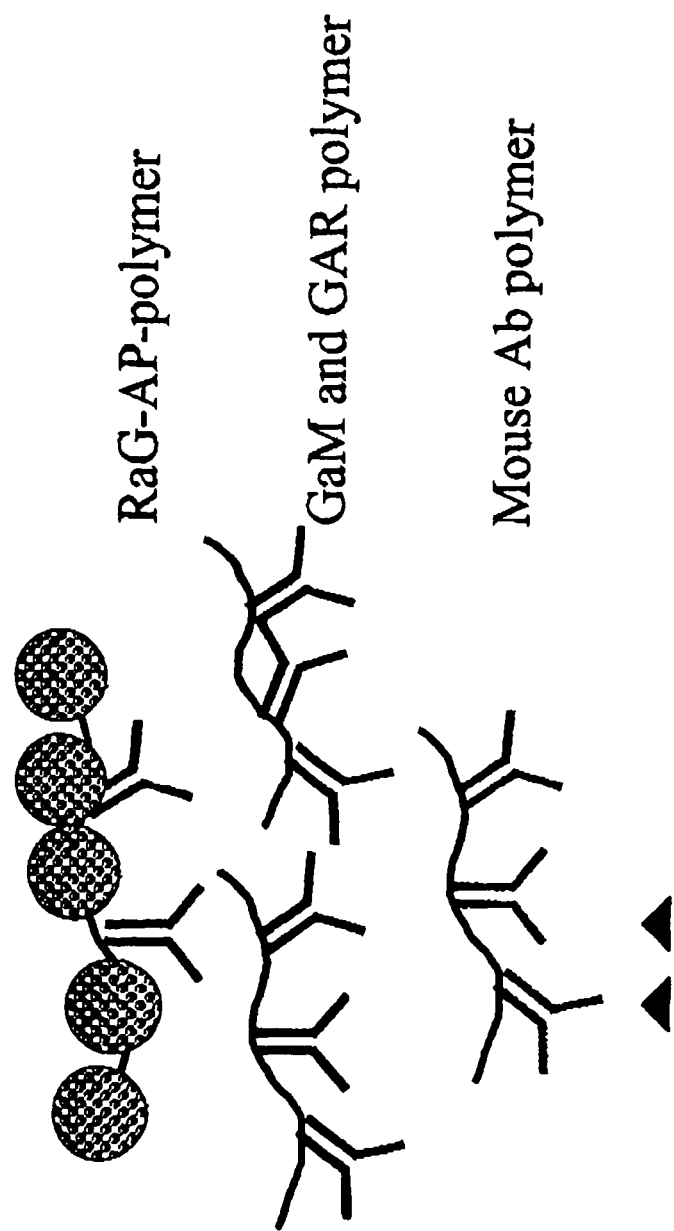

Antibody, as used herein, means an immunoglobulin or a part thereof, and encompasses any polypeptide comprising an antigen-binding site regardless of the source, method of production, and other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can still bind antigen, for example, an Fab, F(ab')$_2$, Fv, scFv. The origin of the antibody is defined by the genomic sequence irrespective of the method of production.

Biological marker, as used herein, refers to any molecule present in a biological sample. The marker may include a protein, including a glycoprotein or lipoprotein, phosphoprotein, methylated protein, or a protein fragment, e.g., a peptide or a polypeptide, a nucleic acid, e.g., DNA, RNA, a lipid, a glyco-lipid, a sugar, a polysaccharide, a starch. The marker may be expressed on the surface of the biological sample, e.g., membrane bound. The marker may be contained in the interior of the biological sample, i.e., within the cell membrane, e.g., within the cytoplasm, within the nucleus, within an intracellular compartment or organelle.

First binding agent, as used herein, refers to a first molecule which specifically binds to a biological marker in a sample, e.g., a primary antibody, a nucleic acid probe, a ligand or receptor.

Second binding agent, as used herein, refers to a second molecule which specifically binds to a first binding agent, e.g., a secondary antibody, an MHC molecule, a c1q molecule, a molecule having at least one leucine zipper domain, fos/jun or the like.

Third binding agent, as used herein, refers to a third molecule which specifically binds a second binding agent, e.g., a tertiary antibody, an MHC molecule, a c1q molecule, a molecule having at least one leucine zipper domain, fos/jun or the like or a hapten molecule, e.g., FITC, biotin, strepavidin, avidin, myc tag.

Dual linked binding agent, as used herein, refers to at least 2 second binding agents each of which is unlinked or linked to the same or its own polymer, or each of which is derivatized and polymerized without the addition of a polymer backbone, and each of which specifically binds a different first binding agent, e.g., primary antibody. An example of a dual linked binding agent includes a polymer conjugate comprising a goat anti-mouse antibody conjugated to a first polymer backbone and a polymer conjugate comprising a goat anti-rabbit antibody conjugated to a first or second polymer backbone.

Hapten, as used herein, refers to a molecule, which can be linked to a larger molecule, and which can specifically bind a second molecule such as an antibody. Examples of haptens include FITC, DNP, myc, Digoxigenin, nitrotyrosine biotin, avidin, streptavidin and anti-dye antibodies to e.g. tetramethylrhodamine, Texas Red, dansyl, Alexa Fluor 488, BODIPY™ FL (4,4-difluoro-5,7-dimethyl-4-bora-3$a$,4$a$-diaza-s-indacene-3-pentanoic acid), lucifer yellow and Alexa Fluor 405/Cascade Blue fluorophores.

Primary antibody, as used herein, refers to an antibody that specifically binds to a biological marker of interest present within the biological sample. In certain embodiments the primary antibody may be polymerized. Primary antibodies may be derived from any warm blooded species, e.g. mammals, birds.

Sample, as used herein, refers to a sample derived from any living organism, e.g., animal, plant, bacteria. It may be comprised of eukaryotic cells or prokaryotic cells. It may be comprised of a tissue specimen derived from an organ. It may be comprised of a cell sample, e.g., a cell smear. It may also include a viral particle, or portions thereof, e.g., a nucleic acid, a protein, a peptide. The viral particle may be a free viral particle, i.e., not associated with any other molecule or it may be associated with any biological sample described above.

Secondary antibody, as used herein, refers to an antibody that has an antigen binding domain that specifically binds to a first binding agent, e.g., a primary antibody.

Tertiary antibody, as used herein, refers to an antibody that has an antigen binding domain that specifically binds to a second binding agent (e.g., a secondary antibody) or a hapten linked to a second binding agent or a hapten linked to polymer conjugated to a second binding agent.

Sometimes an antibody may function both as a secondary and a tertiary antibody.

B. Conjugated Polymers

In certain embodiments, the invention provides compositions useful in the detection of a biological marker in a sample. The composition may comprise conjugated polymers, e.g., a binding agent, such as an antibody, conjugated to a polymer backbone. The composition may comprise a polymerized binding agent, e.g., a derivatized binding agent that is polymerized without the addition of a polymer backbone. In some embodiments, a conjugated polymer may be comprised of a secondary antibody and a polymer and optionally a detectable substance. The detectable substance may be linked to the polymer or the secondary antibody or both the polymer and the secondary antibody. In some embodiments, the conjugated polymer comprises a secondary antibody and a polymer and a hapten. The hapten may be linked to the polymer or the secondary antibody or both the polymer and the secondary antibody. In certain embodiments, the conjugated polymer has a molecular weight less than 10 million Daltons. In other embodiments, the conjugated polymer has a molecular weight less than 2 million Daltons.

In some embodiments, the conjugated polymer is comprised of a third binding agent, e.g., a tertiary antibody. The third binding agent may be conjugated to a polymer backbone. The third binding agent may be derivatized and polymerized without the addition of a polymer backbone. The third binding agent may also comprise a detectable substance. The detectable substance may be linked to the polymer or the third binding agent or both the polymer and the third binding agent.

1. Polymers

The polymer may be a soluble molecule or an insoluble molecule. The polymer may be any molecule which facilitates attachment of a protein, a binding entity or hapten, a biologically active compound, and a detectable substance while providing the advantageous properties of the construct, e.g., the ability to detect a biological marker in a sample. Examples of suitable polymers include polysaccharides such as dextrans, carboxy methyl dextran, dextran polyaldehyde, carboxymethyl dextran lactone, and cyclodextrins; pullulans, schizophyllan, scleroglucan, xanthan, gellan, O-ethylamino guaran, chitins and chitosans such as 6-O-carboxymethyl chitin and N-carboxymethyl chitosan; derivatized cellulosics such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenans, alginates, and agarose; synthetic polysaccharides such as FICOLL™ neutral, highly-branched, hydrophilic sucrose polymer and carboxymethylated FICOLL™; vinyl polymers including poly(acrylic acid), poly(acryl amides), poly(acrylic esters), poly(2-hydroxy ethyl methacrylate), poly(methyl methacrylate), poly(maleic acid), poly(maleic anhydride), poly(acrylamide), poly(ethyl-co-vinyl acetate), poly(methacrylic acid), poly(vinylalcohol), poly(vinyl alcohol-co-vinyl chloroacetate), aminated poly(vinyl alcohol), and co block polymers thereof; poly ethylene glycol (PEG) or polypropylene glycol or poly(ethylene oxide-co-propylene oxides) containing polymer backbones including linear, comb-shaped or hyperbranched polymers and dendrimers, including branched PAMAM-dendrimers; poly amino acids including polylysines, polyglutamic acid, polyurethanes, poly(ethylene imines), pluriol; proteins including albumins, immunoglobulins, and virus-like proteins (VLP), and polynucleotides, DNA, PNA, LNA, oligonucleotides and oligonucleotide dendrimer constructs. Also contemplated is the use of mixed polymers, i.e., a polymer comprised of one or more of the above examples including any of the polymers, the co-block polymers and random co-polymers.

The choice of polymer depends, for example, on the application of the protein construct. Of course, properties of the polymer can be varied, depending on the desired application to optimize performance. Examples of these parameters include the length of the polymer and branching of the polymer. Furthermore, the polymer may carry various substituents. The substituents may be chemically protected and/or activated, allowing the polymer to be derivatized further.

2. Detectable Substances

The detectable substance may include any molecule which may be detected directly or indirectly. In direct detection only one detectable substance is used, i.e., a primary detectable substance. Thus direct detection means that the detectable substance may be detected per se without the need for the addition of a second molecule. Examples of primary detectable substances which may be detected directly include fluorescent dyes and radioactive substances and metal particles. In contrast, indirect detection requires the application of one or more additional molecules, i.e., secondary detectable substances, after application of the primary detectable substance. Thus the detection is performed by the detection of the binding of the secondary detectable substance to the primary detectable substance. Examples of primary detectable substances requiring addition of a secondary detectable substance include enzymatic detectable substances and hapten detectable substances.

In some embodiments, the detectable substance is conjugated to at least one polymer. The polymer may be conjugated with at least one first binding agent, i.e., an agent which will bind the primary antibody, e.g., a secondary antibody, an MHC molecule. The polymer may be conjugated with a second binding agent, i.e., an agent which will bind a second binding agent or a hapten. In some embodiments, 1-500 detectable substance molecules are linked to each polymer molecule. In some embodiments, the detectable substance is an enzyme and the number of enzyme molecules linked to each polymer molecule is 1-200, 2-50, 2-25. In some embodiments, the detectable substance is a gold particle, a dye, a low molecular weight fluorochrome and the number of detectable substances linked to each polymer molecule is 1-500, 2-200. In some embodiments, the detectable substance is a protein fluorochrome and the number of detectable substances linked to each polymer molecule is 1-50, 2-20. In some embodiments, the number of detectable substance molecules linked to each polymer is 1-200, 2-50, 2-25. In some embodiments, the detectable substance may further be attached via a suitable linker. Many such linkers are known in the art. Examples include polyethylene glycol and poly amides.

Examples of detectable substances which may be used in the invention include fluorescent labels, enzyme labels, radioisotopes, chemiluminescent labels, electrochemiluminescent labels, bioluminescent labels, polymers, polymer particles, metal particles, haptens, antibodies, and dyes.

Examples of fluorescent labels which may be used in the invention include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particles labels which may be used in the invention include micro particles or latex particles of polystyrene, PMMA or silica, which can be embedded with fluorescent dyes, or polymer micelles or capsules which contain dyes, enzymes or substrates.

Examples of metal particles labels which may be used in the invention include gold particles and coated gold particles, which can be converted by silver stains.

Examples of haptens which may be used in the invention include DNP, fluorescein isothiocyanate (FITC), biotin, and digoxiginin.

Examples of enzymatic labels which may be used in the invention include horse radish peroxidase (HRP), alkaline phosphatase (ALP or AP), beta-galactosidase (GAL), glucose-6-phosphate dehydrogenase, beta-N-acetylglucosamimidase, β-glucuronidase, invertase, Xanthine Oxidase, firefly luciferase and glucose oxidase (GO).

Examples of commonly used substrates for horse radish peroxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), α-naphtol pyronin (α-NP), o-dianisidine (OD), 5-bromo-4-chloro-3-indolylphosphate (BCIP), Nitro blue tetrazolium (NBT), 2-(p-iodophenyl)-3-p-nitrophenyl-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels which may be used in the invention include luminol, isoluminol, acridinium esters, 1,2-dioxetanes and pyridopyridazines. Examples of electrochemiluminescent labels include ruthenium derivatives.

Examples of radioactive labels which may be used in the invention include radioactive isotopes of iodide, cobalt, selenium, tritium, carbon, sulfur and phosphorous.

Detectable substances may be linked to any molecule which specifically binds to a biological marker of interest, e.g., an antibody, a nucleic acid probe, or a polymer which is conjugated to any molecule which specifically binds to a biological marker of interest.

3. Binding Agents

In certain embodiments, the invention provides three types of binding agents: a first binding agent, a second binding agent and a third binding agent. The first binding agent is used to contact the sample. It may be comprised of any molecule which will specifically bind to a biological marker of interest contained within the sample. In some embodiments, the first binding agent is an antibody, i.e., a primary antibody. A skilled artisan Will appreciate that antibodies recognizing numerous biological markers are commercially available (see for example DakoCytomation general product Catalogue, DakoCytomation, Carpinteria, Calif. The skilled artisan will also appreciate that methods of making antibodies with specific antigen binding sites are know in the art. These methods are described below in section 4. In some embodiments the first binding agent is a nucleic acid probe. Methods of making nucleic acid probes are described below in section 5.

The second binding agent may be any molecule that binds the first binding agent. The second binding agent may include a secondary antibody. The secondary antibody may have an antigen binding domain that specifically binds to the first binding agent, e.g., the constant region of a primary antibody.

The second binding agent may include c1q a protein in the classical pathway of the complement cascade which can bind an antibody constant region, a MHC molecule, e.g., MHC class I and MHC class II and non conventional MHC, a molecule having a specific binding partner, such as molecules involved in cellular signaling pathways such as molecules having leucine zipper domains, e.g., fos/jun, myc, GCN4, molecules having SH1 or SH2 domains, such as Src or Grb-2. The second binding agent may be an immunoglobulin receptor, e.g., an Fc receptor. A second binding agent may also be comprised of a chimeric protein, i.e., a protein engineered to combine the features of two or more specific binding partners, e.g., a leucine zipper could be engineered into a Fc region of an antibody, an SH2 domain could be engineered to be expressed in a Fc region of an antibody. In other embodiments, fusion proteins can be engineered comprising an Fc portion of an antibody with a substituted variable domain (see e.g. U.S. Pat. No. 5,843,725).

The second binding agent may also include a hapten. The hapten may be linked to the second binding agent. Haptens may be small molecules thus permitting multiple copies to be attached to a single second binding agent molecule. The hapten provides a convenient target molecule for the third binding agent. The bound multiple copies provides for enhanced sensitivity, e.g., increased signal strength. Examples of suitable haptens include FITC, DNP, myc Digoxigenin, nitrotyrosine biotin, avidin, streptavidin and anti-dye antibodies to e.g. tetramethylrhodamine, Texas Red, dansyl, Alexa Fluor 488, BODIPY™ FL (4,4-difluoro-5,7-dimethyl-4-bora-3a, 4a- diaza-s-indacene-3-pentanoic acid), lucifer yellow and Alexa Fluor 405/Cascade Blue fluorophores.

The third binding agent may be any molecule that binds the second binding agent. The third binding agent may include a tertiary antibody. The tertiary antibody may have an antigen binding domain that specifically binds to the second binding agent, e.g., the constant region of a secondary antibody. The third binding agent may be comprised of any of the specific binding partners described above for the second binding agent, so long as it specifically binds the second binding agent. It may also include chimeric proteins and fusion proteins.

In certain embodiments additional fourth and fifth etc. binding agents similar to the binding agents described above may be comprised. The fourth and fifth binding agent may, in some embodiments, be linked to a polymer, or be polymerizable themselves. In some embodiments the fourth and/or fifth binding agent may be comprised of an antibody.

4. Antibodies

Antibodies used in the invention, including primary antibodies, secondary antibodies and tertiary antibodies, may be derived from any mammal species, e.g., a rat, a mouse, a goat, a guinea pig, a donkey, a rabbit, horse, lama, camel, or any avian species e.g., chicken, duck. Derived from any mammal or avian species, as used herein, means that at least a part of the nucleic acid sequence encoding a particular antibody originated from the genomic sequence of a specific mammal, e.g., a rat, a mouse, a goat, or a rabbit or a specific bird e.g., chicken, duck. The antibody may be of any isotype, e.g., IgG, IgM, IgA, IgD, IgE or any subclass, e.g., IgG1, IgG2, IgG3, IgG4.

In certain embodiments the primary antibody contains an antigen binding region which can specifically bind to a biological marker expressed by cells comprising a biological sample. The marker may be expressed on the cell surface or within the cell membrane, i.e., on the interior of the cell, e.g., within the cytoplasm, within the nucleus, within the endoplasmic reticulum. In some embodiments the biological marker is secreted from the cell and thus is present in solution, e.g., in cell culture media, in blood or plasma.

In certain embodiments, the secondary antibody contains an antigen binding region which specifically binds to the primary antibody, e.g., the constant region of the primary antibody. In certain embodiments, the secondary antibody is conjugated to a polymer. In some embodiments, the polymer is conjugated with 2-20 secondary antibodies. In other embodiments, the polymer is conjugated with 2-10 secondary antibodies.

In certain embodiments, the tertiary antibody contains an antigen binding region which specifically binds to the secondary antibody, e.g., a constant region of the secondary antibody, or a hapten linked to the secondary antibody or a polymer conjugated to the secondary antibody. In certain embodiments, the tertiary antibody is conjugated to a polymer. In some embodiments, the polymer is conjugated with 1-20 tertiary antibodies. In other embodiments, the polymer is conjugated with 1-5 tertiary antibodies.

The antibodies that may be used in the methods and compositions of the invention include monoclonal and polyclonal antibodies, engineered antibodies including chimeric, CDR-grafted and artificially selected antibodies produced using phage display or alternative techniques.

Various techniques for producing antibodies have been described, see, e.g., Kohler and Milstein, (1975) *Nature* 256: 495; Harlow and Lane, *Antibodies: a Laboratory Manual*, (1988) (Cold Spring Harbor Press, Cold Spring Harbor, N.Y.) incorporated herein by reference. Techniques for the preparation of recombinant antibody molecules is described in the above references and also in, for example, EP 0623679; EP 0368684; and EP 0436597.

Antibodies may be produced recombinantly or synthetically. Nucleic acids encoding antibodies may be isolated from a cDNA library. Nucleic acids encoding antibodies may be isolated from a phage library (see e.g. McCafferty et al. 1990, *Nature* 348:552, Kang et al. 1991, *Proc. Natl. Acad. Sci. USA* 88:4363; EP 0 589 877 B1). Nucleic acids encoding antibodies can be obtained by gene shuffling of known sequences (Mark et al. 1992, *Bio/Technol.* 10:779). Nucleic acids encoding antibodies can be isolated by in vivo recombination (Waterhouse et a. 1993, *Nucl. Acid Res.* 21:2265). The antibodies used in the methods and compositions of the invention include humanized immunoglobulins (U.S. Pat. No. 5,585, 089, Jones et al. 1986, *Nature* 332:323).

The antibodies may be altered antibodies comprising an effector protein such as a toxin or a label, e.g., a detectable substance.

Antibodies may be obtained from animal serum, or, in the case of monoclonal antibodies or fragments thereof, produced in cell culture. Recombinant DNA technology may be used to produce the antibodies according to established procedure, in bacterial, yeast, insect or mammalian cell culture. In certain embodiments, the selected cell culture system preferably secretes the antibody product.

Growing of hybridoma cells or mammalian host cells in vitro may be carried out in suitable culture media, for example Dulbecco's Modified Eagle Medium (DMEM) or RPMI 1640 medium, optionally replenished by a mammalian serum, for example fetal calf serum, or trace elements and growth sustaining supplements. In some embodiments, feeder cells, such as normal mouse peritoneal exudate cells, spleen cells, bone marrow macrophages, can be used to enhance cell growth in culture. Additives can also be used to enhance cell growth including 2-aminoethanol, insulin, transferrin, low density lipoprotein, oleic acid.

Bacterial cells or yeast cells are grown, for example, in suitable culture media known in the art. Examples of bacteria media include LB, NZCYM, NZYM, NZM, Terrific Broth, SOB, SOC, 2xYT, or M9 Minimal Medium (see Sambrook et al. *Molecular Cloning: A Laboratory Manual*, 2 ed., Cold Spring Harbor Laboratory Press (1989) (incorporated herein by reference). Examples of media suitable for growing yeast include YPD, YEPD, Minimal Medium, or Complete Minimal Dropout Medium (Ibid).

Recombinantly produced antibodies may be cloned and expressed in insect cells. Insect cells provide a high probability of obtaining a correctly folded and biologically active antibody when compared to bacterial or yeast expression systems. Insect cells may be cultured in serum free medium. Recombinant baculovirus may be used as an expression vector, and the construct used to transfect a host cell line, which may be any of a number of lepidopteran cell lines, including *Spodoptera frugiperda* Sf9. (see e.g. Altmann et al. (1999), *Glycoconj J* 1999,16:109; Kost and Condreay (1999), *Curr Opin Biotechnol*, 10:428).

The skilled artisan will appreciate that antibodies produced recombinantly, or by other means, for use in the invention include any antibody fragment which can still bind antigen, e.g. an Fab, an F(ab)$_2$, Fv, scFv. In certain embodiments, the antibody, or antibody fragment, may be recombinantly engineered to include a hapten, e.g, a peptide. In certain specific embodiments the hapten may be a myc tag. Inclusion of a hapten in an antibody or antibody fragment facilitates subsequent binding of a binding agent, e.g. a secondary antibody, a tertiary antibody, or a specific binding partner of the hapten. FIG. 1J illustrates one embodiment of the invention where a myc tag is used to detect a biological marker. Myc specific antibodies may be used in this embodiment. Myc specific antibodies are known in the art, e.g. anti-myc clone 9E10 and 4A6.

In vitro production provides relatively pure antibody preparations and allows scale-up to give large amounts of the desired antibodies. Techniques for bacterial cell, yeast, insect and mammalian cell cultivation are known in the art and include homogeneous suspension culture, for example, in an airlift reactor or in a continuous stirrer reactor, or immobilized or entrapped cell culture, for example, in hollow fibres, microcapsules, on agarose microbeads or ceramic cartridges.

Large quantities of the desired antibodies can also be obtained by growing antibody producing mammalian cells in vivo. For this purpose, hybridoma cells producing the desired antibodies are injected into histocompatible mammals, e.g., a mouse, to cause growth of antibody-producing tumors. Optionally, the animals are primed first with a hydrocarbon such as a mineral oil. Examples of mineral oil include pristane (tetramethyl-pentadecane). After one to three weeks, the antibodies are isolated from the body fluids of those mammals. For example, hybridoma cells obtained by the fusion of suitable myeloma cells with an antibody-producing spleen cells from Balb/c mice, or transfected cells derived from the hybridoma cell line Sp2/0 that produce the desired antibodies may be injected intraperitoneally into Balb/c mice, optionally pretreated with pristane, and, after one to two weeks, ascitic fluid is taken from the animals.

For isolation of the antibodies, the antibodies in the culture supernatants or in the ascitic fluid may be concentrated, for example by precipitation with ammonium sulphate, by dialysis against hygroscopic material such as polyethylene glycol, or by filtration through selective membranes, or the like. If necessary and/or desired, the antibodies may be purified by the customary chromatography methods, for example, gel filtration, ion-exchange chromatography, chromatography over DEAE-cellulose and/or immunoaffinity chromatography, for example, affinity chromatography over a column or other solid support containing a protein which specifically binds to the antigen binding domain of the antibody, or over a column or solid support containing Protein-A.

The cell culture supernatants may be screened for the desired antibodies by immunofluorescent staining of cells expressing the desired target, by immunoblotting, by an enzyme immunoassay, for example, a sandwich assay or a dot-assay, or a radioimmunoassay.

5. Nucleic Acid Probes

A first binding agent may comprise a nucleic acid probe, e.g., a DNA molecule, an RNA molecule, for use in in situ hybridization. Nucleic acid probes may be synthesized chemically or produced recombinantly in cells (see e.g. Sambrook et al. (1989) *Molecular Cloning: A Laboratory Manual,* 2nd ed. Cold Spring Harbor Press). In some embodiments, the probe is comprised of a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g. Nielson, 2001, *Current Opinion in Biotechnology* 12:16) (hereby incorporated by reference). In other embodiments, the probe is comprised of locked nucleic acids (LNA) (Sorenson et al. 2003, Chem. Commun. 7(17):2130). In some embodiments, the nucleic acid probe specifically binds to the biological marker, e.g., a nucleic acid molecule contained within the biological sample.

The nucleic acid probe, in particular embodiments, comprises at least a sequence that specifically hybridizes to a sequence in the biological sample. In some embodiments, the nucleic acid probe hybridizes to a target sequence in a sample, e.g., a nucleic acid sequence such as a genomic DNA sequence or an mRNA sequence, under specific conditions of stringency. As used herein, the term "hybridization under stringent conditions," is intended to describe conditions for hybridization and washes under which nucleotide sequences that are significantly complementary to each other remain bound to each other. The conditions are such that sequences at least 70%, at least 80%, at least 85-90% complementary remain bound to each other. The percent complementary is determined as described in Altschul et al. (1997) *Nucleic Acids Res.* 25:3389-3402 (hereby incorporated by reference).

Specified conditions of stringency are known in the art and can be found in *Current Protocols in Molecular Biology*, John Wiley & Sons, Inc. (Ausubel et al. 1995 eds.), sections 2, 4, and 6 (hereby incorporated by reference). Additionally, specified stringent conditions are described in Sambrook et al. (1989) Molecular Cloning: A Laboratory Manual, 2nd ed. Cold Spring Harbor Press, chapters 7, 9, and 11 (hereby incorporated by reference). In some embodiments, the hybridization conditions are high stringency conditions. An example of high stringency hybridization conditions is hybridization in 4X sodium chloride/sodium citrate (SSC) at 65-70° C. or hybridization in 4X SSC plus 50% formamide at 42-50° C, followed by one or more washes in 1X SSC, at 65-70° C. It will be understood that additional reagents may be added to hybridization and/or wash buffers, e.g., blocking agents (BSA or salmon sperm DNA), detergents (SDS), chelating agents (EDTA), FICOLL™ neutral, highly-branched, hydrophilic sucrose polymer, PVP, etc.

In some embodiments, the nucleic acid probes hybridize to a target sequence in a sample under moderately stringent conditions. Moderate stringency, as used herein, include conditions that can be readily determined by those having ordinary skill in the art based on, for example, the length of the DNA. Exemplified conditions are set forth by Sambrook et al. *Molecular Cloning: A Laboratory Manual,* 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the nucleic acid probes hybridize to a target sequence in a sample under low stringent conditions. Low stringency conditions may include, as used herein, conditions that can be readily determined by those having ordinary skill in the art based on, for example, the length of the DNA. Low stringency may include, for example, pretreating the DNA for 6 hours at 40° C. in a solution containing 35% formamide, 5 x SSC, 50 mM Tris-HCl (pH 7.5), 5 mM EDTA, 0.1% PVP, 0.1% FICOLL™ neutral, highly-branched, hydrophilic sucrose polymer, 1% BSA, and 500 µg/ml denatured salmon sperm DNA. Hybridizations are carried out in the same solution with the following modifications: 0.02% PVP, 0.02% FICOLL™ neutral, highly-branched, hydrophilic sucrose polymer, 0.2% BSA, 100 µg/ml salmon sperm DNA, 10% (wt/vol) dextran sulfate, and 5-20x10$^6$ CPM probe is used. Samples are incubated in hybridization mixture for 18-20 hours at 40° C., and then washed for 1.5 h at 55° C in a solution containing 2 x SSC, 25 mM Tris-HCl (pH 7.4), 5 mM EDTA, and 0.1% SDS. The wash solution is replaced with fresh solution and incubated an additional 1.5 h at 60° C.

6. Methods of Making Polymer Conjugates

Many methods of forming polymeric conjugates are known in the art and can be used to make the polymeric conjugates of the invention. In some embodiments, the binding agent, e.g., a first binding agent, a second binding agent, a third binding agent and a detectable substance, if desired, can be chemically linked, or conjugated, to a polymeric backbone. In some embodiments, the polymer conjugate is formed by covalent coupling amino groups to conjugated double bonds. The polymer may be activated with vinylsulfon and mixed with a binding agent and detectable substance to form the polymer conjugate. In other embodiments, aldehydes are used to activate a polymeric backbone, e.g., dextrans which are then mixed with the binding agent and an optional detectable substance. Yet another method of preparing polymeric conjugates is by using so called chemo selective coupling schemes for coupling the components together, e.g., enzymes or other molecules can be derivatized with thiol reactive maleimide groups before being covalent coupled to an thiol modified polymeric carrier or backbone. Other embodiments described below permit the reagents themselves to form conjugates, e.g. the detectable substance, the binding agent.

In some embodiments no exogenous polymeric backbone is required. In these embodiments the binding agent and the detectable substance are derivatized, e.g., with vinyl groups. Polymerization occurs by addition of a radical, which results in polymerization of the vinyl groups to form a polymeric conjugate. The conjugate thus will contain a poly vinyl backbone or blocks of poly vinyl. Active esters of acrylic acid can be used to activate proteins and other molecules. Generating free radicals can polymerize the derivatized molecules. Small molecule linkers with more than one vinyl group can be further added to help form a polymeric conjugate.

In some embodiments, the binding agent and detectable substance can be derivatized with a cross-linker. Examples of this method include the use of homobifunctional cross linkers such as glutaric dialdehyde, hexan di isocyanate, dimethylapimidate, 1,5-difluoro-2,4-dinitrobenzene, heterobifunctional cross linkers like e.g. N-gamma-maleimidobytyroloxy succinimide ester, and zero length cross linkers such as 1-ethyl-3-(3-dimethylaminopropyl)cabodiimide. By choosing the correct reaction conditions, the cross linkers can form bridges between various functional groups in, e.g., the detectable substances and binding agents to form a polymeric conjugate.

C. Methods of Detecting Biological Markers in a Sample

The invention relates to a method of detecting at least one biological marker in a biological sample comprising contacting the sample with the composition of the invention. The method can be applied to a variety of known detection formats including immuno-histochemistry, immuno cytochemistry, in situ hybridization, flow cytometry, enzyme immuno-assay (EIA), and enzyme linked immuno-assay (ELISA).

Multistaining, that is, staining several biological markers in a sample is important. In histochemistry, the localization of several stained markers in combination with counter stain and morphological data allows the examiner to extract more valuable information than from single marker stains. The invention, thus, also provides a method of detecting multiple biological markers. e.g., two, three, in a given sample and thus provides a method of obtaining data, e.g., diagnostic information, concerning expression of multiple proteins, multiple genes or a combinations of one or more proteins and one or more genes. As an example, but not as a limitation, HER2 protein and the HER2 gene can be screened simultaneously in a cancer diagnostic assay, e.g., an assay for breast cancer. Another non-limiting example may include screening for three markers, e.g., to detect cervical cancer. The markers may include Ki67/mib-1, as well as the cellular proliferation marker, p16(INK4a), along with a marker, e.g., a protein or nucleic acid, for human papilloma virus. Yet another non-limiting example includes screening for multiple markers associated with prostate cancer. These markers may include AMACR P504S, high molecular weight cytokeratin (HMW-CK), and p63. Screening this combination of markers provides a method to distinguish benign prostate tumors from malignant ones. It will also permit the detection of prostatic adenocarcinoma and high grade intraepithelial neoplasm.

It is desirable to minimize cross reactivity between binding agents, e.g, where multiple markers are detected. This can be accomplished by using antibodies derived from different species. An example of such a system is depicted in FIG. 1L where a first protein marker is detected using a mouse antibody, a secondary polymer conjugated goat anti-mouse antibody and a tertiary polymer conjugated rabbit anti-goat antibody. The detectable substance is alkaline phosphatase. The second marker, in this case a nucleic acid, is detected using a hapten labeled oligonucleotide probe and a polymer conjugated rabbit anti-hapten antibody and a polymer conjugated swine anti-rabbit antibody. The detectable substance is horse radish peroxidase. Staining of multiple markers may be particularly advantageous in distinguishing benign and malignant prostate tumors. Thus prostatic adenocarcinoma and high-grade prostatic intra-epithelial neoplasm may be identified by staining for multiple markers. Suitable markers may include AMACR P504S, high molecular weight cytokeratin (HMW-CK) and p63.

Using combinations of e.g. secondary antibodies against antibodies and haptens can minimize unwanted cross reactivity between different species. This is illustrated in FIGS. 1 L and M, where two markers are visualized using the system of the invention and with a minimum of unwanted cross reactivity between the markers. A mouse antibody and the other marker visualize the first marker by a hapten labeled probe against a DNA marker. The figure further illustrates the feasibility of visualizing protein and gene markers by the present invention.

It should be clear that some dyes including fluorescent dyes can also function as haptens. This allows for both direct detection and for further enhancement of the signal. The enhancement can give a fluorescent or chromogenic stain. This is illustrated in various combinations in FIG. 1-M, S and T.

Also, it is beneficial to be able to add extra amplification layers or to convert one signal into another signal. The signal could e.g. be changed from a fluorescent to a chromogenic stain.

Combination of conjugates are also contemplated to increase the signal, e.g. by adding an extra layer onto the first layer. In automated instruments, this will allow for the use of a general visualization system, e.g. an Envision™ type system with GAR and GAM conjugates and HRP. If the target is difficult to visualize or a stronger signal is desired, one can add one or two or more layers on top of the first general visualization system. This is illustrated in several version in e.g. FIGS. 1-N, R, S and T.

Yet another embodiment of the present invention is the use of one or more layers which may recognize several targets. In one embodiment, the same conjugate can contain e.g. several primary and secondary antibodies for detecting several targets. In another embodiment, the conjugate can contain two or more secondary antibodies, which can form a bridge between different layers. Thus in some embodiments the conjugate may serve as a double adhesive tape or carpet tape between components. For example, this may be a second binding agent or a tertiary, etc depending on the numbers of layers used.

Figure 1J:
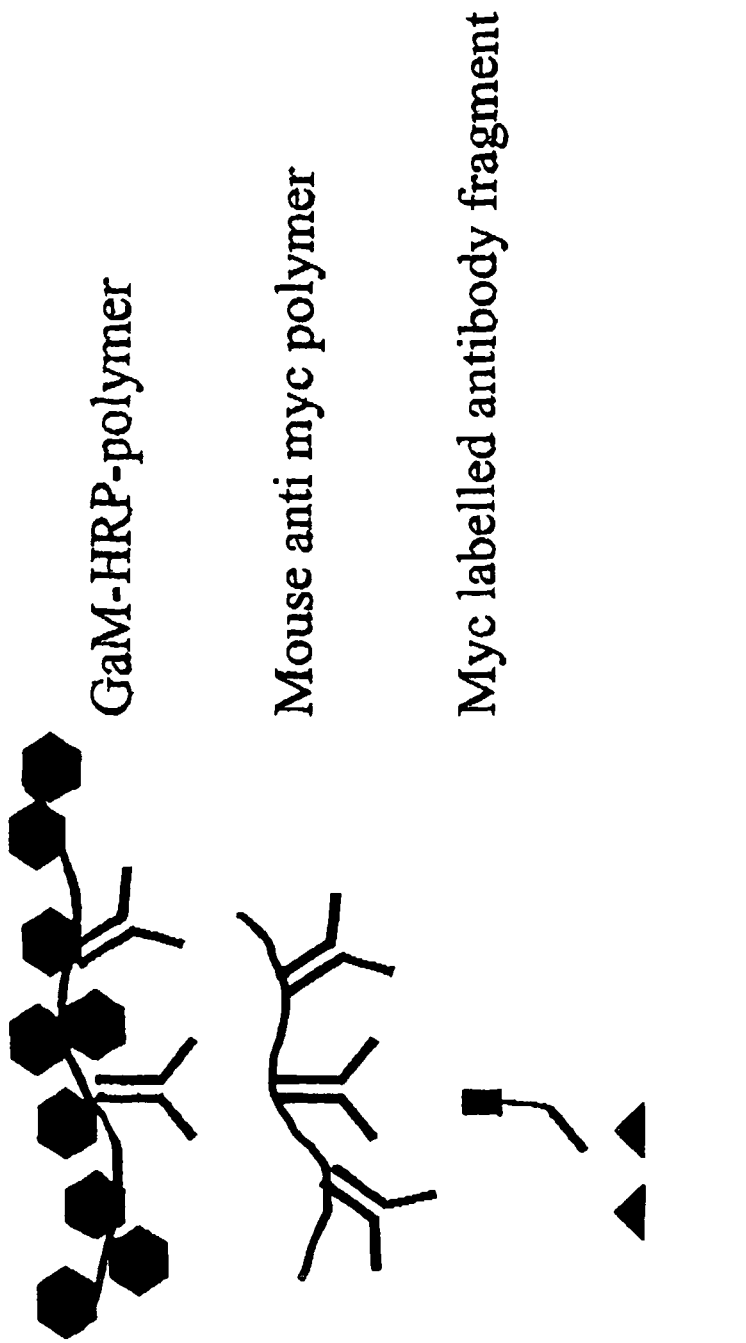

This is illustrated in FIG. 1O and P, where one conjugate contains a secondary antibody against the antibody below, and contains an antibody against a conjugate with a detectable substance, in FIG. 1-O and P, it is AP and HRP. It should be understood, that the secondary antibody could also be directed against the detectable substance.

Figure 1K:
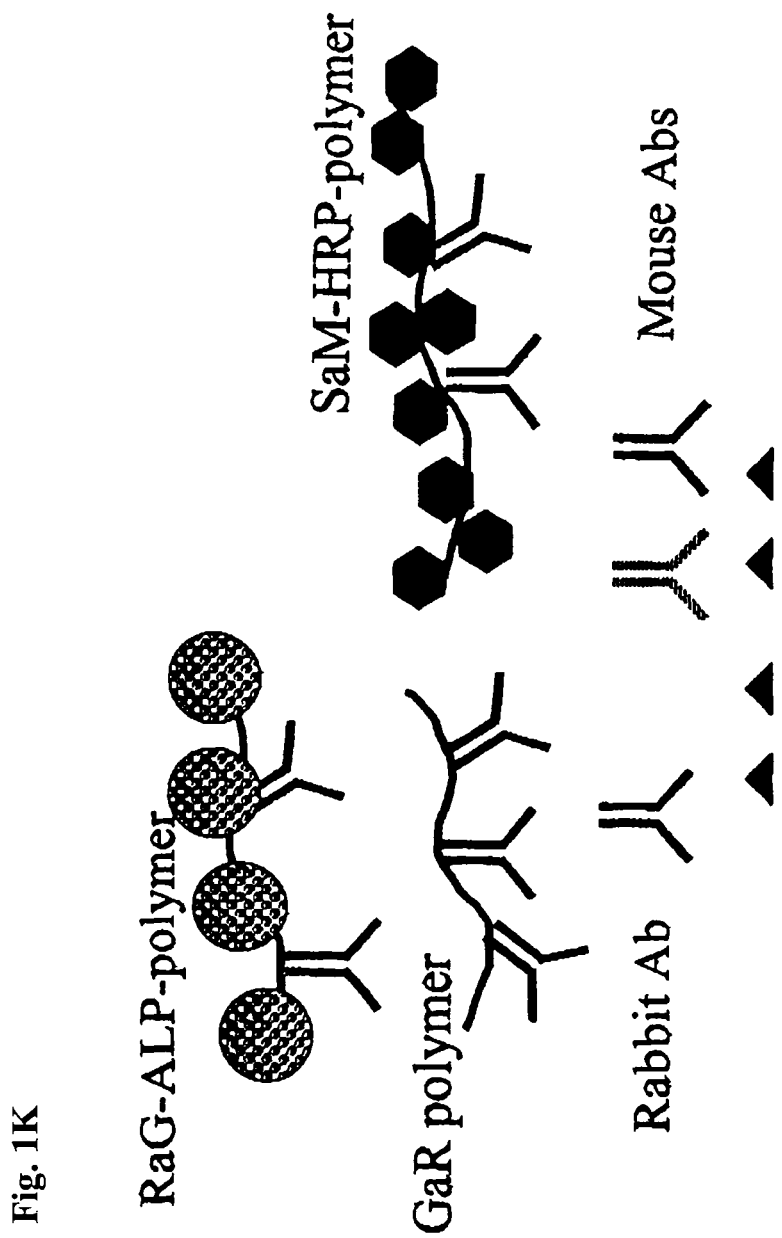
Figure 1L:
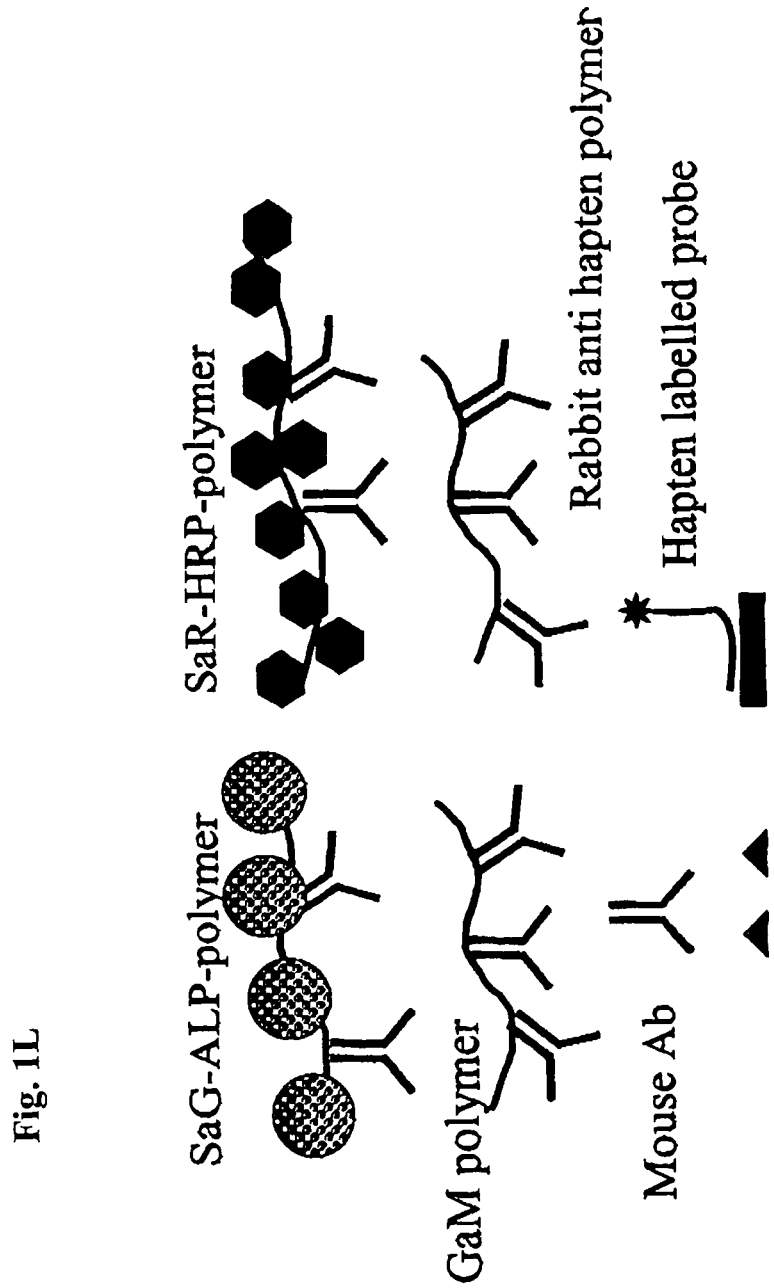
Figure 1M:
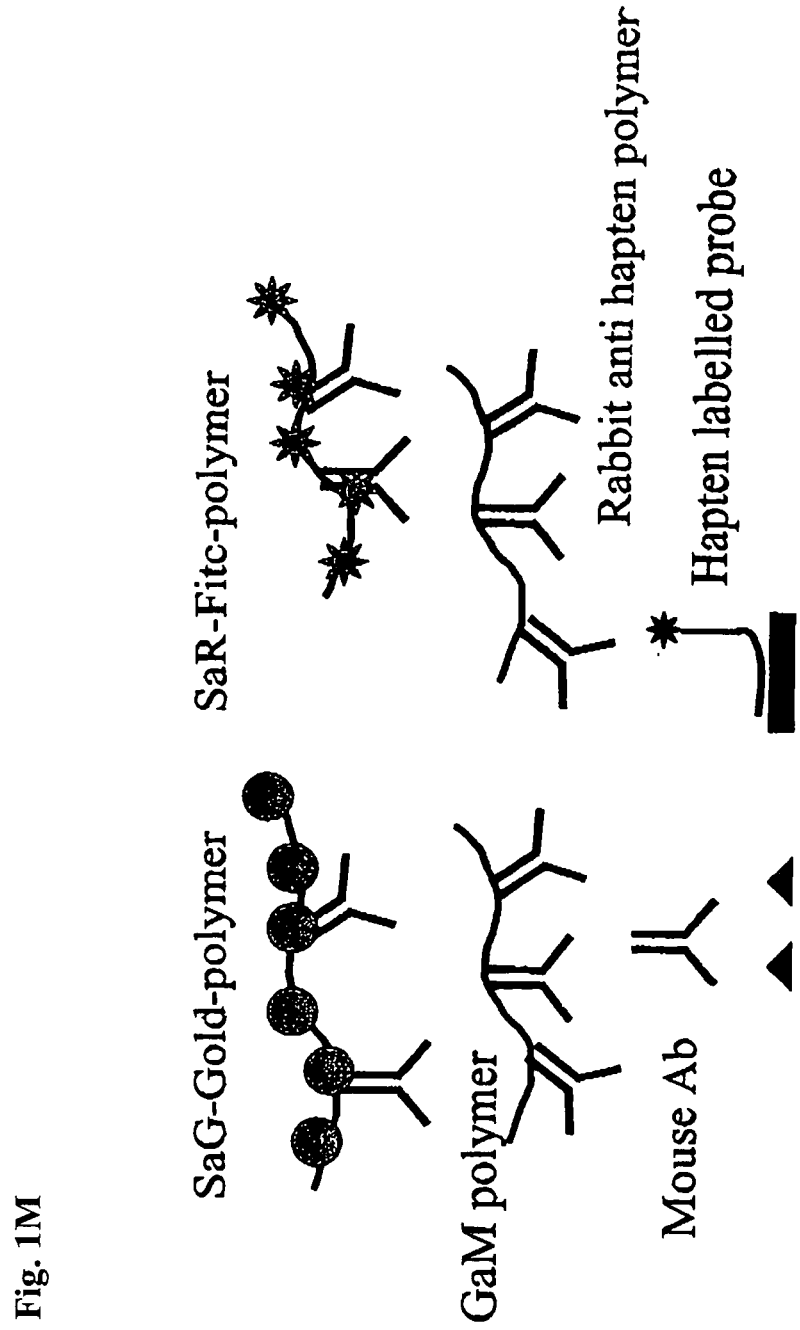
Figure 1N:
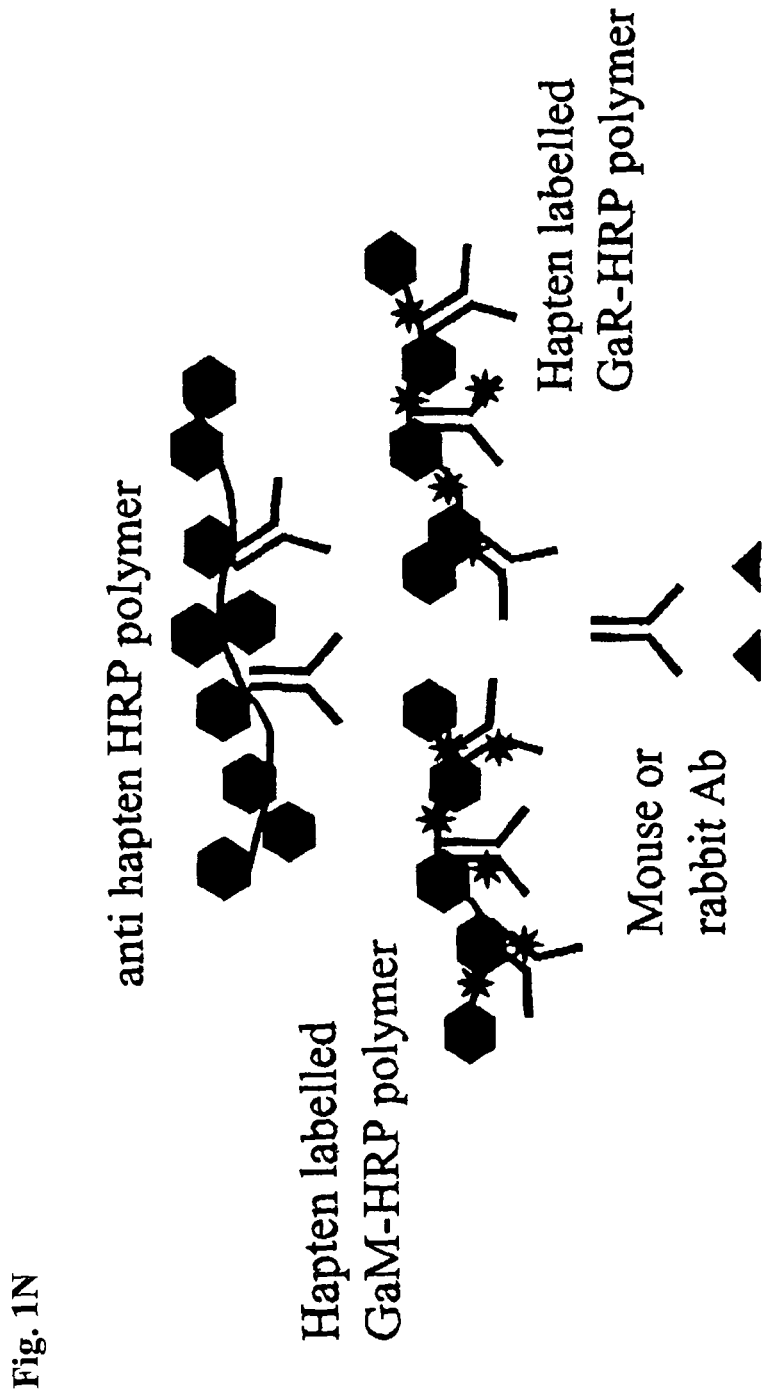
Figure 10:
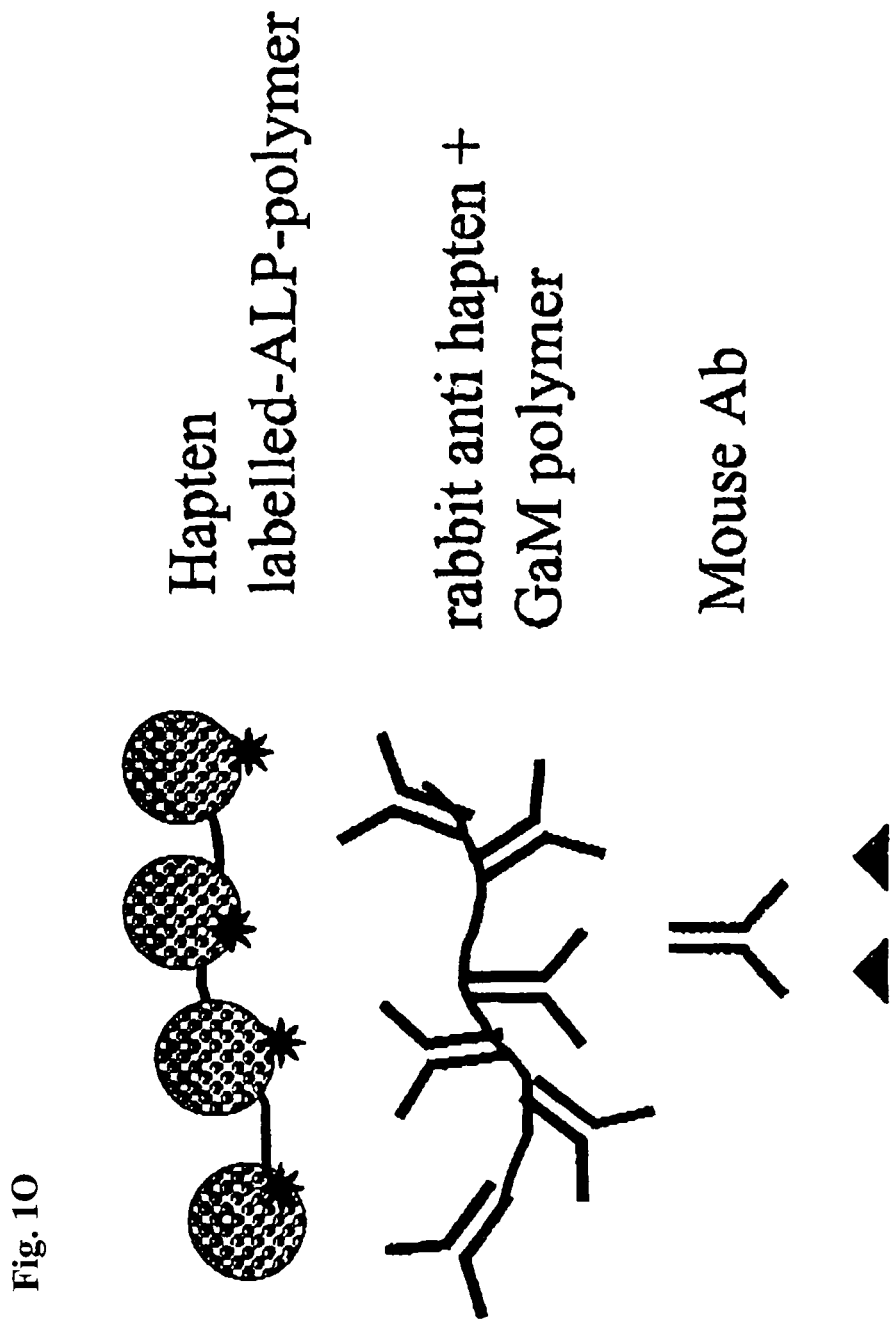
FIG. 10A to D are microphotographs of the Advance AP/Fuchsin stained melanoma and lymph node imprints taken at 10 times magnification: anti Vientiane stained imprint of melanoma samples using Advance AP (A) and EnVison™ AP (B), and anti CD3 stained imprint of lymph node samples using Advance AP (C) and EnVison™ AP (D), respectively.
Figure 1P:
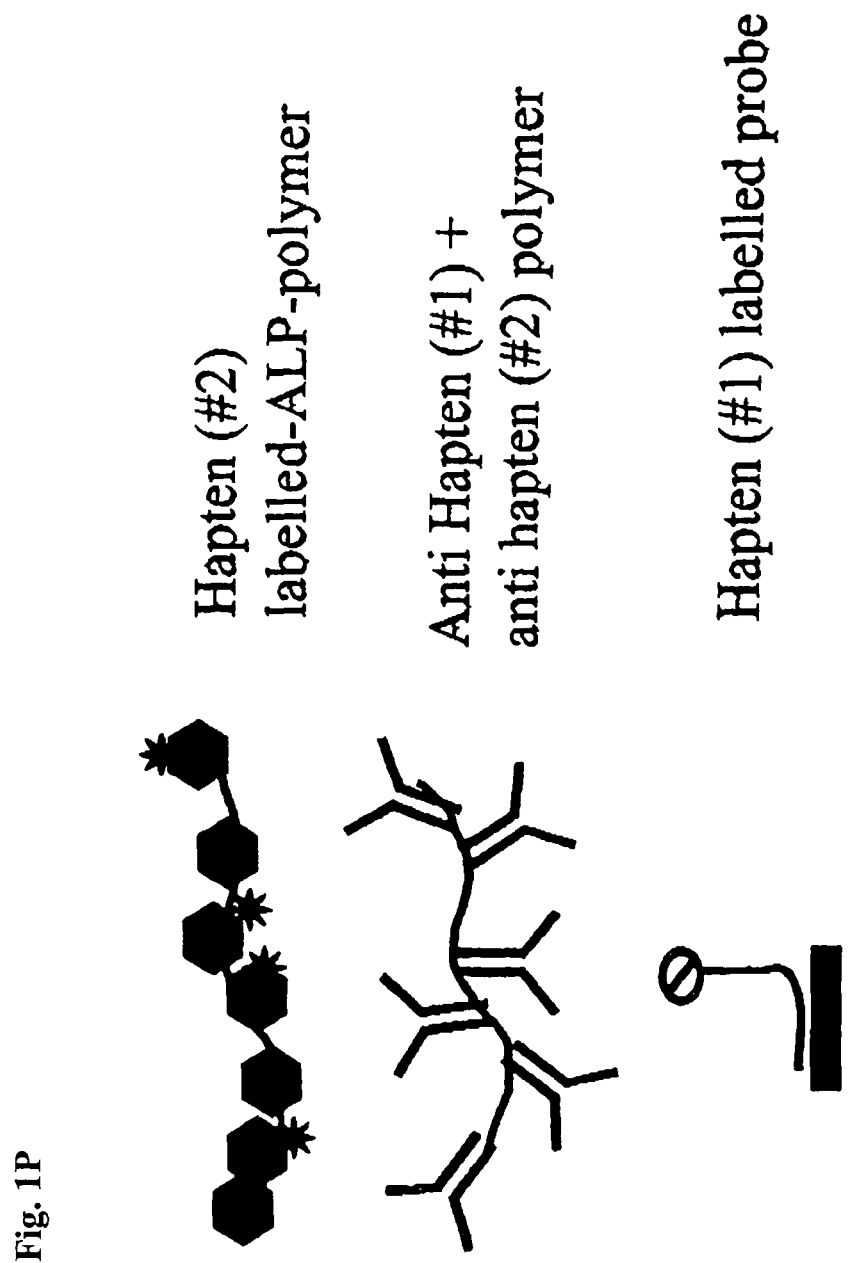
Figure 1R:
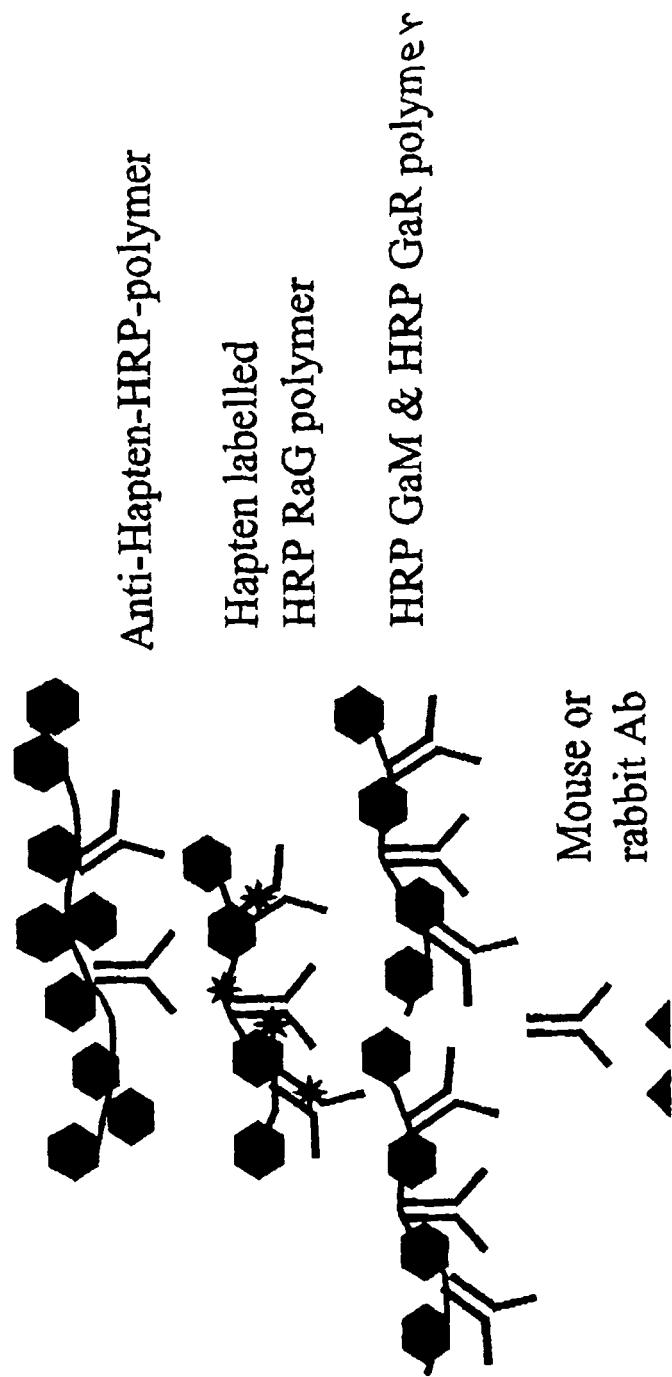
Figure 1S:
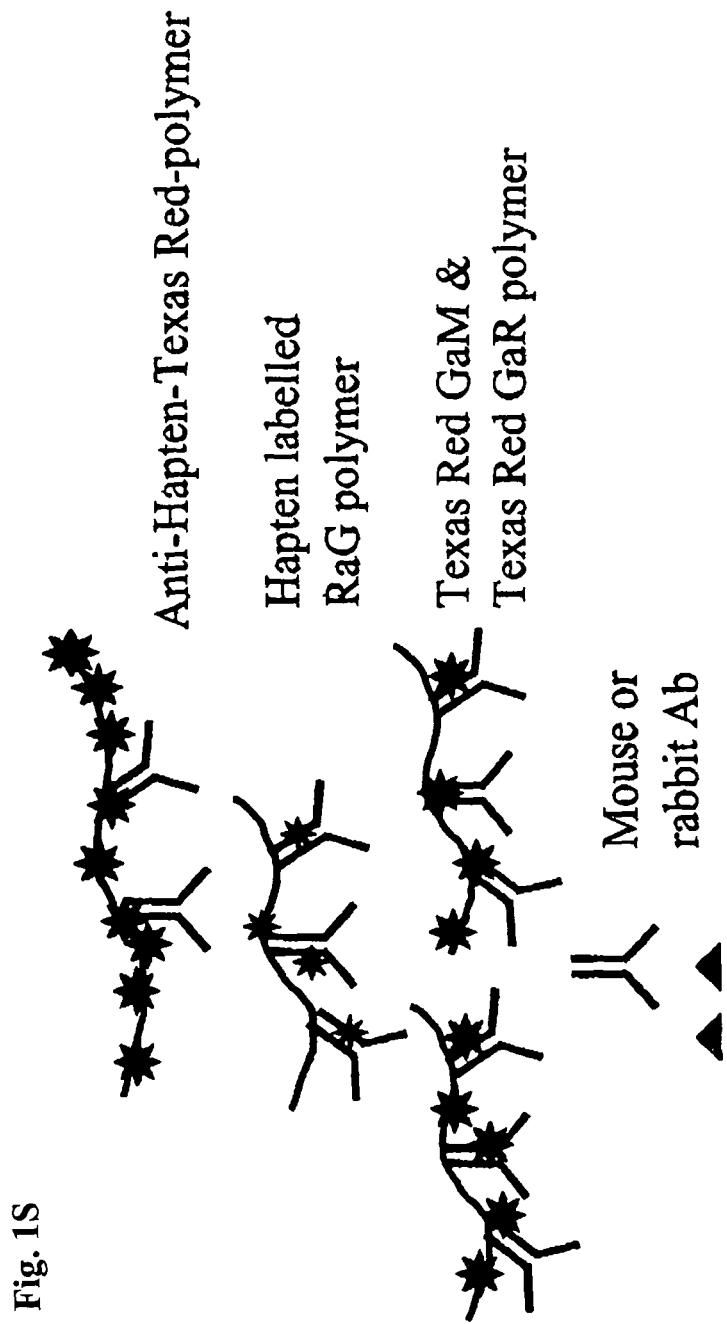
Figure 1T:
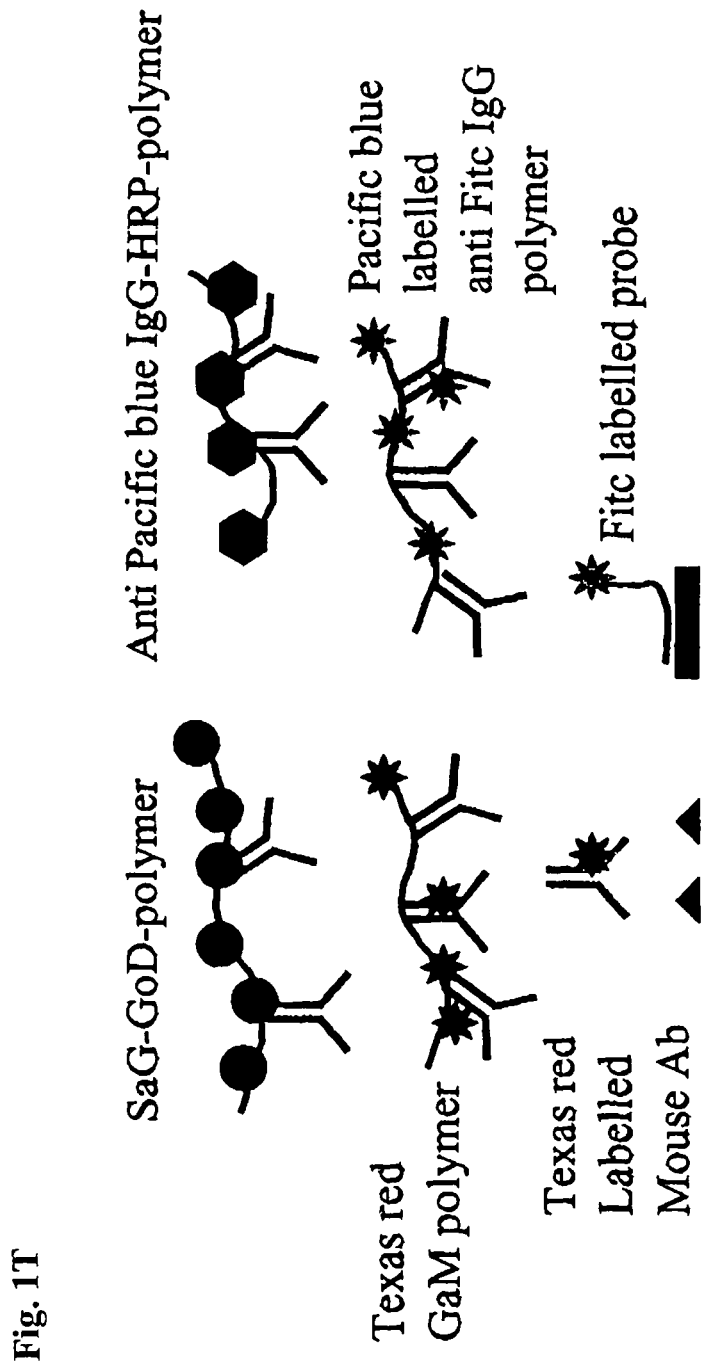
Figure 2A:
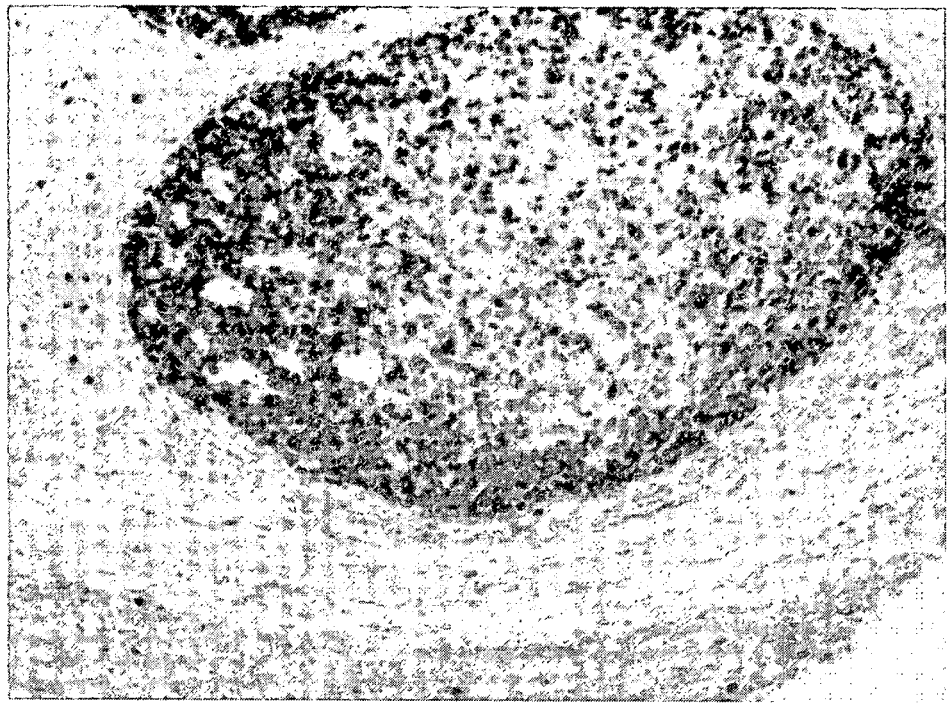
FIG. 2A-D are photomicrographs of the Ki67 stained tonsil tissue using the combination of conjugate 1 and Envision™+ (A) (Dakocytomation, Carpenteria, Calif.), unconjugated RaM (B), Envision™+ (C), or the PowerVision+™ (Immunovision, Springdale, Ariz.) system (D).
Figure 2B:
Figure 2C:
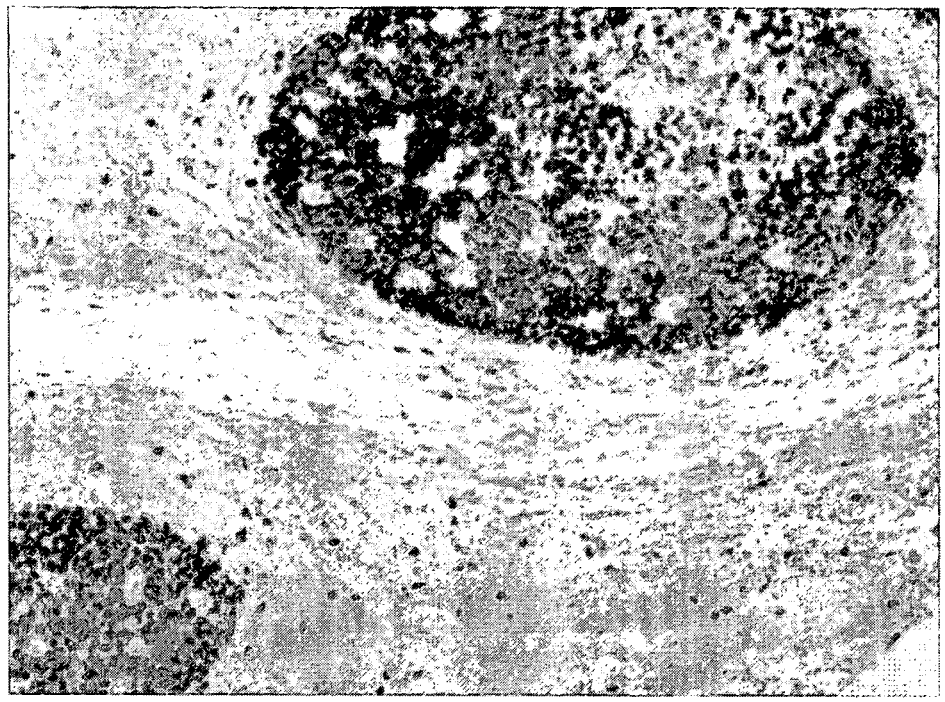
Figure 2D:
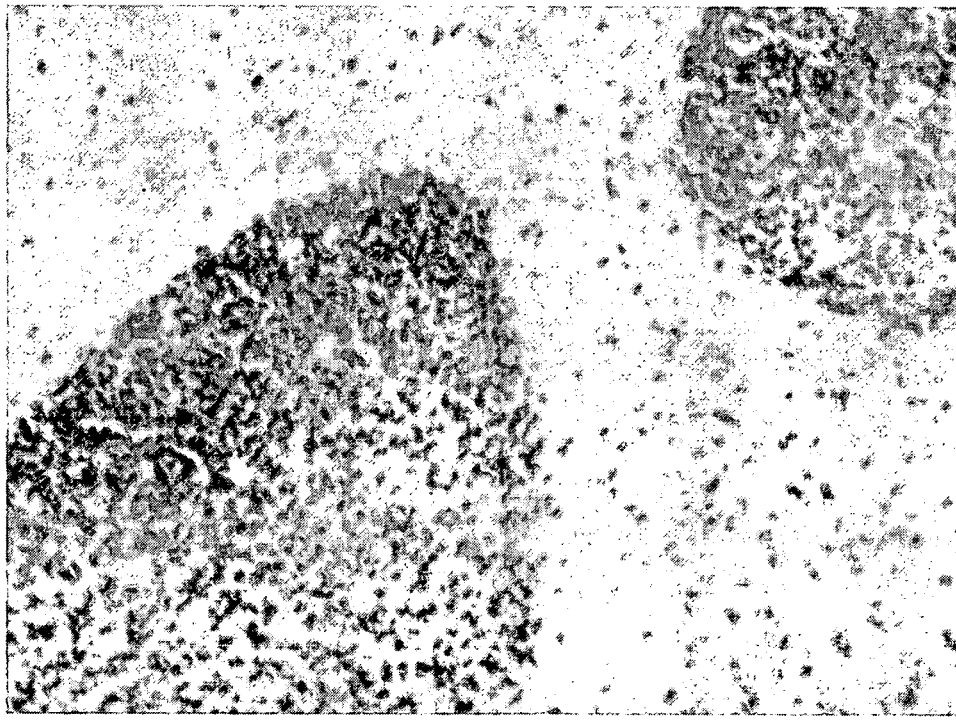
Figure 3A:
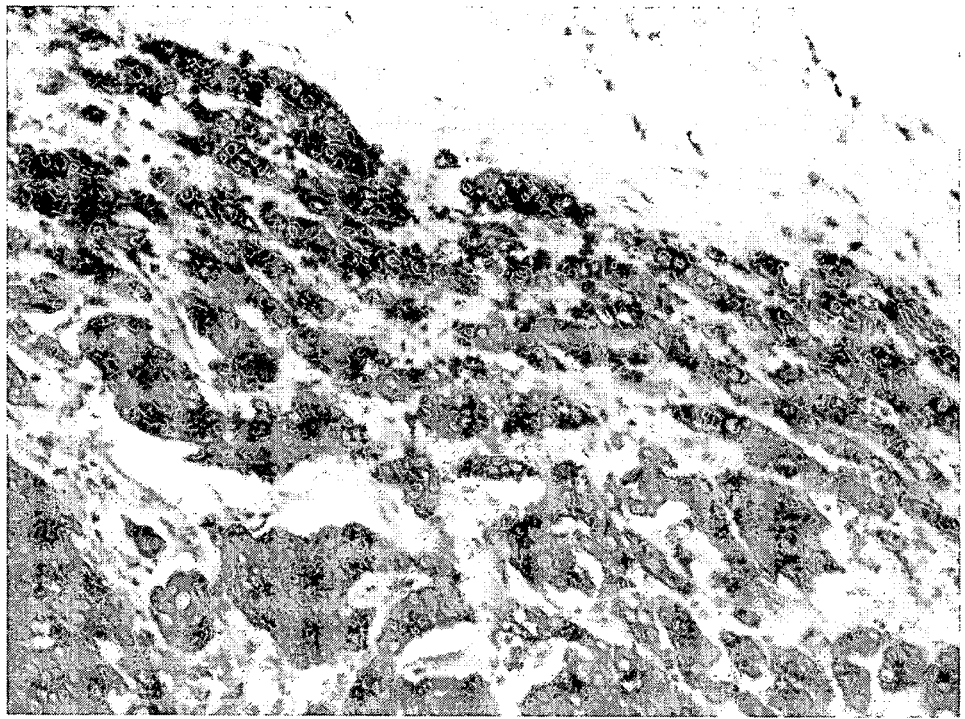
FIG. 3A-D are photomicrographs of the cytokeratine stained Mammae carcinoma tissue using the combination of Conjugate No. 1 and Envision™+(A) (Dakocytomation, Carpenteria, Calif.), unconjugated RaM and Envision™+(Dakocytomation, Carpenteria, Calif.) (B), Envision™+ (Dakocytomation, Carpenteria, Calif.) (C), or PowerVision+™ (Immunovision, Springdale, Ariz.) (D).
Figure 3B:
Figure 3C:
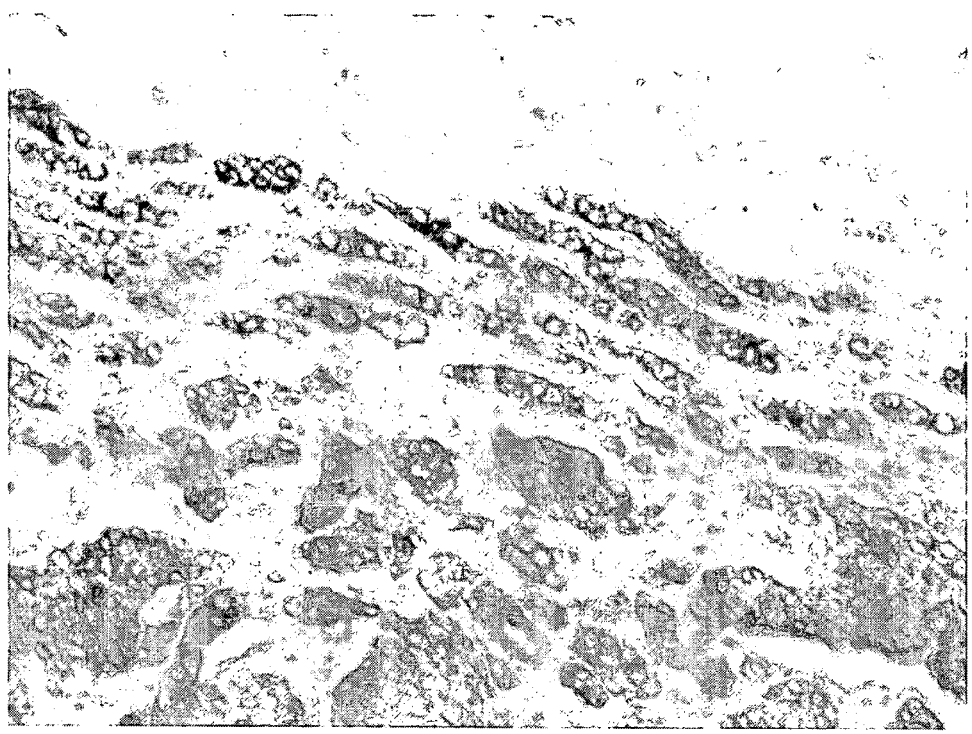
Figure 3D:
Figure 4A:
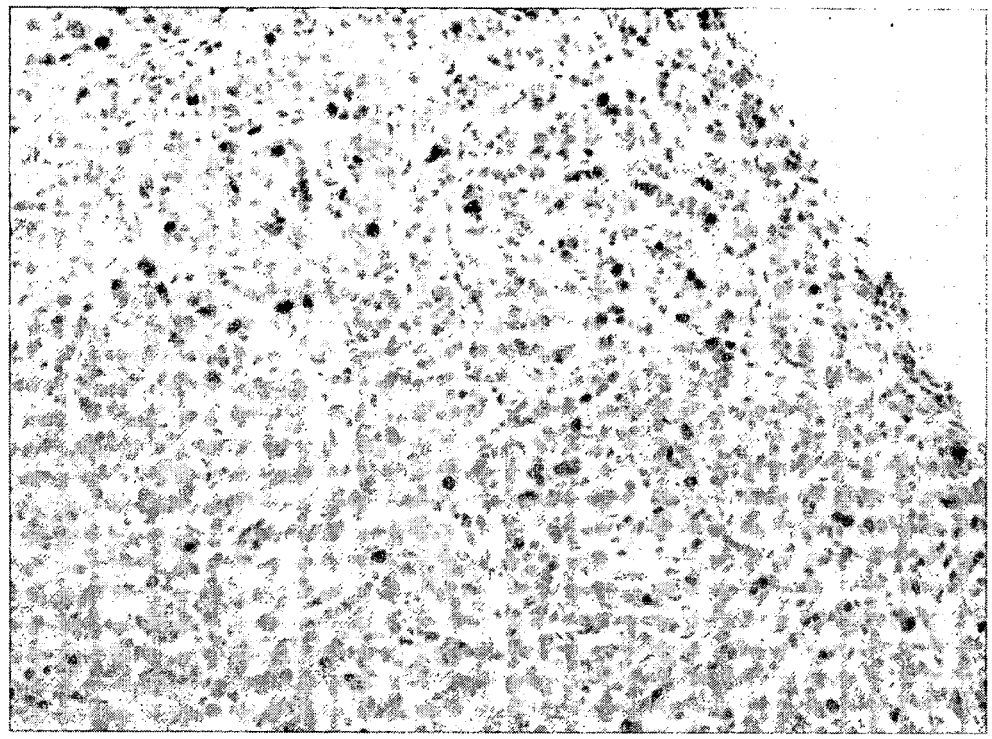
FIGS. 4A-D are photomicrographs of the Ki-67 stained Mammae carcinoma tissue using the combination of Conjugate No. 4 and Envision™+(Dakocytomation, Carpenteria, Calif.) (A), unconjugated RaM and Envision™+(Dakocytomation, Carpenteria, Calif.) (B), Envision™+ (Dakocytomation, Carpenteria, Calif.) (C), or PowerVision+™ (Immunovision, Springdale, Ariz.) (D).
Figure 4B:
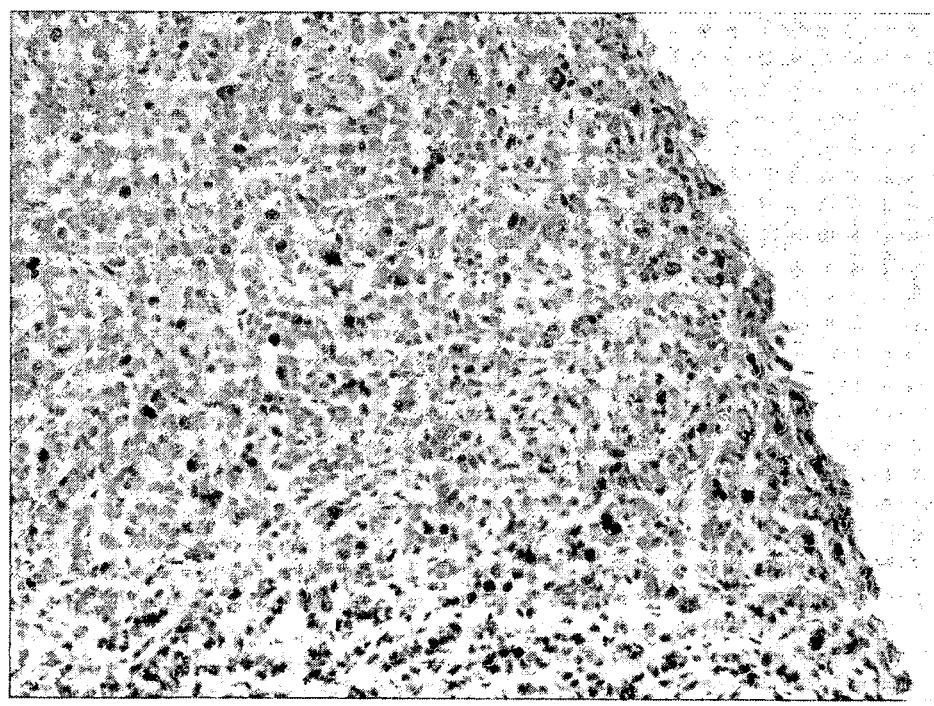
Figure 4C:
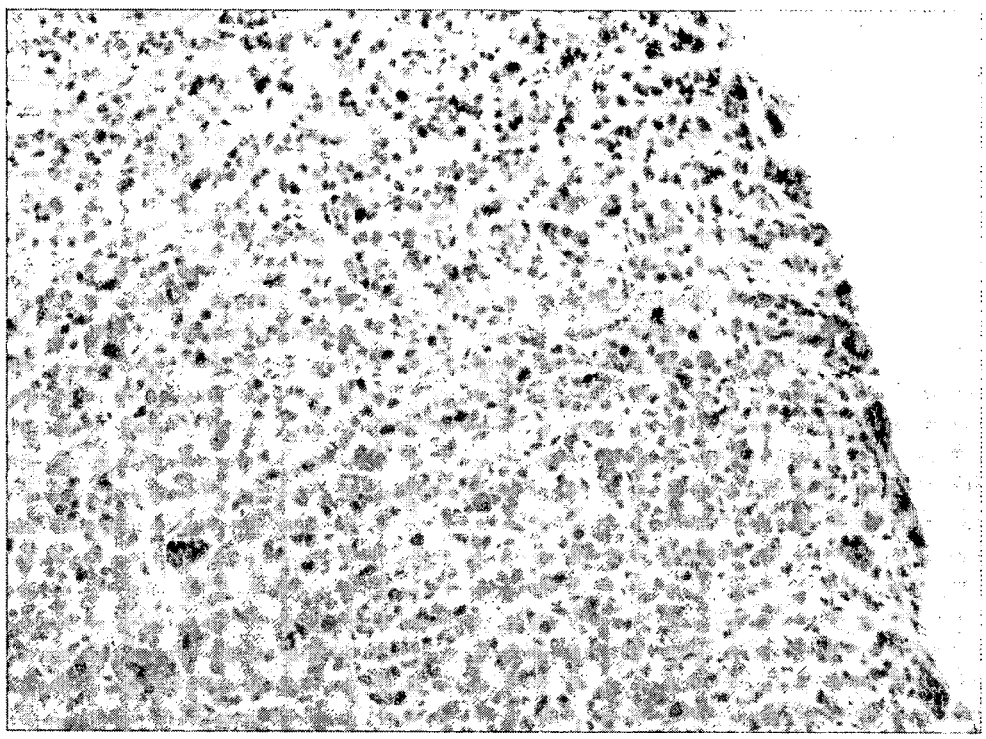
Figure 4D:
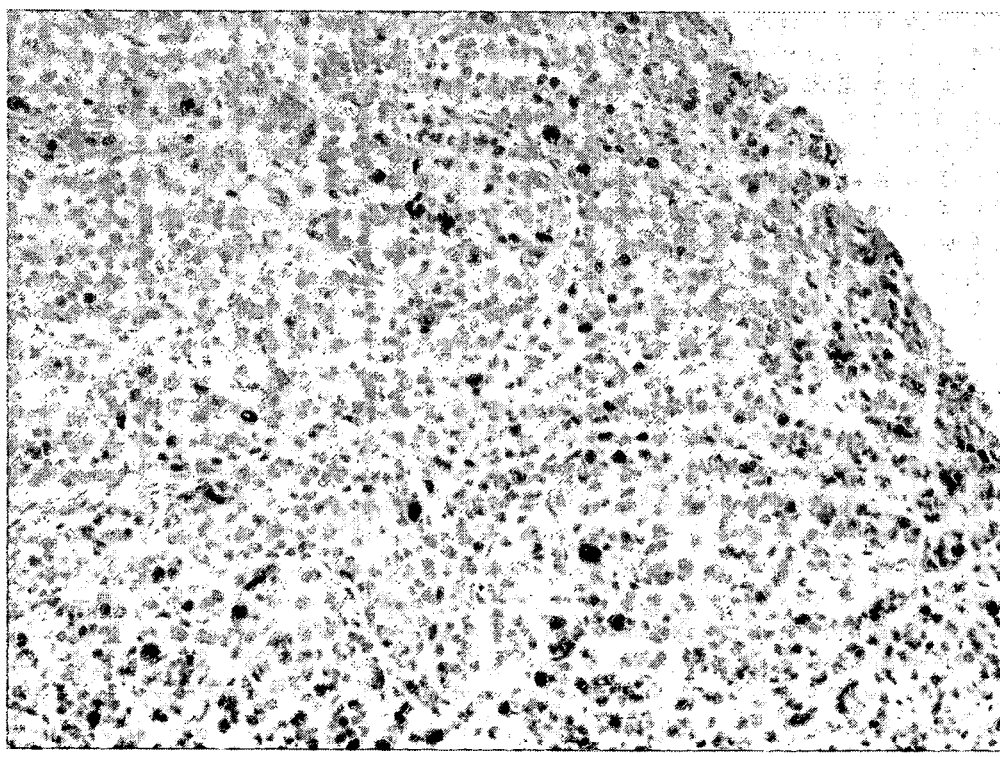
Figure 5A:
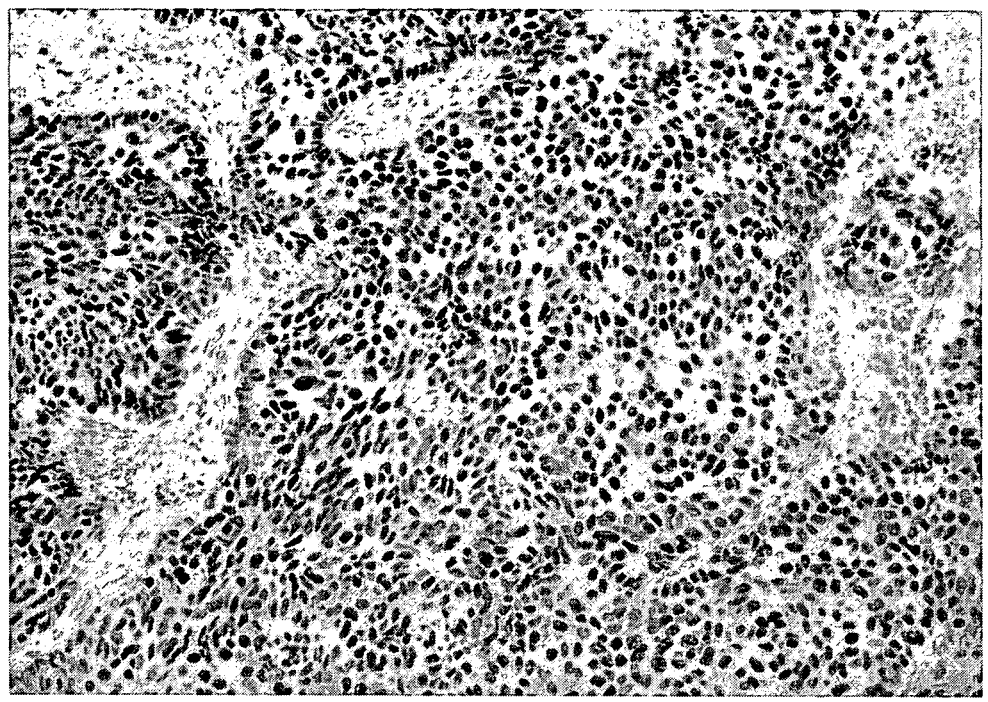
FIG. 5A-D are photomicrographs of the first estrogen receptor stained breast tissue: specific staining was obtained using the estrogen receptor antibody visualized with a mixture of polymeric goat anti rabbit and goat anti mouse secondary antibody and followed by a polymeric conjugate containing rabbit anti goat and horse radish peroxidase (NDS-1) (A), or PowerVision+™ (Immunovision, Springdale, Ariz.) (B); Negative antibody control staining was performed using NDS-1 (C), or PowerVision+™ (Immunovision, Springdale, Ariz.) (D).
Figure 5B:
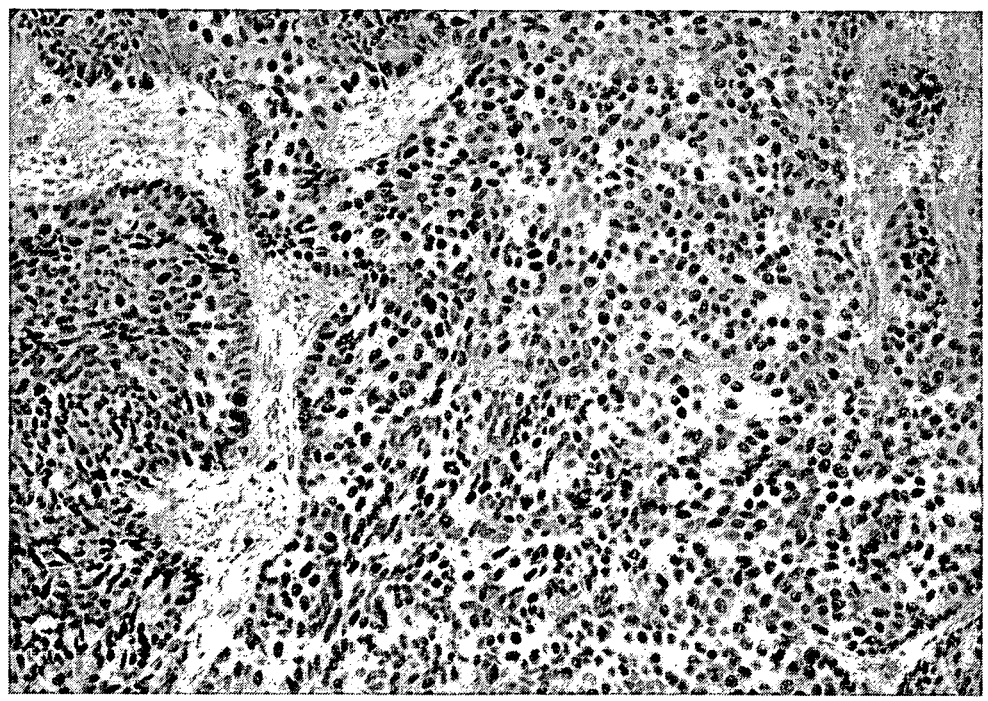
Figure 5C:
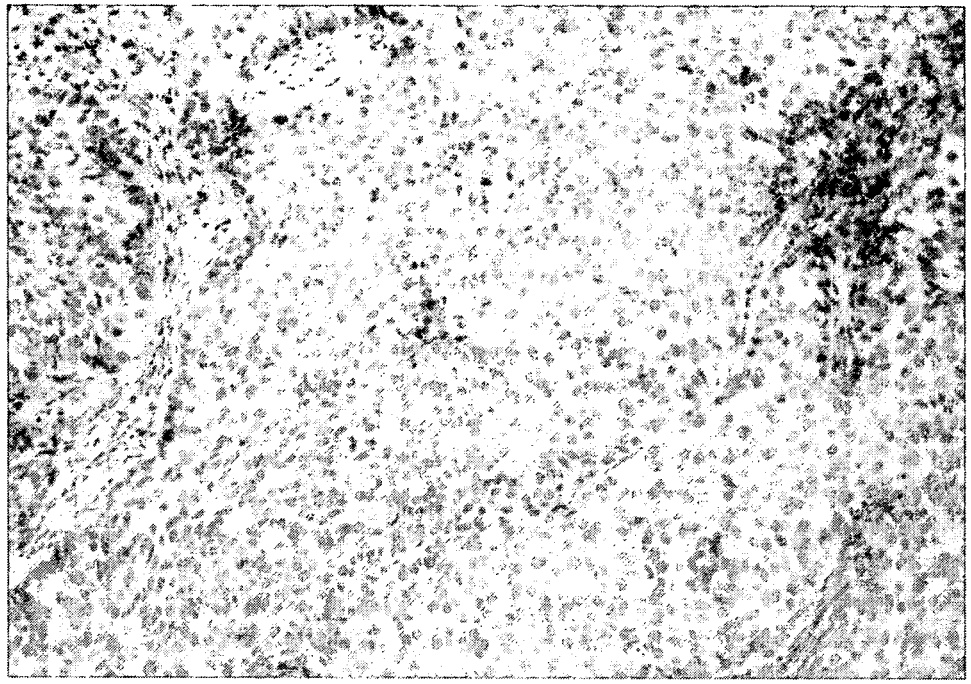
Figure 5D:
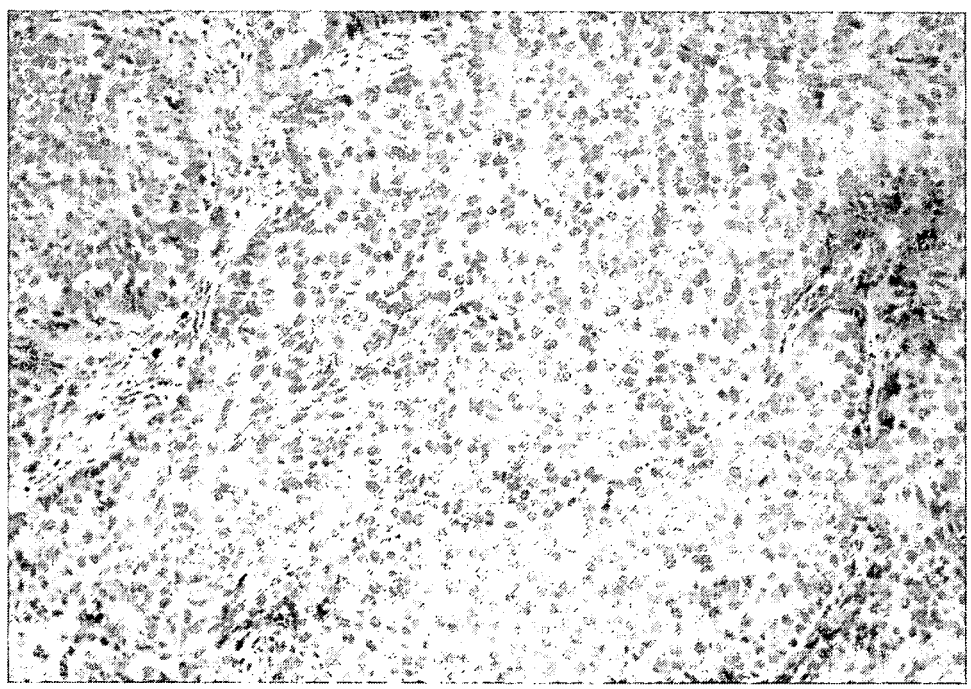
Figure 5E:
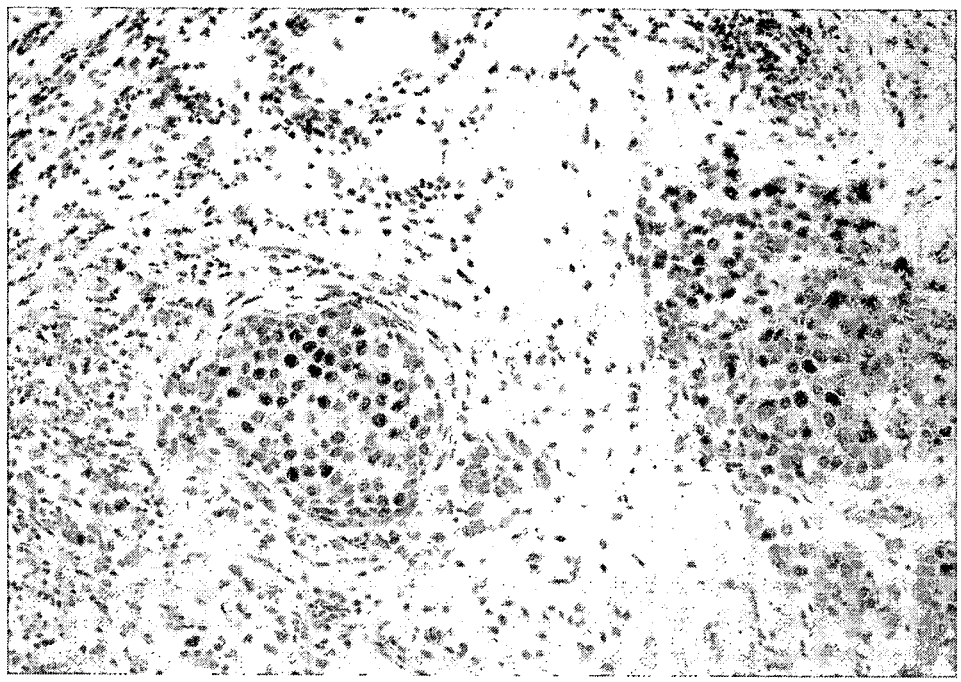
FIG. 5E-H are photomicrographs of the second estrogen receptor stained breast tissue: Specific staining was obtained using the estrogen receptor antibody visualized with a mixture of polymeric goat anti rabbit and goat anti mouse secondary antibody and followed by a polymeric conjugate containing rabbit anti goat and horse radish peroxidase (NDS-1) (E), or the PowerVision+™ (Immunovision, Springdale, Ariz.) (F). Negative antibody control staining was performed using the NDS-1 (G), or PowerVision+™ (Immunovision, Springdale, Ariz.) (H). All the photomicrographs were taken at 20-times magnification.
Figure 5F:
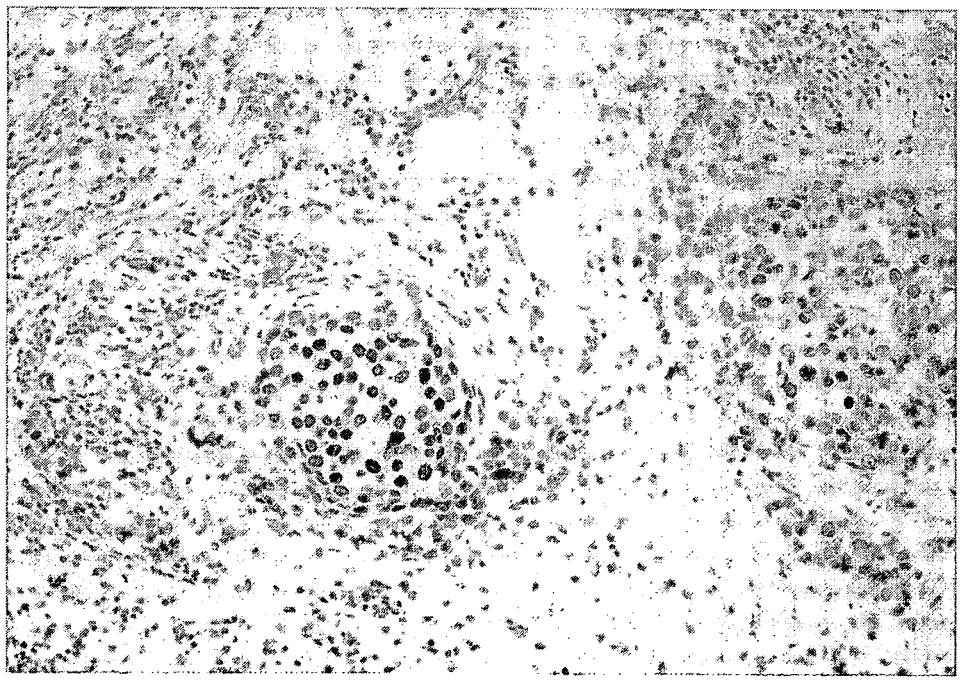
Figure 5G:
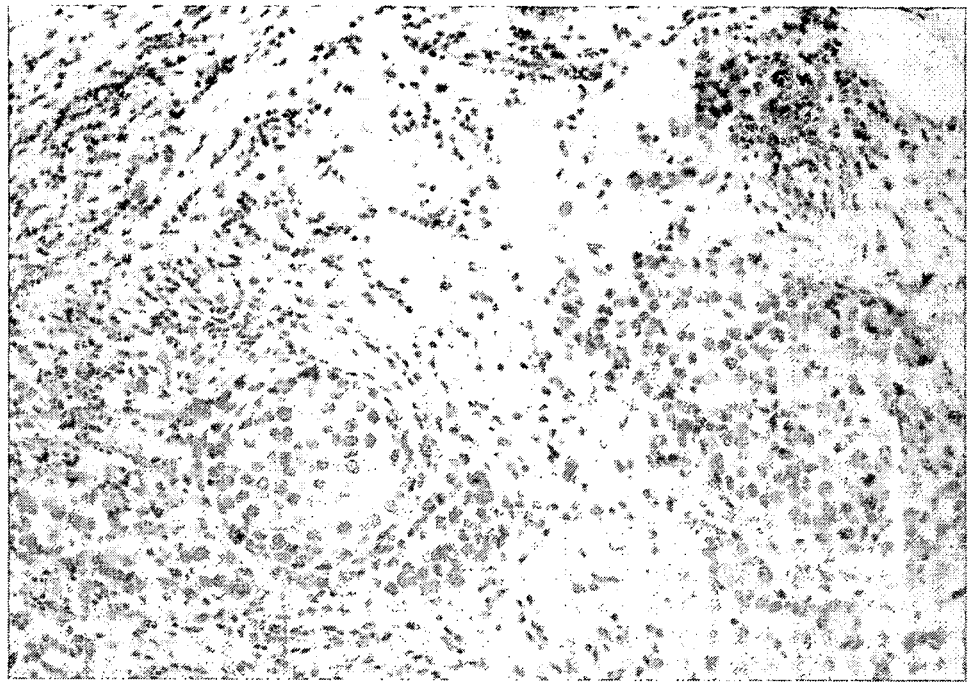
Figure 5H:
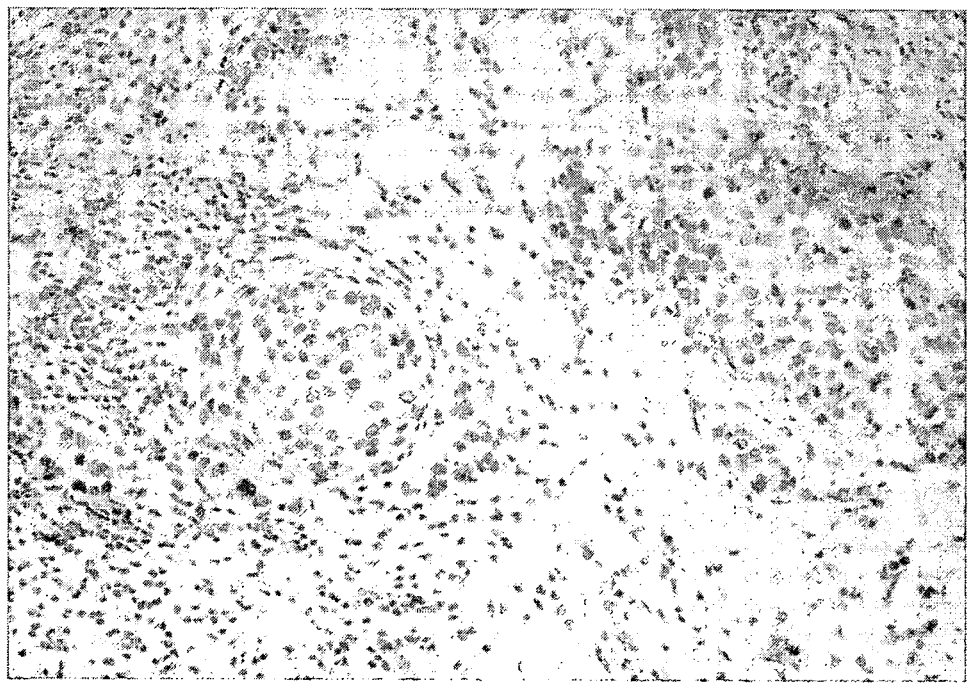
Figure 6A:
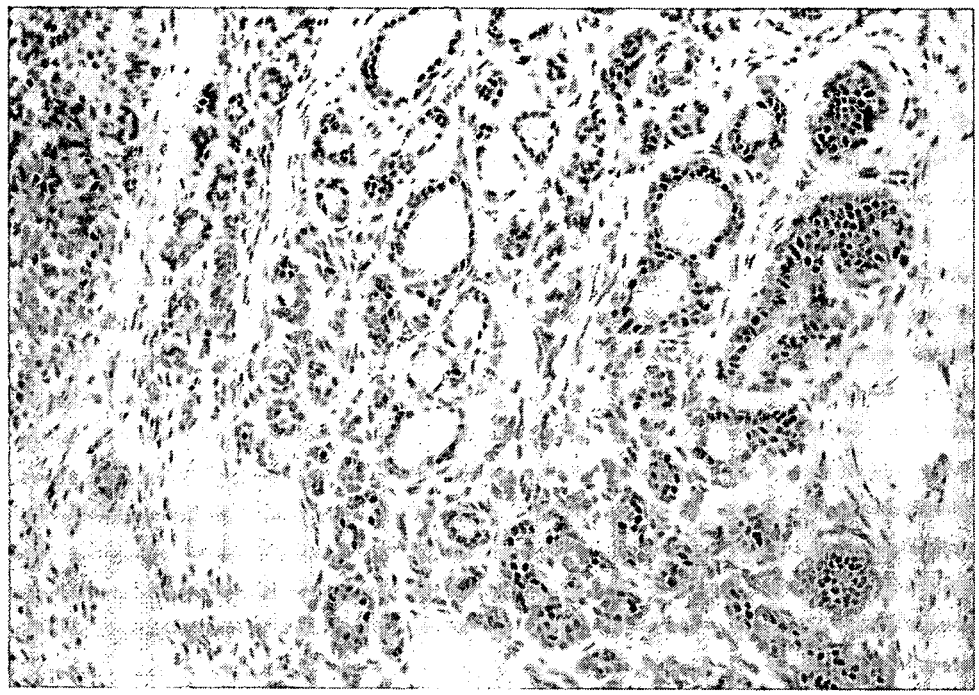
FIG. 6A-D are photomicrographs of the first progesterone receptor stained breast tissue: Specific staining was obtained using the progesterone receptor antibody: visualized with a mixture of polymeric goat anti rabbit and goat anti mouse secondary antibody and followed by a polymeric conjugate containing rabbit anti goat and horse radish peroxidase (NDS-1) (A), or PowerVision+™ (Immunovision, Springdale, Ariz.) (B). Negative antibody control staining was performed using NDS-1 (C), or PowerVision+™ (Immunovision, Springdale, Ariz.) (D).
Figure 6B:
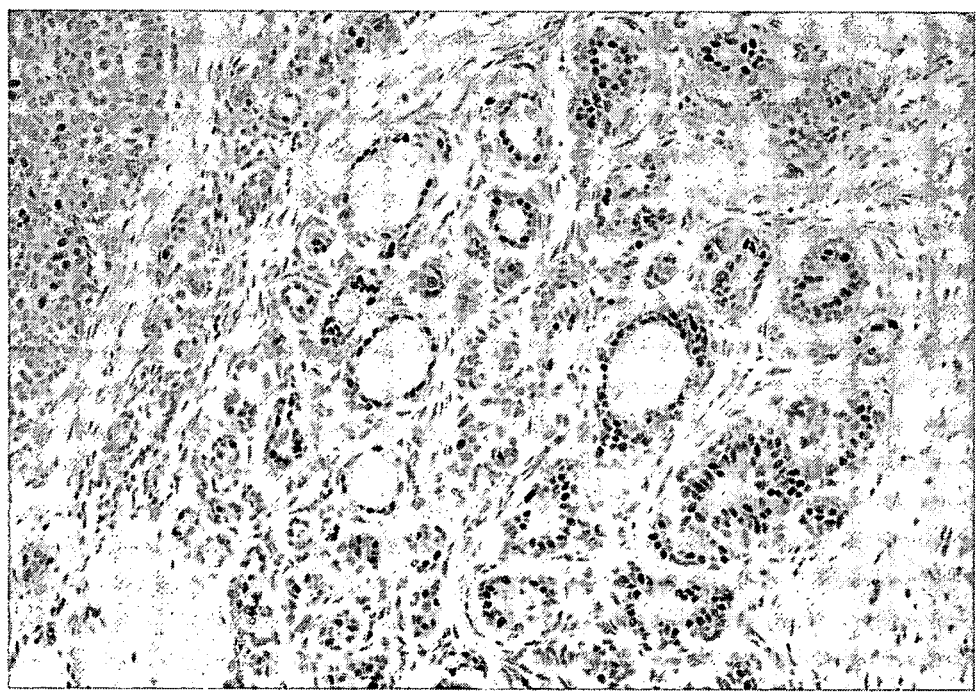
Figure 6C:
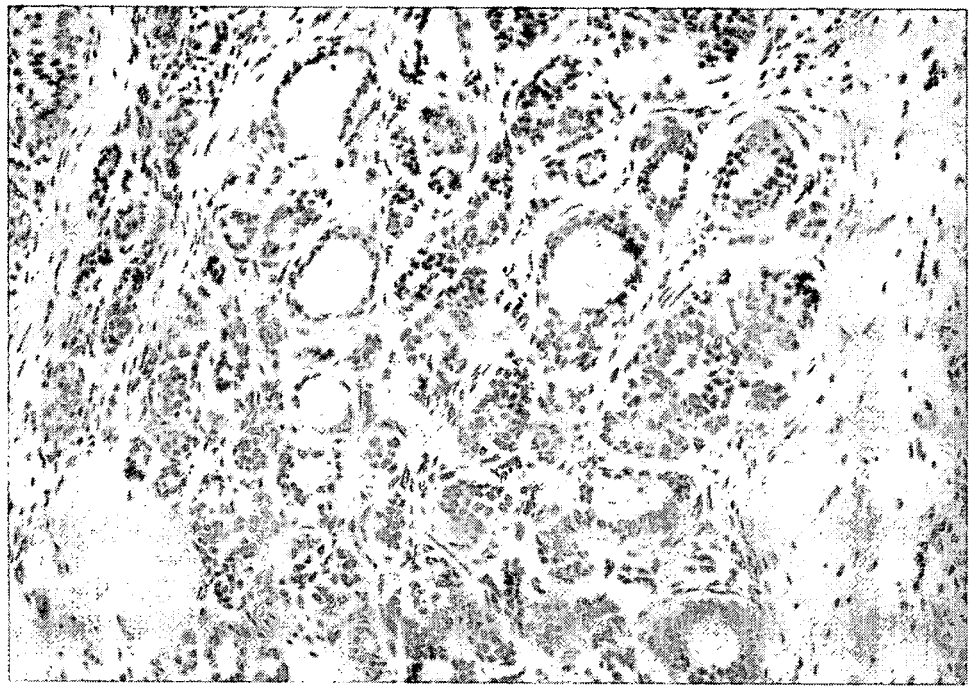
Figure 6D:
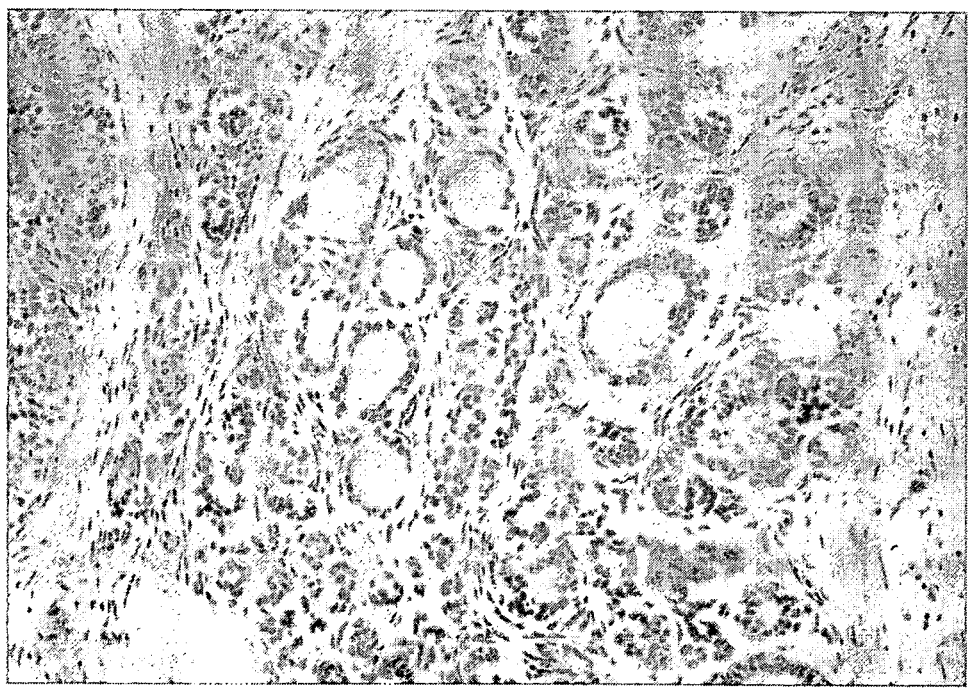
Figure 6E:
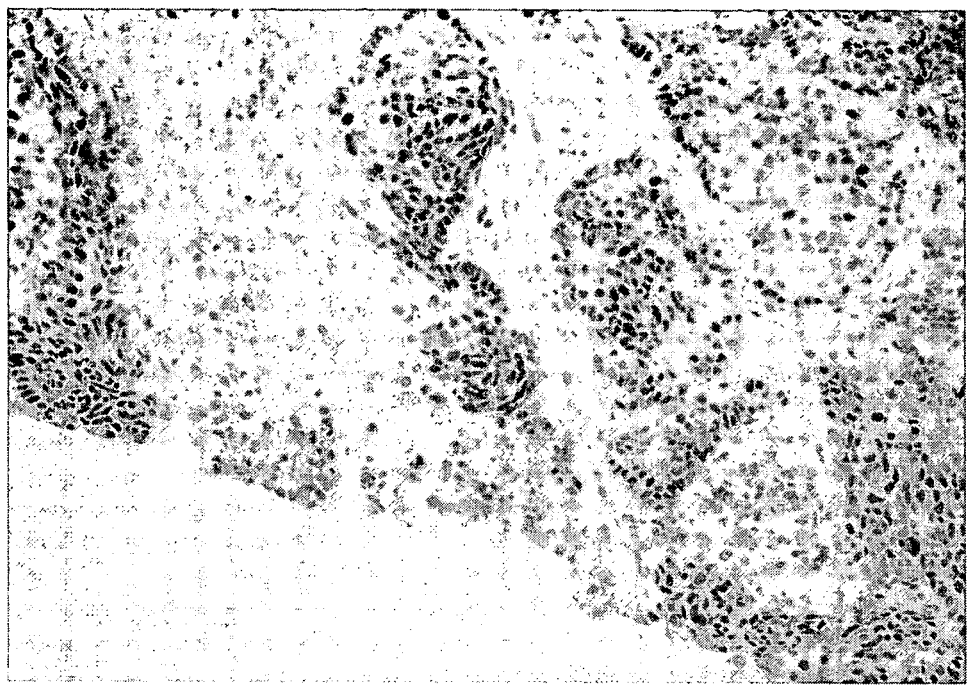
FIG. 6E-H are photomicrographs of the second progesterone receptor stained breast tissue: Specific staining was obtained using the progesterone receptor antibody: visualized with a mixture of polymeric goat anti rabbit and goat anti mouse secondary antibody and followed by a polymeric conjugate containing rabbit anti goat and horse radish peroxidase (NDS-1) (E), or the PowerVision+™ (Immunovision, Springdale, Ariz.) (F). Negative antibody control staining was performed using NDS-1 (G), or PowerVision+™ (Immunovision, Springdale, Ariz.) (H). All the photomicrographs were taken at 20-times magnification.
Figure 6F:
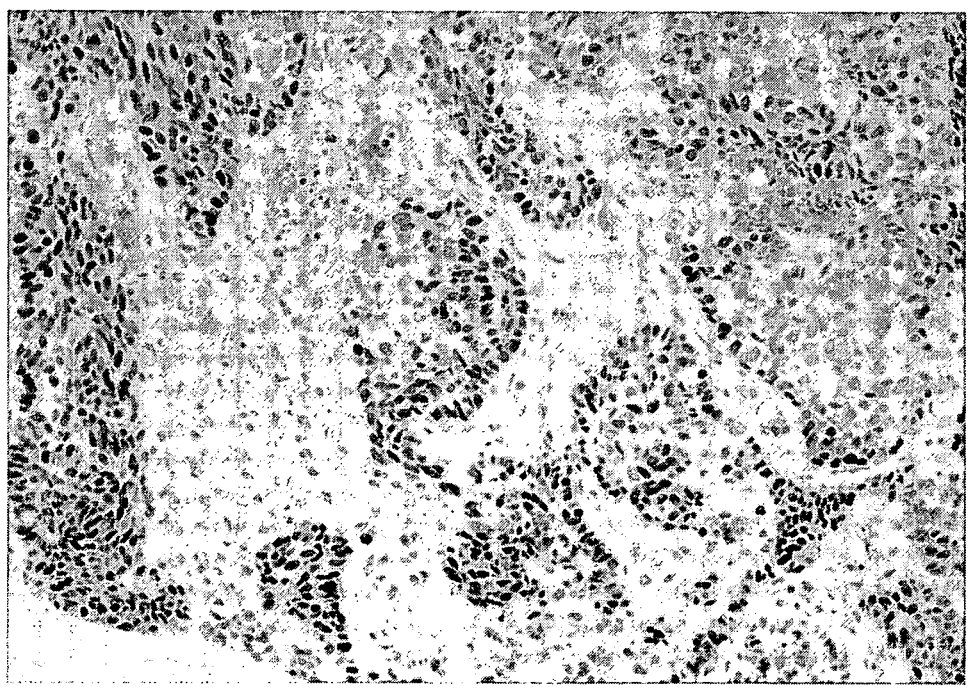
Figure 6G:
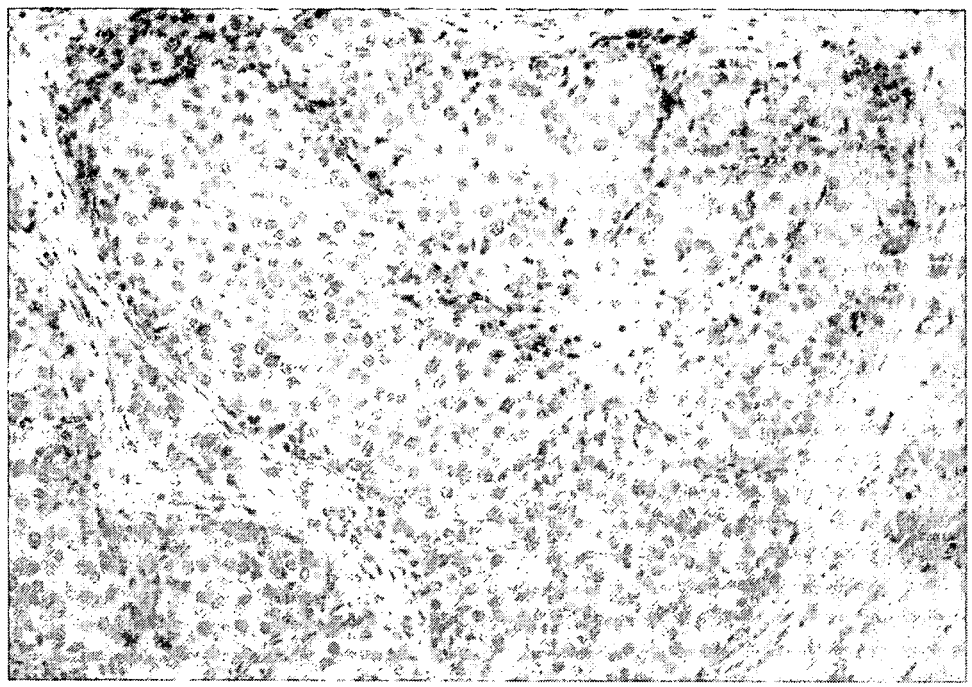
Figure 6H:
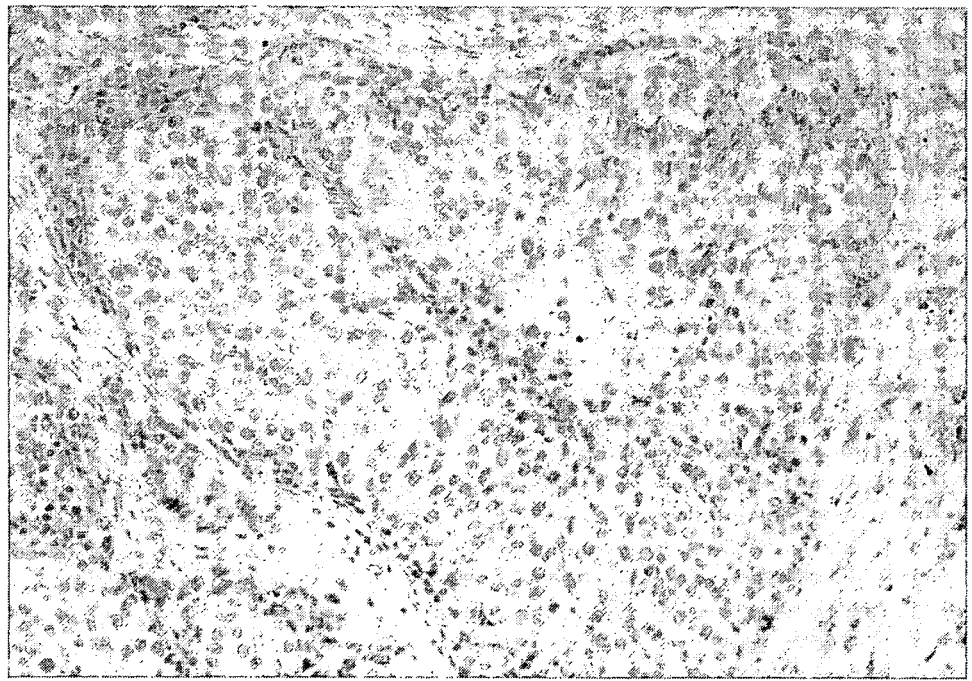
Figure 7A:
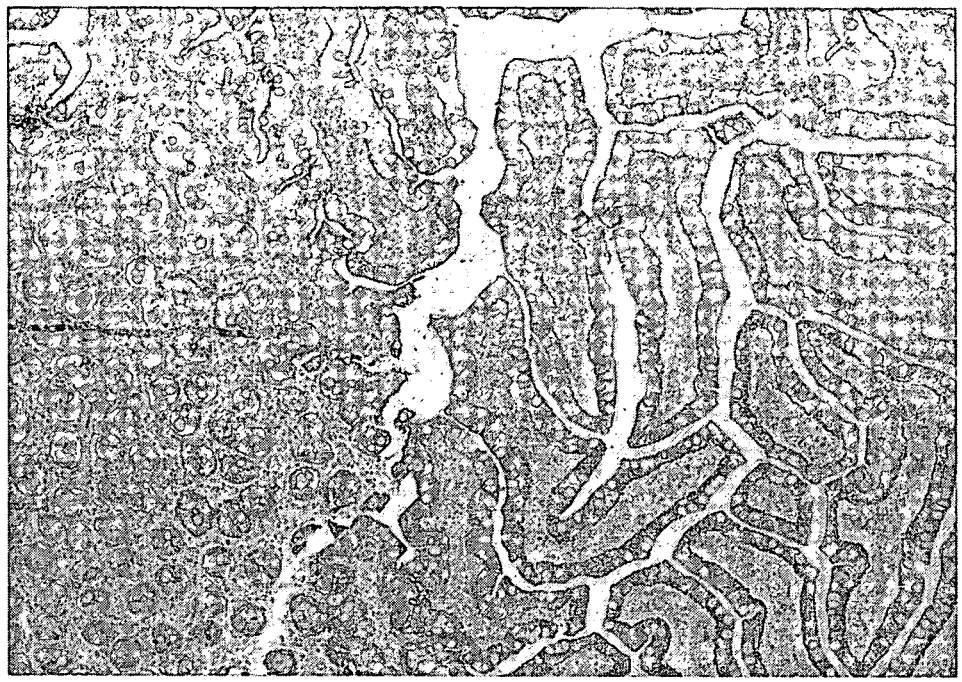
FIG. 7A-F are photomicrographs of stained breast tissue using a mixture of polymeric goat anti rabbit and goat anti mouse secondary antibody followed by a polymeric conjugate containing rabbit anti goat and horse radish peroxidase (NDS-1) in a fast protocol: Specific staining using the anti CK20 antibody: diluted 1:600 (A), diluted 1:3000 (B), and negative control (C). Specific staining using the anti progesterone receptor antibody: diluted 1:200 (D), diluted 1:1000 (E), and negative control (F).
Figure 7B:
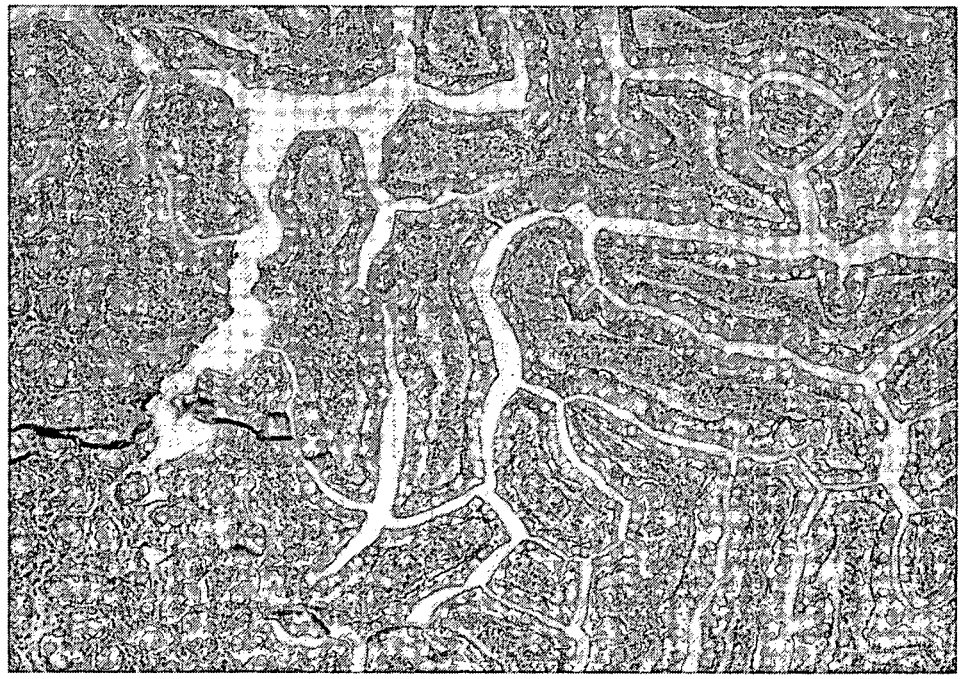
Figure 7C:
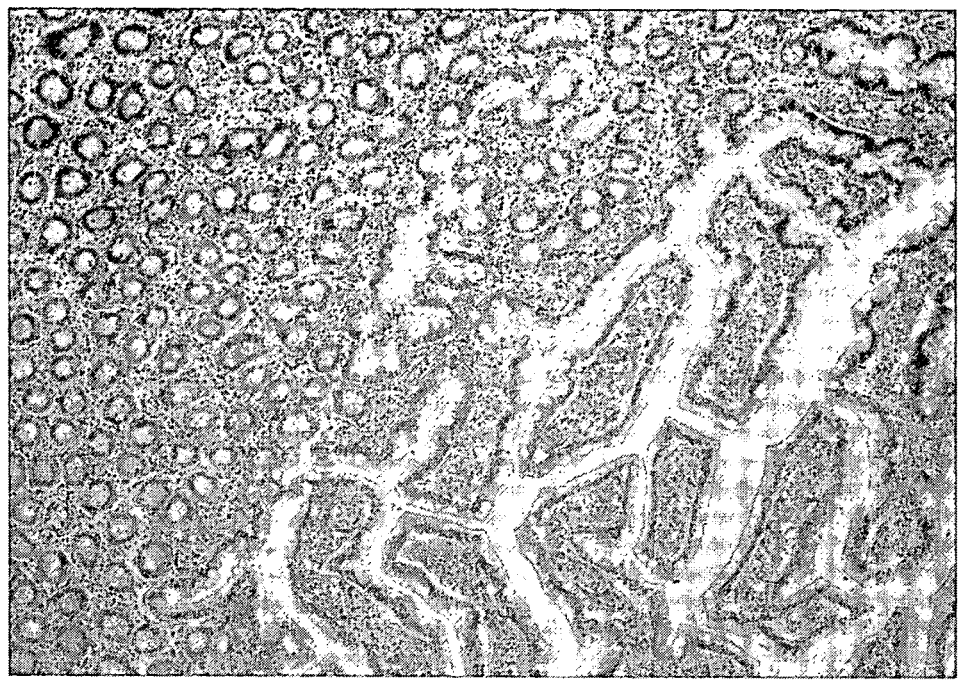
Figure 7D:
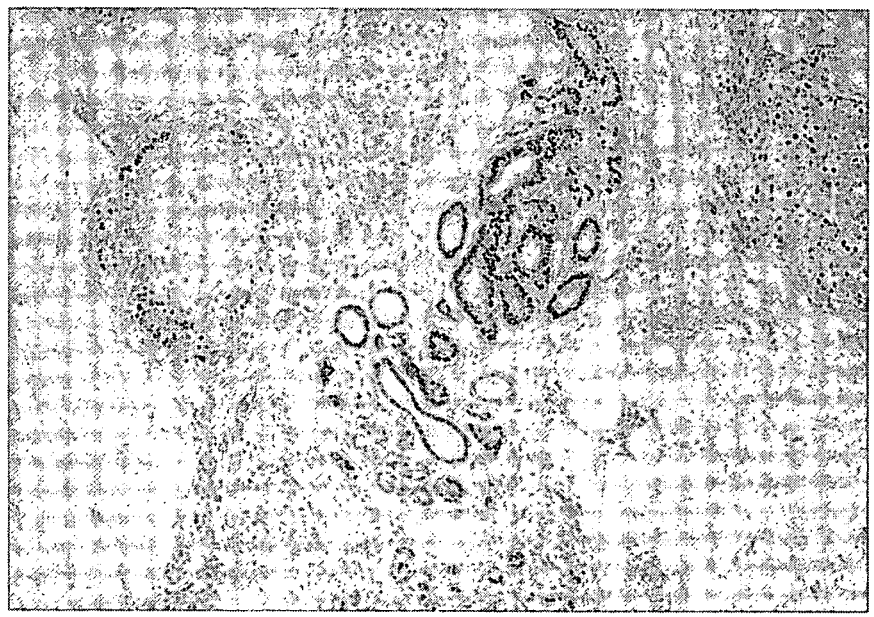
Figure 7E:
Figure 7F:

Automated stainers may be used in various embodiments of the invention, including embodiments which provide methods of detecting multiple markers. Detection of multiple markers frequently requires balancing of the signals emanating from the different detectable substances. When multiple markers are to be detected it may thus be advantageous to provide different amplification potential. An example of one such system is depicted in FIG. 1K and also described in Example 28, infra. In this embodimenta more sensitive detection system using a primary, secondary and tertiary binding agent (e.g., antibody) is balanced against the less sensitive system using a cocktail of rabbit antibodies and a secondary antibody linked to a polymer comprising horse-radish peroxidase, e.g., Envision™.

The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, *Immunocytochemistry: Theory and Practice*, (CRC Press, Boca Raton, Fla.); *Methods in Molecular Biology*, vol. 80 1998, John D. Pound (ed.) (Humana Press, Totowa, N.J.).

1. Sample Preparation

IHC and ISH techniques usually require a series of treatment steps conducted on a tissue section mounted on a suitable solid support for microscopic inspection, or the production of photomicrographs, e.g., a glass slide or other planar support, to highlight by selective staining certain morphological indicators of disease states or detection of biological markers.

Thus, for example in IHC, a sample is taken from an individual, fixed and exposed to antibodies which specifically bind to the biological marker of interest. The sample processing steps may include, for example, antigen retrieval, exposure to a primary antibody, washing, exposure to a secondary antibody (optionally coupled to a suitable detectable substance), washing, and exposure to a tertiary antibody linked to a detectable substance. Washing steps may be performed with any suitable buffer or solvent, e.g., phosphate-buffered saline (PBS), tris buffered saline (TBS), distilled water. The wash buffer may optionally contain a detergent, e.g., Tween 20.

There are in general two categories of histological samples: (a) preparations comprising fresh tissues and/or cells, which generally are not fixed with aldehyde-based fixatives, and (b) fixed and embedded tissue specimens, often archived material.

One IHC staining procedure may involve the steps of: cutting and trimming tissue, fixation, dehydration, paraffin infiltration, cutting in thin sections, mounting onto glass slides, baking, deparaffination, rehydration, antigen retrieval, blocking steps, applying primary antibody, washing, applying secondary antibody—enzyme conjugate, washing, applying a tertiary antibody conjugated to a polymer and linked with an enzyme, applying a chromogen substrate, washing, counter staining, applying a cover slip and microscopic examination.

In ISH, a sample is taken from an individual, fixed and exposed to a nucleic acid probe which hybridizes by virtue of complementary base pairing to the nucleic acid of interest. The biological sample typically comprises a detectable nucleic acid, such as DNA and RNA, including messenger RNA. Detection of DNA/RNA levels may indicate the level of expression of a particular gene, and hence may be used to detect a condition (such as a disease condition) of a cell, tissue, organ or organism. The nucleic acid in the sample is typically denatured to expose binding sites. The probe is typically a double or single stranded nucleic acid, such as a DNA or RNA, and is labeled using radioactive labels such as $^{31}P$, $^{33}P$ or $^{32}S$, or non-radioactively, using labels such as digoxigenin, or fluorescent labels, a great many of which are known in the art. By using hapten labeled DNA probes, these can be visualized by the current invention, by, e.g., using a primary antibody against the label and further adding a polymeric conjugate containing a secondary antibody and further adding a polymeric conjugate containing a tertiary antibody and an enzyme or fluorescent label. The enzyme or fluorescent label can generate the signal necessary for detection.

The amount of the relevant antigen or nucleic acid detected by such techniques is then assessed to determine whether it is above a certain pre-determined minimum threshold or compared to a known standard, and therefore, diagnostically relevant. Suitable treatment may then be planned for the individual if necessary.

2. Methods of Fixation

Many methods of fixing and embedding tissue specimens are known, for example, alcohol fixation and formalin-fixation and subsequent paraffin embedding (FFPE).

Fixatives are needed to preserve cells and tissues in a reproducible and life-like manner. To achieve this, tissue blocks, sections, or smears are immersed in a fixative fluid, or in the case of smears, are dried. Fixatives stabilize cells and tissues thereby protecting them from the rigors of processing and staining techniques.

Any suitable fixing agent may be used, for example, ethanol, acetic acid, picric acid, 2-propanol, 3,3'-diaminobenzidine tetrahydrochloride dihydrate, acetoin (mixture of monomer) and dimer, acrolein, crotonaldehyde (cis+trans), formaldehyde, glutaraldehyde, glyoxal, potassium dichromate, potassium permanganate, osmium tetroxide, paraformaldehyde, mercuric chloride, tolylene-2,4-diisocyanate, trichloroacetic acid, tungstic acid. Other examples include formalin (aqueous formaldehyde) and neutral buffered formalin (NBF), glutaraldehyde, acrolein, carbodiimide, imidates, benzoequinone, osmic acid and osmium tetraoxide.

Fresh biopsy specimens, cytological preparations (including touch preparations and blood smears), frozen sections and tissues for immunohistochemical analysis are commonly fixed in organic solvents, including ethanol, acetic acid, methanol and/or acetone.

3. Antigen Retrieval

To facilitate the specific recognition in fixed tissue, it is often necessary to retrieve or unmask the targets, i.e., the biological markers of interest, through pre-treatment of the specimens to increase reactivity of the majority of targets. This procedure is referred to as "antigen retrieval", "target retrieval" or "epitope retrieval", "target unmasking" or "antigen unmasking." An extensive review of antigen retrieval (antigen unmasking) may be found in Shi et al. 1997, *J Histochem Cytochem*, 45(3):327.

Antigen retrieval includes a variety of methods by which the availability of the target for interaction with a specific detection reagent is maximized. The most common techniques are enzymatic digestion with a proteolytic enzyme (for example proteinase, pronase, pepsin, papain, trypsin or neuramimidase) in an appropriate buffer or heat induced epitope retrieval (HIER) using microwave irradiation, heating in a water bath, a steamer, a regular oven, an autoclave or a pressure cooker in an appropriately pH stabilized buffer, usually containing EDTA, EGTA, Tris-HCl, citrate, urea, glycin-HCl or boric acid. Detergents may be added to the HIER buffer to increase the epitope retrieval or added to the dilution media and/or rinsing buffers to lower non-specific binding.

The antigen retrieval buffer is most often aqueous, but may also contain other solvents, including solvents with a boiling point above that of water. This allows for treatment of the tissue at more than 100° C. at normal pressure.

Additionally, the signal-to-noise ratio may be increased by different physical methods, including application of vacuum and ultrasound, or freezing and thawing of the sections before or during incubation of the reagents.

Endogenous biotin binding sites or endogenous enzyme activity (for example phosphatase, catalase or peroxidase) may be removed as a step in the staining procedure, e.g., endogenous biotin and peroxidase activity may be removed by treatment with peroxides. Endogenous phosphatase activity may be removed by treatment with levamisole. Endogenous phosphatases and esterases may be destroyed by heating.

Blocking of non-specific binding sites with inert proteins like, HSA, BSA, ova-albumin, fetal calf serum or other sera, or detergents like Tween20, Triton X-100, Saponin, Brij or Pluronics may be used. Blocking non-specific binding sites in the tissue or cells with unlabeled and target non-specific versions of the specific reagents may also be used.

4. Free Floating Technique

Samples may also be prepared and stained using the free floating technique. In this method a tissue section is brought into contact with different reagents and wash buffers in suspension or freely floating in appropriate containers, for example micro centrifuge tubes.

The tissue sections may be transferred from tube to tube with different reagents and buffers during the staining procedure using for example a "fishing hook like" device, a spatula or a glass ring. The different reagents and buffer can also be changed by gentle decantation or vacuum suction. Alternatively, containers with the tissue sections can be emptied into a special staining net, like the Corning "Netwells" (Corning,) and the tissue section washed before being transferred back into the tube for the next staining step.

All the steps, including for example fixation, antigen retrieval, washing, incubation with blocking reagents, immuno-specific reagents and the enzymatic catalyzed development of the colored stains, are done while the tissue section is floating freely or withheld on nets. After development of the stain, the tissue section is mounted on slides, dried, before being counterstained and covered with a cover slip before being analyzed, e.g., by light microscopy.

In some embodiments, the tissue section may be mounted on slides following the critical incubation with the immuno-specific reagents. The rest of the staining process is then conducted on the slide mounted tissue sections.

D. Kits

The invention provides a kit for detecting a biological marker in a sample. In certain embodiments, the kit provides a first and second binding agent, at least one of which is conjugated to a polymer or is polymerizable itself and at least one detectable substance. The detectable substance may be linked to at least one of the other components of the kit, e.g., the first binding agent, the second binding agent, a polymer. The detectable substance may be polymerizable with the binding agent, e.g., derivatized and polymerized. The kit may further comprise at least one container. The kit may optionally comprise a primary antibody and instructions.

In some embodiments the invention provides a kit comprising a secondary antibody, a tertiary antibody, and optionally a primary antibody and at least one detectable substance. The secondary antibody may be conjugated without the addition of a polymeric backbone or with the addition of a polymeric backbone. The tertiary antibody may be conjugated without the addition of a polymeric backbone or with the addition of a polymeric backbone.

In certain embodiments, the invention provides a kit for performing immuno-histochemistry on a sample comprising a) at least one secondary antibody optionally linked to a first polymer; b) at least one tertiary antibody linked to a second polymer and a first detectable substance linked to at least one of i) the at least one tertiary antibody; ii) the first polymer; and iii) both the first polymer and the tertiary antibody; c) optionally a primary antibody; d) at least one container and optionally, instructions. The kit may further comprise a first secondary antibody linked to a first polymer and a second secondary antibody linked to a second polymer and a second detectable substance linked to at least one of a) the secondary antibody; b) the second polymer; and c) both the secondary antibody and the second polymer. In some embodiments, the first and second detectable substances are different. In some embodiments, the first and second detectable substances are the same.

In some embodiments, the kit comprises at least one hapten molecule linked to at least one of a) a secondary antibody; b) a second polymer; and c) both a secondary antibody and a second polymer.

EXAMPLES

Example 1

Preparation of Polymeric Conjugates

Dextran polymers were prepared for conjugation with antibodies and detectable substances to be used in the detection of biological markers in a sample. Dextrans of various sizes were activated with divinylsulfone, followed by coupling to horseradish peroxidase and antibodies.

Dextrans of different molecular sizes (70 and 150 kDa) (Pharmacosmos, Viby, Denmark) were activated with divinylsulfon (DVS, Vinyl sulfone), (Sigma-Aldrich, St. Louis, Mo.) according to the method of Lihme and Boenisch (WO 93/01498). This resulted in activation of 25% of the dextran monomers. The activated dextran was stored in the dark at 2-8° C. before use.

Example 2

Conjugation of Antibodies to Activated Dextran

Affinity purified rabbit anti mouse (RaM) antibody (Dakocytomation, Carpenteria, Calif.), affinity purified goat anti rabbit (GaR) immunoglobulin (Dakocytomation, Carpenteria, Calif.) or affinity purified goat anti mouse (GaM) immunoglobulin (Dakocytomation, Carpenteria, Calif.), or affinity purified rabbit anti DNP Fab2 immunoglobulin (anti Dinitrophenyl, Fab2,) (Dakocytomation, Carpenteria, Calif.) or affinity purified primary antibody mouse anti human Bcl-2 Oncoprotein immunoglobulin (clone 124, Isotype: IgG1 kappa) (Dakocytomation, Carpenteria, Calif.) was dialyzed overnight against 0.10 M NaCl buffer using dialysis tubing having a molecular weight cut off of 10 kDa at a temperature of 2-4° C. One liter of buffer was used. The buffer was changed three times. The concentration of antibody was 100 mg in a volume of 5 ml. After dialysis the antibody was concentrated on centrifuge filters (10 kDa Mw cut off) to more than 30 mg/ml before conjugation to the activated dextran.

The conjugation was performed by addition of antibody to vinylsulfon-activated dextran. The antibody solution, at a concentration of 21.25 mg/ml, was added to a solution of vinylsulfon-activated dextran at a concentration of 1.60 mg dextran/ml, in 25 mM carbonate, 0.10 M NaCl, pH 8.5 and stirred overnight in a water bath at 30° C. for 18 hours. This was done for each of the immunoglobulins. For the Fab2 antibodies, the concentration was 13.70 mg/ml in the conjugation mixture.

Any remaining reactive groups on the dextran were quenched by addition of $\frac{1}{10}$ volume reaction mixture of a cysteine containing buffer (110 mM cysteine, 50 mM HEPES, 0.1 M NaCl, pH 7.0) and stirred for 60 minutes at 30° C.

The polymeric conjugates were purified from unbound antibody by gel filtration using FPLC (Pharmacia, Uppsala, Sweden), with an S-200 gel SEC column and a buffer of 0.1 M HEPES, 0.1 M NaCl at pH 7.0 (Pharmacia, Peapack, N.J.).

The number of antibodies per dextran molecule, and conjugate concentration was calculated from the UV absorbance of the fractions containing the conjugate and the fraction containing unconjugated antibody. Absorbance measurements were measured at 280 nM.

Some of the polymeric conjugates were further labeled with DNP. The polymeric conjugates were dialyzed overnight against 0.10 M NaCl buffer as described above. After dialysis the polymeric conjugates were concentrated on centrifuge filters (10 kDa Mw cut off) to more than 30 mg/ml before reaction with Sangers reagent.

The coupling reaction was made by sequential mixing of water, polymeric conjugate, F-DNP (Sangers reagent, 2,4-dinitro-1-fluorobenzene) (Sigma, St Louis, Mo.) dissolved in dry NMP (0.30 g/l) and carbonate buffer (0.80 M, pH 9.0). The reaction mixture (1.6 g protein/ml, 10 equivalent DNP per IgG, 25 mM carbonate and total volume of 0.5 mL) was mixed at room temperature for 19 hours before being stopped by adding ethanolamine (in total 10 mM). The mixture was purified by dialysis overnight (1000 ml, 10 kDa MwCO, 0.1 M NaCl, 10 mM HEPES, pH 7.2). The buffer was changed three times.

The number of DNP per conjugate, and total conjugate concentration was calculated from the UV absorbance at 280 nm and 349 nm. The results are presented below in Table 1. Azide (15 mM) was added to all the conjugates as a microbial preservative.

TABLE 1

| Conjugate no | Dextran size kDa | Antibody type | Antibody per dextran Average | DNP per conjugate Average | Concentration $10^{-8}$ M dextran |
|---|---|---|---|---|---|
| 1 | 150 | RaM | 5.8 | 0 | 329 |
| 2 | 70 | GaR | 3.3 | 0 | 150 |
| 3 | 70 | GaM | 3.7 | 0 | 150 |
| 8 | 70 | DNP labeled GAM | 3.7 | 6.7 | 400 |
| 9 | 70 | (Fab)2 Rabbit anti DNP | 4.3 | 0 | 81 |
| 10 | 70 | Mouse anti BCL2 | 3.7 | 0 | 80 |

Example 3

Preparation of HRP-IgG-Dextran Conjugates

The preparation of both HRP and AP conjugates is described below.

HRP Conjugates:

Horseradish peroxides (HRP) (Faizyme, Cape Town, Rep. of South Africa) and affinity purified rabbit anti mouse (Ram) antibody (DakoCytomation, Carpenteria, Calif.) or affinity purified rabbit anti goat (RaG) antibody (IgG) (DakoCytomation, Carpenteria, Calif.) or affinity purified swine anti mouse immunoglobulin (SaM) (Dakocytomation, Carpenteria, Calif.) or affinity purified rabbit anti DNP Fab2 immunoglobulin (anti Dinitrophenyl, Fab2) (Dakocytomation, Carpenteria, Calif.) were dialyzed overnight against 1000 ml 0,10 M NaCl, at 2-4° C. with 3 changes of buffer. Enzyme or antibody concentration was 100 mg in a volume of 5 ml. The dialysis tubing had a molecular weight cut off of 10 kDa. After dialysis the protein was concentrated on centrifuge filters with 10 kDa Mw cut off to more than 60 mg/ml.

The conjugation was performed by sequential addition of HRP and antibody to activated dextran. The HRP solution was added to a solution of vinylsulfon activated dextran (70 kDa) in 25 mM carbonate, 0.1 M NaCl, pH 9.5. The concentration of HRP and dextran was 40.0 mg/ml and 1.6 mg/ml, respectively. The mixture was stirred in a water bath at 30° C. for 3.0 hours. The antibody solution was added to the reaction mixture and stirred overnight in a water bath at 30° C. for 18 hours. The final concentration of antibody was 5.87 mg/ml. The final concentration of dextran and HRP was 1.06 mg/ml and 26.67 mg/ml, respectively.

Any remaining reactive groups were quenched by addition of 1/10 volume reaction mixture of a cysteine-containing buffer (110 mM cysteine, 50 mM HEPES, 0.1 M NaCl, pH 7.0) and stirred for 30 minutes at 30° C.

The conjugate was separated from unconjugated antibody and HRP by gel filtration using an FPLC with an S-200 column and a buffer of 0.1 M HEPES, 0.1 M NaCl, pH 7.2 (Pharmacia, Peapack, N.J.).

The number of antibodies and HRP molecules per dextran molecule, and the conjugate concentration was calculated from the UV absorbance at 280 and 403 nm of the fraction containing the conjugate and the fraction containing unconjugated antibody and HRP. Bovine serum albumin was added to the conjugates as a protein stabilizer. An anti microbial agent was also added to the samples.

AP Conjugates:

The polymeric conjugates containing alkaline phosphatase (AP) and immunoglobulin were prepared by first introducing thiol groups onto AP followed by coupling to vinylsulfon-activated dextran (270 kDa). The AP-Dextran intermediate was coupled with the immunoglobulin in high salt conditions and purified. The procedure is analogous to the procedure for making the EnVision™ AP conjugates.

In more detail, alkaline phophatase (RDS, Switzerland) was dialyzed against 0.50 M potassium phosphate, pH 8.0 at 2-8° C. and concentrated on centrifuge filters (10 kDa MWCO). It was then reacted with SPDP (10 equivalents SPDP per AP, 10 mg AP/ml, 0.50 M potassium phosphate, pH 8) while being mixed at 30° C. for 30 minutes. The disulfide was reduced by addition of (±)-threo-1,4-Dimercapto-2,3-butanediol (DTT, Cleland's reagent) (Aldrich, St Louis, Mo.), at a concentration of 20 mM at room temperature for 30 minutes. The thiol modified AP was purified on G25 column and the protein concentration calculated from UV measurement at 280 nm.

The modified AP was coupled to vinylsulfon-activated dextran (270 kDa) by incubating at room temperature (3.5 AP/ml, 20 equivalents AP per dextran chain, 0.50 M potassium phosphate, pH 8.0) while mixing. After 20 hours, excess thiols were quenched with N-ethyl maleimide (NEM) (Aldrich, St Louis Mo.) (20% in NMP, in total 10 mM) and mixed for 20 minutes. The reaction mixture was dialyzed against water and concentrated on centrifuge filters. The AP-Dextran conjugate was purified on Sephacryl S-300 column and concentrated again. The protein concentrations were measured by UV absorbance at 280 nm.

Affinity purified rabbit anti goat (RaG) antibody (IgG) (DakoCytomation, Carpenteria, Calif.) was dialyzed as described above. The AP-Dextran was coupled with the dialyzed IgG by reaction at high salt conditions for 18 hours at room temperature and constant mixing (30 equivalent IgG per vinylsulfone AP-dextran, 2.5 mg IgG/ml, 1.75 potassium phosphate, 10 mM Magnesium chloride, 1 mM Zinc chloride, pH 7.9). The precipitated conjugate was isolated by centrifugation and resuspended in water and purified from unbound protein on a Sephacryl S-300 column.

The number of antibodies and AP molecules per dextran molecule, and conjugate concentration was calculated from the UV absorbance at 280 of the fractions. The conjugate was diluted with a buffer containing 50 mM Tris/HCl, 0.10 M NaCl, 0.1 mM zinc chloride, 1 mM magnesium chloride and an anti microbial agent.

The results of the conjugation experiments are presented in Table 2, below.

TABLE 2

| Conjugate no | Dextran size KDa | Antibody type | Antibody per dextran Average | Enzyme | Enzyme per dextran Average | Concentration 10-8M dextran |
|---|---|---|---|---|---|---|
| 4 | 70 | RaM | 1.1 | HRP | 7.0 | 225 |
| 5 | 70 | RaG | 1.4 | HRP | 9.4 | 119 |
| 6 | 270 | RaG | 3.3 | AP | 6.7 | 80 |
| 7 | 70 | Fab2 Anti DNP | 1.66 | HRP | 8.72 | 110 |
| 11 | 70 | SAM | 1.74 | HRP | 8.66 | 100 |

The conjugates used in the examples that follow are described in Table 3, below.

TABLE 3

| Conjugate no | Dextran backbone kDa | Antibody type | Enzyme | Directed against: |
|---|---|---|---|---|
| 1 | 150 | RaM | | Mouse IgG |
| 2 | 70 | GaR | | Rabbit IgG |
| 3 | 70 | GaM | | Mouse IgG |
| 4 | 70 | RaM | HRP | Mouse IgG |
| 5 | 70 | RaG | HRP | Goat IgG |
| 6 | 270 | RaG | AP | Goat IgG |
| 7 | 70 | (Fab)2 Rabbit anti DNP | HRP | DNP |
| 8 | 70 | DNP labeled GAM | | Mouse IgG |
| 9 | 70 | (Fab)2 Rabbit anti DNP | | DNP |
| 10 | 70 | Mouse anti Bcl-2 | | Bcl-2 protein |
| 11 | 70 | SAM | HRP | Mouse IgG |

Example 4

Fixation of Biological Samples For IHC Staining tissue samples were fixed in neutral buffered formalin, (NBF) using 20 mL, of 10 mM $NaH_2Po_4/Na_2HPO_4$, (Merck, Whitehouse Station, N.J.) and 0.145 M NaCl (Merck, Whitehouse Station, N.J.), pH 7,0, adjusted to 4% formaldehyde from a 37% formaldehyde stock (Merck, Whitehouse Station, N.J.). The samples were incubated overnight (18 hours) in a ventilated laboratory hood at room temperature.:

Example 5

Sample Dehydration and Paraffin Embedding

The tissue samples were gently wrapped in microscope lens cleansing paper (Leica, Bannockburn, Ill.) and placed in a marked plastic histocapsule (Sekura, Japan), before being dehydrated and embedded in paraffin. The tissue samples were dehydrated by sequential incubation with 70% ethanol two times for 45 minutes, 96% ethanol two times for 45 minutes, 99% ethanol two times for 45 minutes, xylene two times for 45 minutes, and then transferred to melted paraffin (melting point 56-58° C.) (Merck, Whitehouse Station, N.J.). The samples were incubated overnight (12-16 hours) at 60° C. The paraffin-infiltrated samples were transferred to fresh warm paraffin and incubated for an additional 60 minutes before being embedded with paraffin in a cast (Sekura, Japan). The samples were cooled to form the final paraffin blocks. The marked paraffin blocks containing the embedded tissue samples were stored at 2-8° C. in the dark before being cut, mounted, deparaffinated and stained.

Example 6

Cutting, Mounting and Deparaffination of Embedded Samples

The paraffin blocks were mounted in a microtome (0355 model RM2065, Feather S35 knives, set at 4.0 micrometer) (Leica, Bannockburn, Ill.). The first few mm were cut and discarded. Paraffin sections were then cut, at room temperature, into sections 4-micrometers thick and collected. The paraffin sections were gently stretched on a 45-60° C. hot water bath before being collected and mounted onto marked microscope glass slides (Superfrost plus) (Fisher, Medford, Mass.). The slides were then dried and baked in an oven at 60° C. The excess and melted paraffin was wiped away with a tissue.

The slides were deparaffinated by incubating two times in xylene for 2-5 minutes, two times in 96% ethanol for 2-5 minutes, two times in 70% ethanol for 2-5 minutes and once in tris buffered saline (TBS) (50 mM Tris-HCl, 150 mM NaCl, pH 7.6) (Crystal Chem Inc., Downers Grove Ill.) for 5 minutes. After mounting on slides, the tissue samples were antigen retrieved (AR) using any one of the methods described below and blocked for endogenous peroxidase activity.

Example 7

Antigen Retrieval by Microwave Oven

The slides were antigen retrieved by immersing the slides in Antigen Retrieval Solution, pH 6.0 (DakoCytomation, Carpenteria, Calif.) diluted 10× in distilled water in a special container with a perforated lid. The container was placed in the middle of a microwave oven and the slides heated for 10 minutes. The container containing the slides was removed from the oven and allowed to cool at room temperature for 20 minutes. The slides were rinsed in TBS for 2 minutes.

Example 8

Antigen Retrieval by Proteinase K Digestion

The slides were antigen retrieved using proteinase K (Dakocytomation, Carpenteria, Calif.) according to the manufacturer's instructions. The ready to use proteinase K solution was applied to the tissue samples on the slide and incubated for 5 minutes at room temperature. The slides were washed in TBS for 2 minutes.

Example 9

Antigen Retrieval by Waterbath Incubation

The slides were antigen retrieved by immersing the slides in a beaker containing a pH 6 citrate antigen retrieval solution (DakoCytomation, Carpenteria, Calif.) diluted 10×. The slides were incubated for 20 minutes in a water bath at 97° C. The beaker containing the slides was removed from the water bath and allowed to cool at room temperature. The slides were then rinsed in deionised water.

Example 10

Endogenous Peroxidase Blocking and Application of Rubber Barrier

All the slides were incubated with a 3% hydrogen peroxide solution for 5 minutes to quench endogenous peroxide activity using Peroxidase-Blocking Solution (DakoCytomation, Carpenteria, Calif.). The slides were then washed once with tris buffered saline (TBS) for 5 minutes. To ensure good coverage of reagent on the sample, the area on the slide with tissue was encircled with a silicone rubber barrier using DakoPen (DakoCytomation Carpenteria, Calif.). The slides were transferred to a rack in a small and closed chamber to avoid desiccation before staining.

Example 11

Manual Staining Protocol

The samples were prepared on Superfrost plus slides (Fisher, Medford, Mass.). The slides were washed in TBS wash buffer for 5 minutes and then incubated with the primary antibody (100 microliters) for 30 minutes at ambient temperature. The concentration was adjusted by dilution according to the specific example. After washing for 5 minutes, the first conjugate was added and incubated 20 minutes at ambient temperature. Following another 5-minute wash, the second conjugate was added and incubated for 30 minutes at ambient temperature. The slides were washed in the wash buffer for 5 minutes, followed by incubation with a diaminobenzidine chromogenic substrate system (DAB+) (DakoCytomation Carpenteria, Calif.) for 10 minutes according to the manufacturer's instructions. The slides were then washed with distilled water for 5 minutes and counterstained with Hematoxylin (DakoCytomation, Carpenteria, Calif.) for 5 minutes and washed in tap water for 5 minutes, according to the manufacturer's instructions.

A cover slip was applied to the slides using 120 microliters of an aqueous mounting media, (Faramount) (DakoCytomation Carpenteria, Calif.). The slides were left to dry and harden and examined in a bright field microscope (Leica DM LB, Bannockburn, Ill.) at 10×, 20× or 40× magnification, using light strength setting 8. The slides were digitally photographed using an Olympus DP50-CU (Olympus, Melville, N.Y.) and the pictures white background corrected. This is done by adjusting the camera settings against an empty spot on the slide.

In the cases where the majority of cells displayed only one intensity this single staining intensity were recorded. In the cases where the majority of the cells displayed a staining intensity range a distribution rather than a single intensity was recorded.

Example 12

Automated Staining Protocol

The protocol was performed using a Dakocytomation Autostainer (Dakocytomation, Carpeteria, Calif.). The slides were Superfrost (Fisher, Medford, Mass.) Following the antigen retrieval step, the wet slides were set up in the racks of an Autostainer (DakoCytomation, Carpeteria, Calif.). The slides were incubated with the diluted primary antibody (200 microliter, 30 minutes) at ambient temperature. The slides were washed by gently flushing wash buffer (DakoCytomation, Carpeteria, Calif.) diluted 10-fold over the slide, before excess buffer was removed with a gently air flow.

The first conjugate was added to the slide (200 microliter) and incubated 30 minutes at room temperature before being washed as described above. The second conjugate was added to the slide (200 microliter) and incubated for 30 minutes at room temperature before being washed as described above.

Two hundred microliters of DAB+ chromogenic substrate system (DakoCytomation, Carpenteria, Calif.) prepared according to the manufacturer's instructions was applied to each slide and incubated for 30 minutes. The slides were then washed in deionized water for 5 minutes. The total process time was 2 hours and 22 minutes.

The slides were taken off the Autostainer and placed in racks and counter stained with hematoxylin (DakoCytomation, Carpenteria, Calif.) according to the manufacturer's instructions for 2 minutes and then washed in deionized water for 5 minutes. A cover slip was applied to the slides using 120 microliters of an aqueous mounting media, (Faramount) (DakoCytomation Carpenteria, Calif.). The slides were left to dry and harden and examined in a bright field microscope using a Nikon Eclipse E400 (Nikon) at 40×, 100× and 200× magnification.

The slides were digitally photographed (RT color Spot, Diagnostic Instruments Inc.) and the picture's white background corrected.

Example 13

Rapid Manual Staining Protocol

Following the antigen retrieval step, the slides were incubated with 200 microliter of the diluted primary antibody for 10 minutes at ambient temperature. The slides were washed by gently flushing wash buffer (DakoCytomation, Carpenteria, Calif.) diluted 10-fold over the slide. Excess buffer was removed as in Example 11. The first conjugate was added to the slide (200 microliter) and incubated 10 minutes at room temperature before being washed as before. The second conjugate was added to the slide (200 microliter) and incubated for 10 minutes at room temperature before being washed as before. DAB chromogenic substrate system prepared as in Example 11 was applied to the slides and incubated for 10 minutes. The slides were then washed in deionized water for 5 minutes. The total process time was reduced to 55 minutes as compared to staining Example 11. The slides were counterstained with hematoxylin, covered with a cover slip and evaluated as in Example 12 above.

Example 14

Envision™+ Plus Dual Link Staining Protocol

The staining, using Envision™+ was performed according to the manufacturer's instructions (DakoCytomation, Carpenteria, Calif.). In short, the staining was performed as described in Example 11—except for the addition of the first conjugate (A) and the subsequent 5 minute wash. DAB staining, haematoxylin counterstaining, and application of the cover slip were as described in Example 11.

Example 15

PowerVision+™ Staining Protocol

The staining was performed, up to the DAB step, as described in the instruction manual in the PowerVision+™ staining kit (ImmunoVision Technologies, Co., Daly City, Calif.). The kit consists of Ready-to-use solutions including pre-antibody Blocking, Post-antibody Blocking ("Polymer Penetration Enhancer"), Poly-HRP anti-Mouse/Rabbit IgG, DAB Solution A, 1× and DAB Solution B, 35×.

The procedure, after blocking of endogenous peroxidase and antigen retrieval, consisted of incubation with the pre-antibody blocking solution for 10 minutes followed by incubation with the diluted primary antibody (200 microliter, 30 minutes) at ambient temperature. The slides were washed with TBS for 5 minutes and then incubated with post-antibody blocking for 20 minutes, followed by TBS washing. The slides were next incubated with Poly-HRP anti-Mouse/Rabbit IgG, for 30 minutes, before being washed with TBS for 5 minutes.

To better compare the various systems, the DAB staining, hematoxylin counterstaining and the cover slipping were done according to the protocol described in Example 11.

Example 16

Comparative Staining of Ki-67 Protein

The example describes immunovisualization of the nuclear marker Ki-67 clone MIB-1 protein on tonsils using Conjugate No. 1, a polymeric dextran (150 kDa) conjugate containing rabbit anti mouse antibody, followed by a polymeric dextran conjugate mixture containing horseradish peroxidase and goat anti mouse or goat anti rabbit antibodies and staining with a HRP chromogen (Envision™+ plus). The assay components are illustrated in FIG. 1-A.

The experiment compared staining with one embodiment of the invention with the Envision™+ or PowerVision+™ (ImmunoVision Technologies, Co., Daly City, Calif.) detection systems. The tissues used were formalin fixed and paraffin embedded block (FFPE) human tonsil, colon, mammae carcinoma and kidney. Cutting, mounting and deparaffination of tissue sections was done according to the protocol described in Example 6. Microwave antigen retrieval and endogen peroxidase blocking was done as described above in Examples 7 and 10 respectively. Immunovisualization was done as described above in Example 11.

In summary, the primary monoclonal antibody was Ki67 clone MIB-1 (DakoCytomation, Carpenteria, Calif.). It was diluted 1:200 in TBS with 0.2% BSA before application. After application of the primary antibody the sample was incubated with Conjugate No. 1 comprising rabbit anti mouse antibodies diluted 1:1000 in TBS buffer with 0.2% BSA. After application of the first conjugate the sample was incubated according to the manufacturer's instructions, with a polymeric dextran conjugate mixture (Envision™+) (Dako-Cytomation, Carpenteria, Calif.) containing horse radish peroxidase and goat anti mouse or rabbit immunoglobulins.

In parallel, immunovisualization was done using an unconjugated rabbit anti mouse immunoglobulins (RaM) (Dako-Cytomation, Carpenteria, Calif.) diluted 1600 times in a TBS buffer containing 0.2% BSA, instead of the polymeric RaM Conjugate No 1. A second in parallel experiment was done using Envision™+ or PowerVision+™ (ImmunoVision Technologies, Co., Daly City, Calif.), according to the protocol described in Examples 14 and 15, respectively.

The staining was evaluated at 40×, 100× and 200× magnification. FIG. 2 A-D are photomicrographs of the Ki67 stained tonsil tissue using the combination of Conjugate No. 1 and Envision™+ (A), unconjugated RaM and Envision™+ (B), Envision™+ (C), or the PowerVision+™ (D).

The samples were evaluated blindly (i.e. the Examiner did not know the method used to prepare the slide). A scale from 0 to 4 in quarter grade increments, in total giving 17 subtle levels of staining intensity was used. The staining intensity was scored to 4.0; 3.5; 3.0; and 4.0, respectively. The staining pattern and localization is almost identical for the four different stainings.

The staining intensity is slightly stronger using the polymeric RaM (A) and PowerVision+™ (ImmunoVision Technologies, Co., Daly City, Calif.). The use of polymeric RaM or monomeric RaM link increases the staining intensity slightly as compared to Envision™+. Immunostaining using a mouse IgG served as a negative control. The mouse antibody is raised against *aspergilius Niger*, which is not present in human tissue (DakoCytomation, Carpentaria, Calif.) and did not result in a detectable signal using any of the tested systems.

The negative controls were acceptable and scored to "O" in intensity.

Example 17

Comparative Staining of Cytokeratin on Mammae Carcinoma

The example describes immunovisualization of the cytoplasmic cytokeratin on Mammae carcinoma tissue using the same tissue block, link conjugate and Envision™+ conjugates as in the previous example 16. The assay set up is also as illustrated in FIG. 1-A.

The experiment compared staining using one embodiment of the invention with staining using rabbit anti mouse as a middle link, the Envision™+, or PowerVision+™ (ImmunoVision Technologies, Co., Daly City, Calif.) detection systems.

Cutting, mounting and deparaffination of tissue sections was done according to the protocol described in Example 6. The tissue pretreatment was the same as in example 16, except for the antigen retrieval was done using the proteinase K method, as described in Example 8. Immunovisualization was done as described above in Example 11.

In summary, the primary rabbit antibody was anti-cytokeratine clone AE1/AE3 (DakoCytomation, Carpenteria, Calif.). It was diluted 1:1000 in TBS with 0.2% BSA before application. After application of the primary antibody the samples were incubated with Conjugate No. 1 comprising Rabbit anti Mouse antibodies conjugated to a 150 kDa dextran and diluted 1:5000 in TBS buffer with 0.2% BSA. After application of Conjugate No. 1, the samples were incubated, according to the manufacturer's instructions, with a polymeric dextran conjugate mixture (Envision™+), DakoCytomation, Carpenteria, Calif.) containing horseradish peroxidase and goat anti mouse or rabbit immunoglobulins.

In parallel, immunovisualization was done using unconjugated rabbit anti-mouse immunoglobulins (RaM) (DakoCytomation, Carpenteria, Calif.), diluted 1600 times in a TBS buffer containing 0.2% BSA, instead of the polymeric RaM Conjugate No. 1. A second in parallel experiment was done using Envision™+ or PowerVision+™ (ImmunoVision Technologies, Co., Daly City, Calif.), according to the protocol described in Examples 14 and 15, respectively.

The staining was evaluated at 40×, 100× and 200× magnification. FIG. 3A-D are photomicrographs of the cytokeratine stained Mammae carcinoma tissue using the combination of Conjugate No. 1 and Envision™+ (A), unconjugated RaM and Envision™+ (B), Envision™+ (C), or PowerVision+™ (ImmunoVision Technologies, Co., Daly City, Calif.) system (D).

The samples were evaluated blindly (i.e. the Examiner did not know the method used to prepare the slide). A scale of from 0 to 4 in quarter grade increments, in total giving 17 subtle levels of staining intensity was used. The staining intensity was scored to 3.0; 3.5; 2.0 and 4.0, respectively. The staining pattern and localization is almost identical for the four different stainings. The staining intensity was strongest using the PowerVision+™, the unconjugated RaM link and polymeric RaM link, in that order. The Envision™+ system alone was the weakest of the four assay systems tested. Immunostaining using a mouse IgG served as a negative control. The negative control mouse antibody specifically recognized *aspergiliius Niger*, (DakoCytomation, Carpentaria, Calif.), which is not present in human tissue. It did not result in a detectable signal using any of the tested systems.

The negative controls were acceptable and scored to "O" in intensity.

Example 18

Comparative Staining of Ki-67 Protein Using a Secondary Antibody Conjugate Linked with HRP The example describes immunovisualization of the Ki-67 protein on mammae carcinoma using link Conjugate No. 4, containing a polymeric dextran (70 kDa) conjugate containing secondary rabbit anti-mouse and horse radish peroxidase, followed by a polymeric dextran conjugate mixture containing horse radish peroxidase and secondary goat antibody and staining with a HRP chromogen (Envision™+). The assay setup is illustrated in FIG. 1-B. The staining was compared to staining using unconjugated rabbit anti mouse as a link, the Envision™+ or PowerVision+™ (ImmunoVision Technologies, Co., Daly City, Calif.) staining systems.

The cutting of mammae carcinoma tissue sections, mounting, deparaffination, antigen retrieval, peroxidase blocking and manual staining protocol was done according to the general procedure described in example 16.

The primary monoclonal antibody was clone MIB-1 (DakoCytomation, Carpenteria, Calif.). It was diluted 1:400 in TBS with 0.2% BSA before application. After application of the primary antibody the sample was incubated with Conjugate No. 4 containing rabbit anti-mouse antibodies and HRP. Conjugate No. 4 was diluted 1:1000 in TBS buffer with 0.2% BSA and applied to the sample. After application of Conjugate No. 4, the sample was incubated, according to the manufacturer's instructions, with a polymeric dextran conjugate mixture (Envision™+), (DakoCytomation, Carpenteria, Calif.) containing horse radish peroxidase and secondary goat anti mouse or rabbit immunoglobulins.

In parallel, immunovisualization was done using unconjugated rabbit anti mouse immunoglobulins (RaM) (DakoCytomation, Carpenteria, Calif.), diluted 1600 times in a TBS buffer containing 0.2% BSA, instead of the polymeric RaM-HRP Conjugate No. 4. A second in parallel experiment was done using Envision™+ or PowerVision+™ (ImmunoVision Technologies, Co., Daly City, Calif.), according to the protocol described in Examples 14 and 15, respectively.

The staining was evaluated in at 40×, 100× and 200× magnification. FIGS. 4A-D are photomicrographs of the Ki-67 stained Mammae carcinoma tissue using the combination of Conjugate No. 4 and Envision™+ (A), unconjugated RaM and Envision™+ (B), Envision™+ (C) or PowerVision+™ (ImmunoVision Technologies, Co., Daly City, Calif.) (D).

The samples were evaluated blindly (i.e. the Examiner did not know the method used to prepare the slide). A scale of from 0 to 4 in quarter grade increments was used. The staining intensity was scored to 4.0; 4.0; 3.5 and 4.0, respectively. The staining pattern and localization is almost identical for the four different stainings. The staining intensity is similar using the RaM-HRP conjugate (a), the unconjugated RaM (b) and PowerVision+™ (ImmunoVision Technologies, Co., Daly City, Calif.) (d). The Envision™+ gave the weakest staining intensity. Immunostaining using a mouse IgG served as a negative control (as described above) (DakoCytomation, Carpentaria, Calif.) and did not result in a detectable signal using any of the tested systems.

Example 19

Comparative Staining of Estrogen Receptor (ER) in Breast Tissue

The example describes immunovisualization of the estrogen receptor in FFPE breast tissue using a mixture of link Conjugate No. 2 and link Conjugate No. 3, polymeric dextran conjugates containing secondary Goat anti rabbit antibody and secondary Goat anti mouse antibody, respectively, followed by a polymeric dextran conjugate containing horseradish peroxidase and secondary rabbit anti goat antibody, Conjugate No. 5, and staining with a HRP chromogen. The assay set up is illustrated in FIG. 1-C. 4-micrometer sections of breast tissue from two different patients were used.

Cutting of the tissue sections, mounting, deparaffination, antigen retrieval using waterbath and S1700 (DakoCytomation, Carpenteria, Calif.) and peroxidase blocking was as described previously in Examples 6, 9, and 10. Immunovisualization was done as described above in the general section according to the automated protocol described in Example 12.

The primary monoclonal antibody, clone 1D5, which recognizes the estrogen receptor (DakoCytomation, Carpenteria, Calif.) was diluted 1:2700 in buffer diluent (DakoCytomation, Carpenteria, Calif.). Conjugate No. 2, was mixed with Conjugate No. 3, in a total dilution of 1:275 and 1:15, respectively. Conjugate No. 5 was diluted 1:30. The buffer was the same as in example 16.

In parallel, immunovisualization was done using PowerVision+™ (ImmunoVision Technologies, Co., Daly City, Calif.), according to the method previously described in Example 15. The primary antibody was used at the same dilution. A second experiment was run in parallel, using a negative control antibody (Mouse IgG negative control, DakoCytomation, no. XO931) instead of the specific antibody and in the same dilution. The staining was evaluated in a Nikon Microscope (Nikon, Melville, N.Y.) at 20×, 100× and 200× magnification.

FIG. 5A-D are photomicrographs of the first ER stained breast tissue. Specific staining using the ER antibody was seen using the combination of Conjugate No. 2, 3 and 5 (A), or PowerVision+™ (B). The samples were evaluated blindly (i.e. the Examiner did not know the method used to prepare the slide). A scale of from 0 to 4 in quarter grade increments was used. The staining intensity was scored as 3.0 and 3.0, respectively. No signal was detected using the Negative antibody control in combination with Conjugate No. 2, 3 and 5 (C), or PowerVision+™ (D). Accordingly, the staining intensity was scored to 0 for both.

FIG. 5E-H are photomicrographs of the second ER stained breast tissue. Specific staining using the ER antibody was seen using the combination of Conjugate No. 2, 3 and 5 (E), or PowerVision+™ (F). The staining intensity was scored to 2.0-3.0 and 2.0-3.0, respectively. No signal was detected using the negative control antibody in combination with Conjugate No. 2, 3 and 5 (G), or PowerVision+™ (H). The staining intensity was scored 0 for both. All the photomicrographs were taken at 20-time magnification.

The photomicrographs all demonstrate strong specific staining and no staining with the negative control. The staining intensity was marginally stronger in FIGS. 5A and E, compared with the staining intensity in FIGS. 5B and F. This strong staining intensity is, obtained with a dilution of the primary antibody that is 54 times the recommended dilution for the ER antibody for Envision™ (DakoCytomation, Carpenteria, Calif.) and 18 times the dilution recommended for Envision™+ (DakoCytomation, Carpenteria, Calif.). In conclusion, the staining, using Conjugate No. 2, 3 and 5 was specific and equivalent or slightly stronger, compared to PowerVision+TM.

Example 20

Comparative Staining of Progesterone Receptor (PR) in Breast Tissue

In this example, Progesterone receptor in FFPE breast tissue was visually detected using the same mixture of conjugates as in the previous example 19, that is, polymeric dextran conjugates containing secondary Goat anti mouse antibody and Goat anti rabbit antibody, respectively, followed by a polymeric dextran conjugate containing horse radish peroxidase and rabbit anti goat antibody and staining with a HRP chromogen.

Tissue pretreatment was done as described in the Example 19. Immunovisualization was done as described above in Example 12. The primary monoclonal antibody specific for the Progesterone receptor was clone PR636 (DakoCytomation, Carpenteria, Calif.). It was diluted 1:2400 in buffer diluent (DakoCytomation, Carpenteria, Calif.). The conjugate dilutions were as in Example 19, a dilution that is 54 times the recommended dilution for Envision™ (DakoCytomation, Carpenteria, Calif.) and 18 times the dilution recommended for Envision™+(DakoCytomation, Carpenteria, Calif.).

In parallel, immunovisualization was done using PowerVision+™, according to the method previously described in Example 15. A second experiment was run in parallel using a negative control antibody of the same original species (NP015 mouse IgG) (DakoCytomation, Carpenteria, Calif.) instead of the specific antibody. The negative control was diluted 1:2400.

FIG. 6A-D are photomicrographs of the first PR stained breast tissue. Specific staining was seen using the PR antibody in combination with Conjugate No. 2, 3 and 5 (A), or PowerVision+™ (B). The samples were evaluated blindly (i.e. the Examiner did not know the method used to prepare the slide). A scale from 0 to 4 in quarter grade increments was used. The staining intensity was scored to 2.0-3.5 and 2.0-3.25, respectively. No signal was detected using the negative control antibody in combination with Conjugate No. 2, 3 and 5 (C), or PowerVision+™ (D). The staining intensity was scored 0 for both.

FIG. 6E-H are photomicrographs of the second PR stained breast tissue. Specific staining was seen using the PR antibody in combination with Conjugate No. 2, 3 and 5 (E), or PowerVision+™ (F). The samples were evaluated blindly (i.e. the Examiner did not know the method used to prepare the slide). A scale from 0 to 4 in quarter grade increments was used. The staining intensity was scored to 2.0-3.25 and 2.0-3.5, respectively. No signal was detected using the Negative control antibody in combination with Conjugate No. 2, 3 and 5 (G), or PowerVision+™ (H). The staining intensity was scored 0 for both.

All the photomicrographs were taken at 20-times magnification. The photomicrographs all demonstrated strong specific staining and no staining using the negative control antibody. The staining intensity was stronger in FIGS. 6A and F, compared with the staining intensity in FIGS. 6B and E. The strong staining intensity was obtained with a primary antibody dilution that is 48 times the recommended dilution for Envision™ (Dakocytomation, Carpeteria, Calif.) and 16 times the recommended dilution for EnVision Dual link+ HRP (Dakocytomation, Carpeteria, Calif.). In conclusion, the staining intensity was specific and stronger compared to PowerVision+TM.

Example 21

Sensitivity Limits in the Detection of Two Proteins

The example describes a short protocol for immunovisualization of the CK20 and Progesterone Receptor on FFPE breast tissue using a conjugate combination as in Example 19. The primary antibody solution was diluted out to assess the sensitivity limits of the assay.

Immunovisualization was done as described above in Example 13. The primary monoclonal antibody against cytokeratin 20 (CK20) was clone Ks20.8 a murine IgG2a kappa (DakoCytomation, Carpenteria, Calif.). It was diluted 1:600 and 1:3000 in buffer diluent (DakoCytomation, Carpenteria, Calif.). The primary monoclonal antibody against the progesterone receptor was clone PR636 (DakoCytomation, Carpenteria, Calif.). It was diluted 1:200 and 1:1000, in the same buffer. The conjugate dilutions were as in Example 1.9. The first tested dilution of primary antibodies are approximately 5× the recommended dilution for EnVision® and comparable to the recommended for EnVision+®. The second dilution of the primary antibodies are 25× the recommended dilution for EnVision®. Simultaneously the incubation times for this short protocol and EnVision® are both 10 minutes whereas EnVision+® is 30 minutes. This example demonstrates therefore, the effect of incubation time and primary antibody dilution on signal.

A second experiment was run in parallel using a negative control antibody of the same original species (NP015 mouse IgG) (DakoCytomation, Carpenteria, Calif.) instead of the specific antibody. The negative control was diluted 1:200. FIG. 7A-F are photomicrographs of the stained breast tissue. Specific staining was seen using the anti CK20 antibody: diluted 1:600 (A), diluted 1:3000 (B). The negative control is shown in (C). The staining intensity was scored to 2.5; 0.75 and 0, respectively. The samples were evaluated blindly (i.e. the Examiner did not know the method used to prepare the slide).

Specific staining was seen using the anti PR antibody: diluted 1:200 (D), diluted 1:1000 (E). The negative control is shown in (F). The staining intensity was scored to 3.5; 1.75 and 0, respectively. The samples were evaluated blindly (i.e. the Examiner did not know the method used to prepare the slide). The photomicrographs all demonstrated strong specific staining and no staining with the negative control. The staining intensity was stronger in FIGS. 7A and D, compared with the staining intensity in FIGS. 7B and E, using a more dilute primary antibody solution. In conclusion, despite the shorter protocol, and diluted primary antibody solution, the staining intensity is surprisingly strong. The Example illustrates the possibility of using the signal amplification method of some embodiments of the invention to allow a shorter staining protocol, and still obtain a good staining intensity.

Example 22

Comparative Detection of Cellular Proteins Located in Various Cellular Compartments The Example describes immunovisualization of several different protein targets on FFPE tissues using the same automated procedure as described in Examples 20 and 21. The various targets of diagnostic interest were located in various compartments of the tissue and were immunovisualized by DAB stain using mouse or rabbit primary antibodies.

Tissue pretreatment was done as in Examples 20 and 21. Immunovisualization was done as described above in Example 12, using the same conjugates as in Example 20 and 21. The various primary antibodies were all obtained from DakoCytomation (Dakocytomation, Carpenteria, Calif.) and diluted in buffer diluent (DakoCytomation, Carpenteria, Calif.). The antibodies used are described below:
Mouse Anti-Human Cytokeratin 20, clone Ks20.8, (mouse IgG2a, kappa),
Rabbit Anti-Human Carcinoembryonic Antigen (CEA)
Rabbit Anti-Human Chromogranin A
Mouse Anti-Human p53 Protein, clone DO-7, (mouse IgG2b, kappa)
Mouse Anti-Human p63 protein clone 4A4, (mouse IgG2a, kappa)
Mouse Anti-Human Thyroid Transcription Factor (TTF-1), clone 8G7G3/1, (mouse IgG1, kappa)
Rabbit Anti-Human Prostate Specific Antigen (PSA)
Mouse Anti-Human CD68, Macrophage, clone PG-M11 (Mouse IgG3)
Mouse Anti-Human ALK Protein, clone ALK-1 (Mouse IgG3)
Mouse Anti-Human Cyclin D1 also called bcl-1, clone DCS-6 (Mouse IgG2a)
Mouse Anti-Human BCL6, clone PG-B6p (Mouse IgG1, kappa)
Mouse Anti-Human CD20, B-cell, clone L26 (Mouse IgG2a, kappa)
Rabbit Anti Terminal Deoxynucleotidyl Transferase The conjugate dilutions were as described in Example 19 and 20. The assay set up was called "NDS-1" and is illustrated in FIG. 1-C. In parallel, immunovisualization was done using PowerVision+™, according to the method described in Example 15. A second in parallel experiment was done using a negative control antibody of the same original species (Universal Negative Control, UNC, NP001, rabbit IgG and NP015 mouse IgG), (DakoCytomation, Carpenteria, Calif.) instead of the specific antibody.

Figure 8A:
FIG. 8AA-ND depict colon (AA-BF), pancreas (CA-CD, EA-FD), prostate (DA-DD, HA-HF), tonsil (1A-JD, LA-MD), head and neck squamous carcinoma LHNSC) (KA-KD), or thymus (GA-GD, NA-ND) tissues immunovisualized using CK20 (AA-AB), CEA (BA-BD), Chromogranin A (CA-CD), p53 (DA-DB), p63 (EA-EB, FA-FB), TTF-1 (GA-GB), PSA (HA-HD), CD68 (IA-IB), ALK-1 (JA-JB), bcl-1 (KA-KB), bcl-6 (LA-LB), CD20 (MA-MB), or TdT (NA-NB) primary antibodies followed by either 1) a mixture of polymeric goat anti rabbit and polymeric goat anti mouse secondary antibody followed by a polymeric conjugate containing rabbit anti goat and horseradish peroxidase ("NDS-1") (AA, AC, BA, BC, BE, CA, CC, DA, DC, EA, EC, FA, FC, GA, GC, HA, HC, HE, IA, IC, JA, JC, KA, KC, LA, LC, MA, MC, NA, NC) or 2) PowerVision+™ (Immunovision, Springdale, Ariz.) ("PV") (AB, AD, BB, BD, BF, CB, CD, DB, DD, EB, ED, FB, FD, GB, GD, HB, HD, HF, IB, ID, JB, JD, KB, KD, LB, LD, MB, MD, NB, ND); negative controls: AC-AD, BE-BF, DC-DD, EC-ED, FC-FD, GC-DG, HE-HF, IC-ID, JC-JD, KC-KD, LC-LD, MC-MD, NC-ND.
Figure 8A:
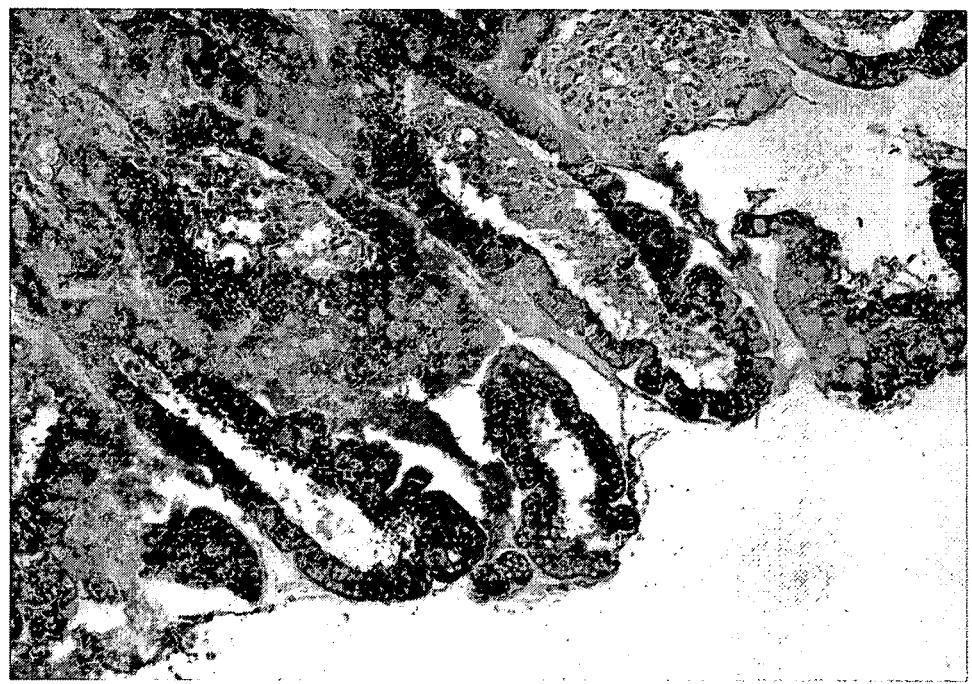
Figure 8A:
Figure 8A:
Figure 8B:
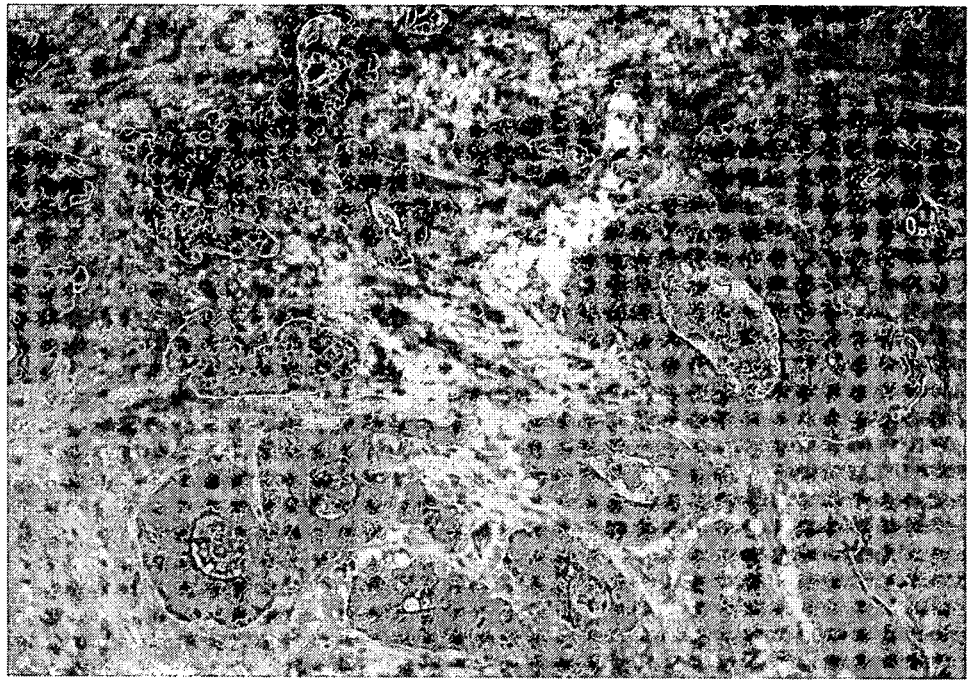
Figure 8B:
Figure 8B:
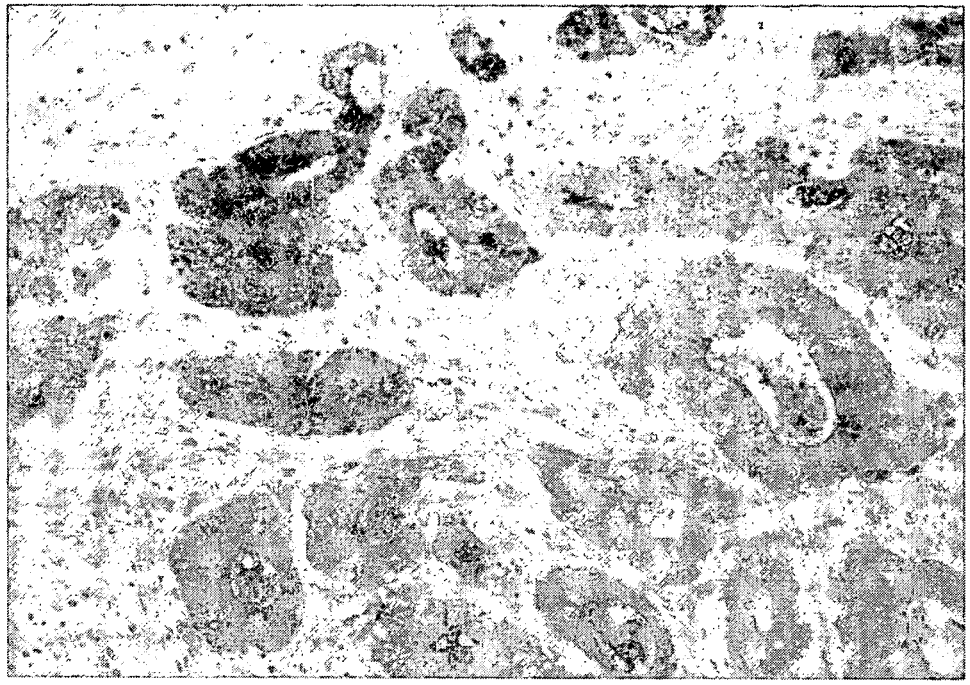
Figure 8B:
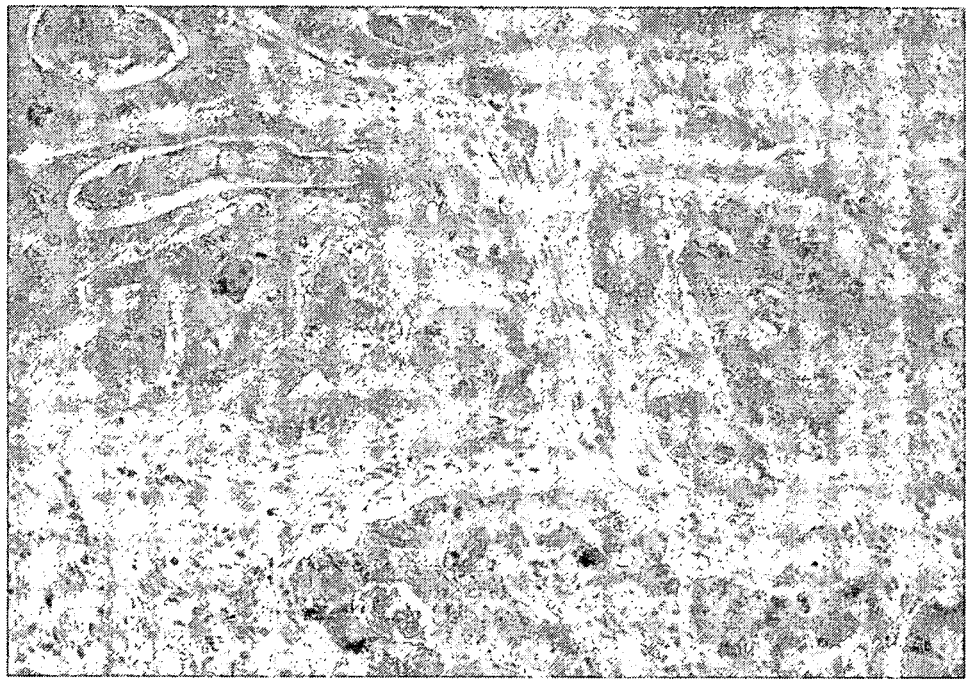
Figure 8B:
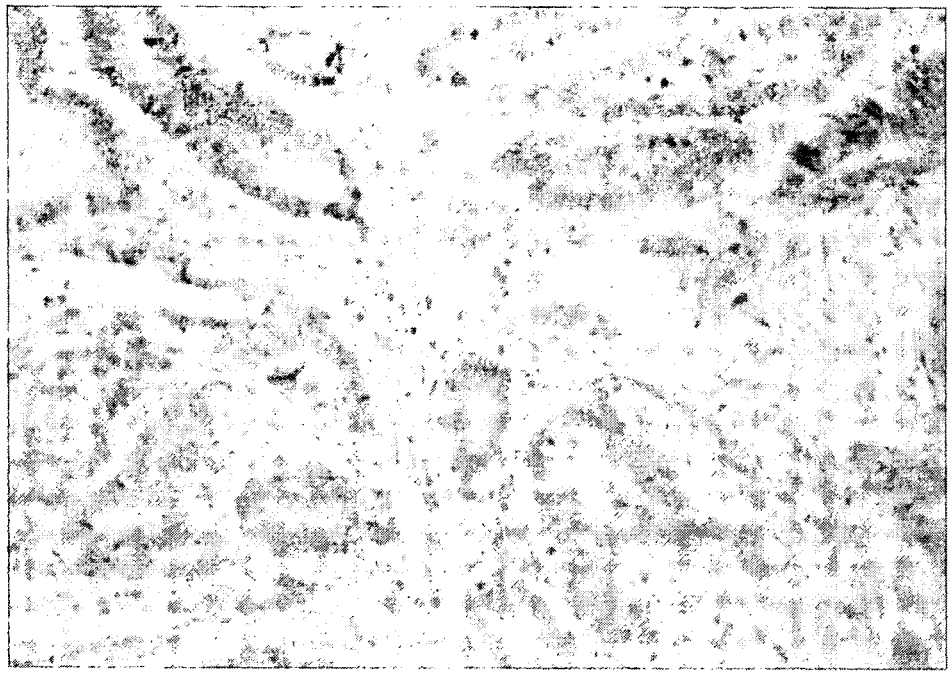
Figure 8B:
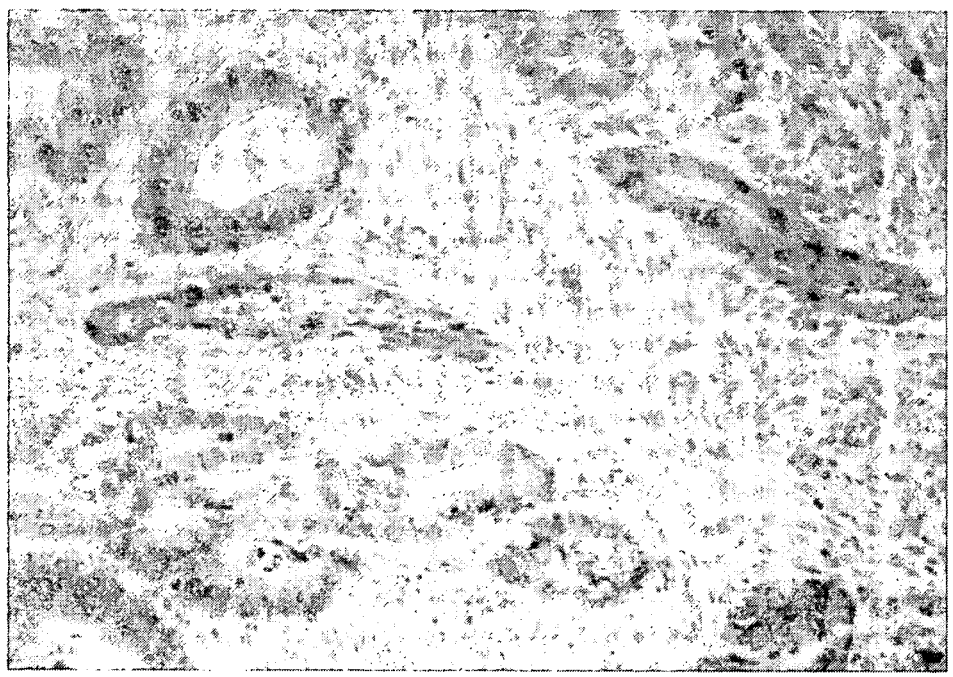
Figure 8C:
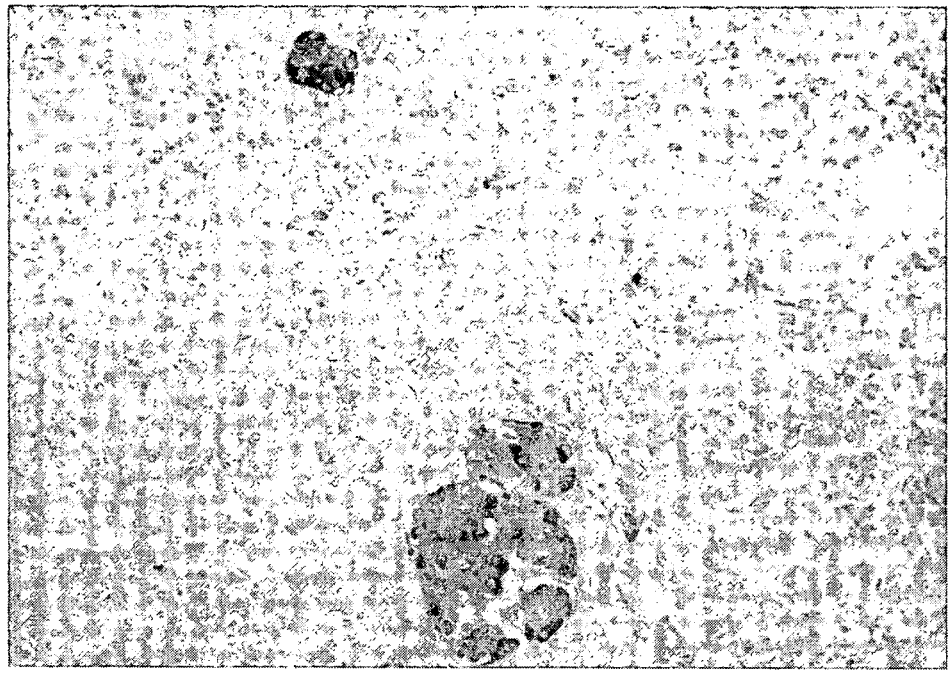
Figure 8C:
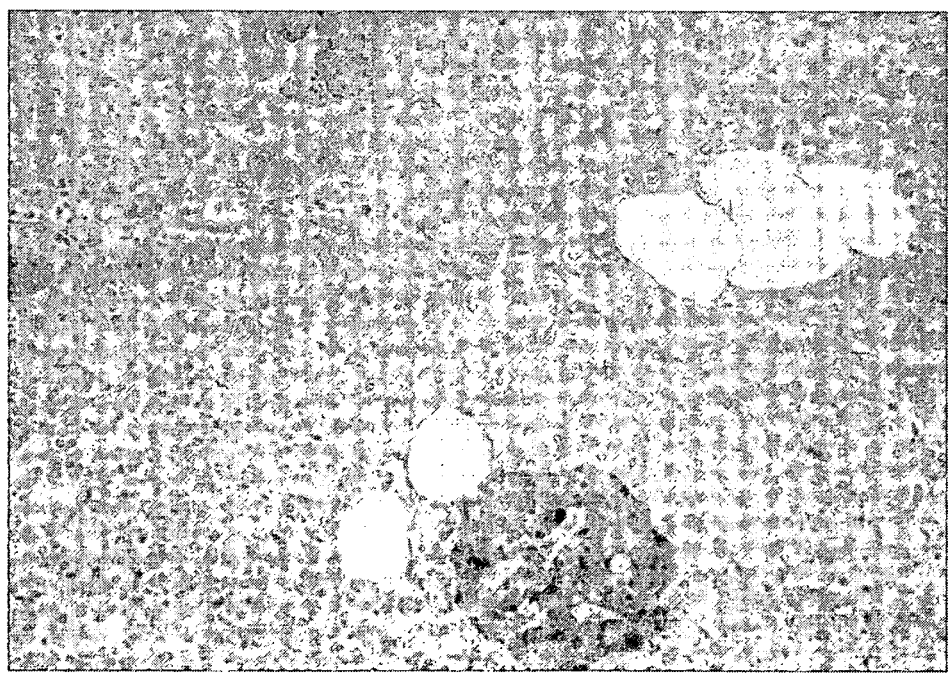
Figure 8C:
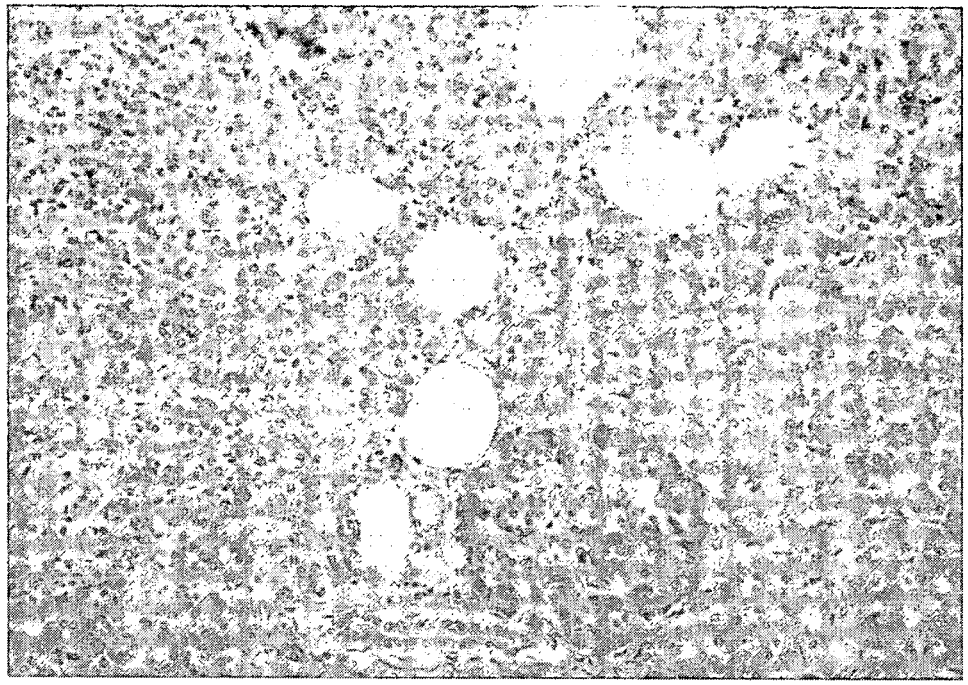
Figure 8C:
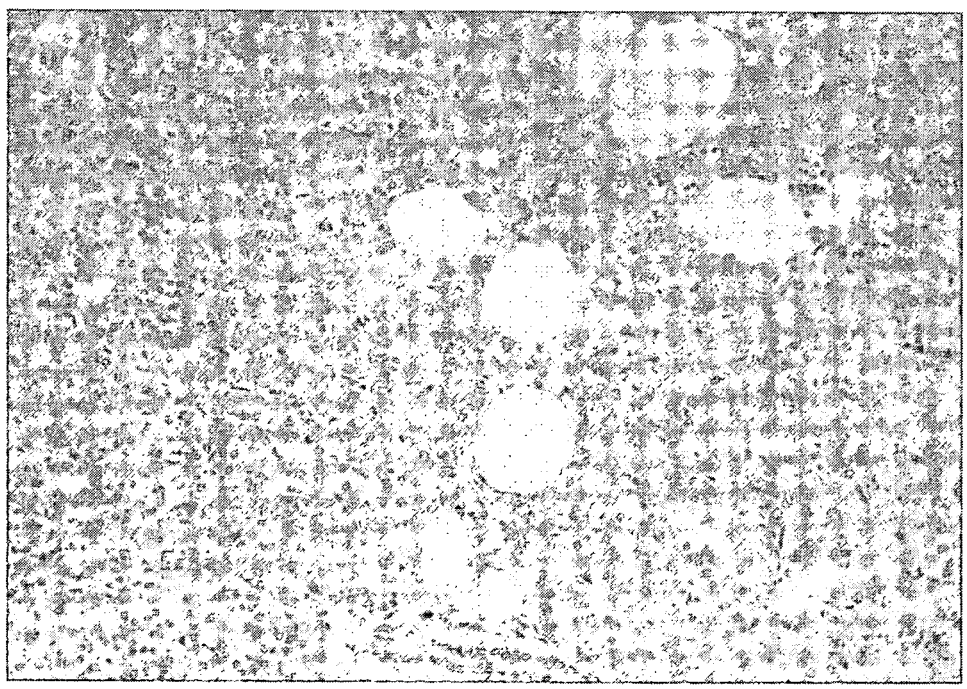
Figure 8D:
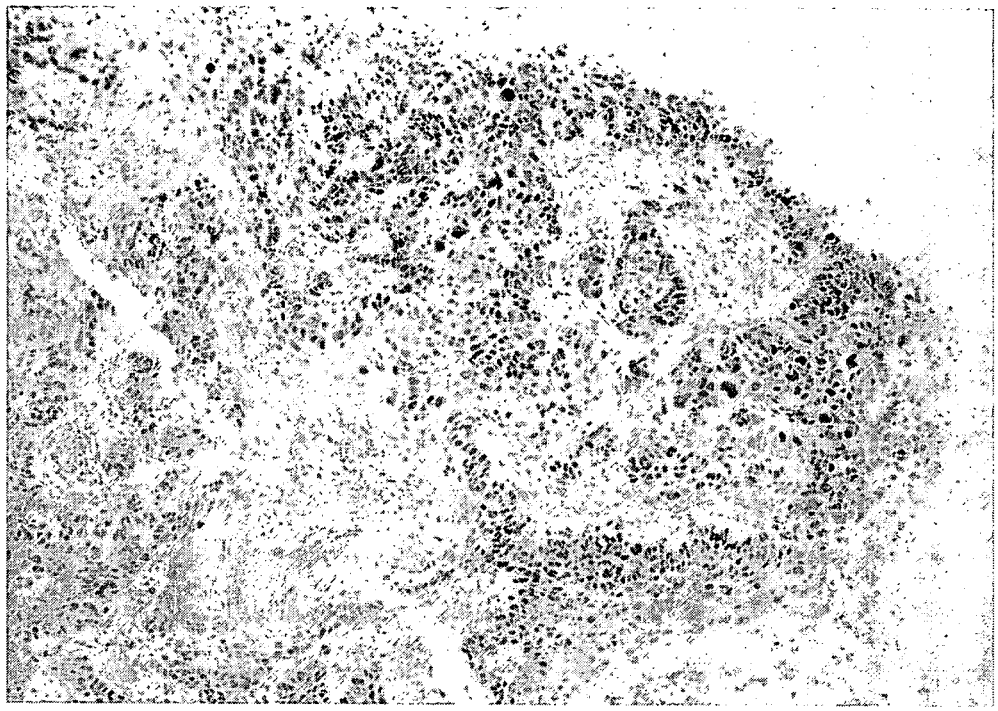
Figure 8D:
Figure 8D:
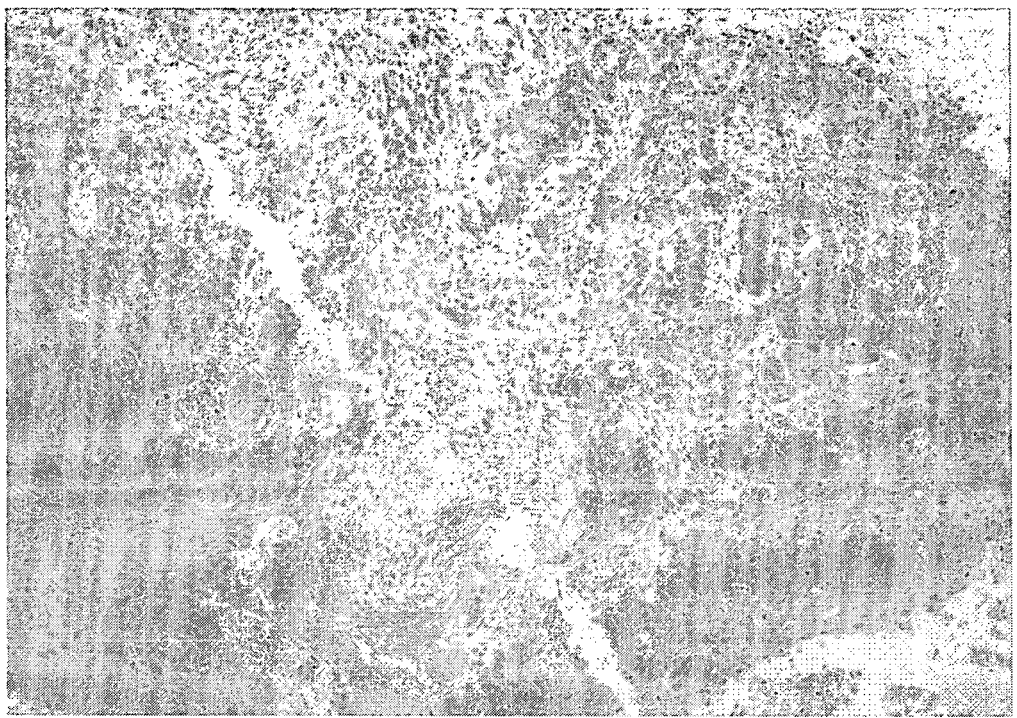
Figure 8D:
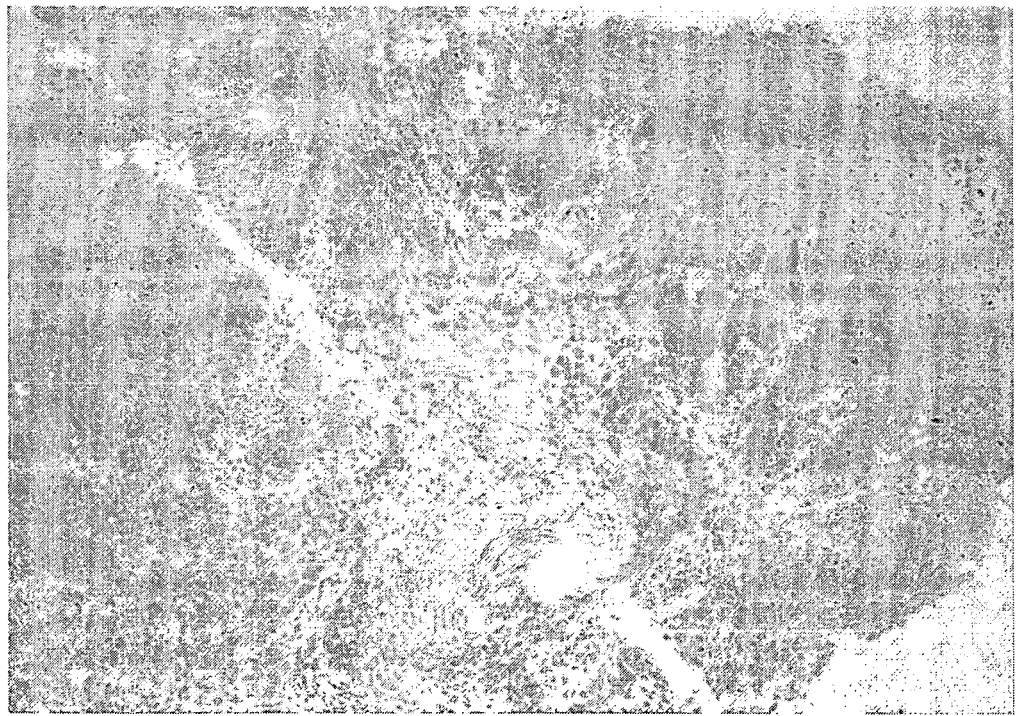
Figure 8E:
Figure 8E:
Figure 8E:
Figure 8E:
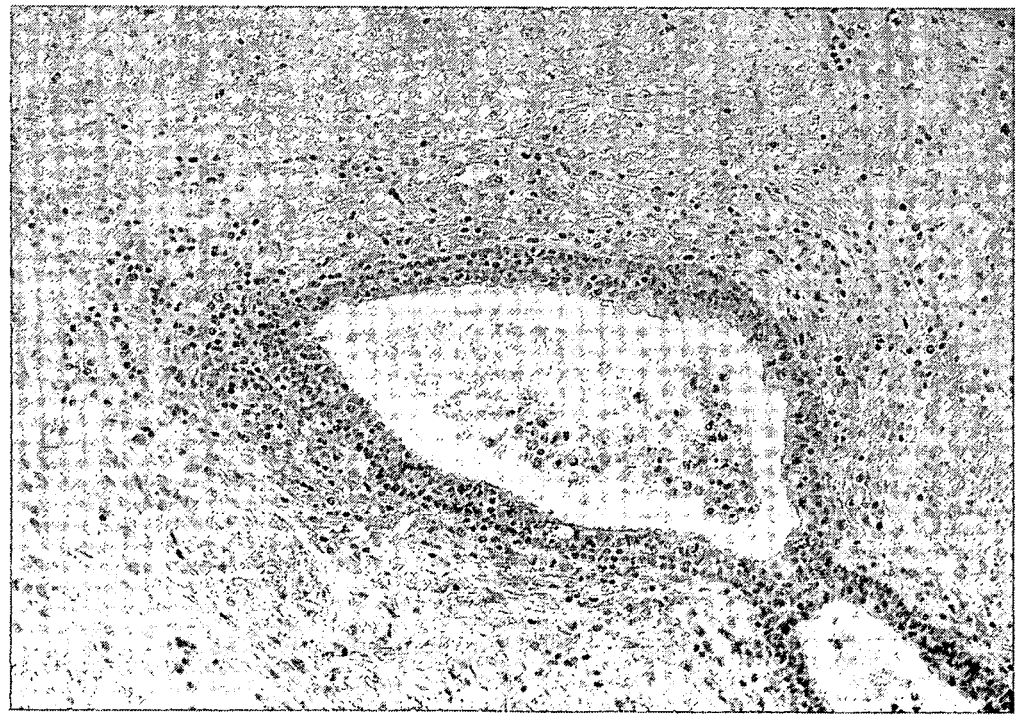
Figure 8F:
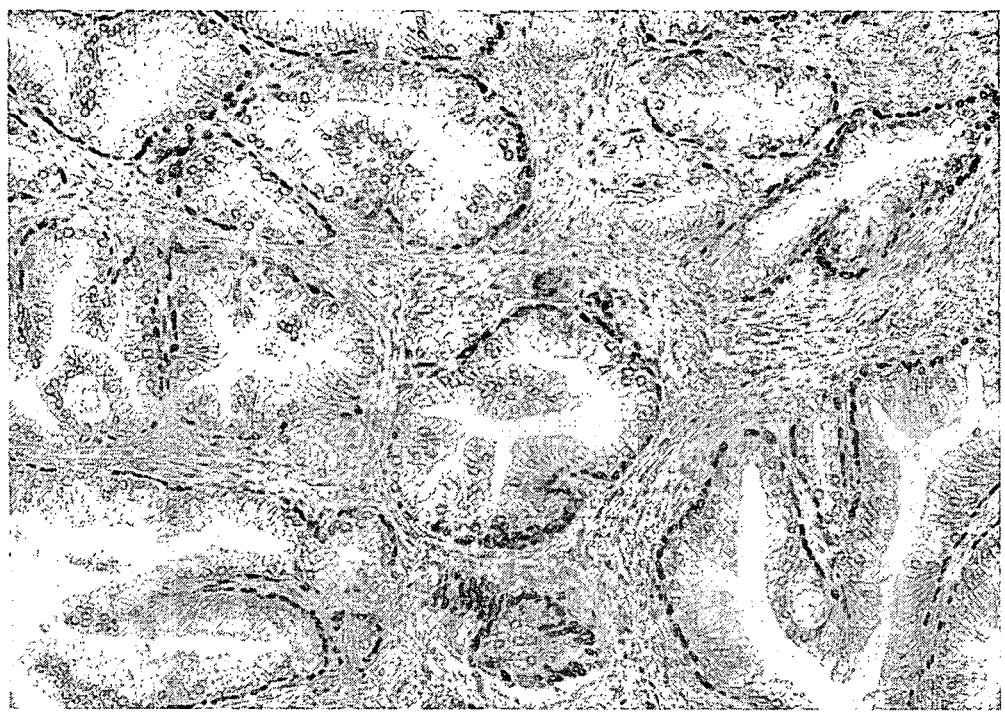
Figure 8F:
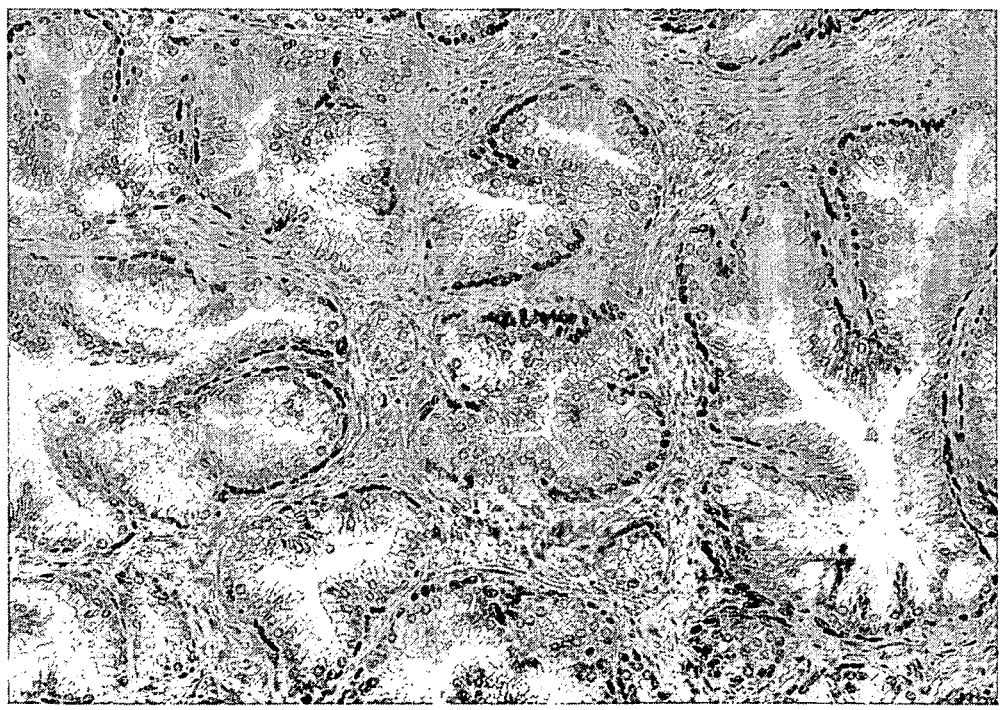
Figure 8F:
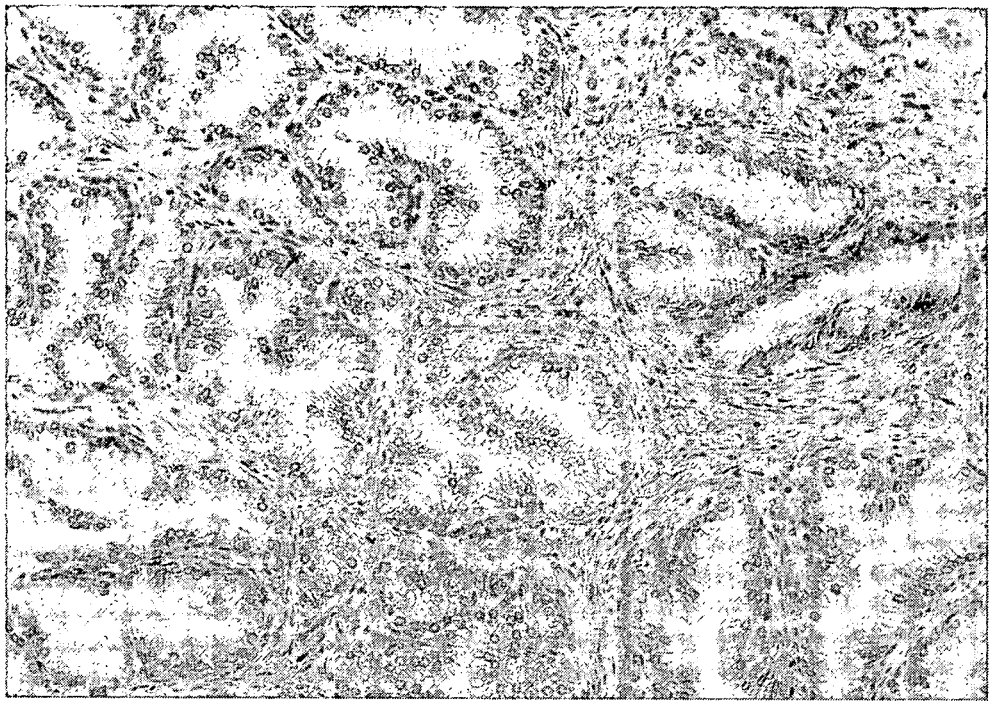
Figure 8F:
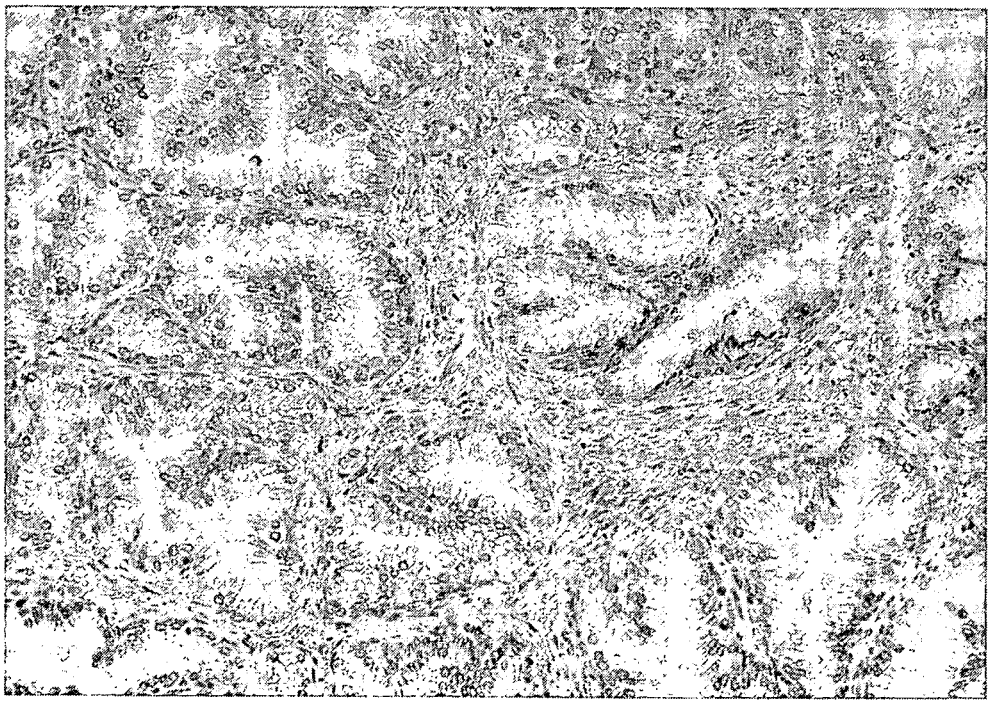
Figure 8G:
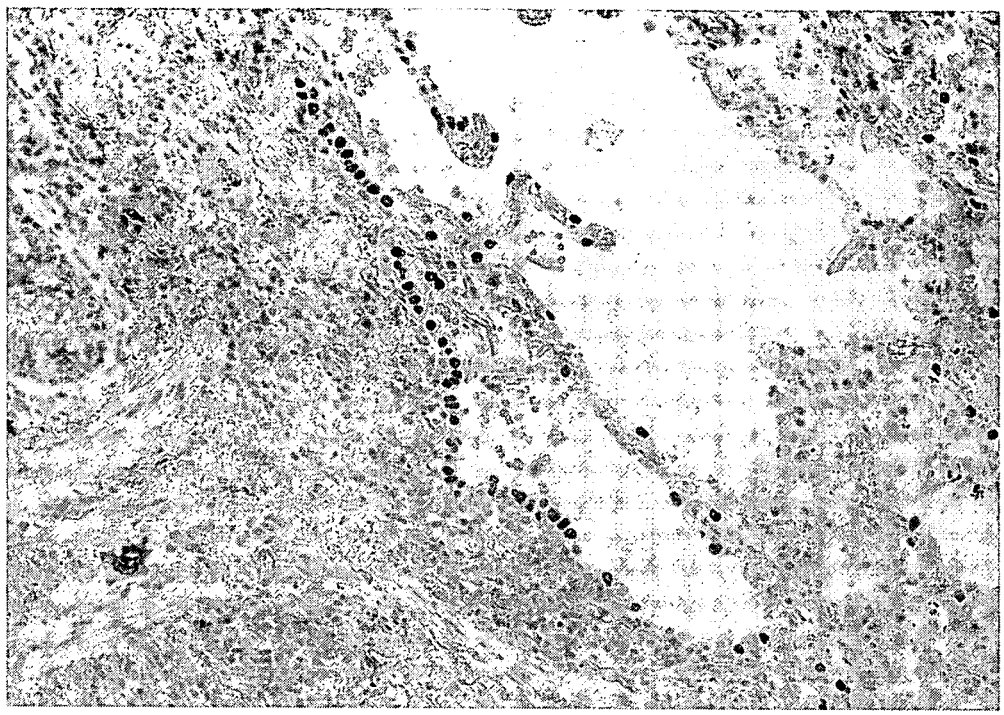
Figure 8G:
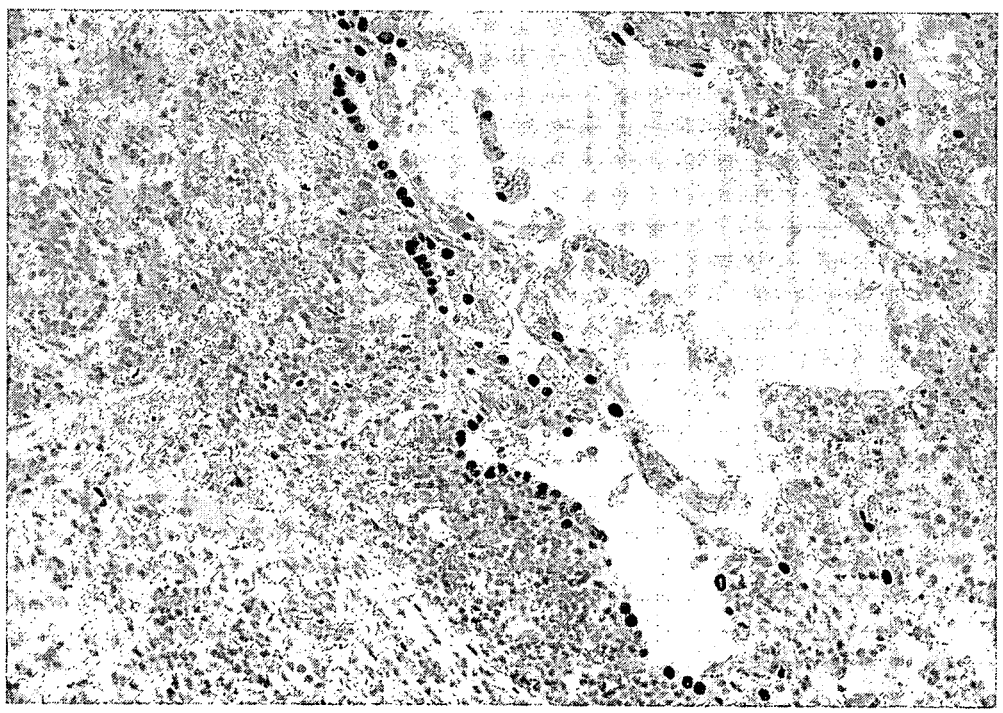
Figure 8G:
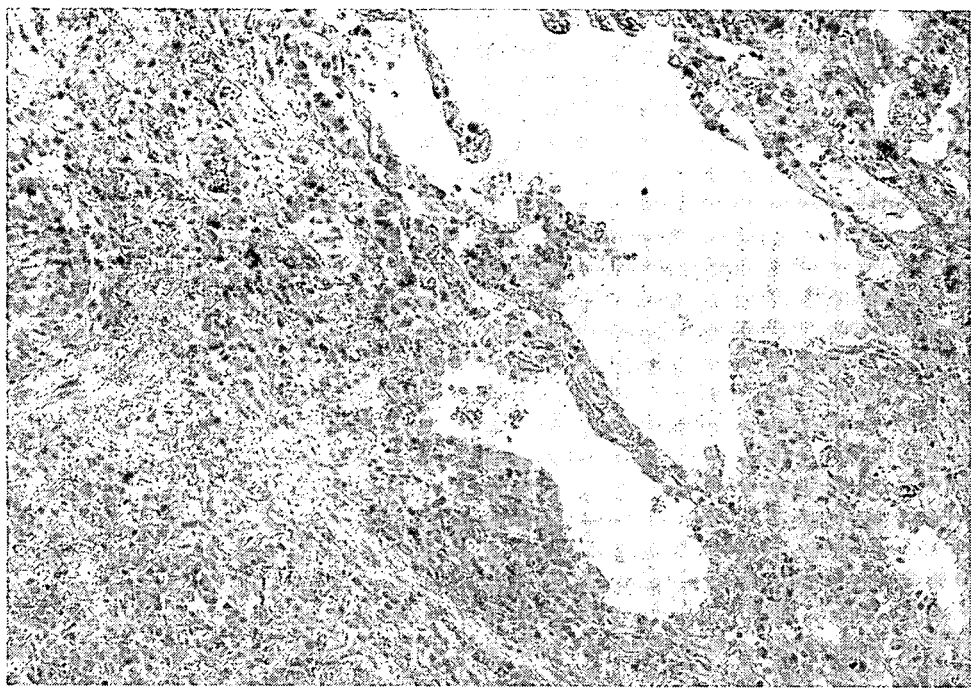
Figure 8G:
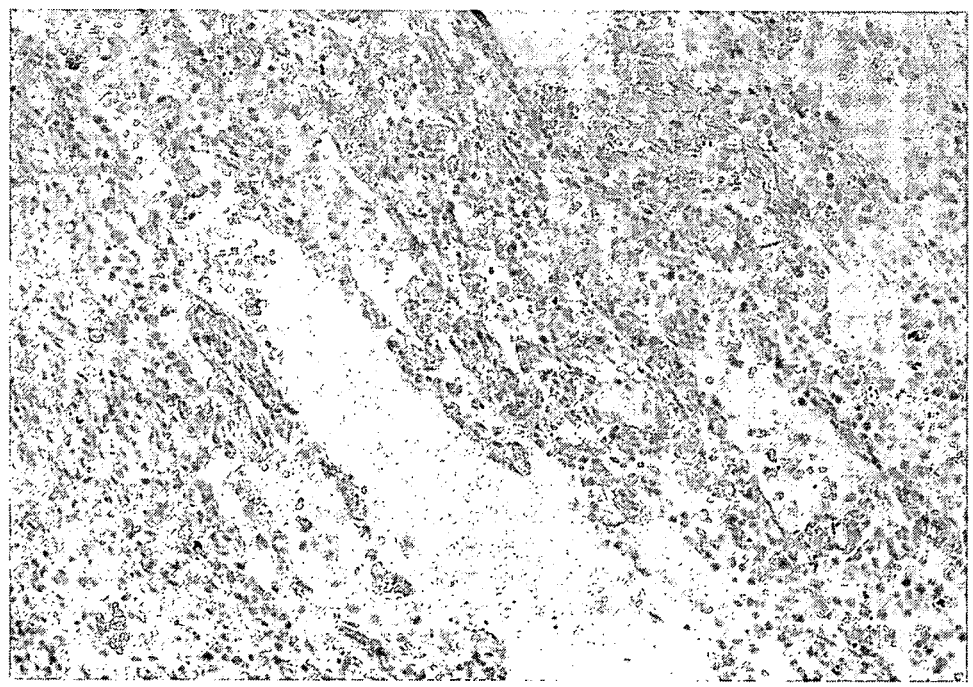
Figure 8H:
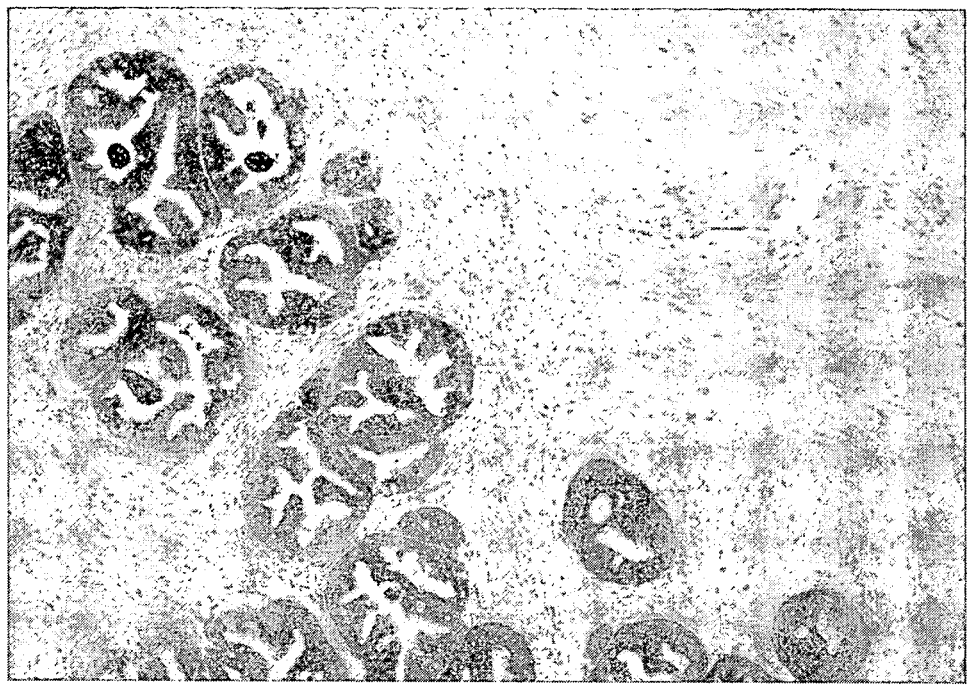
Figure 8H:
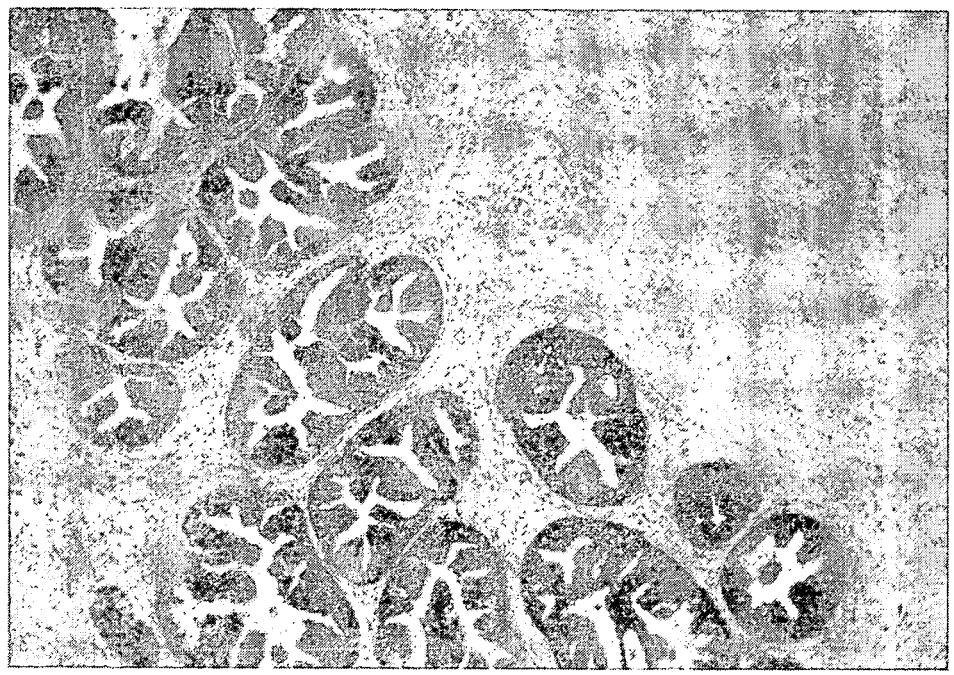
Figure 8H:
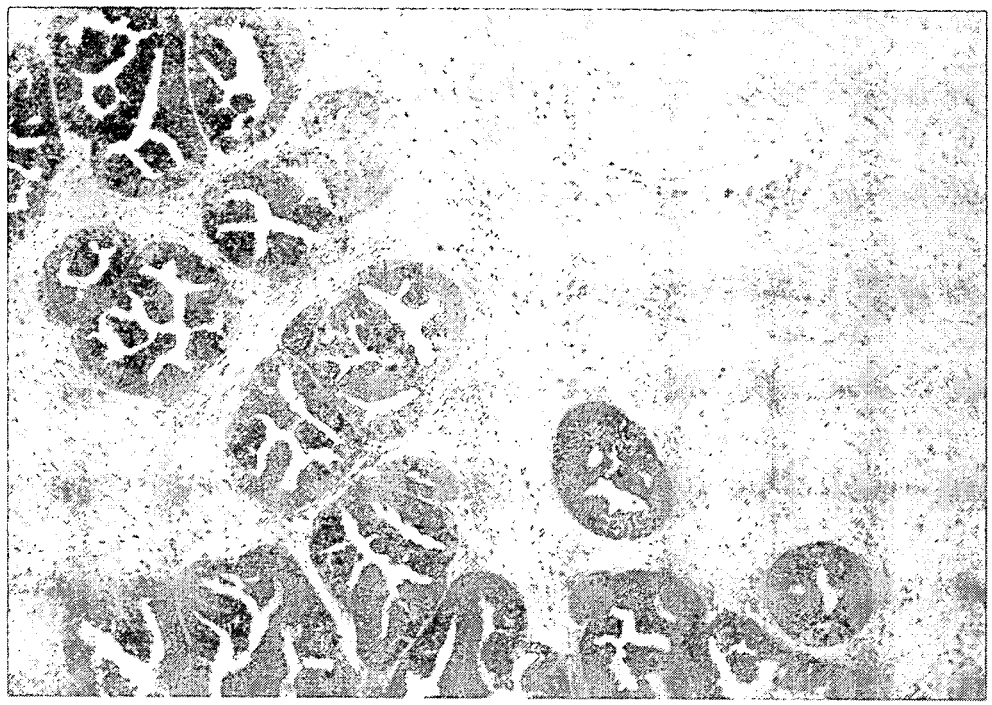
Figure 8H:
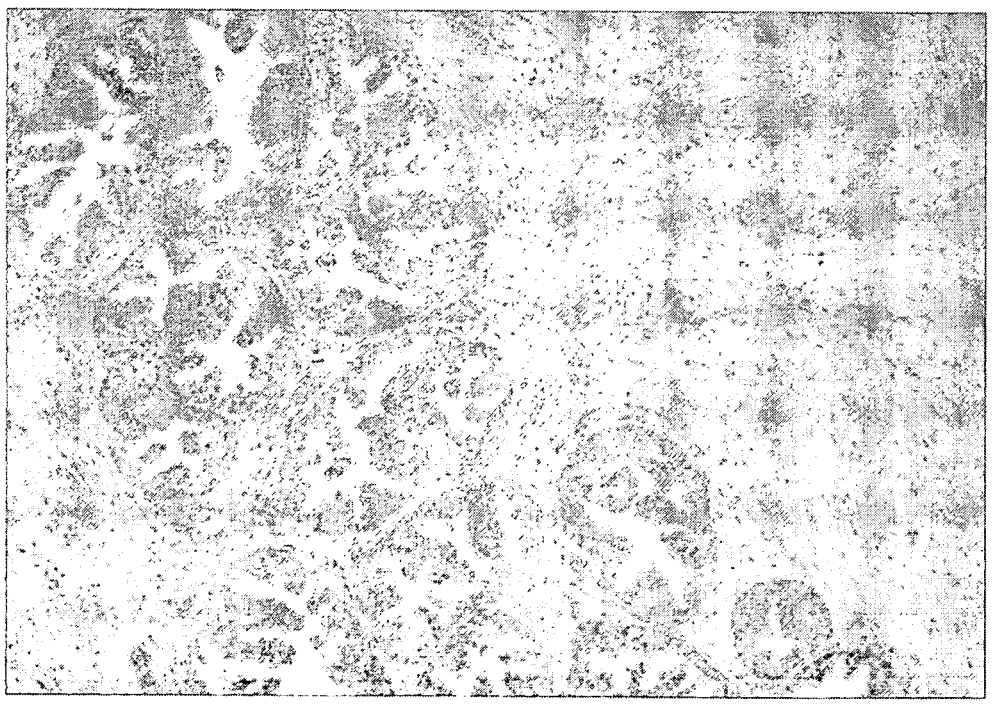
Figure 8H:
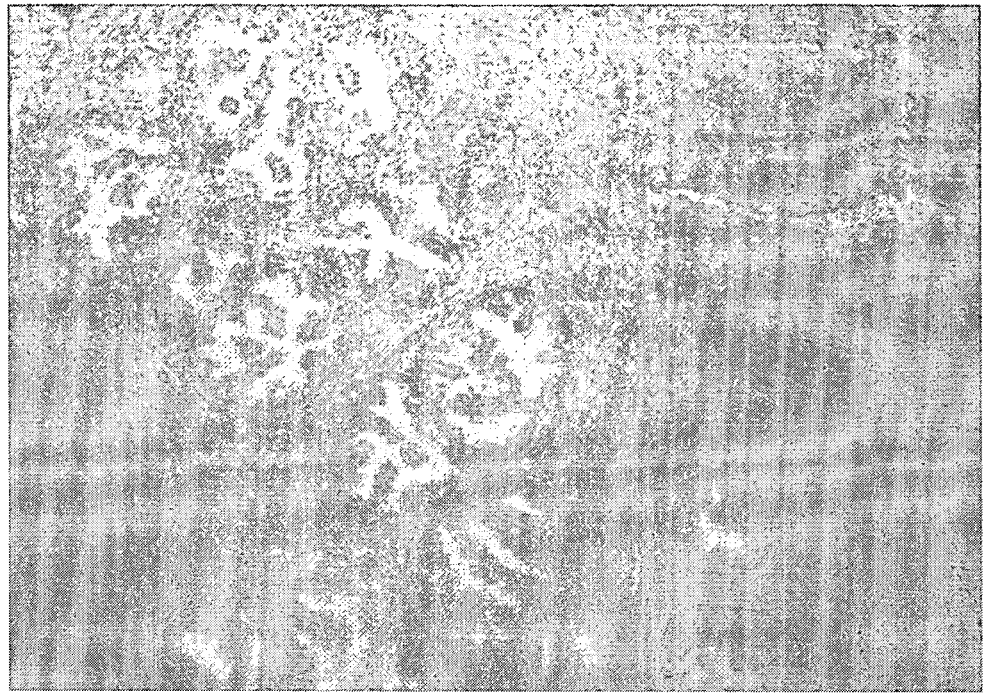
Figure 8H:
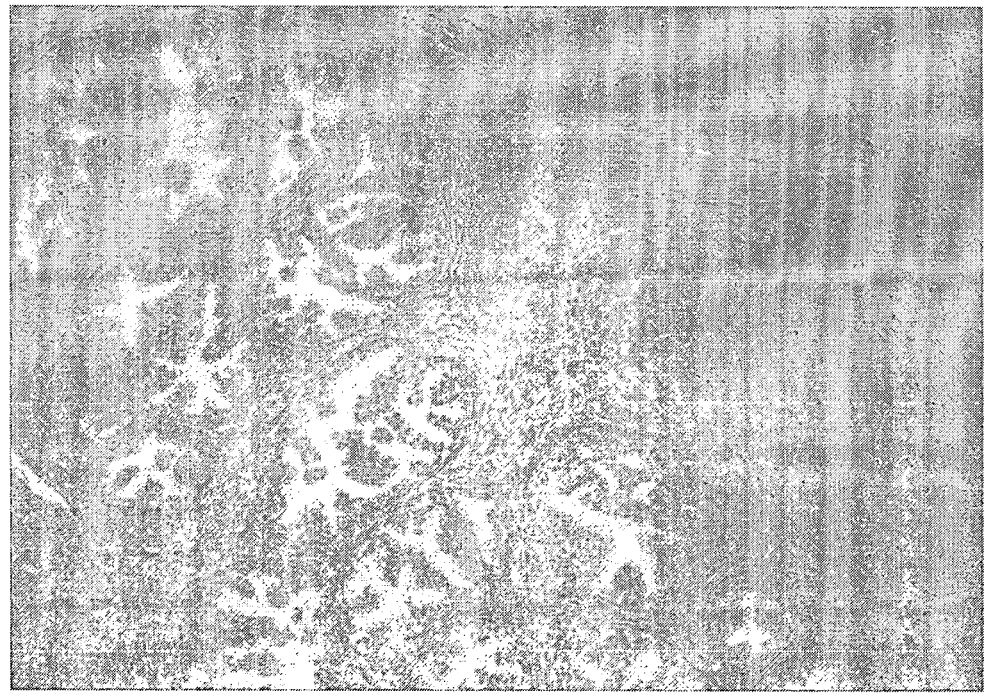
Figure 8I:
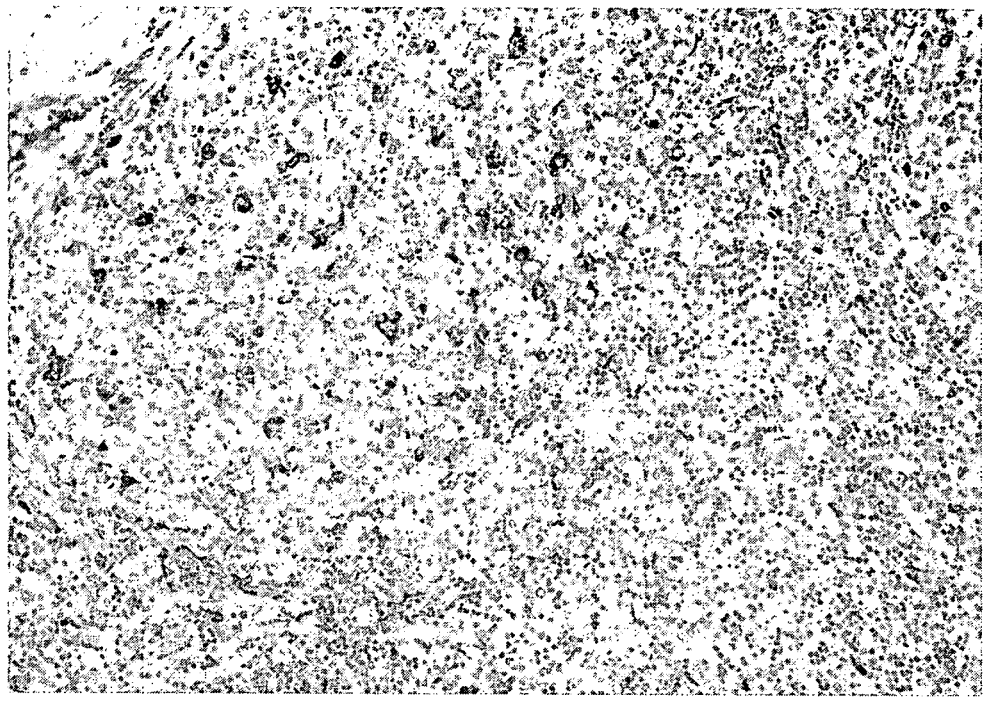
Figure 8I:
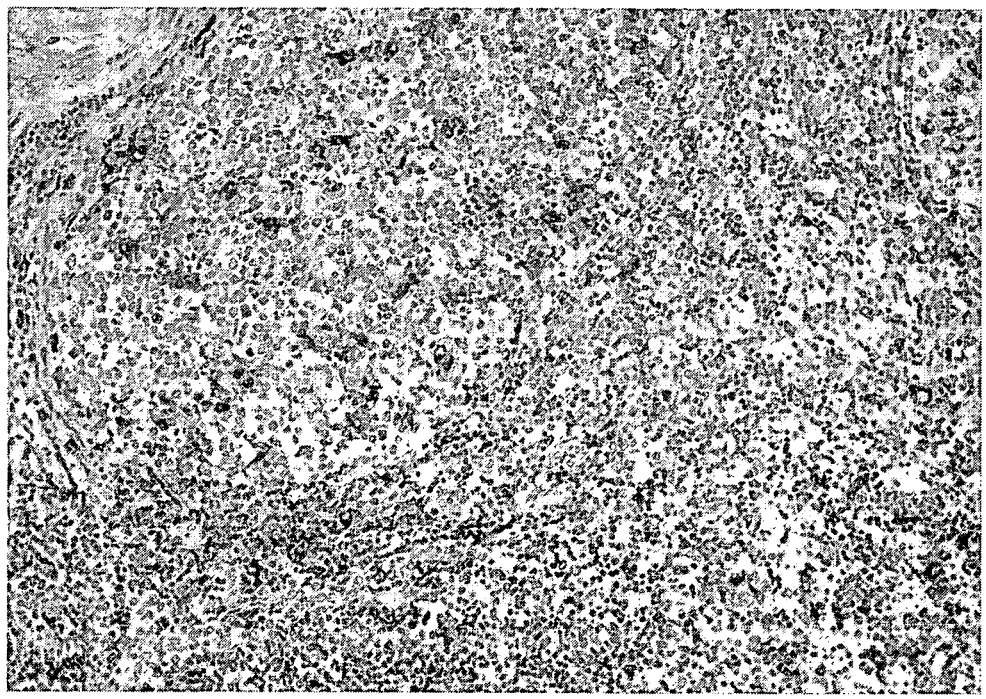
Figure 8I:
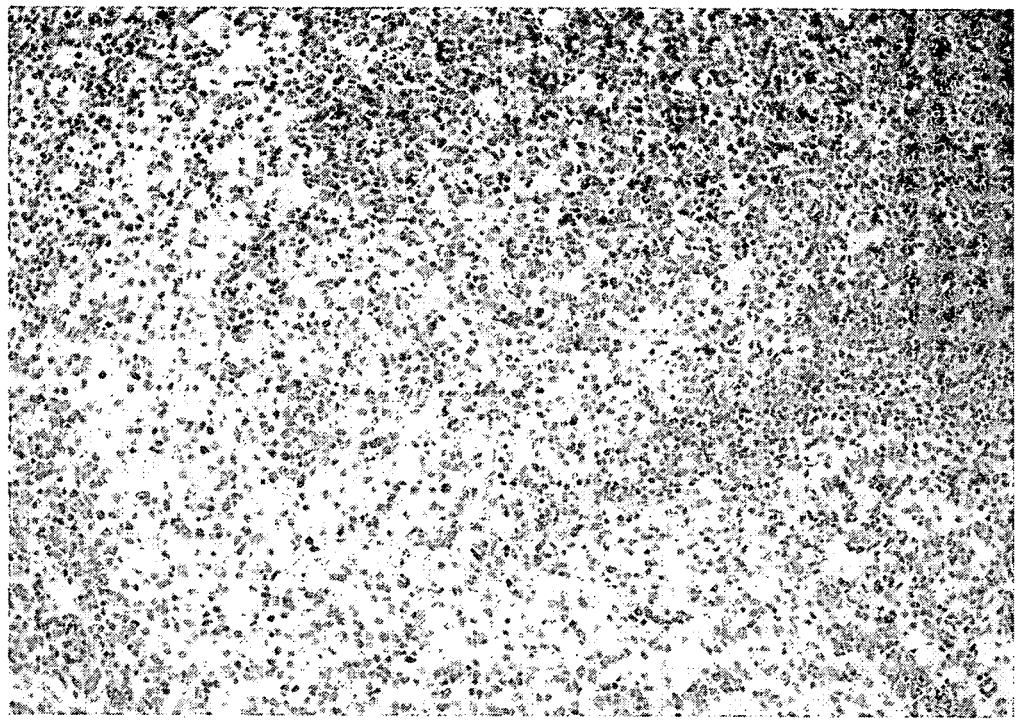
Figure 8I:
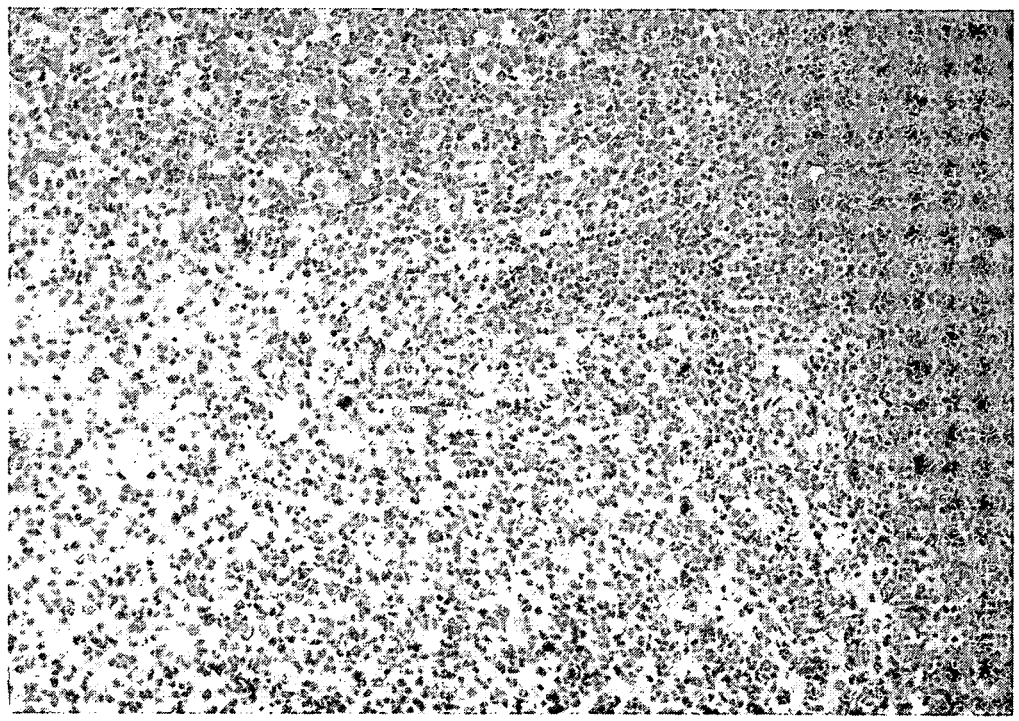
Figure 8J:
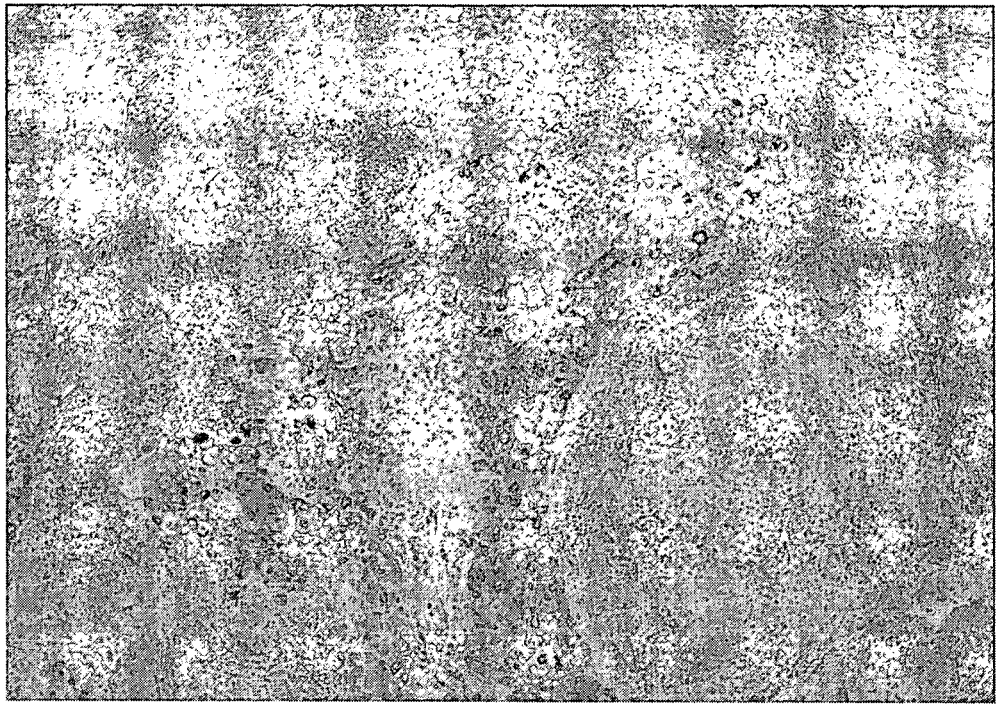
Figure 8J:
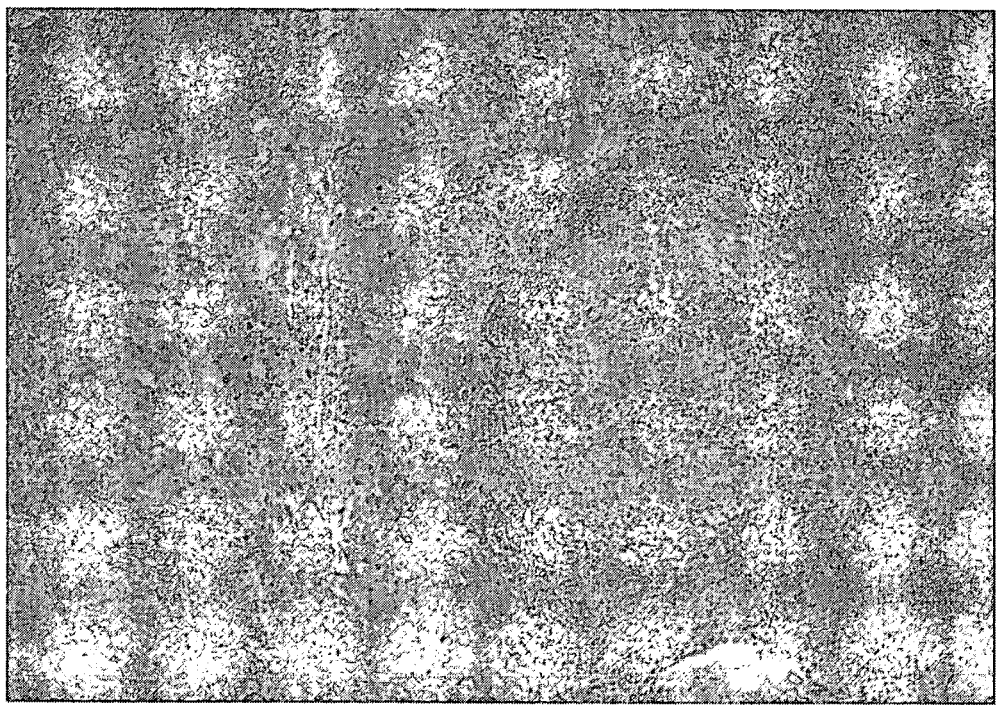
Figure 8J:
Figure 8J:
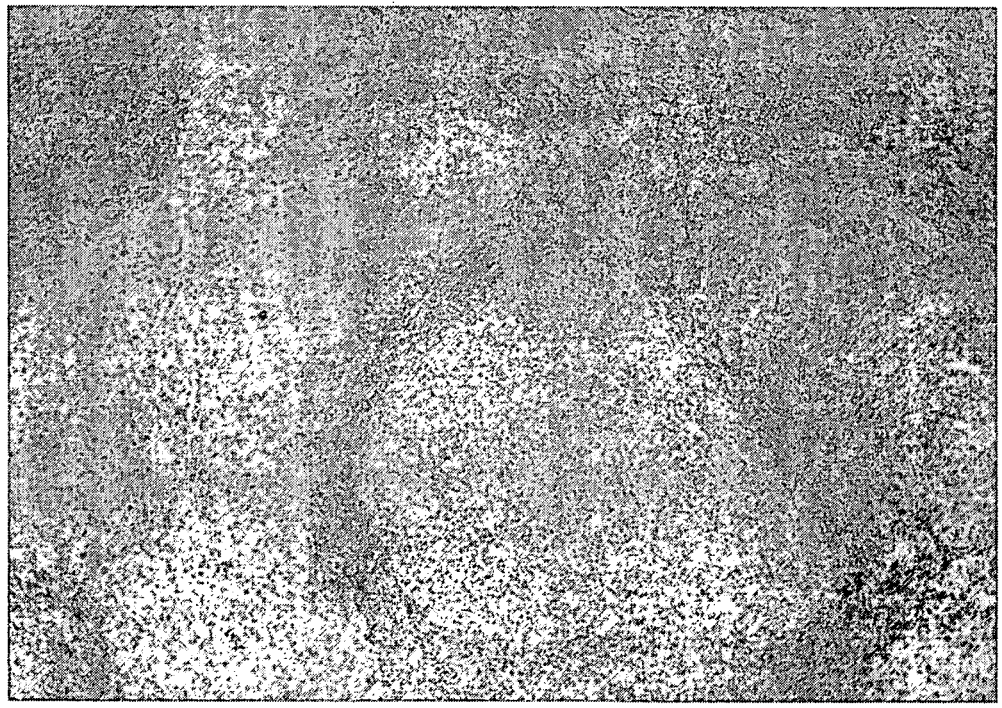
Figure 8K:
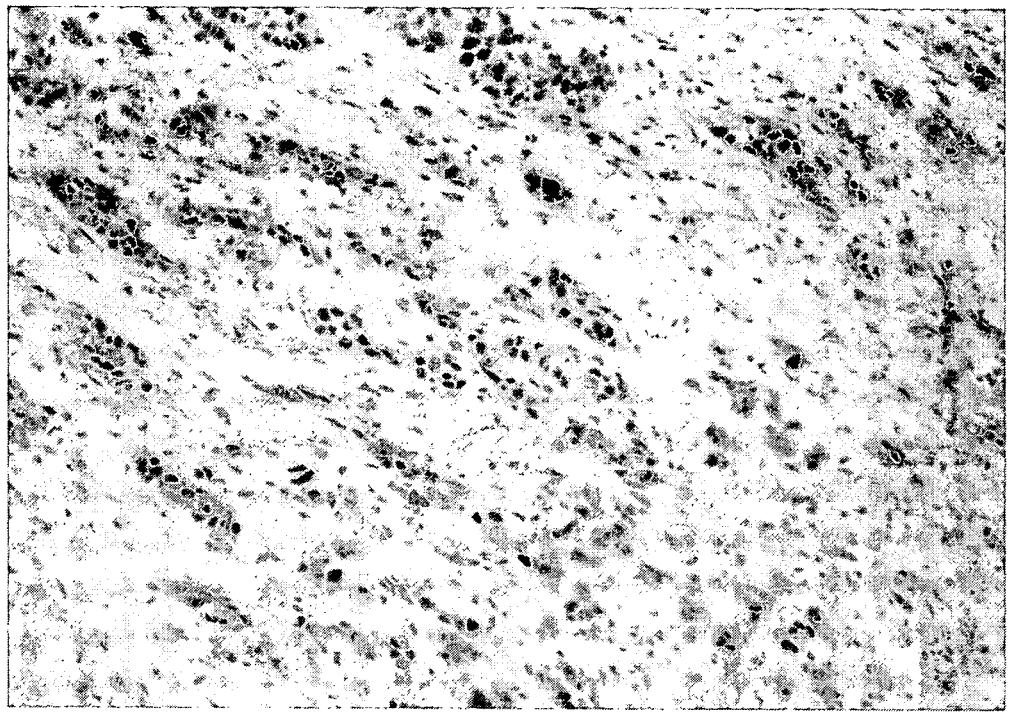
Figure 8K:
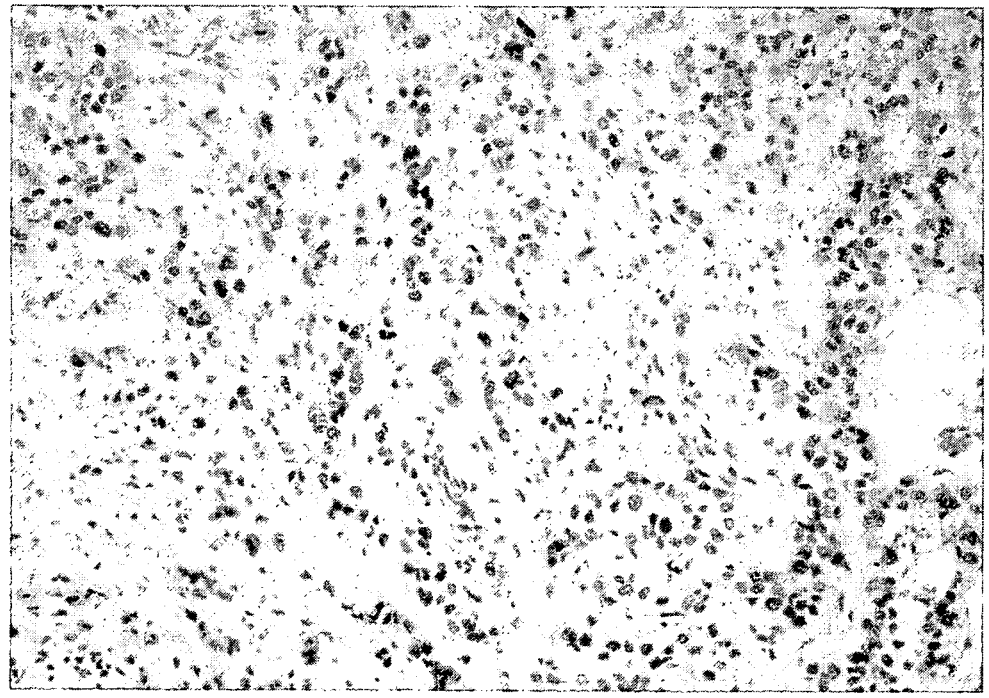
Figure 8K:
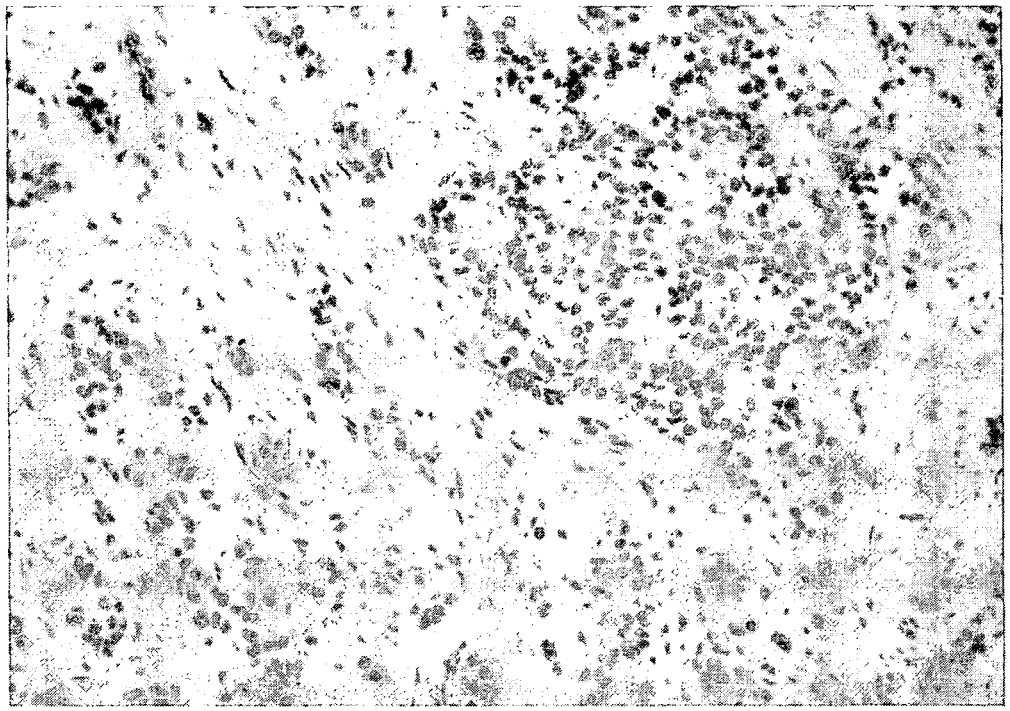
Figure 8K:
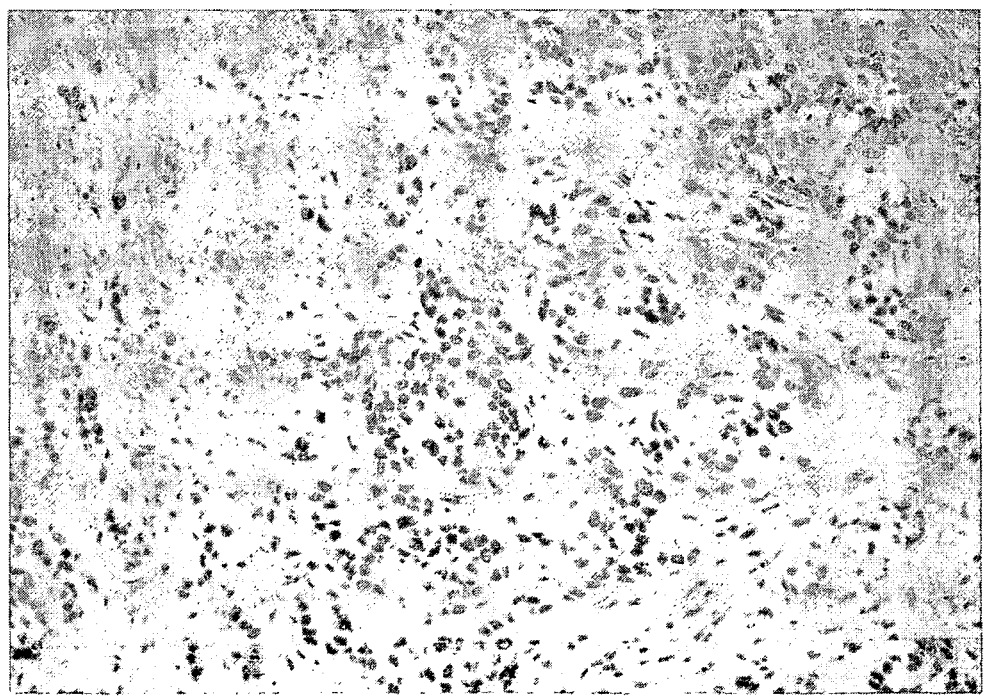
Figure 8L:
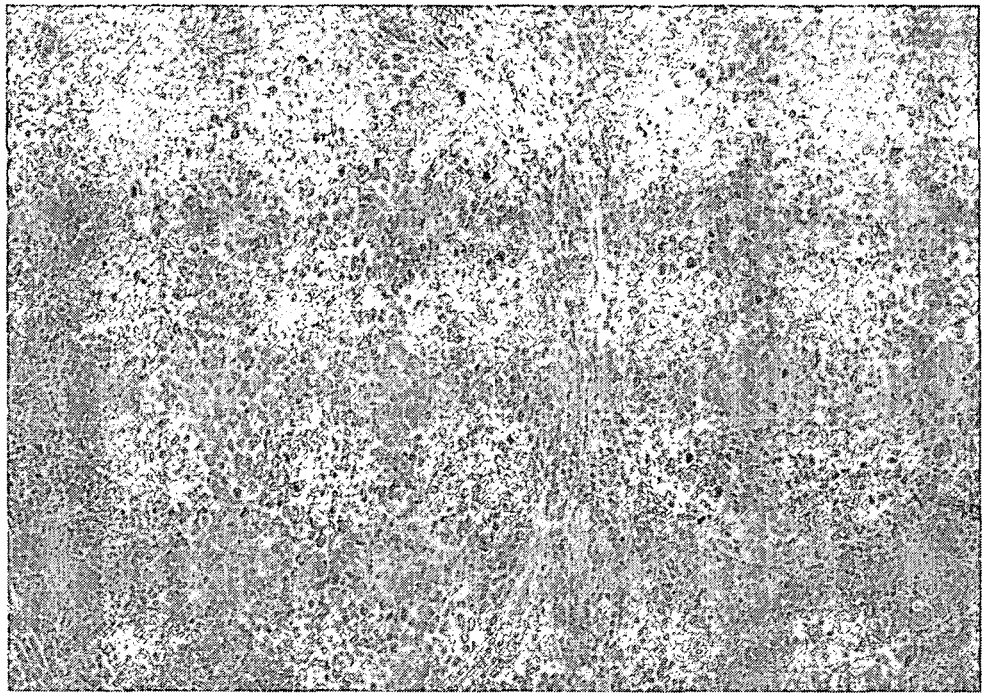
Figure 8L:
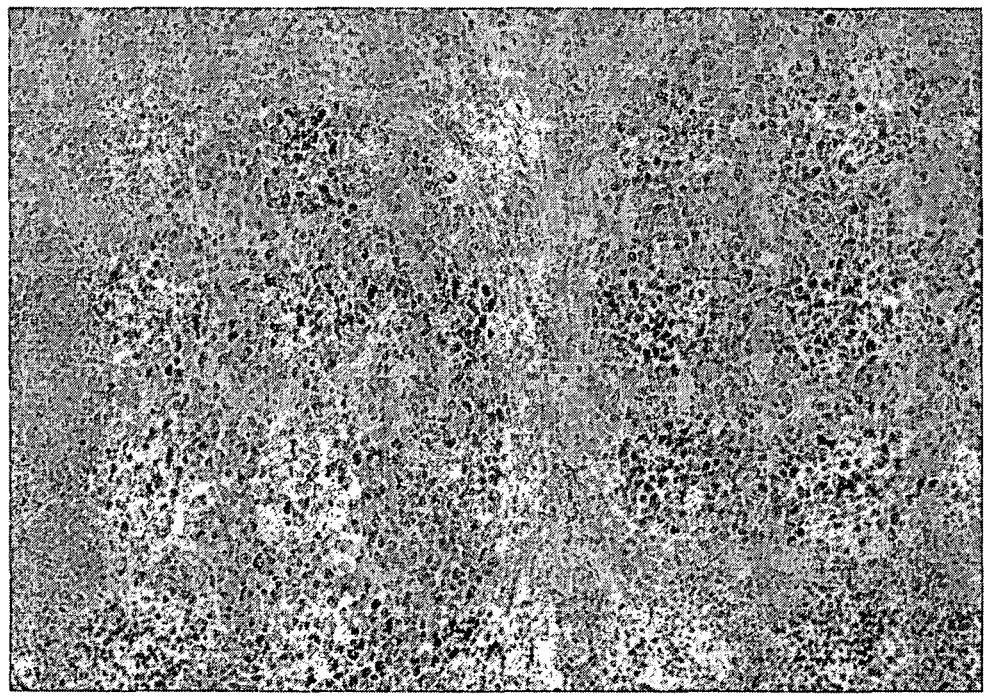
Figure 8L:
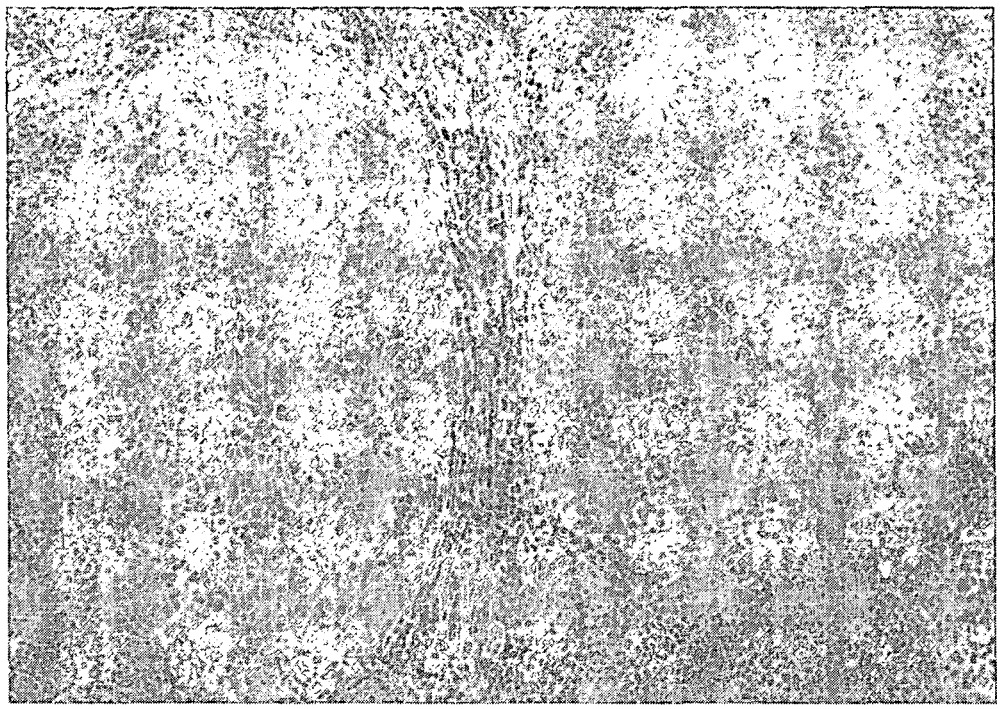
Figure 8L:
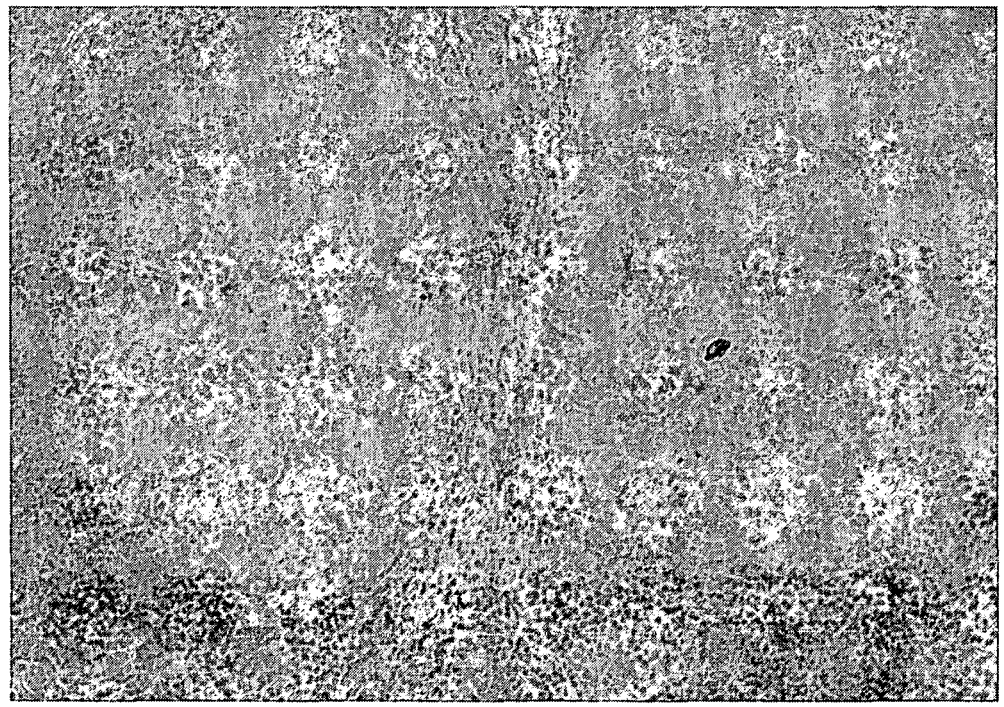
Figure 8M:
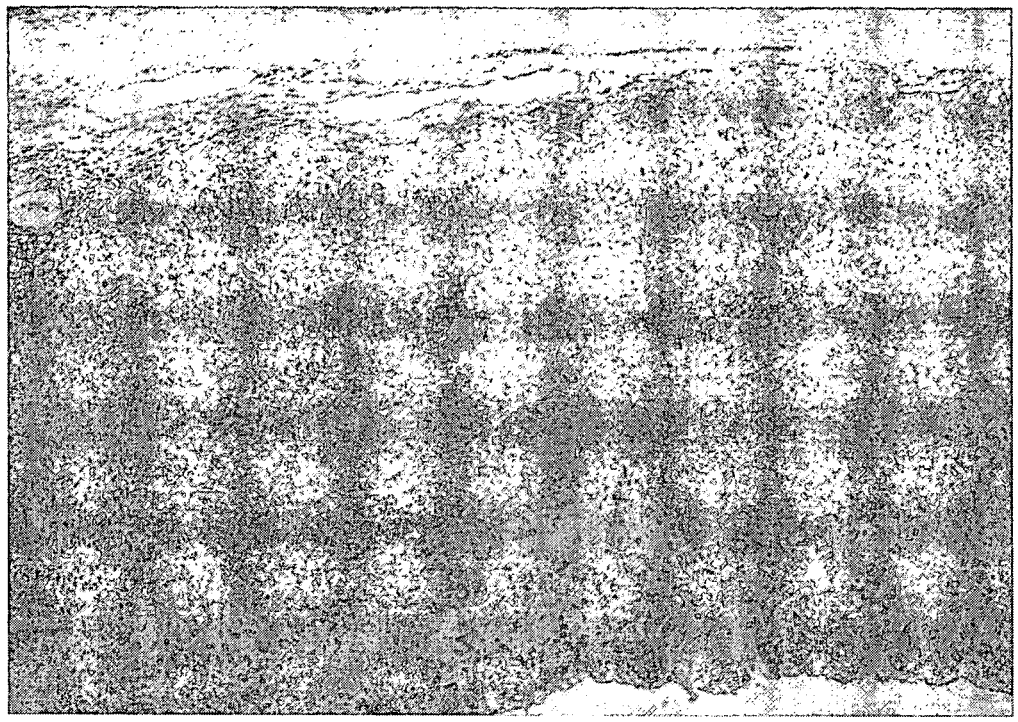
Figure 8M:
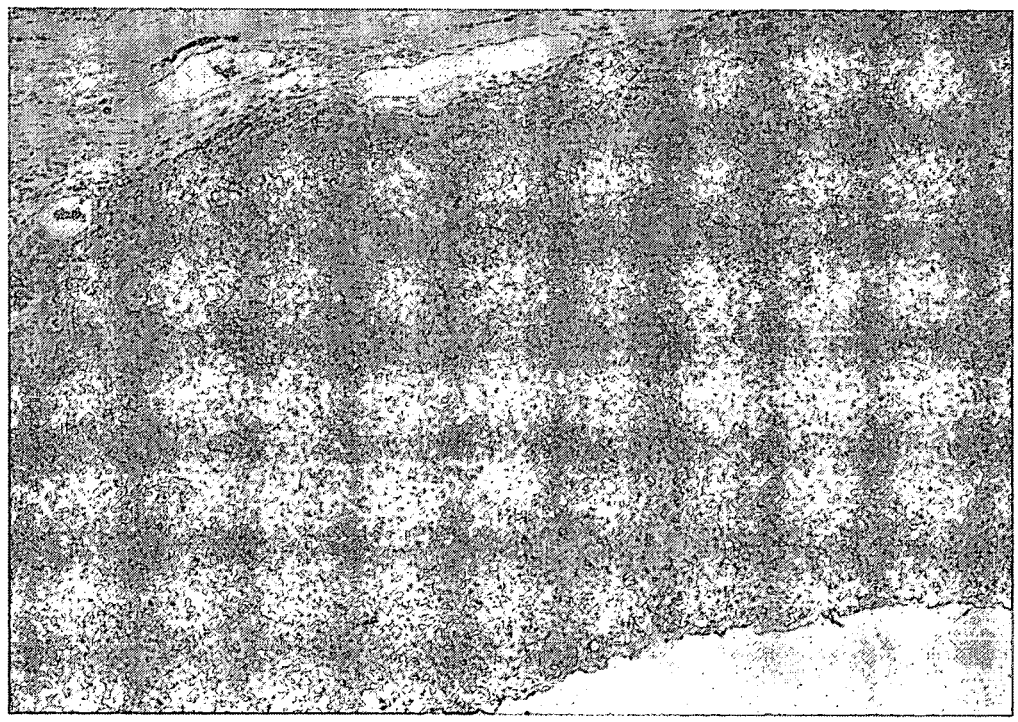
Figure 8M:
Figure 8M:
Figure 8N:
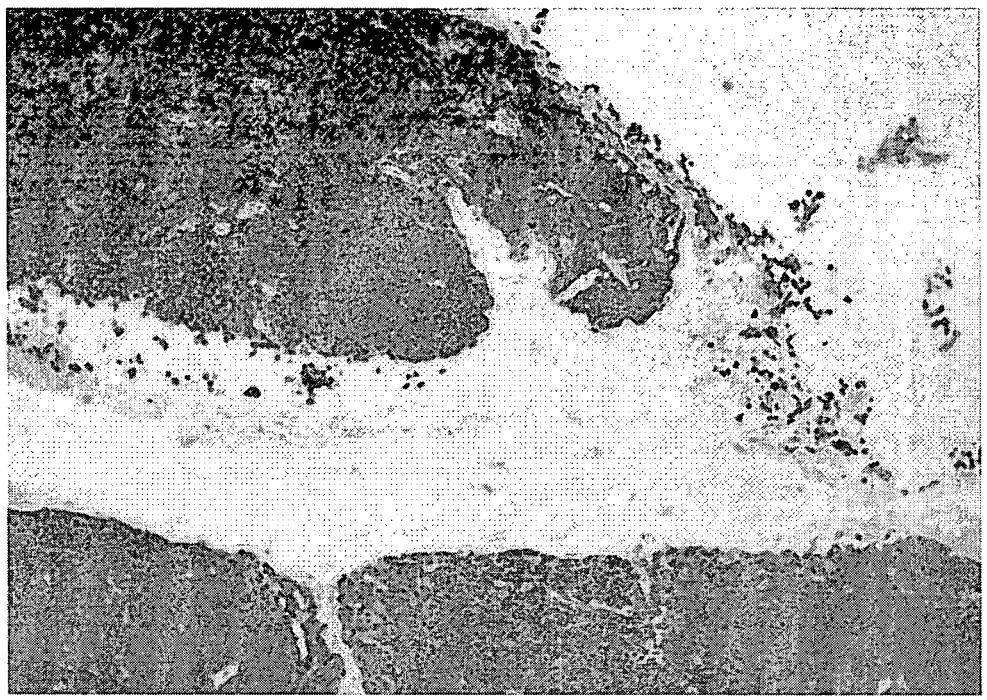
Figure 8N:
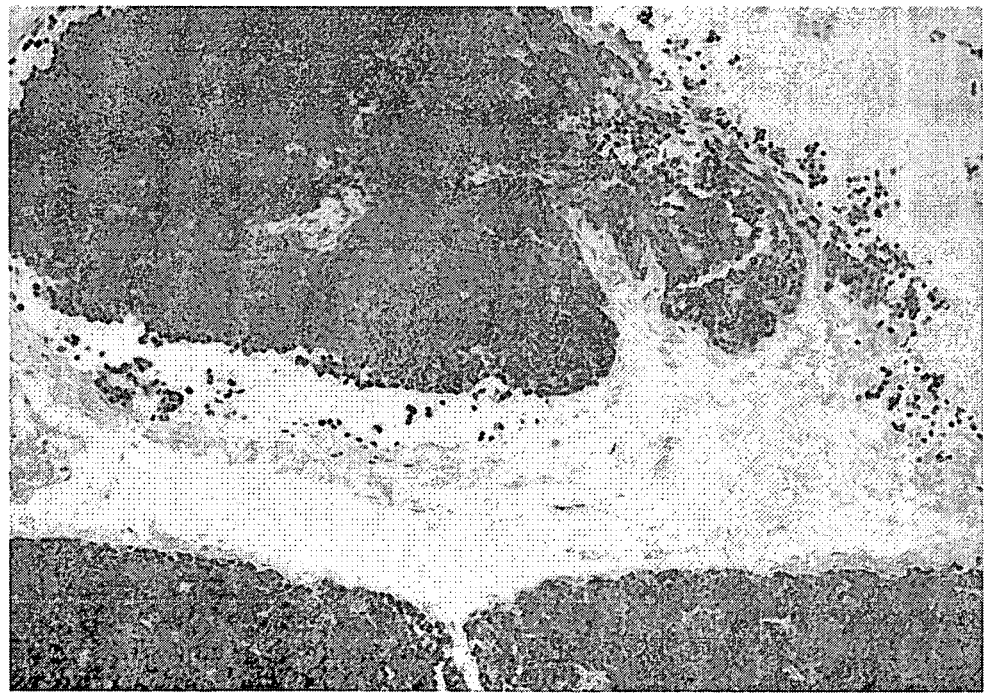
Figure 8N:
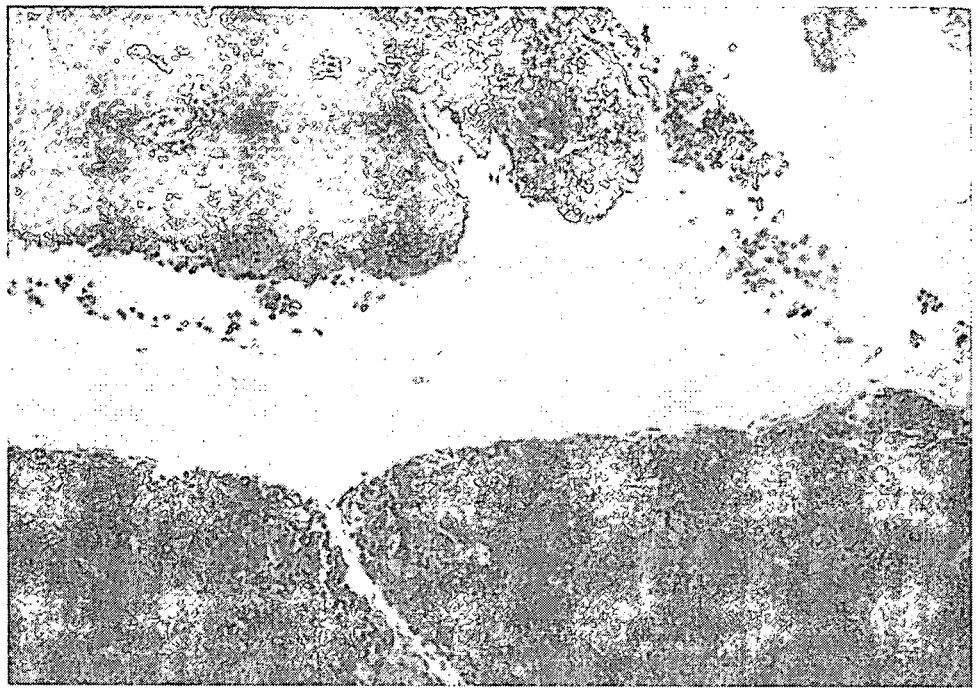
Figure 8N:
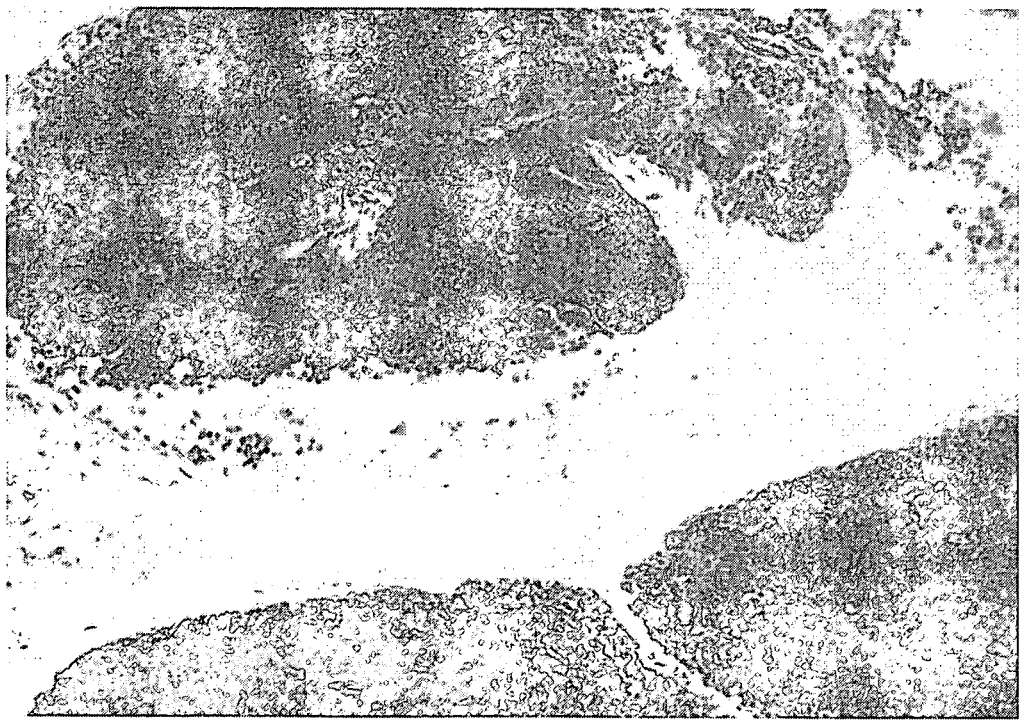

Table 4 below summarizes the staining experiments, with respect to slide number, primary antibody, primary antibody dilution, tissue sample type, visualization system used, optical magnification, and resulting staining intensity score. The slides are denoted 8-AA to 8-ND. FIG. 8AA to 8ND are photomicrographs of the DAB stained tissues taken at 10 or 20-times magnification.

TABLE 4

| Figure No. | Primary Antibody | Ab dilution 1:X | Tissue | Visualization Set up | Magnif. | Score |
|---|---|---|---|---|---|---|
| 8-AA | CK-20 | 10800 | Colon | NDS-1 | 20 | 2.0-3.25 |
| 8-AB | CK-20 | 10800 | Colon | PV | 20 | 2.0-3.5 |
| 8-AC | Negativ control | 10800 | Colon | NDS-1 | 20 | |
| 8-AD | Negativ control | 10800 | Colon | PV | 20 | 1.75 |
| 8-BA | CEA | 34000 | Colon | NDS-1 | 20 | 2.0-3.5 |
| 8-BB | CEA | 34000 | Colon | PV | 20 | 1.0-1.75 |
| 8-BC | CEA | 68000 | Colon | NDS-1 | 20 | 1.0-3.0 |
| 8-BD | CEA | 68000 | Colon | PV | 20 | 0-1.5 |
| 8-BE | Negativ control | 34000 | Colon | NDS-1 | 20 | 0 |
| 8-BF | Negativ control | 34000 | Colon | PV | 20 | 0 |
| 8-CA | Chromogranin A | 7200 | Pancreas | NDS-1 | 20 | 2.5-3.5 |
| 8-CB | Chromogranin A | 7200 | Pancreas | PV | 20 | 1.0-2.0 |
| 8-CC | Chromogranin A | 14400 | Pancreas | NDS-1 | 20 | 1.0 |
| 8-CD | Chromogranin A | 14400 | Pancreas | PV | 20 | 0 |
| 8-DA | p53 | 30000 | Prostate | NDS-1 | 10 | 2.0-3.5 |
| 8-DB | p53 | 30000 | Prostate | PV | 10 | 2.0-3.0 |
| 8-DC | Negativ control | 30000 | Prostate | NDS-1 | 10 | 0 |
| 8-DD | Negativ control | 30000 | Prostate | PV | 10 | 0 |
| 8-EA | p63 | 200 | Pancreas | NDS-1 | 20 | 3.5 |
| 8-EB | p63 | 200 | Pancreas | PV | 20 | 3.5 |
| 8-EC | Negativ control | 200 | Pancreas | NDS-1 | 20 | 0 |
| 8-ED | Negativ control | 200 | Pancreas | PV | 20 | 0 |
| 8-FA | p63 | 200 | Pancreas | NDS-1 | 20 | 3.0 |
| 8-FB | p63 | 200 | Pancreas | PV | 20 | 3.25 |
| 8-FC | Negativ control | 200 | Pancreas | NDS-1 | 20 | 0 |
| 8-FD | Negativ control | 200 | Pancreas | PV | 20 | 0 |
| 8-GA | TTF-1 | 250 | Thymus | NDS-1 | 20 | 3.5 |
| 8-GB | TTF-1 | 250 | Thymus | PV | 20 | 3.25-3.5 |
| 8-GC | Negativ control | 250 | Thymus | NDS-1 | 20 | 0 |
| 8-GD | Negativ control | 250 | Thymus | PV | 20 | 0 |
| 8-HA | PSA | 30000 | Prostate | NDS-1 | 10 | 2.25 |
| 8-HB | PSA | 30000 | Prostate | PV | 10 | 1.75 |
| 8-HC | PSA | 120000 | Prostate | NDS-1 | 10 | 1.0 |
| 8-HD | PSA | 120000 | Prostate | PV | 10 | 0 |
| 8-HE | Negativ control | 30000 | Prostate | NDS-1 | 10 | 0 |
| 8-HF | Negativ control | 30000 | Prostate | PV | 10 | 0 |
| 8-IA | CD68 | 800 | Tonsil | NDS-1 | 20 | 2.75 |

TABLE 4-continued

| Figure No. | Primary Antibody | Ab dilution 1:X | Tissue | Visualization Set up | Magnif. | Score |
|---|---|---|---|---|---|---|
| 8-IB | CD68 | 800 | Tonsil | PV | 20 | 2.75 |
| 8-IC | Negativ control | 800 | Tonsil | NDS-1 | 20 | 0.25 |
| 8-ID | Negativ control | 800 | Tonsil | PV | 20 | 0.75 |
| 8-JA | ALK-1 | 250 | Tonsil | NDS-1 | 10 | 2.0-3.0 |
| 8-JB | ALK-1 | 250 | Tonsil | PV | 10 | 1.0-2.0 |
| 8-JC | Negativ control | 250 | Tonsil | NDS-1 | 10 | 0 |
| 8-JD | Negativ control | 250 | Tonsil | PV | 10 | 0 |
| 8-KA | bcl-1 | 1000 | H&N Sq. Carcinoma | NDS-1 | 20 | 2.0-3.5 |
| 8-KB | bcl-1 | 1000 | H&N Sq. Carcinoma | PV | 20 | 1.75-3.0 |
| 8-KC | Negativ control | 1000 | H&N Sq. Carcinoma | NDS-1 | 20 | 0 |
| 8-KD | Negativ control | 1000 | H&N Sq. Carcinoma | PV | 20 | 0 |
| 8-LA | bcl-6 | 200 | Tonsil | NDS-1 | 20 | 1.75 |
| 8-LB | bcl-6 | 200 | Tonsil | PV | 20 | 2.25 |
| 8-LC | Negativ control | 200 | Tonsil | NDS-1 | 20 | 0 |
| 8-LD | Negativ control | 200 | Tonsil | PV | 20 | 0-0.25 |
| 8-MA | CD20 | 10000 | Tonsil | NDS-1 | 10 | 2.5 |
| 8-MB | CD20 | 10000 | Tonsil | PV | 10 | 2.25 |
| 8-MC | Negativ control | 10000 | Tonsil | NDS-1 | 10 | 0 |
| 8-MD | Negativ control | 10000 | Tonsil | PV | 10 | 0 |
| 8-NA | TdT | 75 | Thymus | NDS-1 | 20 | 2.75-3.0 |
| 8-NB | TdT | 75 | Thymus | PV | 20 | 2.25-2.75 |
| 8-NC | Negativ control | 75 | Thymus | NDS-1 | 20 | 0 |
| 8-ND | Negativ control | 75 | Thymus | PV | 20 | 0 |

The photomicrographs all demonstrated strong specific staining and no staining with the negative control using the NDS-1 set up, except for the 8-AC using the CK20 on colon and 8-IC using CD68 on tonsil. The PowerVision+™ gave no staining for the negative control, except for slide 7-AD using CK20 on tonsil, 7-ID using CD68 on tonsil and slide 7-LD, bcl-6 on tonsil, which both gave unacceptable background. The PowerVision+™ gave high unspecific background on slide 7-AB, CK20 on colon, and slide 7-IB, CD68 on tonsil, whereas the NDS-1 visualization system did not show the same unspecific staining. In general, the NDS-1 visualization system resulted in the same or higher staining intensity than PowerVision+™. This staining intensity was significantly stronger for the CEA on colon, Chromoganin A on pancreas, PSA on prostate, and only slightly stronger for ALK on tonsil, bcl-1 on HNSC, TdT on thymus.

The CEA, Chromogranin A and PSA were all rabbit primary antibodies, indicating that the NDS-1 system is a truly dual link visualization system, giving high staining intensity for all mouse and rabbit primary antibodies.

The stronger intensity compared with PowerVision+™ was further illustrated when the primary antibody was diluted out. Detection was seen using NDS-1 at a 1:68000 dilution of anti CEA on colon and a 1:120000 dilution of anti PSA on prostate tissue. The PowerVision+TM could barely stain the tissue above the background in these samples.

For bcl-6 on tonsil and CK-20 on colon with PowerVision+™ seemed to give a stronger staining. This is an artifact, as the general background is higher than for the NDS-1 system. This is shown by the clear staining using the negative control primary antibody. In summary, the staining intensity was specific and as strong as or stronger than PowerVision+™ for all the various tissues and targets. The background was generally lower than PowerVision+™.

Example 23

Comparative Staining of Various Targets in FFPE Preparations Using Secondary Antibody Conjugate Linked with Alkaline Phosphatase The example describes immunovisualization of various protein targets in 4-micrometer FFPE sections of various tissues using a mixture of link Conjugate No. 2 and Conjugate No. 3. Thus, polymeric dextran conjugates containing secondary Goat anti rabbit antibody and secondary Goat anti mouse antibody, respectively, followed by a polymeric dextran conjugate containing alkaline phosphatase and tertiary rabbit anti goat antibody, (conjugate no. 6) were used. The results were visualized by staining with a red AP chromogen, Fuchsin+ (DakoCytomation, Carpenteria, Calif.). The assay set up is illustrated in FIG. 1-F and described in the following as "Advance AP".

The staining was compared to staining using the HRP ChemMate/DAB (DakoCytomation, Carpenteria, Calif.), AP Envision™+ (DakoCytomation, Carpenteria, CA), AP LSAB+ (DakoCytomation, Carpenteria, Calif.), APAAP (DakoCytomation, Carpenteria, Calif.) or AP PowerVision+™ (ImmunoVision Technologies, Co., Daly City, Calif.) staining systems all performed according to the maufacturer's instructions using a DakoCytomation Autostainer (DakoCytomation, Carpenteria, Calif.).

The staining protocol was similar to the HRP system described in example 12. In short, the slides were deparaffinated with xylene and rehydrated as described previously. Target retrieval was performed according to the specification sheet recommendations for the individual primary antibody. After the target retrieval, the slides were rinsed and placed in the wash buffer. The slides were incubated with primary antibody or negative control antibody for 30 minutes at room temperature. Excess buffer was removed and the slides were washed three times. The slides were incubated with a cocktail of conjugate Nos. 2 and 3 (Advance AP link), containing goat anti rabbit and goat anti mouse dextran polymer (diluted 1:220 and 1:25, respectively, in the antibody dilution buffer, (DakoCytomation, Carpenteria, Calif.) (300 µL per slide) for 30 min (+/−1 min). Excess buffer was removed and the slides were washed three times.

The slides were incubated with conjugate no. 6 containing rabbit anti goat and alkaline phosphatase (Advance AP enzyme reagent) diluted 1:13.6 in the same buffer used for AP Envision™+ (DakoCytomation, Carpenteria, Calif.), containing BSA, stabilizers, anti microbial agents, zinc, magnesium and salt at pH 7.2.

Conjugate No. 6 was incubated on the slide (300 μL per slide) for 30 minutes. (+/−1 min.). Excess buffer was removed and the slides were washed three times before being treated with the Fuchsin+AP chromogen for 10 minutes (+/−1 min.) according to the manufacturer's instructions (DakoCytomation, Carpenteria, Calif.).

All slides were counterstained with Mayers Hematoxylin for 1 minute before being mounted with a cover slide as in the previous examples.

In table 5 the protein marker, cellular localization, clone no., code number from supplier and various dilution ratios are summarized.

TABLE 5

| Marker | Localization | Clone | Code Number | Dilution |
|---|---|---|---|---|
| CD3 | membranous | Poly | A0452 | 1:100/400/1600 |
| Chromo. A | cytoplasmatic | Poly | A0430 | 1:250/1000/4000 |
| Pan CK | cytoplasmatic | AE1/AE3 | M3515 | 1:50/200/800 |
| Ki67 | nuclear | MIB1 | M7240 | 1:50/200/800 |
| S100 | nuclear & cytoplasmatic | Poly | Z0311 | 1:250/1000/4000 |
| Cyclin D1 | nuclear | SP4 rabbit | RM-9104-R7 | 1:50/200/800 |
| CD45 | membranous | 2B11 + PD7/26 | A4502 | 1:300/600/1200 |
| Neg control | | Diluent | S0809 | RTU |

Antigen retrieval (HIER) pre-treatment was done by heating in Target Retrieval Solution pH 9 (DakoCytomation, Carpenteria, Calif.) in a microwave oven at 700 watt for 7 minutes, followed by 15 minutes at 300 watt. The slides were cooled down to approximately 60° C. before being further processed.

For the S100 antibody, the antigen retrieval method was treatment with Proteinase K (DakoCytomation S3020) for 4 minutes at room temperature.

All the primary antibodies were from DakoCytomation (DakoCytomation, Carpenteria, Calif.), except for Cyclin D1, which was supplied from NeoMarker (AH Diagnostics, Aarhus V, Denmark). The antibodies were diluted in the standard antibody diluent (DakoCytomation, Carpenteria, Calif.).

The immunohistochemical reaction was performed on serial sections of FFPE multi blocks containing various normal tissue types and tumors with different levels of the antigen of interest.

For each marker the slides were processed (sectioning, drying, deparaffination & epitope retrieval) simultaneously and finally stained in two DakoCytomation Autostainers (DakoCytomation, Carpenteria, Calif.) to secure optimal conditions for all detection systems and to reduce variations due to different section handling i.e. HIER etc.

The staining of the ChemMate EnVision™/HRP and EnVision/AP protocol was such performed in Autostainer 1 and the other methods were performed in Autostainer 2. Identical antibody solutions and reagents were used in both stainers.

Both specific and background reaction were scored. Each slide was assessed and given a score based on an average of the stainings in the various tissues in the multi blocks. A scale from 0 to 3 in quarter grade increments was used. The scoring system was summarized as: no staining or very weak (score 0), weak staining (score 1), moderate staining (score 2) and intense staining (score 3). All slides were evaluated blindly and by three individuals.

The score was given for the specific staining and the background staining. e.g. 3/1 indicates specific staining intensity of 3 and background staining of 1. Some staining was very weak or diffuse, and was scored as a borderline 1 score in intensity. This is indicated by a "(1)".

Table 6, provides a summary of the results.

TABLE 6

| NO | CD3 | 1:100 | 1:400 | 1:1600 |
|---|---|---|---|---|
| 1 | ChemMate/DAB | 3/2 | 3/1 | 2/0 |
| 2 | EnVision | 2/1 | 1/0 | 0/0 |
| 3 | LSAB | 2/1 | 2/1 | 1/0 |
| 4 | APAAP | n.a. | n.a | n.a |
| 5 | NDS Advance | 3/2 | 3/1 | 3/(1) |
| 6 | PowerVision+ | 3/2 | 3/1 | 1/0 |
| NO | CD45 | 1:100 | 1:400 | 1:1600 |
| 7 | ChemMate/DAB | 3/0 | 3/0 | 2/0 |
| 8 | EnVision | Error | Error | Error |
| 9 | LSAB | 2/0 | 1/0 | 1/0 |
| 10 | APAAP | 3/0 | 2/0 | 1/0 |
| 11 | NDS Advance | 3/(1) | 3/0 | 2/0 |
| 12 | PowerVision+ | 3/(1) | 3/0 | 2/0 |
| No | AE1/AE3 | 1:50 | 1:200 | 1:800 |
| 13 | ChemMate/DAB | 3/0 | 2/0 | 1/0 |
| 14 | EnVision | 2/0 | 1/0 | 0/0 |
| 15 | LSAB | 2/0 | 2/0 | 1/0 |
| 16 | APAAP | 2/0 | 1/0 | 1/0 |
| 17 | NDS Advance | 3/0 | 3/0 | 2/0 |
| 18 | PowerVision+ | 3(1) | 3/0 | 2/0 |
| NO | KI67 | 1:50 | 1:200 | 1:800 |
| 19 | ChemMate/DAB | 3/0 | 3/0 | 2/0 |
| 20 | EnVision | 2/0 | (1)/0 | 0/0 |
| 21 | LSAB | 2/0 | 1/0 | 1/0 |
| 22 | APAAP | 3/0 | 2/0 | 1/0 |
| 23 | NDS Advance | 3/(1) | 3/0 | 2/0 |
| 24 | PowerVision+ | 3/0 | 3/0 | 3/0 |
| No | CGA | 1:250 | 1:1000 | 1:4000 |
| 25 | ChemMate/DAB | 3/2 | 3/0 | 2/0 |
| 26 | EnVision | 2/1 | 1/0 | 1/0 |
| 27 | LSAB | 2/1 | 1/1 | 1/0 |
| 28 | APAAP | n.a. | n.a. | n.a. |
| 29 | NDS Advance | 3/2 | 3/1 | 2/0 |
| 30 | PowerVision+ | 3/1 | 3/1 | 1/0 |
| NO | CYCLIN D1 | 1:50 | 1:200 | 1:800 |
| 31 | ChemMate/DAB | 3/0 | 3/0 | 1/0 |
| 32 | EnVision | 1/0 | 0/0 | 0/0 |
| 33 | LSAB | 2/1 | 2/1 | 1/0 |
| 34 | APAAP | n.a. | n.a. | n.a. |
| 35 | NDS Advance | 3/(1) | 3/(1) | 2/0 |
| 36 | PowerVision+ | 2/0 | 2/0 | 1/0 |
| NO | S100 | 1:250 | 1:1000 | 1:4000 |
| 37 | ChemMate/DAB | 3/(1) | 3/0 | 2/0 |
| 38 | EnVision | 3/0 | 2/0 | 1/0 |
| 39 | LSAB | 3/1 | 2/0 | 1/1 |
| 40 | APAAP | n.a. | n.a. | n.a. |
| 41 | NDS Advance | 3/(1) | 3/(1) | 2/0 |
| 42 | PowerVision+ | 3/0 | 2/0 | 2/0 |

One of the trials (no. 8) gave no staining, presumably due to an experimental procedure error.

In this experiment, the Advance/AP detection system was the most sensitive detection system compared to the other AP-systems. Compared to the 2-step method EnVision™/AP K4017, the Advance AP provided a significant increase in sensitivity—even with a difference of 8-16× the primary antibody titer. The Advance AP system provided a superior result in all of the 7 tested markers. Notably, the Advance AP system was able to stain structures/cells such as cytokeratin positive follicular dendritic cells, and CD45 positive microglia cells. EnVision™ was not able to do this.

Both the 3-step methods APAAP (K0670) and LSAB+ (K0678) were inferior to Advance AP with regard to sensitivity. More importantly, Advance AP could visualize both rabbit and mouse primary antibodies. In contrast, APAAP was only was able to detect primary mouse antibodies.

The staining of Advance AP was in general comparable to PowerVision+ for the monoclonal mouse antibodies specific to anti-CD45 and anti-pan cytokeratin. With respect to the monoclonal mouse anti-Ki67 PowerVision+appeared more sensitive—in this set-up a signal strength approximately 4 times greater.

By comparing polyclonal rabbit and monoclonal rabbit (SP4), Advance AP was consistently more sensitive than PowerVision+ with an improvement of the sensitivity of approximately 4 fold. Both nuclear anti Cyclin D1 clone SP4 (rabbit), and cytoplasmic markers were amplified with Advance AP.

No reproducible unspecific reaction was seen using Advance AP. Occasionally focal background reaction was seen in e.g., the surface epithelium and muscle layer in the appendix. This phenomenon was also seen in the negative reactions. The reaction was also seen using PowerVision+.

FIG. 9A to K are representative microphotographs of the obtained staining results taken at 20 times magnification.

Figure 9A:
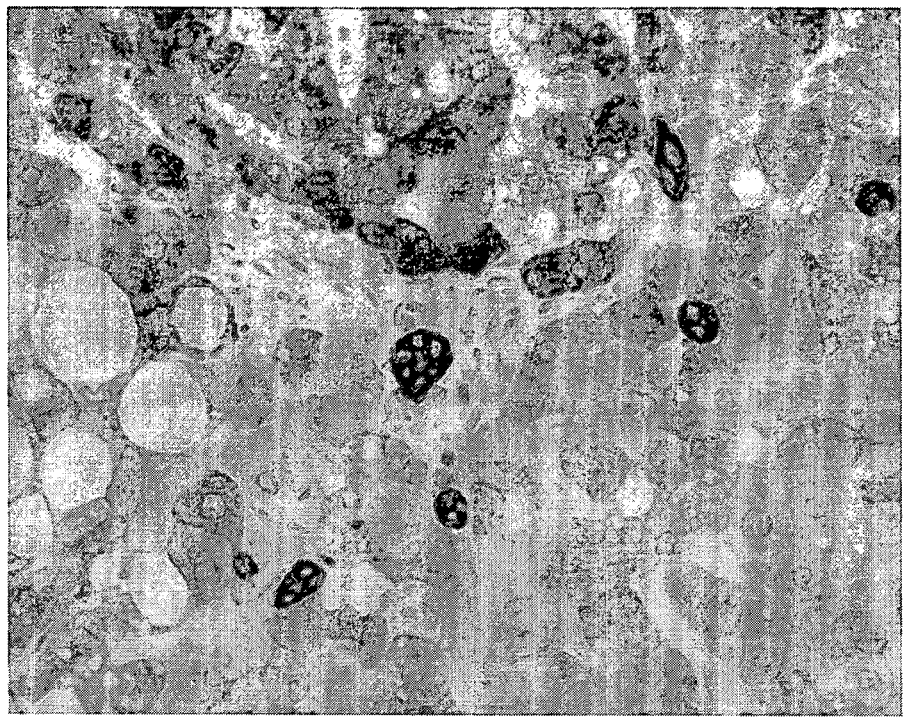
FIG. 9A-9K are photomicrographs of the Advance AP/Fuchsin stained FFPE tissue taken at 20 times magnification: Cytokeratine stained liver FFPE samples using Advance AP (A), EnVison™ AP (B), LSAB AP (C), and PowerVision™ AP (D); Cytokeratine (clone AEI/AE3) stained colon adenocarcinoma FFPE samples using Advance AP (E), EnVison™ AP (F), LSAB AP (G), and PowerVision™ AP (H); and Cyclin D1 stained tonsil FFPE samples using Advance AP (I), LSAB AP (J), and PowerVision™ AP (K).
Figure 9B:
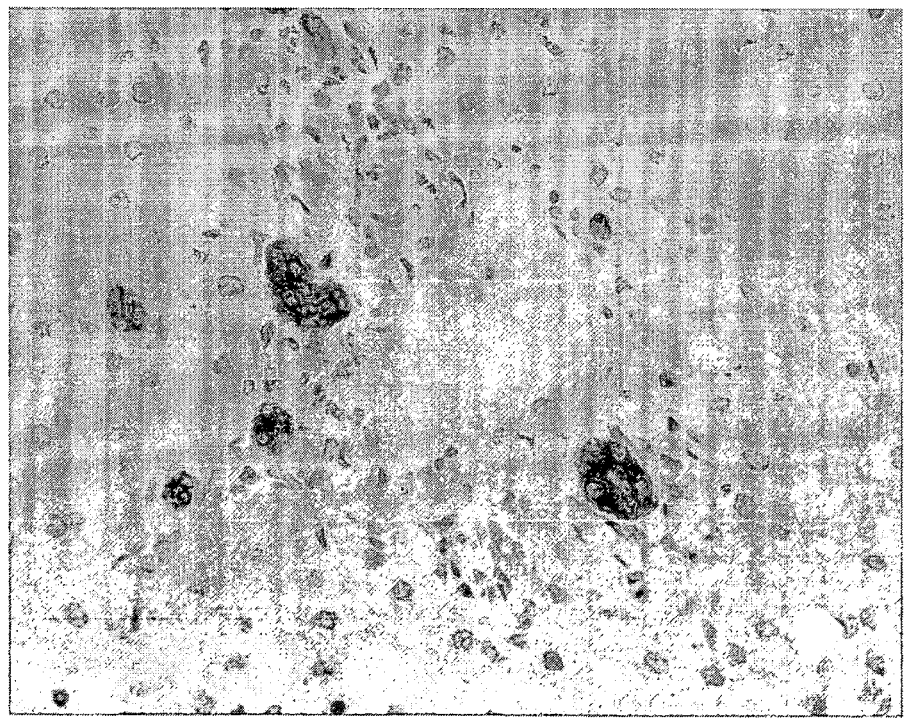
Figure 9C:
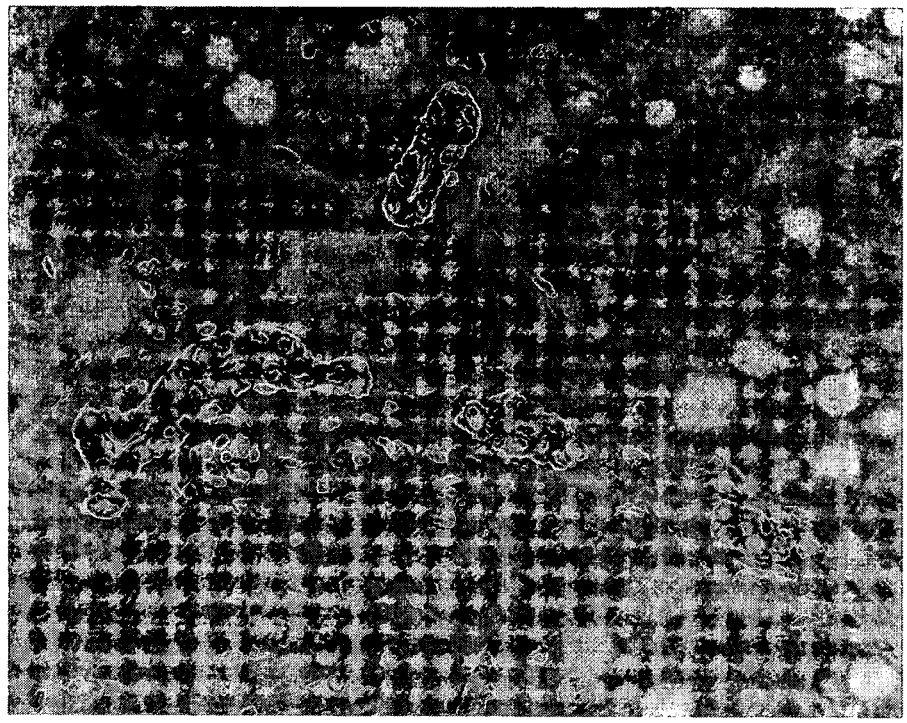
Figure 9D:
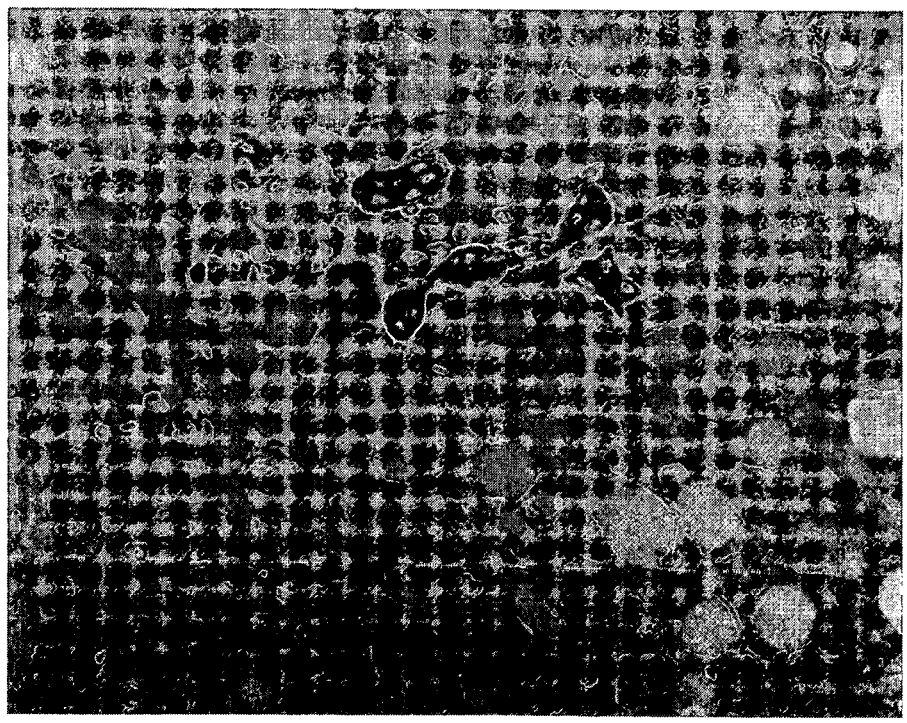

FIG. 9A, B, C and D are photomicrographs of anti Pan cytokeratine AE1/AE3 (diluted 1:200) stained liver FFPE samples using Advance AP (A); EnVison AP (B), LSAB AP (C) and PowerVision AP (D)

Figure 9E:
Figure 9F:
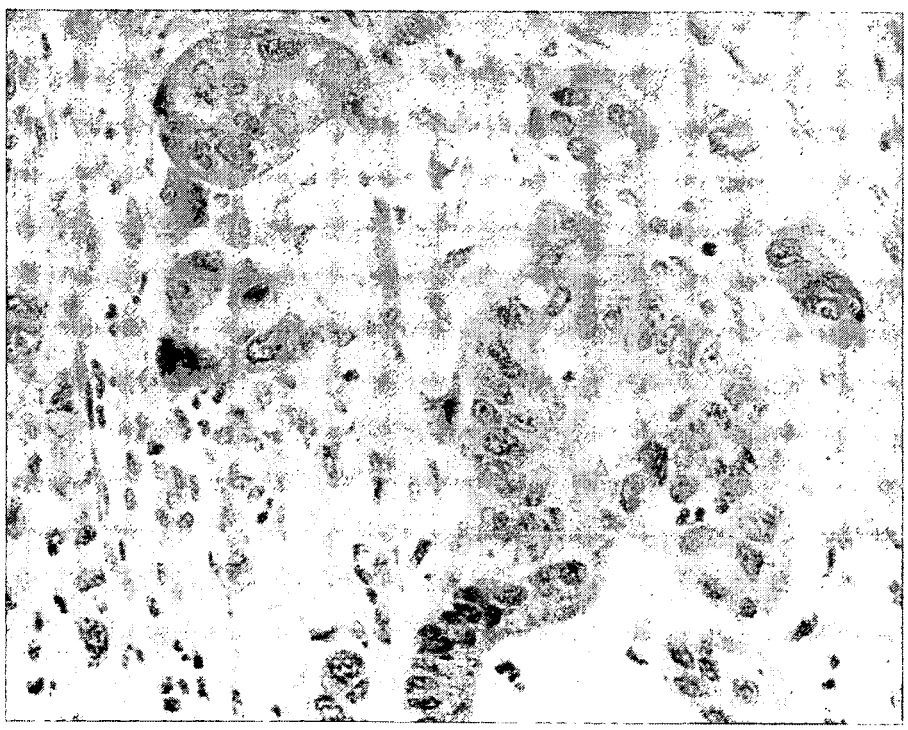
Figure 9G:
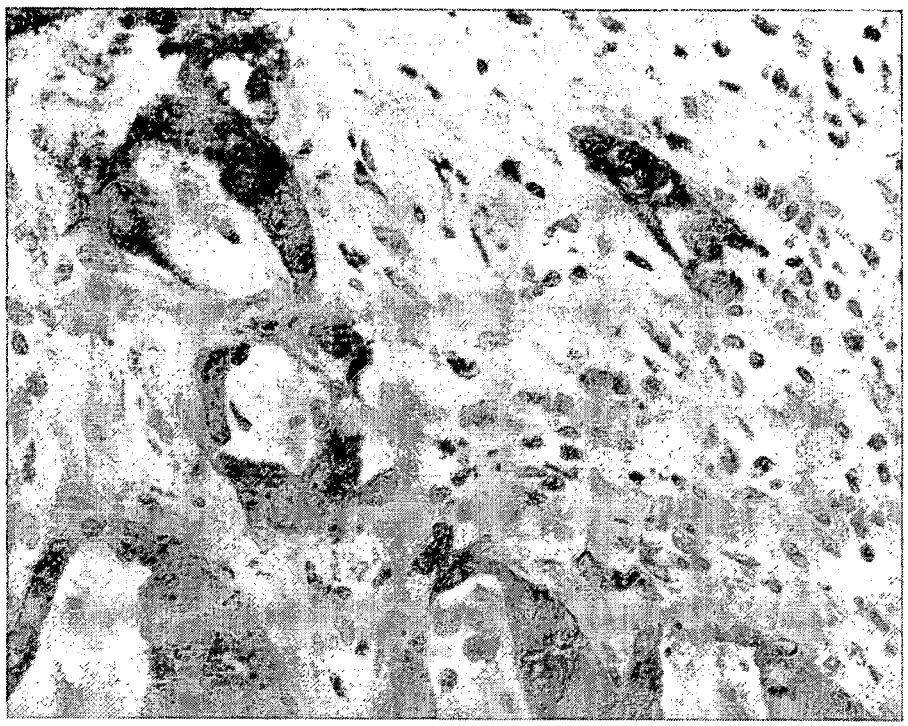
Figure 9H:
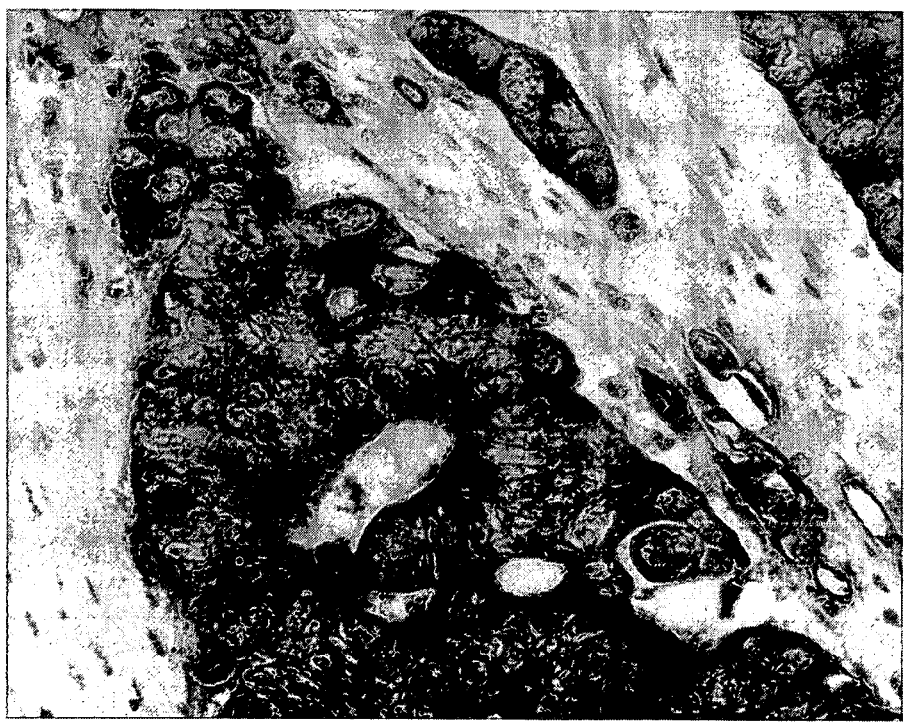

FIGS. 9E, F, G and H are photomicrographs of anti Pan cytokeratine clone AE1/AE3 (diluted 1:200) stained colon adenocarcinoma FFPE samples using Advance AP (E); EnVison AP (F), LSAB AP (G) and PowerVision AP (H)

Figure 9I:
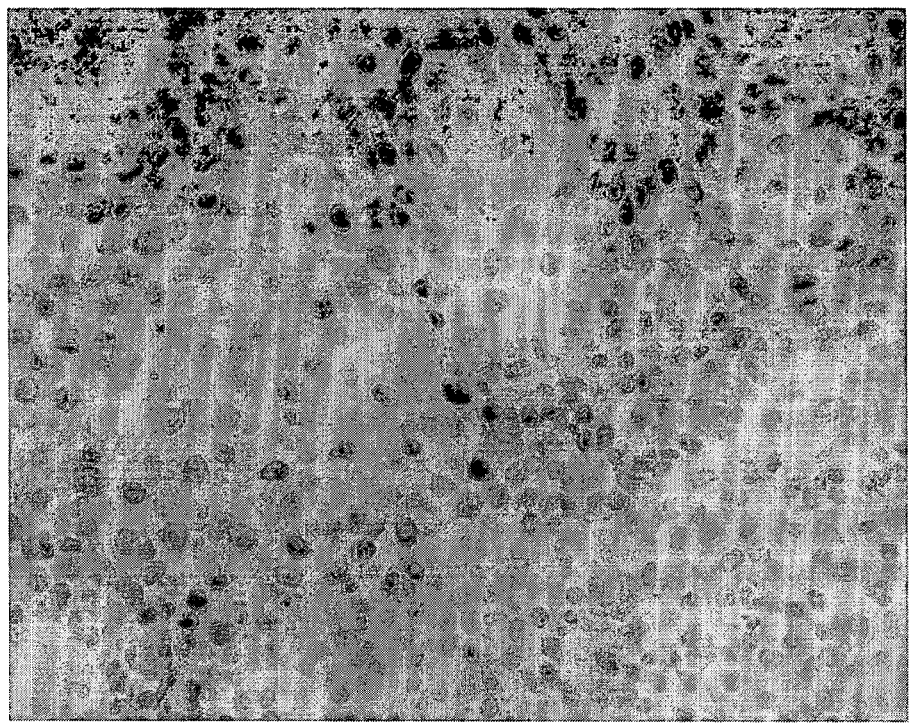
Figure 9J:
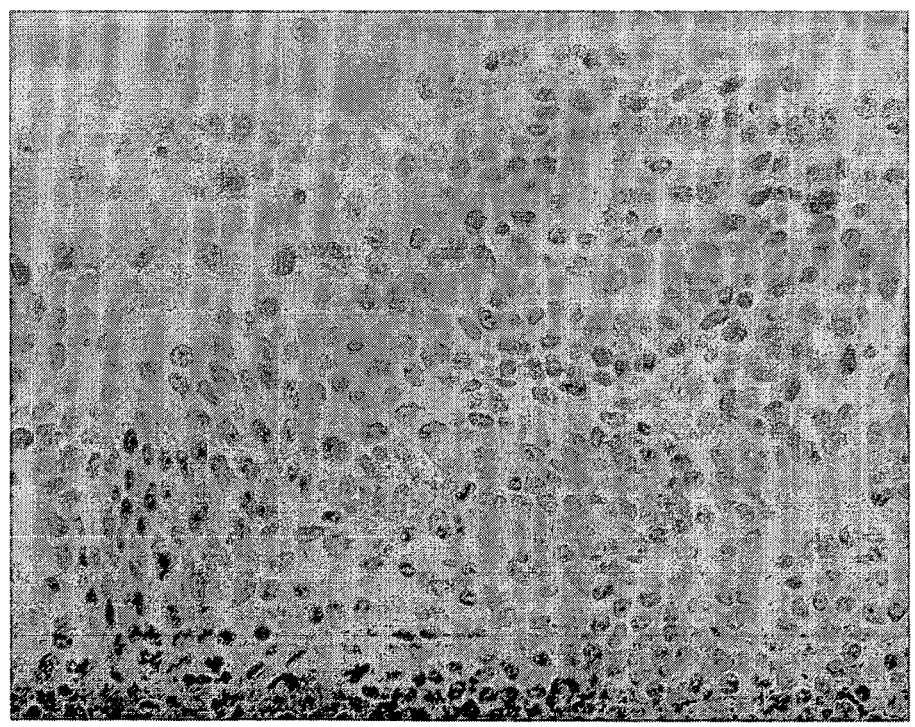
Figure 9K:
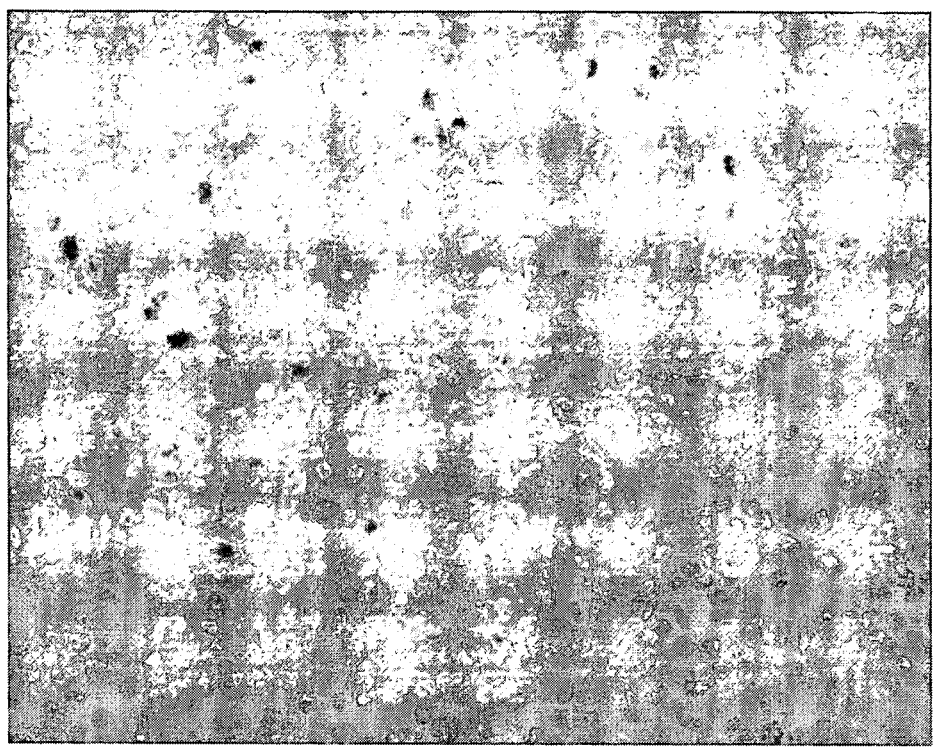

FIG. 9I, J and K are photomicrographs of Cyclin D1 SP4 (diluted 1:200) stained tonsil FFPE samples using Advance AP (I); LSAB AP (K) and PowerVision AP (L)

In conclusion, the system described in this example has at least comparable sensitivity to ChemMate EnVision K5007 using HRP and DAB. The Advance AP eliminates problems with endogenous brown pigment (such as HMB45, Melan-A). The significant increase in sensitivity compared to EnVision/AP and LSAB+/AP should be highly attractive to most laboratories by reducing the risk of false negative reactions. Compared to APAAP, the Advance AP both amplifies the sensitivity and makes it possible to use the same system for both mouse and rabbit antibodies, which gives flexibility in the protocol set-up.

The Advance AP amplifies both mouse and rabbit antibodies which is superior to PowerVision+AP and the described system could be preferable to the next generation of rabbit monoclonal antibodies such as anti-Cyclin D1 clone SP4, anti-p504s clone etc.

Example 24

Comparative Staining of Targets on Imprint Samples Using an Antibody Conjugate Linked with Alkaline Phosphatase The following example used the same AP visualization system and staining procedure as described in example 23 above. The staining intensity of various imprint samples using Advance AP and EnVision AP were compared.

Both detection systems in this example used Fuchsin+ (DakoCytomation, Capenteria, Calif.) as a chromogen. The staining was performed on the Autostainer Plus (DakoCytomation, Carpenteria, Calif.) using the wash buffer S3006 (DakoCytomation, Capenteria, Calif.).

Table 7 provides a summary of the markers examined, as well as the results obtained.

TABLE 7

| No | Marker | Clone | Code Number | Dilution | Intensity Advance AP | Intensity AP EnVision |
|---|---|---|---|---|---|---|
| 1 | CD3 | PS1 | NCL-PS1 | 1:100 | 3+ | 0 |
| 2 | CD20 | L26 | M0755 | 1:200 | 3+ | 0 |
| 3 | CD45 | 2B11 + PD7/26 | M701 | 1:200 | 3+ | 0 |
| 4 | Vim | 3B4 | M7020 | 1:200 | 3+ | 0 |
| 5 | Melan A | A103 | M7196 | 1:100 | 3+ | 0 |
| 6 | S100 | Poly | Z0311 | 1:500 | 3+ | 0 |
| 7 | Neg. control | | S0809 | RTU | 0 | 0 |

Nos. 1, 2 and 3 examined an imprint of lymph node fixed in acetone for 90 seconds. Nos. 4, 5 and 6 examined an imprint of melanoma fixed in 10% neutral buffered formalin (NBF) for 10 minutes, followed by HIER in a 10 mM citrate buffer at pH 6 in a microwave oven at 700 watts for 5 minutes, followed by 350 Watts for 10 minutes.

The antibodies were all from Dakocytomation, except for mouse anti CD3 which was from Novocastra (TriChem, Frederikssund, Denmark). All antibodies were diluted in the standard antibody diluent (DakoCytomation, Carpenteria, Calif.).

FIG. 10A to D are representative microphotographs of the obtained staining results taken at 10× magnification.

Figure 10A:
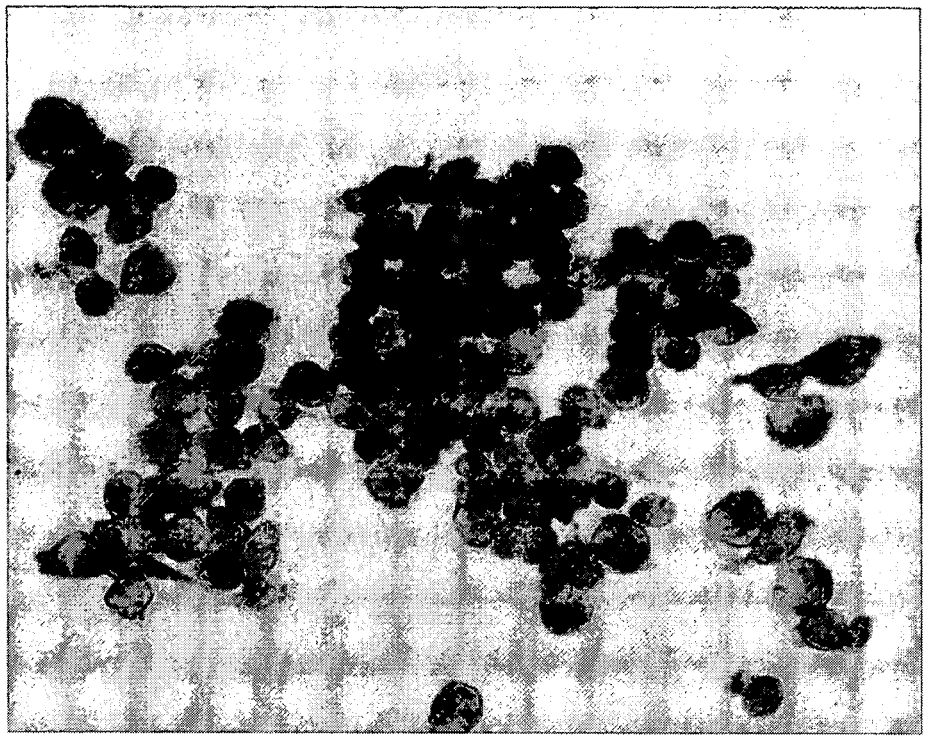
Figure 10B:
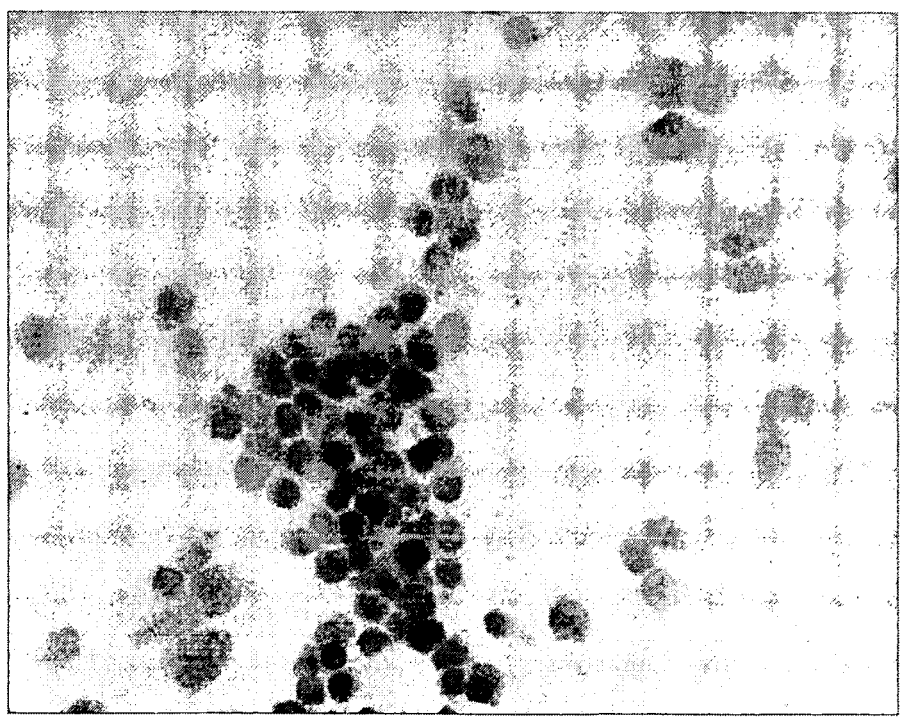

FIGS. 10A and B, are photomicrographs of anti Vimentin stained imprint of melanoma samples using Advance AP (A) and EnVison™ AP (B), respectively.

Figure 10C:
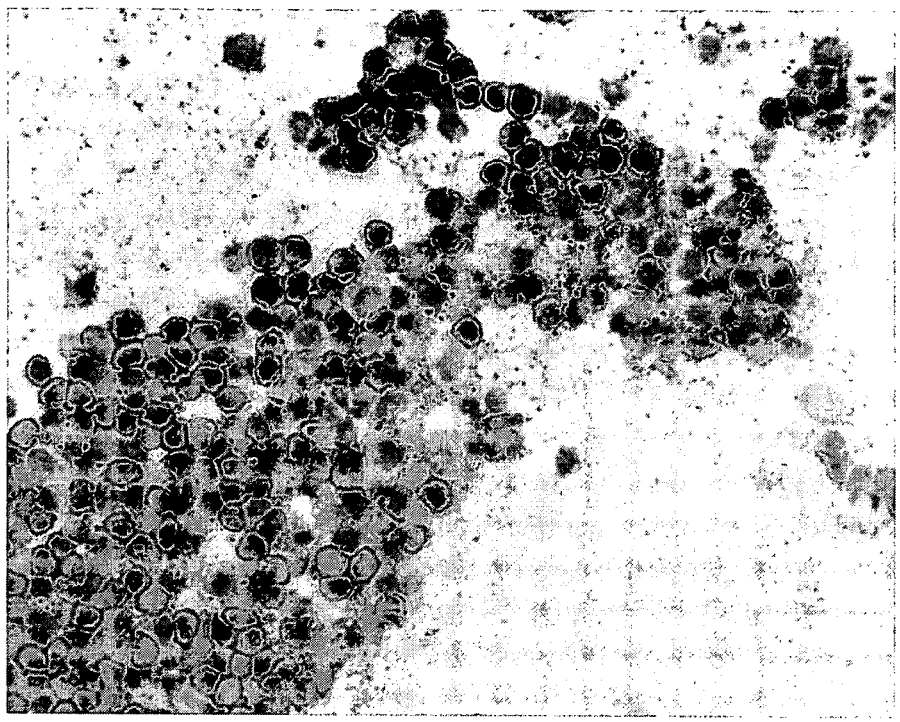
Figure 10D:
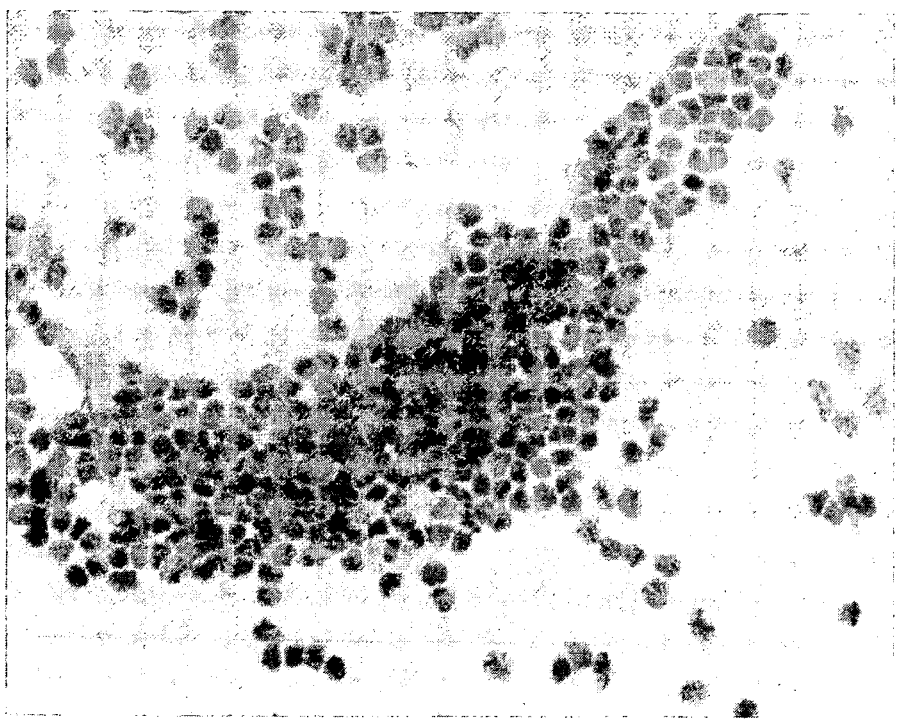

FIGS. 10C and D, are photomicrographs of anti CD3 stained imprint of lymph node samples using Advance AP (C) and EnVison™ AP (D), respectively.

The negative control antibody was DakoCytomation code no. S0809 (DakoCytomation, Carpenteria, Calif.) and produced no detectable staining.

The results obtained with Advance AP were generally superior to the results obtained with EnVision™ AP. The intensity of the reactions was both stronger and more distinct using Advance AP. Staining CD3 on T-cells using EnVision™ AP was practically negative but easily identified with Advance AP. A similar result was seen in the anti-Vimentin sample in the melanoma cells. Thus, Advance AP produced a detectable signal while EnVision™ did not.

Strong AP-based systems may be preferred to HRP-systems due to the endogenous enzyme peroxidase activity. The AP system also provides for the contrast of the crisp red Fuchsin+/Fast Red TR and the blue hematoxylin stained nuclei.

Example 25

Staining of Tonsil Using Hapten Labeled Secondary Antibody Conjugate and Polymeric Anti Hapten Conjugate with Horseradish Peroxidase The example describes immunovisualization of the nuclear marker Bcl-2 Oncoprotein on tonsils in a FFPE sample preparation using Conjugate No. 8, a polymeric dextran conjugate containing DNP labeled secondary Goat anti mouse antibody, followed by Conjugate No. 7, a polymeric dextran conjugate containing horse radish peroxidase and rabbit Fab2 anti DNP antibody and staining with a HRP chromogen (DAB plus). The assay set up is illustrated in FIG. 1-G.

In short, the sample was a FFPE multiblock with various tissues, including tonsils. The sample was cut, mounted, deparaffinated, and rehydrated as described in example 11. The slides were antigen retrieved using Tris-EDTA pH 9.0 according to the manufacturer's instructions (DakoCytomation, Carpenteria, Calif.). The manual general staining procedure was as described in example 11. In short the primary antibody, mouse anti Bcl-2 (Dakocytomation, Carpenteria, Calif.) was diluted 1:200 in buffer S2022 (DakoCytomation, Carpenteria, Calif.) and 200 microliters was applied and incubated 30 minutes at room temperature. The slide was washed twice in the wash buffer (containing TBS and tween20, (Dakocytomation, Carpenteria, Calif.). The DNP labeled GAM polymer was diluted 1:10 in the conjugate buffer, containing BSA and antimicrobial agents, and 200 microliter was applied and incubated 30 minutes at room temperature. The slide was washed twice in S3006 before being incubated 30 minutes with conjugate 7 (diluted 1:10 in the same conjugate buffer as above) at room temperature. The slide was washed twice in S3006 before being visualized for 10 minutes with DAB+ (Dakocytomation, Carpenteria, Calif.) according to the manufacturer's instructions. The slide was washed and counterstained and cover slipped as described previously.

In parallel, slides were immunostained using Envision™ (Dakocytomation, Carpenteria, Calif.) according to the manufacturer's instructions.

Figure 11A:
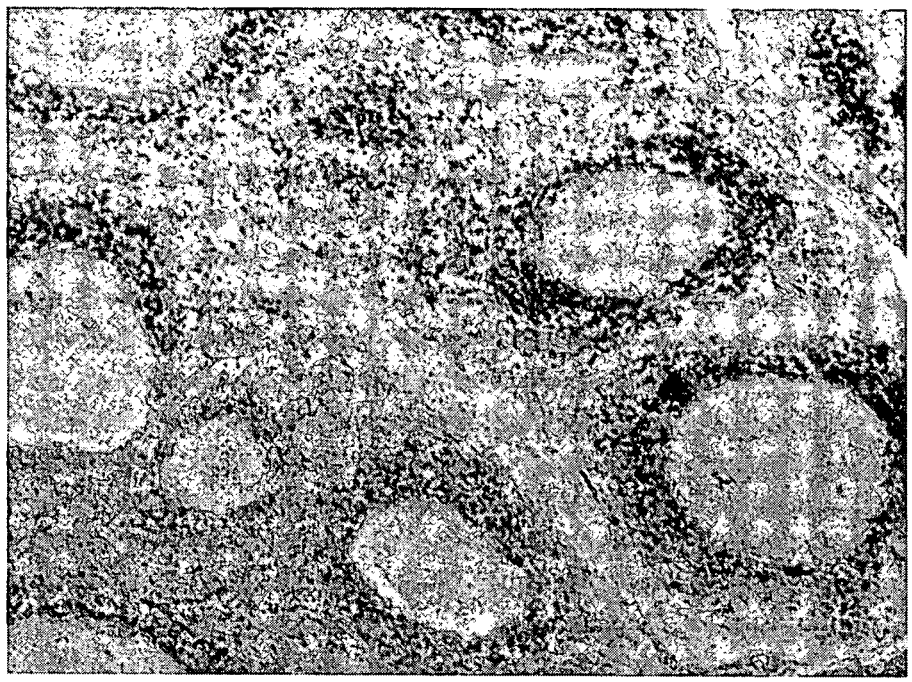
FIGS. 11A and B, are photomicrographs taken at 4 times magnification of anti bcl-2 DAB stained tonsil FFPE samples using the DNP labeled GAM polymer and rabbit anti DNP-HRP polymer (A) and EnVision™ (B), respectively.
Figure 11B:

FIGS. 11A and B, are photomicrographs taken at 4 times magnification of anti bcl-2 stained tonsil FFPE samples using the hapten labeled GAM polymer and anti DNP-HRP polymer (A) and EnVision (B), respectively.

The staining pattern was as expected for both systems. The system in this example showed very strong, specific and clean staining (3+) with no detectable background. The reference system was at almost the same staining strength.

This is surprising, as the reference system is an optimized system, based on lengthy development work. The example illustrates the feasibility of using hapten encoded polymeric layers of the invention. This is important for e.g. multi staining systems and in amplified visualization systems.

Example 26

Staining of Bcl-2 Oncoprotein Using a Hapten Labeled Primary Antibody, Polymeric Anti Hapten Conjugate and an Antibody Conjugate Linked with Horseradish Peroxidase The example describes immunovisualization of the nuclear marker Bcl-2 Oncoprotein on tonsils using DNP labeled mouse anti Bcl-2, a polymeric dextran conjugate containing rabbit anti DNP Fab2 antibody (Conjugate no. 9), followed by a polymeric dextran conjugate containing horseradish peroxidase and goat anti rabbit IgG antibodies (EnVision™ K4003) (Dakocytomation, Carpenteria, Calif.) and staining with a HRP chromogen (DAB plus). The assay components are illustrated in FIG. 1-H.

Affinity purified primary antibody mouse anti human Bcl-2 Oncoprotein immunoglobulin (clone 124, Isotype IgG1 kappa), (Dakocytomation, Carpenteria, Calif.) was DNP labeled using the method described in example 2, for the polymeric conjugates. The method provided 2.7 DNP molecules per IgG on average and an antibody concentration of 700 $10^{-8}$ M. The manual staining was done as described in example 25 above.

The DNP labeled antibody was diluted 1:100 and the rabbit anti DNP conjugate no. 9 was diluted 1:10. The conjugate was used according to the manufacturer's instructions (DakoCytomation, Carpenteria, Calif.).

In parallel, slides were stained with an unmodified primary antibody for bcl-2 (Dakocytomation, Carpenteria, Calif.) diluted 1:200 and Envision™ (DakoCytomation, Carpenteria, Calif.)) and DAB+.

Figure 12A:
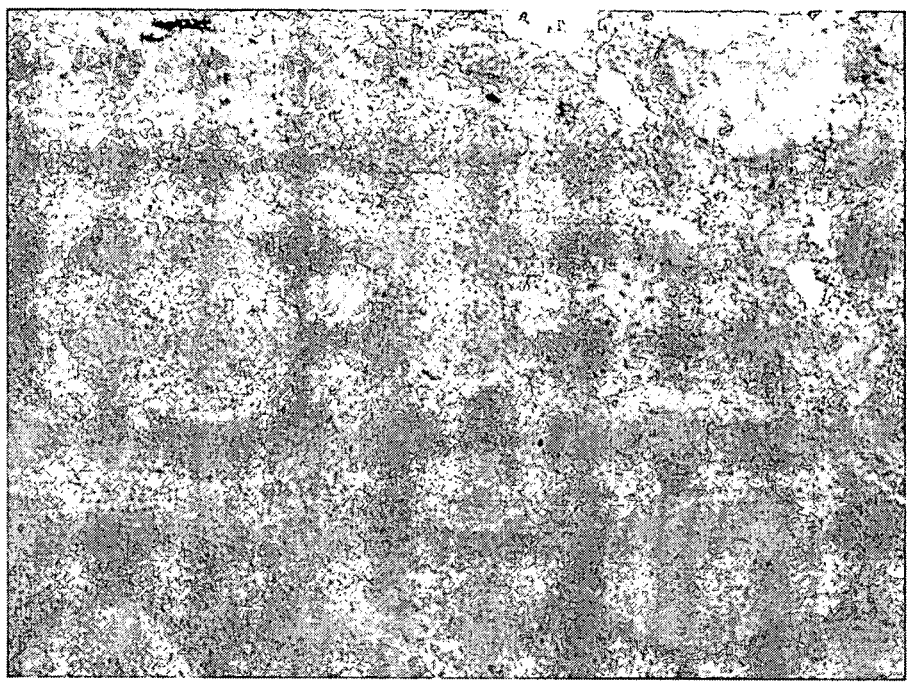
FIGS. 12A and B, are photomicrographs taken at 4 times magnification of anti bcl-2 DAB stained tonsil FFPE samples using the DNP labeled bcl-2 antibody, rabbit anti DNP polymer and goat anti rabbit HRP conjugate (A) and staining using the un-conjugated primary antibody and EnVision™ (K4007) (B), respectively.
Figure 12B:
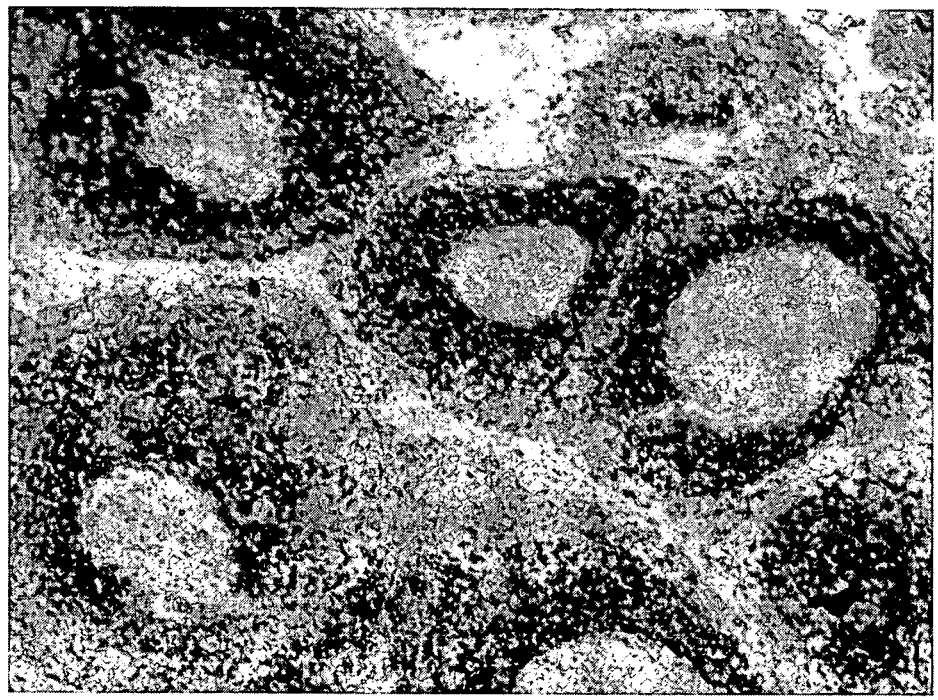

FIGS. 12A and B, are representative photomicrographs taken at 4 times magnification of anti bcl-2 stained tonsil FFPE samples using the hapten labeled bcl-2 antibody, anti DNP polymer and goat anti rabbit HRP conjugate (A) and staining using the un-conjugated primary antibody and EnVision™ (DakoCytomation, Carpenteria, Calif.) (B), respectively.

The results showed the expected localization of staining but was somewhat weak (0.5+). The reference was strongly stained (3+) with the expected staining pattern. The example illustrates the feasibility of using a labeled primary antibody or reagent and as part of the visualization system of the invention.

By using hapten encoded primary antibodies or probes, it will be possible to construct assay configurations with more flexibility than for those configurations using only secondary or tertiary antibodies directed against other IgGs.

Example 27

Staining of Bcl-2 Oncoprotein Using a Polymeric Primary Mouse Antibody, Polymeric Secondary Conjugate Against Mouse and Secondary Antibody Conjugate Linked with Alkaline Phosphatase The example describes manual immunovisualization of the Bcl-2 Oncoprotein on tonsils in a FFPE sample using Conjugate No. 10, a polymeric dextran conjugate containing mouse anti human Bcl-2, followed by the same conjugate cocktails as described in example 23 and 24, i.e., the Advance AP. A cocktail containing polymeric conjugates containing GAR and GAM (conjugate no. 2 and 3), and the polymeric conjugate containing rabbit anti goat and alkaline phosphatase (conjugate no. 6) was used. The assay set up is illustrated in FIG. 1-I.

The sample and antigen retrieval used were as desribed in example 25. The first conjugate (conjugate no. 10, diluted 1:100 in the conjugate diluent) was incubated for 30 minutes at room temperature. The next steps were as described in example 23, except liquid permanent red (Dakocytomation, Carpenteria, Calif.) was used as an AP chromogen. The slides were haematoxylin counter stained and cover slipped as described previously.

In parallel, samples were stained using the un-conjugated antibody (Dakocytomation, Carpenteria, Calif.) diluted 1:200 and Envision™ AP according to the manufacturer's instructions.

Figure 13A:
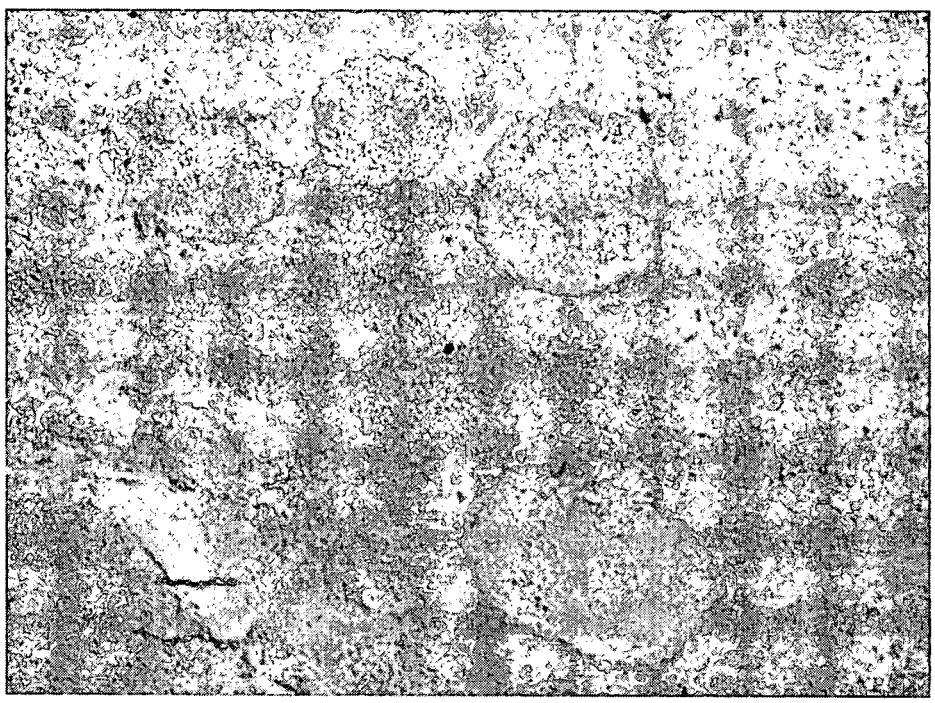
FIGS. 13A and B, are photomicrographs taken at 4 times magnification of bcl-2 liquid permanent red stained tonsil FFPE samples using the anti bcl-2 polymer conjugate and Advance AP (A) and bcl-2 and EnVision™ AP (B), respectively.
Figure 13B:
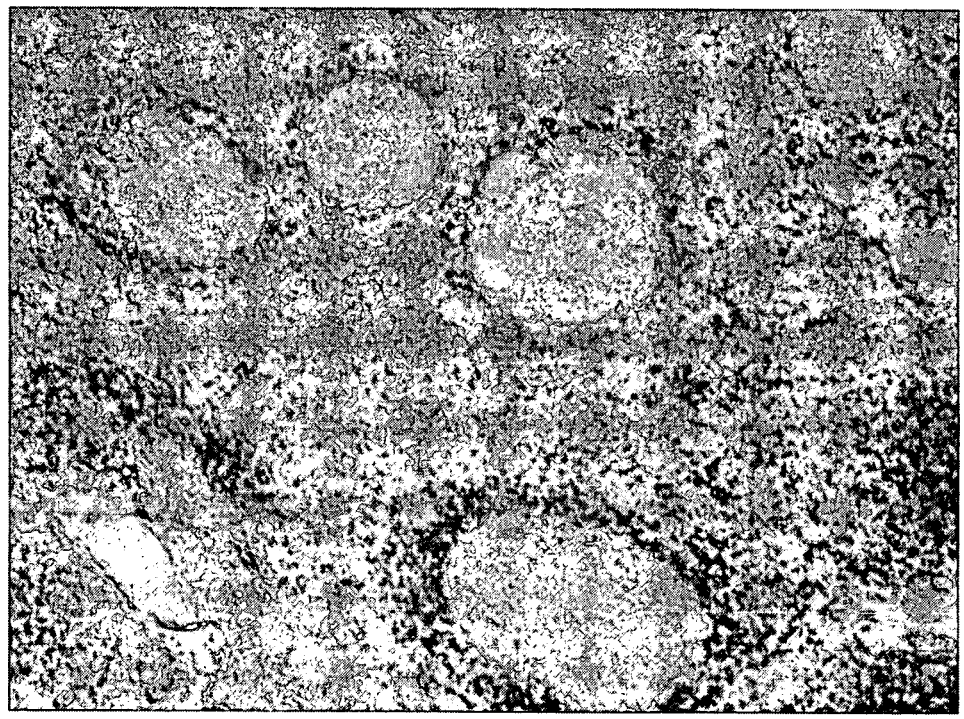

FIGS. 13A and B, are representative photomicrographs taken at 4 times magnification of bcl-2 stained tonsil FFPE samples using the anti bcl-2 polymer conjugate and Advance AP (A) and bcl-2 and EnVison™ AP (B), respectively.

The staining pattern was as expected for both systems. The system in this example showed very strong, specific and clean staining (2.5+) with no detectable background. The reference system was at the same or slightly higher staining intensity, though appeared slightly more sharply localized.

It is somewhat surprising that the larger molecular weight of the conjugate containing the primary antibody did not negatively affect the staining efficiency.

Example 28

Double Staining of FFPE Prostate Samples Using a Mouse and Rabbit Primary Antibody Cocktail and Polymeric Secondary Conjugates Linked with Horseradish Peroxidase or Alkaline Phosphatase The example describes the double immunovisualization of three mouse and rabbit antibodies using a combination of conjugates of the invention. The rabbit antibody was visualized with a combination of a Goat anti mouse dextran conjugate (no. 2) and a conjugate containing Rabbit anti goat and alkaline phosphatase conjugate (No. 6). The two mouse antibodies were visualized using a conjugate containing swine anti mouse IgG and horseradish peroxidase (conjugate No. 11). The assay components are illustrated in FIG. 1-K.

An FFPE prostate samples was cut, mounted and deparaffinated as previously described. Antigen retrieval was done using Target Retrieval Solution S2367 (DakoCytomation, Carpenteria, Calif.). The sample was placed in a water bath at 96° C. for 20 minutes.

After washing in TBS/Tween20 buffer (Dakocytomation, Carpenteria, Calif.), the slides were treated with Dual Endogenous Enzyme Block reagent (DakoCytomation, Carpenteria, Calif.).

The slides were incubated with a cocktail of rabbit and mouse monoclonal antibodies in Dakocytomation dilution buffer (DakoCytomation, Carpenteria, Calif.). The dilutions were as follows: monoclonal Rabbit Anti-Human P504S clone 13H4 was diluted 1:100; monoclonal Mouse Anti-Human p63 Protein clone 4A4 was diluted 1:150; and monoclonal Mouse Anti-Human HMW Cytokeratin clone 34βE12 was diluted 1:100. These antibodies were obtained from Dalocytomation (DakoCytomation, Carpenteria, Calif.).

After washing, the slides were treated with a cocktail of conjugate no. 11 containing swine anti mouse and horse radish peroxidase, and conjugate no. 2, containing goat anti rabbit. After washing, the slides were incubated with conjugate no. 6, containing rabbit anti goat and alkaline phosphatase.

The staining was done by first applying DAB+ (Dakocytomation, Carpenteria, Calif.) and then applying Liquid Permanent Red (Dakocytomation, Carpenteria, Calif.) according to the manufacturer's instructions.

The slides were counterstained with haematoxylin (DakoCytomation, Carpenteria, Calif.) before being cover slipped and examined. The staining was also done with the HRP reagent and the AP reagent only.

Figure 14A:
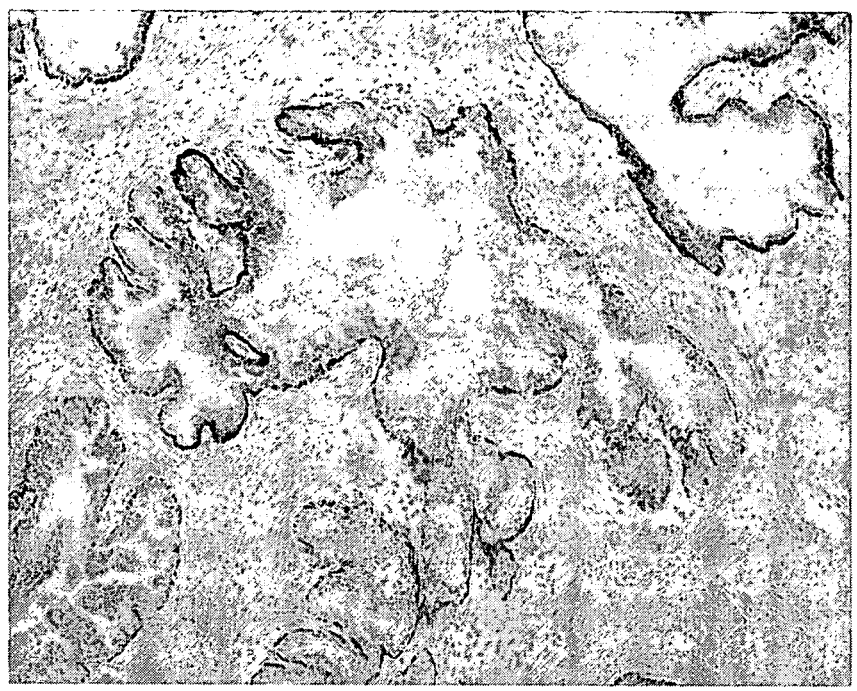
FIG. 14A-C, are photomicrographs of double staining experiments on prostate FFPE samples using a cocktail of Rabbit Anti-Human P504S, Mouse Anti-Human p63 Protein and Mouse Anti-Human HMW Cytokeratin and the combination of swine anti mouse HRP, Goat anti rabbit polymer and rabbit anti goat AP: Separate HRP/DAB stain (A), AP/Liquid Permanent Red stain (B) and combined stains (C).
Figure 14B:
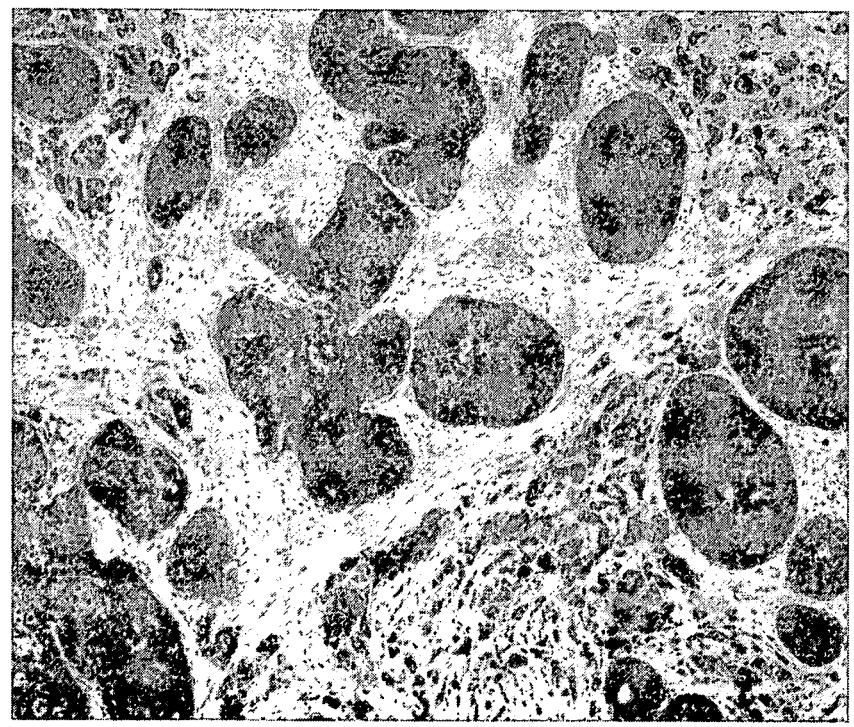
Figure 14C:
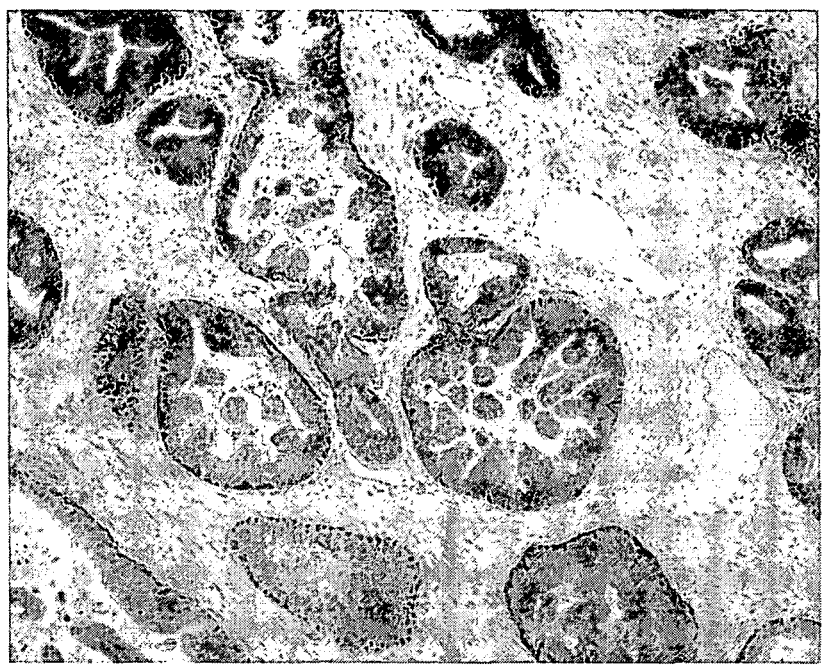

FIG. 14A-C, are representative photomicrographs taken at 4 times magnification. The stained prostate FFPE samples shown use the separate HRP (A), AP (B) and combined stains (C).

FIG. 14(A) shows the specific DAB staining of Benign Prostatic Hyperplasia with demonstrated staining of basal cells surrounding glands.

FIG. 14(B) show the AP Liquid Permanent Red staining on prostatic adenocarcinoma with rabbit monoclonal P504s antibody showing staining in areas of invasive cancer and Prostatic Intraepithelial Neoplasia ("PIN").

FIG. 14(C) show the double staining on prostatic carcinoma. It shows strong nuclear and cytoplasmic staining (DAB, brown) of HMW CK and p63 antibodies in basal cells surrounding the prostate glands. Moderate expression of P504s is seen in areas of PIN (Liquid Permanent Red).

The combination of the new detection components in this example demonstrate the use of multiple antibodies in an easy to use cocktail. The system permits the visualization and identification of more than one marker with very high sensitivity and certainty on a single slide. This provides for an improved diagnostic test. Further, the example illustrates the compatibility of the invention with other visualization systems.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of detecting a biological marker in a sample comprising:
   a. contacting the sample with at least one first binding agent that specifically binds to the biological marker in the sample such that the at least one first binding agent binds to the sample and forms a first complex;
   b. contacting the first complex of a) with at least one second binding agent that specifically binds to the at least one first binding agent such that a second complex is formed, wherein the at least one second binding agent is linked to at least one first polymer;
   c. contacting the second complex of b) with at least one third binding agent that specifically binds to the at least one second binding agent, wherein the at least one third binding agent is linked to at least one second polymer;
   wherein at least one detectable agent is linked to at least one of
      i. the at least one third binding agent;
      ii. the at least one second polymer; or
      iii. both the at least one third binding agent and the at least one second polymer;
   wherein the at least one third binding agent binds to the second complex of b) and forms a third complex; and
   d. detecting the at least one detectable agent of the third complex of c), thereby detecting the biological marker in the sample.

2. The method of claim 1, wherein the at least one first binding agent is a primary antibody or a nucleic acid probe.

3. The method of claim 2, wherein the at least one first binding agent is a primary antibody derived from any mammalian or avian species.

4. The method of claim 3, wherein the primary antibody is derived from a rat, mouse, pig, goat, rabbit, sheep, guinea pig, donkey, llama, camel, or horse.

5. The method of claim 1, wherein the at least one second binding agent is a dual linked binding agent.

6. The method of claim 1, wherein the at least one second binding agent is a secondary antibody.

7. The method of claim 6, wherein the secondary antibody is derived from any mammalian species except the mammalian species from which the primary antibody is derived.

8. The method of claim 7, wherein the secondary antibody is derived from a rat, mouse, pig, goat, rabbit, sheep, guinea pig, donkey, llama, camel, or horse.

9. The method of claim 1, wherein the at least one second binding agent is at least one of fos, jun, major histocompatibility complex (MHC), C1q, an immunoglobulin receptor, or any molecule comprising a leucine zipper domain.

10. The method of claim 9, wherein the at least one second binding agent further comprises an Fc region of an antibody.

11. The method of claim 9, wherein the at least one second binding agent is an MHC molecule, and wherein the MHC molecule is MHC class I, MHC class II, or non-conventional MHC.

12. The method of claim 1, wherein the at least one third binding agent is a tertiary antibody.

13. The method of claim 12, wherein the tertiary antibody is derived from any mammalian species except the mammalian species from which the primary antibody and secondary antibody are derived.

14. The method of claim 13, wherein the tertiary antibody is derived from a rat, mouse, pig, goat, rabbit, sheep, guinea pig, donkey, llama, or horse.

15. The method of claim 12, wherein the tertiary antibody binds to a hapten molecule linked to at least one of:
   i. the at least one second binding agent;
   ii. the at least one first polymer; or
   iii. the at least one second binding agent and the at least one first polymer.

16. The method of claim 15, wherein the hapten is FITC, DNP, Digoxigenin, nitrotyrosine biotin, avidin, streptavidin, or an anti-dye antibody.

17. The method of claim 1, wherein the at least one third binding agent is fos, jun, major histocompatibility complex (MHC), C1q, an immunoglobulin receptor, or any molecule having a leucine zipper domain.

18. The method of claim 17, wherein the at least one third binding agent further comprises an Fc region of an antibody.

19. The method of claim 17, wherein the MHC molecule is MHC class I or MHC class II.

20. The method of claim 1, wherein the sample is a tissue sample.

21. The method of claim 1, wherein the sample is a cell sample.

22. The method of claim 1, wherein the sample is a mammalian sample.

23. The method of claim 22, wherein the mammalian sample is a human sample.

24. The method of claim 1, wherein the biological marker in the sample is a protein.

25. The method of claim 24, wherein the protein in the sample is expressed at higher or lower levels in a cell obtained from a subject having a disease compared to a cell obtained from a subject not having the disease.

26. The method of claim 1, wherein the sample is provided on a solid support.

27. The method of claim 26, wherein the solid support is a microscope slide, a solid support capable of being inspected under a microscope, or a solid support capable of being used to produce photomicrographs.

28. The method of claim 1, wherein the at least one second binding agent linked to the at least one first polymer comprises two different secondary antibodies linked to two different polymers, each of the two secondary antibodies comprising an antigen binding domain which specifically binds to the at least one first binding agent, wherein the at least one first binding agent comprises two different primary antibodies derived from different mammalian sources.

29. The method of claim 28, wherein the primary antibodies are derived from a rat, mouse, pig, goat, rabbit, sheep, guinea pig, donkey, llama, or horse.

30. The method of claim 1, further comprising at least one second detectable agent linked to at least one of
   a. the at least one first polymer;
   b. the at least one second binding agent; or
   c. both the at least one first polymer and the at least one second binding agent.

31. The method of claim 30, wherein the at least one first and second detectable agents are the same agent.

32. The method of claim 30, wherein the at least one first and second detectable agents are different agents.

33. The method of claim 30, wherein the at least one first and second detectable agents are fluorescent labels, enzyme labels, radioisotopes, chemiluminescent labels, bioluminescent labels, polymers, metal particles, haptens, antibodies, or dyes.

34. The method of claim 33, wherein the at least one first and second detectable agents are 5-(and 6)-carboxyfluorescein, 5- or 6 -carboxyfluorescein, 6-(fluorescein)-5-(and 6)-carboxamido hexanoic acid, fluorescein isothiocyanate, rhodamine, tetramethylrhodamine, Cy2, Cy3, Cy5, AMCA, PerCP, R-phycoerythrin (RPE), allophycoerythrin (APC), Texas Red, Princeton Red, Green fluorescent protein (GFP), coated CdSe nanocrystallites, DNP, biotin, digoxiginin, horseradish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), luminol, isoluminol, acridinium esters, 1,2 -dioxetanes, 1,2-pyridopyridazines, or radioactive isotopes of hydrogen, carbon, sulfur, iodide, cobalt, selenium, tritium, or phosphorous.

35. The method of claim 1, wherein at least one of the first binding agent, the second binding agent, and the third binding agent is an antibody.

36. The method of claim 35 wherein the antibody is a monoclonal antibody.

37. The method of claim 1, further comprising two second binding agents wherein each second binding agent is individually linked to at least one separate polymer.

38. The method of claim 1, wherein at least one of the at least one first polymer and the at least one second polymer comprises natural polysaccharides, synthetic polysaccharides, polyethylene glycol-containing polymer backbones, polypropylene glycol-containing polymer backbones, poly(ethylene oxide-co-propylene oxide)-containing polymer backbones, linear dendrimers, comb-shaped dendrimers, branched dendrimers, poly amino acids, proteins, polynucleotides, or oligonucleotide dendrimer constructs.

39. The method of claim 38, wherein the polymer is a mixed polymer comprising two or more of the following: natural polysaccharides, synthetic polysaccharides, polyethylene glycol-containing polymer backbones, polypropylene glycol-containing polymer backbones, poly(ethylene oxide-co-propylene oxide)-containing polymer backbones, linear dendrimers, comb-shaped dendrimers, branched dendrimers, poly amino acids, polynucleotides, or oligonucleotide dendrimer constructs.

40. The method of claim 39, wherein the polysaccharides comprise dextrans, cyclodextrins, pullulans, schizophyllan, scleroglucan, xanthan, gellan, O-ethylamino guaran, chitins, chitosans, derivatized cellulosics, hydroxylated starch, hydroxypropyl starch, hydroxyethyl starch, carrageenans, alginates, or agarose; the synthetic polysaccharides comprise vinyl polymers; the poly amino acids comprise polylysines, polyglutamic acid, polyurethanes, or poly(ethylene imines); the proteins comprise albumins or immunoglobulins; and the polynucleotides comprise DNA, peptide nucleic acid (PNA), locked nucleic acid (LNA), or oligonucleotides.

41. The method of claim 40, wherein the dextrans comprise carboxy methyl dextran, dextran polyaldehyde, or carboxymethyl dextran lactone; the vinyl polymers comprise poly(acrylic acid), poly(acryl amides), poly(acrylic esters), poly(2-hydroxy ethyl methacrylate), poly(methyl methacrylate), poly(maleic acid), poly(maleic anhydride), poly(acrylamide), poly(ethyl-co-vinyl acetate), poly(methacrylic acid), poly(vinylalcohol), poly(vinyl alcohol-co-vinyl chloroacetate), aminated poly(vinyl alcohol), or co block polymers thereof; the chitins comprise 6-O-carboxymethyl chitin; the chitosans comprise N-carboxymethyl chitosan; and the derivatized cellulosics comprise carboxymethyl cellulose, carboxymethyl hydroxyethyl cellulose, hydroxyethyl cellulose, 6-amino-6-deoxy cellulose, or O-ethylamine cellulose.

42. The method of claim 38, wherein if at least one of the at least one first polymer and the at least one second polymer comprises natural polysaccharides, the natural polysaccharides comprise dextrans, cyclodextrins, pullulans, schizophyllan, scleroglucan, xanthan, gellan, O-ethylamino guaran, chitins, chitosans, derivatized cellulosics, hydroxylated starch, hydroxypropyl starch, hydroxyethyl starch, carrageenans, alginates, or agarose; or if at least one of the at least one first polymer and the at least one second polymer comprises synthetic polysaccharides, the synthetic polysaccharides comprise vinyl polymers; or if at a least one of the at least one first polymer and the at least one second polymer comprises poly amino acids, the poly amino acids comprise polylysines, polyglutamic acid, polyurethanes, or poly(ethylene imines); or if at least one of the at least one first polymer and the at least one second polymer comprises proteins, the proteins comprise albumins or immunoglobulins; or if at least one of the at least one first polymer and the at least one second polymer comprises polynucleotides, the polynucleotides comprise DNA, peptide nucleic acid (PNA), locked nucleic acid (LNA), or oligonucleotides.

43. The method of claim 42, wherein if at least one of the at least one first polymer and the at least one second polymer comprises dextrans, the dextrans comprise carboxy methyl dextran, dextran polyaldehyde, or carboxymethyl dextran lactone; or if at least one of the at least one first polymer and the at least one second polymer comprises vinyl polymers, the vinyl polymers comprise poly(acrylic acid), poly(acryl amides), poly(acrylic esters), poly(2-hydroxy ethyl methacrylate), poly(methyl methacrylate), poly(maleic acid), poly(maleic anhydride), poly(acrylamide), poly(ethyl-co-vinyl acetate), poly(methacrylic acid), poly(vinylalcohol), poly(vinyl alcohol-co-vinyl chloroacetate), aminated poly(vinyl alcohol), or co block polymers thereof; or if at least one of the at least one first polymer and the at least one second polymer comprises chitins, the chitins comprise 6-O-carboxymethyl chitin; or if at least one of the at least one first polymer and the at least one second polymer comprises chitosans, the chitosans comprise N-carboxymethyl chitosan; or if at least one of the at least one first polymer and the at least one second polymer comprises derivatized celllulosics, the derivatized cellulosics comprise carboxymethyl cellulose, carboxymethyl hydroxyethyl cellulose, hydroxyethyl cellulose, 6-amino-6-deoxy cellulose, or O-ethylamine cellulose.

44. The method of claim 1, wherein at least one of the first polymer and the second polymer comprises dextran.

45. A method of detecting a biological marker in a sample comprising
   a. contacting the sample with at least one primary mouse or rabbit antibody that specifically binds to the biological marker in the sample, such that the at least one primary antibody binds to the sample forming a first complex;
   b. contacting the first complex of a) with
      i. at least one first secondary goat antibody linked to at least one first polymer, the at least one first secondary goat antibody comprising an antigen binding domain that specifically binds to a mouse antibody; and
      ii. at least one second secondary goat antibody linked to at least one second polymer, the at least one second secondary goat antibody comprising an antigen binding domain that specifically binds to a rabbit antibody,
      such that at least one secondary antibody binds to the first complex of a) forming a second complex;
   c. contacting the second complex of b) with at least one tertiary rabbit antibody linked to at least one third polymer, the at least one tertiary rabbit antibody comprising an antigen binding domain that specifically reacts with a goat antibody;
      wherein at least one horseradish peroxidase molecule is linked to at least one of
         1. the at least one tertiary antibody;
         2. the at least one third polymer; or
         3. both the at least one tertiary antibody and the at least one third polymer;
      wherein the at least one tertiary antibody binds to the second complex of b) and forms a third complex; and
   d. detecting the horseradish peroxidase of the third complex of c), thereby detecting the biological marker in the sample.

46. A method of detecting a biological marker in a sample comprising
   a. contacting the sample with at least one primary mouse antibody that specifically binds to the biological marker in the sample such that the at least one primary mouse antibody binds to the sample forming a first complex;
   b. contacting the first complex of a) with at least one rabbit secondary antibody linked to at least one first polymer, the at least one rabbit secondary antibody comprising an antigen binding domain that specifically reacts with a mouse antibody such that the at least one rabbit antibody specifically binds to the first complex of a) forming a second complex;
   c. contacting the second complex of b) with at least one tertiary goat antibody linked to at least one second polymer, the at least one tertiary goat antibody comprising an antigen binding domain that specifically binds to a rabbit antibody;
      wherein at least one horseradish peroxidase molecule is linked to at least one of
         1. the at least one tertiary antibody;
         2. the at least one second polymer; or
         3. both the at least one tertiary antibody and the at least one second polymer
      wherein the at least one tertiary antibody binds to the second complex of b) and forms a third complex; and
   d. detecting the horseradish peroxidase of the third complex of c), thereby detecting the biological marker in the sample.

47. A method of detecting a biological marker in a sample comprising
   a. contacting the sample with at least one primary mouse antibody that specifically binds to the biological marker in the sample such that the at least one primary mouse antibody binds to the sample forming a first complex;
   b. contacting the first complex of a) with at least one secondary rabbit antibody linked to at least one first polymer, the at least one secondary rabbit antibody comprising an antigen binding domain which specifically reacts with a mouse antibody such that the at least one secondary antibody binds to the first complex of a) forming a second complex;
   c. contacting the second complex of b) with
      i. at least one first tertiary goat antibody linked to at least one second polymer, the at least one first tertiary goat antibody comprising an antigen binding domain that specifically binds to a rabbit antibody; and
      ii. at least one second tertiary goat antibody linked to at least one third polymer, the at least one second tertiary goat antibody comprising an antigen binding domain which specifically reacts with a mouse antibody;
      wherein at least one horseradish peroxidase molecule is linked to at least one of
         1. any tertiary antibody;
         2. the at least one second polymer;
         3. the at least one third polymer;
         4. both the at least one second polymer and the at least one third polymer; or
         5. any tertiary antibody and both the at least one second polymer and the at least one third polymer;
      wherein the at least one first and second tertiary antibodies bind to the second complex of b and form a third complex; and
   d. detecting the horseradish peroxidase of the third complex of c), thereby detecting the biological marker in the sample.

48. The method of claim 47, further comprising at least one horseradish peroxidase molecule linked to
   a. the at least one secondary rabbit antibody;
   b. the at least one first polymer; or
   c. both the at least one secondary rabbit antibody and the at least one first polymer.

49. A method of detecting a biological marker in a sample comprising
   a. contacting the sample with at least one primary mouse or rabbit antibody that specifically binds to the biological marker in the sample, such that the at least one primary antibody binds to the sample forming a first complex;
   b. contacting the first complex of a) with at least one second binding agent comprising
      i. at least one first secondary goat antibody linked to at least one first polymer, the at least one first secondary goat antibody comprising an antigen binding domain that specifically binds to a mouse antibody;
      ii. at least one second secondary goat antibody linked to at least one second polymer, the at least one second secondary goat antibody comprising an antigen binding domain that specifically binds to a rabbit antibody; and
      iii. at least one hapten molecule linked to at least one of
         1. the first or second secondary goat antibodies;
         2. the first or second polymers; or
         3. the first or second secondary goat antibody and the first or second polymers;
      such that at least one secondary antibody binds to the first complex of a) forming a second complex;
   c. contacting the second complex of b) with at least one tertiary rabbit, mouse, rat, pig, or goat antibody, linked to at least one third polymer, the at least one tertiary antibody comprising an antigen binding domain that specifically binds to at least one hapten molecule of b);
      wherein at least one horseradish peroxidase molecule is linked to at least one of
         1. the at least one tertiary antibody;
         2. the at least one third polymer; or
         3. both the at least one tertiary antibody and the at least one third polymer;
      wherein the at least one tertiary antibody binds to the second complex of b) and forms a third complex; and
   d. detecting the horseradish peroxidase of the third complex of c), thereby detecting the biological marker in the sample.

* * * * *

UNITED STATES PATENT AND TRADEMARK OFFICE
CERTIFICATE OF CORRECTION

PATENT NO. : 8,632,994 B2  
APPLICATION NO. : 10/999102  
DATED : January 21, 2014  
INVENTOR(S) : Lars Winther et al.

It is certified that error appears in the above-identified patent and that said Letters Patent is hereby corrected as shown below:

On the Title page, under the "OTHER PUBLICATIONS" heading, "Harlow, E. and Lane, D., Antibodies: A Laboratory Manual (1988) Cold Spring Harbor Laboratory Press, Cold Spring Harbor, NY, pp. 359 and 361-420.*" should read -- Harlow, E. and Lane, D., Antibodies: A Laboratory Manual (1988) Cold Spring Harbor Laboratory Press, Cold Spring Harbor, NY, pp. 319, 321, 344, 359 and 361-420.* --.

In the Claims:

In Claim 41, col. 51, line 17, "poly(vinylalcohol)" should read -- poly(vinyl alcohol) --.

In Claim 42, col. 51, line 34, "or if ata least" should read -- or if at least --.

Signed and Sealed this  
Fifteenth Day of April, 2014

Michelle K. Lee  
*Deputy Director of the United States Patent and Trademark Office*